(12) United States Patent
Voigt et al.

US009040266B2

(10) Patent No.: US 9,040,266 B2
(45) Date of Patent: May 26, 2015

(54) CELL-BASED SYSTEMS FOR PRODUCTION OF METHYL FORMATE

(75) Inventors: Christopher A. Voigt, San Francisco, CA (US); Travis S. Bayer, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 181 days.

(21) Appl. No.: 13/386,205

(22) PCT Filed: Jul. 22, 2010

(86) PCT No.: PCT/US2010/042943
§ 371 (c)(1),
(2), (4) Date: Jun. 21, 2012

(87) PCT Pub. No.: WO2011/011627
PCT Pub. Date: Jan. 27, 2011

(65) Prior Publication Data
US 2012/0258506 A1   Oct. 11, 2012

Related U.S. Application Data

(60) Provisional application No. 61/227,734, filed on Jul. 22, 2009.

(51) Int. Cl.
*C12P 7/62* (2006.01)
*C12P 1/02* (2006.01)
*C12N 9/10* (2006.01)
*C12P 39/00* (2006.01)

(52) U.S. Cl.
CPC ............... *C12N 9/1007* (2013.01); *C12P 7/62* (2013.01); *C12P 39/00* (2013.01); *C12Y 201/01165* (2013.01); *C12P 1/02* (2013.01)

(58) Field of Classification Search
None
See application file for complete search history.

(56) References Cited

U.S. PATENT DOCUMENTS

| | | | |
|---|---|---|---|
| 4,510,243 | A | 4/1985 | Haga et al. |
| 5,514,586 | A | 5/1996 | Hottinger et al. |
| 6,610,504 | B1 | 8/2003 | Yuan |
| 6,649,397 | B1 | 11/2003 | Nakamura |
| 7,160,704 | B2 | 1/2007 | Takeshita et al. |
| 2004/0175805 | A1 | 9/2004 | Leonhartsberger et al. |
| 2004/0265953 | A1 | 12/2004 | Harman et al. |
| 2005/0267023 | A1 | 12/2005 | Sinclair et al. |
| 2006/0235088 | A1 | 10/2006 | Olah et al. |
| 2007/0026505 | A1 | 2/2007 | Madden et al. |
| 2007/0118916 | A1 | 5/2007 | Puzio et al. |
| 2007/0178569 | A1 | 8/2007 | Leschine et al. |

FOREIGN PATENT DOCUMENTS

| | | |
|---|---|---|
| WO | 2009/073557 A2 | 6/2009 |
| WO | 2009/073560 A1 | 6/2009 |

OTHER PUBLICATIONS

Purification and properties of methyl formate synthase a mitochondrial alcohol dehydrogenase, participating in formaldehyde oxydation in methylotropic yeasts Murdano et al App. Environ. Microbiol. 1997, 63(5):1715.*
International Search Report for PCT/US2010/42943, mailed on Sep. 15, 2010, 4 pages.
International Search Report for PCT/US2008/085013, mailed May 28, 2009, 3 pages.
Supplementary European Search Report for EP Patent Application No. 08858165.7, mailed on May 26, 2011, 5 pages.
Attieh et al., "Purification and properties of multiple isoforms of a novel thiol methyltransferase involved in the production of volatile sulfur compounds from *Brassica oleracea*", Archives of Biochemistry and Biophysics, 2000, p. 257-266, vol. 380, No. 2.
Bayer et al., "Synthesis of Methyl Halides from Biomass Using Engineered Microbes", Journal of the American Chemical Society, May 2009, vol. 131, No. 18, p. 6508-6515.
Farooqui et al., "Studies on Compartmentation of S-Adenosyl-L-Methionine in *Saccharomyces Cerevisiae* and Isolated Rat Hepatocytes", Biochimica et Biophysica Acta, 1983, p. 342-351, vol. 757.
Harper, D B., "Halomethane from Halide Ion a Highly Efficient Fungal Conversion of Environmental Significance", Nature, 1985, vol. 315, No. 6014, p. 55-57.
Itoh et al., "Formation and emission of monohalomethanes from marine algae", Phytochemistry, 1997, p. 67-73, vol. 45, No. 1.
Janssen et al., "Microbial dehalogenation", Current Opinion in Biotechnology, 2001, p. 254-258, vol. 12.
Marobbio et al., "Identification and functional reconstitution of yeast mitochondrial carrier for S-adenosylmethionine", The EMBO Journal, 2003, vol. 22, No. 22, p. 5975-5982.
Murdanoto et al., "Purification and Properties of Methyl Formate Synthase, a Mitochondrial Alcohol Dehydrogenase, Participating in Formaldehyde Oxidation in Mehtylotrophic Yeast", Applied and Environmental Microbiology, 1997, p. 1715-1720, vol. 63.
Nakamori et al., "Mechanism of L-methionine overproduction by *Escherichia coli*: the replacement of Ser-54 by Asn in the MetJ protein causes the depression of L-methionine biosynthetic enzymes", Appl Microbiol Biotechnol, 1999, vol. 52, p. 179-185.
Ni et al., "Expression of *Batis maritima* methyl chloride thansferase in *Escherichia coli*", Proceedings of the National Academy of Sciences, Mar. 30, 1999, vol. 96, No. 7, p. 3611-3615.

(Continued)

*Primary Examiner* — Kagnew H Gebreyesus
(74) *Attorney, Agent, or Firm* — Kilpatrick Townsend & Stockton LLP

(57) ABSTRACT

Disclosed is a process in which a recombinant organism, such as a yeast, expressing a heterologous S-adenosylmethionine (SAM)-dependent methyl halide transferase (MHT) protein is combined with a halide and a carbon source in a cultivation medium under conditions in which methyl formate is produced. The cell may genetically modified to express methyl formate synthase, methanol dehydrogenase and/or hydrolytic dehalogenase at levels higher than a cell of the same species that is not genetically modified. The methyl formate may be collected and used in a variety of applications. The halide may be chlorine, bromine or iodine.

19 Claims, 17 Drawing Sheets

(56) References Cited

OTHER PUBLICATIONS

Ni et al., "cDNA cloning of *Batis maritima* methyl chloride transferase and purification of the enzyme", Proceedings of the National Academy of Sciences, 1998, vol. 95, p. 12866-12871.

Saxena et al., "Biochemical characterization of chloromethane emission from the wood-rotting fungus *Phellinus pomaceus*", Applied and Environmental Microbiology, Aug. 1998, vol. 64, No. 8, p. 2813-2835.

Sun et al., "The Catalytic Conversion of Methyl Chloride to Ethylene and Propylene over Phosphorus-Modified Mg-ZSM-5 Zeolites", Journal of Catalysis, 1993, vol. 143, p. 32-44.

Suzuki et al., "Growth of a Tryptophanase-producing thermophile *symbiobacterium-thermophilum* new-genus new-species is dependent on co-culture with a *bacillus*-sp", Journal of General Microbiology, 1988, p. 2353-2362, vol. 134, No. 8.

Wada et al., "Chemiosmotic Coupling of Ion Transport in the Yeast Vacuole: Its Role in Acidification Inside Organelles", Journal of Bioenergetics and Biomembranes, 1994, vol. 26, No. 6, p. 631-637.

Wuosmaa et al., "Methyl Chloride Transferase: a Carbocation Route for Biosynthesis of Halometabolites", Science; 1990, vol. 249, No. 4965, p. 160-162.

Zaheer et al., "Studies on Compartmentation of S-Adenosyl-L-Methionine in *Saccharomyces Cerevisiae* and Isolated Rat Hepatocytes", Biochimica et Biophysica Acta, 1983, vol. 757, p. 342-351.

Janssen et al., "Purification and Characterization of a Bacterial Dehalogenase with Activity Toward Halogenated Alkanes, Alcohols and Ethers," European Journal of Biochemistry, 171: 67-72 (1988).

Murdanoto et al., "Ester Synthesis S by NAD+-Dependent Dehydrogenation of Hemiacetal: Production of Methyl Formate by Cells of Methylotrophic Yeasts," Bioscience, Biotechnology, and Biochemistry, 61(8): 1391-1393 (1997).

* cited by examiner

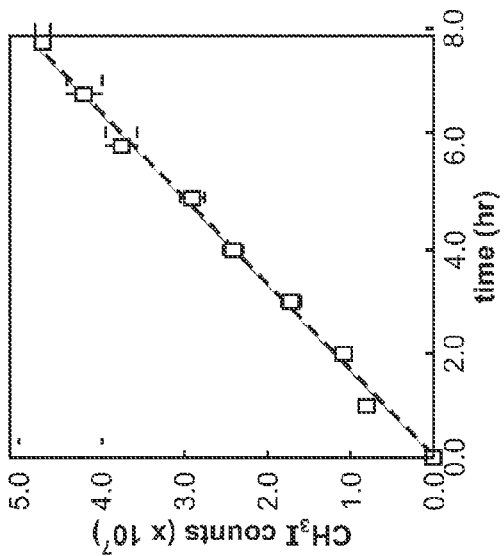
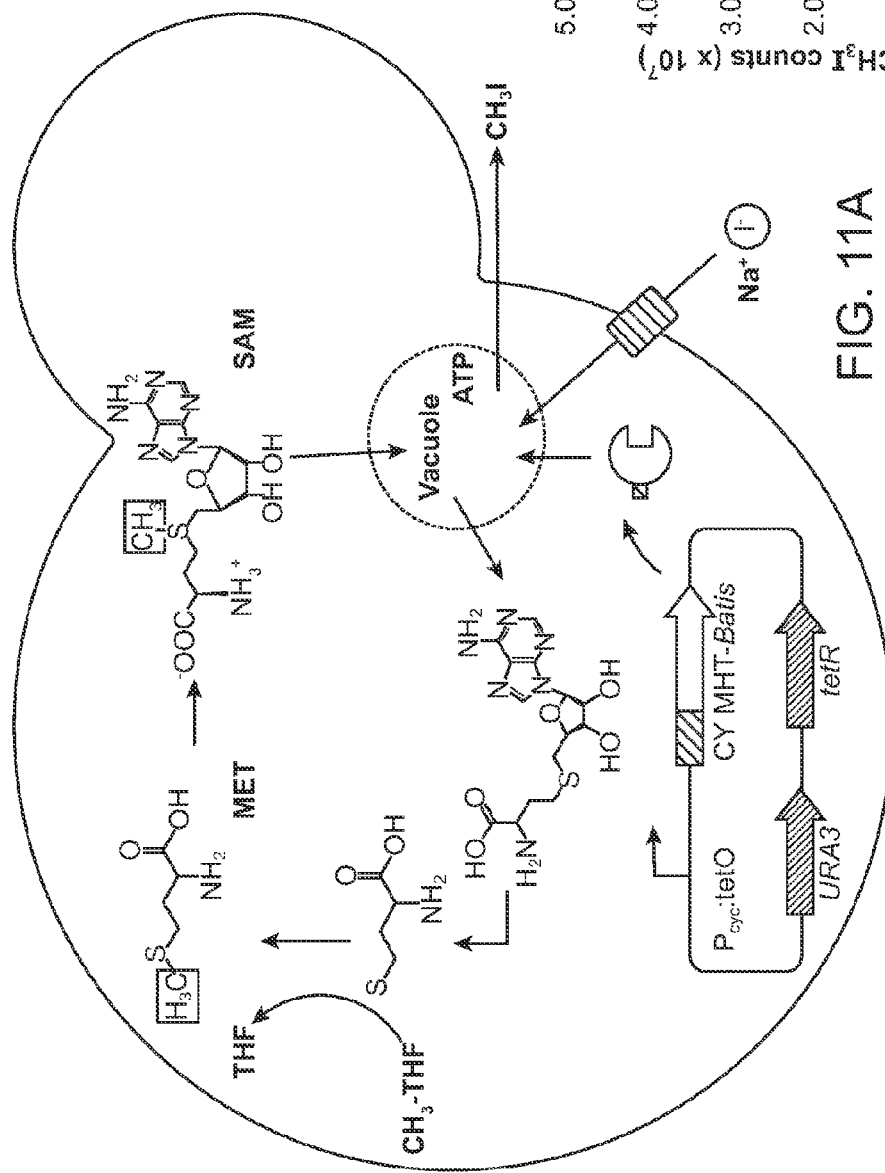
FIG. 11A
FIG. 11B

CELL-BASED SYSTEMS FOR PRODUCTION OF METHYL FORMATE

CROSS-REFERENCE TO RELATED APPLICATIONS

This application is a National Stage of PCT/US2010/042943, filed Jul. 22, 2010, which claims priority to U.S. provisional application No. 61/227,734, filed Jul. 22, 2009, the entire content of which is incorporated herein by reference.

STATEMENT AS TO RIGHTS TO INVENTIONS MADE UNDER FEDERALLY SPONSORED RESEARCH AND DEVELOPMENT

This invention was made with government support under grant no. R01 AI067699 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEST FILE

The Sequence Listing written in file 81906-830165_ST25.TXT, created on Feb. 12, 2012, 216,025 bytes, machine format IBM-PC, MS-Windows operating system, is hereby incorporated by reference.

FIELD OF THE INVENTION

The invention relates to production of biofuels and other methyl halide derivatives by cultivation of genetically modified organisms expressing methyl halide transferase.

BACKGROUND

Methyl halides are reactive one-carbon compounds from which a wide variety of commercially important organic products can be produced. Industrial production of methyl halides has been carried out using chemical methods that often consume high amounts of energy, and involve conditions of high temperature and pressure. For example, a common method for industrial production of methyl halides involves reaction of methanol with gaseous hydrogen chloride in the presence of an aluminum oxide catalyst at elevated temperature and under a pressure of at least 1 bar. See, e.g., McKetta, J., CHEMICAL PROCESSING HANDBOOK, 1993.

Many plants and fungi produce methyl halides and release them into the environment. These organisms contain methyl halide transferases that combine a chlorine, bromine or iodine ion with a methyl group of the metabolite S-adenosylmethionine ("AdoMet" or "SAM") to form the methyl halide and S-adenosyl homocysteine.

BRIEF SUMMARY OF THE INVENTION

The invention includes a process comprising combining (i) an organism comprising a S-adenosylmethionine (SAM)-dependent methyl halide transferase (MHT), (ii) a halide selected from the group comprising chlorine, bromine and iodine; and (iii) a carbon source in a cultivation medium, under conditions in which methyl halide is produced. The methyl halide can optionally be collected. The methyl halide can be converted into a non-halogenated organic molecule or a mixture of non-halogenated organic molecules, which can optionally be collected. The process can be carried out on a commercial scale, for example in a reactor. The invention also provides a genetically modified algae, fungus or bacteria, comprising a heterologous S-adenosylmethionine (SAM)-dependent methyl halide transferase gene, that is genetically modified to increase flux through a S-adenosyl-methionine (SAM) biosynthetic pathway; and/or genetically modified to increase the intracellular halide concentration.

Useful organisms include algae, yeast and bacteria. The recombinant organism can be a gram negative bacterium, e.g., *E. coli, Salmonella, Rhodobacter, Synechtocystis,* or *Erwinia*. Other gram negative bacteria include members from the Methylococcaceae and Methylocystaceae families; *Thermotoga hypogea, Thermotoga naphthophila, Thermotoga subterranean, Petrotoga halophila, Petrotoga mexicana, Petrotoga miotherma,* and *Petrotoga mobilis*. Alternatively, the recombinant organism can be a gram positive bacterium, e.g., *B. subtilis* or *Clostridium*. If desired, the recombinant organism can be a fungus such as *Saccharomyces cerevisae, Pichia pastoris, Hansenula polymorpha, Kluyveromyces lactis, Yarrowia lipolytica, Scizosacchromyces pombe* or *Trichoderma reesei* or other yeast species of genus *Saccharomyces, Pichia, Hansenula, Kluyveromyces, Yarrowia, Trichoderma* or *Scizosacchromyces*. The recombinant organism may be of genus *Geobacillus* (e.g., *Geobacilus thermoleovorans, Geobacillus stearothermophilus*), which may use hydrocarbon or petroleum as an energy source. The recombinant organism can also be a eukaryote such as an algae. Example of algae include *Chlamydomonas*.

The organism optionally comprises a gene encoding a heterologous MHT. The MHT can be a naturally-occurring MHT or a synthetic MHT. If so desired, the expression of the heterologous MHT can be under the control of an inducible promoter. Useful MHTs include, for example and not limitation, MHTs from *Batis maritime, Burkholderia phymatum, Synechococcus elongatus, Brassica rapa, Brassica oleracea, Arabidopsis thaliana, Arabidopsis thaliana, Leptospirillum, Cryptococcus neoformans, Oryza sativa, Ostreococcus tauri, Dechloromonas aromatica, Coprinopsis cinerea, Robiginitalea bofirmata, Maricaulis marls, Flavobacteria bacterium, Vitis vinifera* or *halorhodospira halophila*. Other useful MHTs include (but are not limited to) MHTs from *B. xenovorans, B. rapa chinensis, B. pseudomallei, B. thailandensis,* Marine bacterium HTCC2080, and *R. picketti*. Also see discussion below and FIG. 10A.

The organism can be genetically modified to increase flux through a S-adenosyl-methionine (SAM) biosynthetic pathway. For example, the flux through the SAM biosynthetic pathway can be increased by expression or overexpression of a SAM synthetase. The SAM synthetase can be *E. coli* metK, *Rickettsia* metK, *S. cerevisae* sam1p, or *S. cerevisae* sam2p. The SAM synthetase optionally has at least 80% amino acid identity with *E. Coli* metK.

If desired, the flux through the SAM biosynthetic pathway can be increased by abolishing, inactivating or decreasing the expression and/or activity of at least one gene. In appropriate instances, the gene can be involved in a SAM utilization pathway, e.g., coproporphyrinogen III oxidase, S-adenosyl-methionine decarboxylase, cystathionine beta-synthetase, ribulose 5-phosphate 3-epimerase, glucose-6-phosphate dehydrogenase, L-alanine transaminase, 3',5ɔ bisphosphate nucleotidase, glycine hydroxymethyltransferase, or glycine hydroxymethyltransferase.

The flux through the SAM biosynthetic pathway can also be increased by increasing flux through a methionine biosynthetic pathway. For example, the flux through the methionine biosynthetic pathway can be increased by expression or overexpression of the *E. coli* metL, metA, metB, metC, metE, and/or metH genes. If desired, a gene encoding a repressor of methionine biosynthesis, e.g., *E. coli* metJ, can be inactivated.

If desired, the flux can be increased by expressing a SAM transporter protein such as the Sam5p yeast mitochondrial gene. In another aspect, methyl halide production can be increased by expressing a gene that increases intracellular concentration and/or availability of ATP, and/or by increasing the intracellular halide concentration, for example through the overexpression of a halide transporter protein gene. The halide transporter can be *E. coli* clc transporter or a gene that shares at least 80% amino acid sequence identity with the *E. coli* clc transporter.

The halide for use in the invention can be provided as a halide salt, e.g., sodium chloride, sodium bromide, and sodium iodide. The halide can be present in the cultivation medium at a concentration of 0.05 to 0.3 M. The cultivation medium optionally comprises methionine. The methyl halide produced can be methyl chloride, methyl bromide, and/or methyl iodide. The conversion of methyl halides into other products can be a result of catalytic condensation. Useful catalysts include a zeolite catalyst, for example ZSM-5 or aluminum bromide ($AlBr_3$). The catalytic condensation step results in the production of a halide which can be recycled back to the cultivation medium. The methods of the invention can be used to produce a composition comprising an alkane, e.g., ethane, propane, butane, pentane, hexane, heptane, octane, or a mixture thereof. Other organic molecules that can be produced include, without limitation, olefins, alcohols, ethers and/or aldehydes.

The organism can be genetically modified at multiple (e.g., 2, 3, 4, 5, or 6) loci. The effect of each modification individually can be to increase the production of methyl halide.

In one aspect the invention provides a method including the steps of combining
i) a recombinant yeast comprising a heterologous gene encoding S-denosylmethionine (SAM)-dependent methyl halide transferase (MHT), ii) a halide selected from the group comprising chlorine, bromine and iodine; and iii) a carbon source; in a cultivation medium under conditions in which methyl halide is produced. The method may further include the step of converting the methyl halide into a non-halogenated organic molecule or a mixture of non-halogenated organic molecules. In come embodiments the yeast is from a genus selected from *Saccharomyces, Pichia, Hansenula, Kluyveromyces, Yarrowia, Trichoderma* and *Scizosacchromyces*. For example, the yeast may be *Saccharomyces cerevisiae, Pichia pastoris, Hansenula polymorpha, Kluyveromyces lactis, Yarrowia lipolytica, Trichoderma reesei,* or *Scizosacchromyces pombe*. In some embodiments the MHT is from *Batis maritima*. In some embodiments the carbon source is acetate and/or ethanol produced by a metabolism of cellulose by a cellulolytic microorganism. The cellulolytic microorganism may be a bacterium, such as *Actinotalea fermentans*. In some embodiments the cellulose is microcrystalline cellulose. In some embodiments the cellulose is a chopped or pulverized feedstock (e.g., pulverized switchgrass, bagasse, elephant grass, corn stover, and poplar).

In an aspect the invention provides a co-culture system comprising yeast and cellulosic bacteria, wherein the yeast express at least one heterologous protein. The co-culture system may contain cellulose. In some embodiments the co-culture system contains one species of yeast and one species of bacteria.

In some embodiments of the co-culture system, the yeast can be from a genus selected from the group consisting of *Saccharomyces, Pichia, Hansenula, Kluyveromyces, Yarrowia, Trichoderma* and *Scizosacchromyces,* for example *S. cerevisiae*.

In some embodiments the yeast and bacterium of the co-culture have a symbiotic relationship in culture. In some embodiments the bacterium is *Actinotalea fermentans*.

In an aspect the invention provides a stable in vitro co-culture of two microorganisms adapted to aerobically grow together while maintaining a relatively constant ratio of species populations such that neither microorganism overtakes the other. The co-culture includes (i) a first microorganism component which metabolizes cellulose and produces one or more metabolic products; (ii) a second microorganism component which is recombinantly modified to express a heterologous protein, and which is metabolically incapable of degrading cellulose, where the second microorganism uses the metabolic products of the first microorganism as a carbon source. In one embodiment the first microorganism is a cellulosic bacteria and the second microorganism is a yeast. In one embodiment the yeast expresses a heterologous methyl halide transferase. In some embodiments the yeast is *S. cerevisiae* and the bacterium is *Actinotalea fermentans*.

In certain embodiments, the heterologous gene encodes a fusion protein comprising a MHT sequence and a targeting peptide sequence that targets the MHT sequence to the yeast vacuole. The targeting peptide sequence can be the N-terminal peptide domain from carboxypeptidase Y.

In one aspect the invention provides a method for production of methyhalide comprising culturing a first microorganism which metabolizes cellulose and produces one or more metabolic products together with a second microorganism which does not metabolize cellulose and which is recombinantly modified to express a heterologous methyl halide transferase protein in a medium containing cellulose and a halide, under conditions in which methyl halide is produced. In some embodiments the halide is chlorine, bromine and iodine.

In one aspect the invention provides a recombinant yeast cell comprising a heterologous gene encoding S-adenosyl-methionine (SAM)-dependent methyl halide transferase (MHT). In certain embodiments the MHT is from *Batis maritima, Burkholderia phymatum, Synechococcus elongatus, Brassica rapa, Brassica oleracea, Arabidopsis thaliana, Arabidopsis thaliana, Leptospirillum, Cryptococcus neoformans, Oryza sativa, Ostreococcus Lauri, Dechloromonas aromatica, Coprinopsis cinerea, Robiginitalea bofirmata, Maricaulis marls, Flavobacteria bacterium, Vitis vinifera* or *halorhodospira halophila*. In certain embodiments the MHT is from *B. xenovorans, B. rapa chinensis, B. pseudomallei, B. thailandensis, Marine bacterium* HTCC2080, or *R. picketti* In certain embodiments the recombinant yeast cell is selected from *Saccharomyces cerevisiae, Pichia pastoris, Hansenula polymorpha, Kluyveromyces lactic, Yarrowia lipolytica, Trichoderma reesei,* and *Scizosacchromyces pombe*. For example, the recombinant yeast cell can be a *Saccharomyces cerevisiae* cell expressing a *Batis maritima* methyl halide transferase protein.

In some embodiments the MHT is expressed in the yeast cell as a fusion protein comprising a targeting peptide sequence that targets proteins to the yeast vacuole. In one embodiment the targeting peptide sequence is the N-terminal peptide domain from carboxypeptidase Y.

In another aspect, described herein is a co-culture system comprising a culture medium a cellulosic bacterium component, where the bacteria metabolize cellulose and produce one or more metabolic products, and a yeast component, where the yeast uses at least one metabolic product of the bacteria as a carbon source. In one embodiment the bacteria-yeast co-culture comprises *Actinotalea fermentans* bacteria which metabolize cellulose and produce one or more metabolic products, and *S. cerevisiae* yeast, where the yeast uses at least one metabolic product produced by the bacteria as a carbon source. The culture medium may contain cellulose. In some embodiments the yeast is metabolically incapable of degrading cellulose. In some embodiments the metabolic product(s) is the sole or primary carbon and energy source for the yeast.

In some embodiments the yeast is recombinantly modified to express a heterologous protein or over-express an endogenous protein. In some embodiments the yeast is a recombinantly modified to knock out expression of an endogenous protein. In some embodiments the bacteria and yeast grow together while maintaining a relatively constant ratio of species populations such that neither microorganism overtakes the other. The co-culture system may be maintained under substantially aerobic conditions or under substantially anaerobic conditions.

In various embodiments the yeast is from a genus selected from *Saccharomyces, Pichia, Hansenula, Kluyveromyces, Yarrowia, Trichoderma* and Scizosachromyces. In an embodiment the yeast is *S. cerevisiae*. In various embodiments the bacteria is a *Actinotalea* or *cellulomonas* species. In an embodiment the bacterium is *Actinotalea fermentans*. In an embodiment the yeast is *S. cerevisiae* and the bacterium is *Actinotalea fermentans*. In some embodiments the co-culture comprises only one species of yeast and only one species of bacteria. In some embodiments the yeast and bacterium have a symbiotic relationship in culture.

In some embodiments the carbon source produced by the bacteria is molecule comprising 1-6 carbon atoms, such as, for example, ethanol, acetate, lactate, succinate, citrate, formate or malate.

In some embodiments the yeast expresses a heterologous protein. For example, the heterologous protein may be a mammalian protein such as, for example a human protein used for treatment of patients. In some embodiments the heterologous protein is an enzyme, such as an enzyme that catalyzes a step in a synthetic pathway in the yeast. In an embodiment the heterologous protein is a methyl halide transferase. In some embodiments the yeast is genetically engineered to produce a commercially valuable small molecule compound. In other embodiments the yeast is a naturally occurring or cultivated strain that is not recombinantly modified.

In another aspect, described herein is a yeast culture method comprising culturing cellulosic bacteria and yeast together in a culture medium in the presence of cellulose or a cellulose-source, under conditions in which (i) the bacteria metabolize cellulose and produce one or more metabolic products, and, (ii) the yeast component uses at least one metabolic product of the bacteria as a carbon source. Usually the culture medium is a liquid. In one embodiment the cellulose is microcrystalline cellulose.

In some embodiments the cellulose-source is biomass, such as, without limitation, switchgrass, bagasse, elephant grass, corn stover, poplar (each of which may be pulverized) and mixtures of these and other biomass materials.

In some embodiments the culture is maintained under aerobic conditions. In some embodiments the culture is maintained under anaerobic conditions. In some embodiments the yeast and bacterium have a symbiotic relationship in culture. In some embodiments the yeast is metabolically incapable of degrading cellulose. In some embodiments the carbon source produced by the bacteria is molecule comprising 1-6 carbon atoms, such as, for example, ethanol, acetate, lactate, succinate, citrate, formate or malate.

In various embodiments the yeast in the co-culture is from a genus selected from *Saccharomyces, Pichia, Hansenula, Kluyveromyces, Yarrowia, Trichoderma* and *Scizosachromyces*. In an embodiment the yeast is *S. cerevisiae*. In various embodiments the bacteria is a *Actinotalea* or *Cellulomonas* species. In an embodiment the bacterium is *Actinotalea fermentans*. In an embodiment the yeast is *S. cerevisiae* and the bacterium is *Actinotalea fermentans*. In some embodiments the co-culture comprises only one species of yeast and only one species of bacteria. In some embodiments the yeast and bacterium have a symbiotic relationship in culture.

In some embodiments the yeast is recombinantly modified to express a heterologous protein. For example, the heterologous protein may be a mammalian protein such as, for example a human protein used for treatment of patients. In some embodiments the heterologous protein is an enzyme. In an embodiment the heterologous protein is a methyl halide transferase. In some embodiments the yeast is genetically engineered to produce a commercially valuable small molecule compound. In other embodiments the yeast is a naturally occurring or cultivated strain that is not recombinantly modified.

In some embodiments the yeast is a recombinantly modified to knock out expression of an endogenous protein. In other embodiments the yeast is a naturally occurring or cultivated strain that is not recombinantly modified.

In some embodiments the method includes the step of recovering a product from the culture medium which product is produced by the yeast. Examples of products that may be recovered include, but is not limited to, a recombinant protein expressed by the yeast, a small molecule synthesized by the yeast cell, a drug, food product, amino acid, cofactor, hormone, protein, vitamin, lipid, alkane, aromatic, olefin, alcohol, or biofuel intermediate. In an embodiment the product is a methyl halide. In some embodiments synthesis of the product requires expression of a heterologous protein in the yeast. In some embodiments the synthesis requires expression of an endogenous protein that is overexpressed in the yeast or deletion of one or more endogenous genes of the yeast.

In one aspect the invention provides a method for production of methyhalide comprising culturing a cellulosic bacteria which metabolizes cellulose and produces one or more metabolic products together with a yeast which does not metabolize cellulose and which is recombinantly modified to express a heterologous methyl halide transferase protein in a medium containing a cellulose source and a halide, under conditions in which methyl halide is produced. The halide may be chlorine, bromine and iodine.

In an aspect the invention provides a method comprising combining i) a recombinant yeast comprising a heterologous gene encoding S-adenosylmethionine (SAM)-dependent methyl halide transferase (MHT), ii) a halide selected from the group comprising chlorine, bromine and iodine; and iii) a cellulolytic bacteria that produces a carbon source by metabolism of cellulose; in a cultivation medium under conditions in which methyl halide is produced. In some embodiments the carbon source is a molecule comprising 1-6 carbon atoms such as ethanol, acetate, lactate, succinate, formate, citrate, or malate. In some embodiments the method includes recovering methyl halide from the culture medium and converting the methyl halide into a non-halogenated organic molecule or a mixture of non-halogenated organic molecules. In some embodiments the yeast is *S. cerevisiae* or another yeast described hereinbelow.

In some embodiments the bacteria is *Actinotalea fermentans* or another cellulosic bacteria described hereinbelow. In some embodiments the MHT is from *Batis maritima* or is another MHT described hereinbelow. In one embodiment the yeast is *S. cerevisiae*, the bacteria is *Actinotalea fermentans* and the MHT is from *Batis maritima*.

BRIEF DESCRIPTION OF THE FIGURES

FIG. 9A: diagram of co-culture. *A. fermentans* ferments cellulosic feedstocks to acetate and ethanol, which *S. cerevisiae* can respire as a carbon (and energy) source. FIG. 9B, left panel, growth of yeast in co-culture. Yeast were inoculated on carboxymethylcellulose (CMC) as the sole carbon sources with and without *A. fermentans*. Growth was measured as colony forming units. FIG. 9B, right panel: Growth of bacteria in co-culture. FIG. 9C: $CH_3I$ production from cellulosic feedstocks. Co-cultures were seeded at low density and grown for 36 hours with the indicated feedstock (20 g/L) as the sole carbon source. Sodium iodide was added and $CH_3I$ production was measured by GC-MS as before. $CH_3I$ yields are reported in grams per liter per day, normalized by CFUs per mL of culture. Yields are shown for the *A. fermentans-S. cerevisiae* co-culture on acetate, CMC, switchgrass, corn stover, and poplar. Cultures grown without *A. fermentans* showed no methyl iodide activity.

FIG. 10A: methyl halide activity for MHT library in *E. coli*. Organisms that MHT genes are from are shown at left. Bacteria are shown in red font, plants are in green, fungi are blue, and archae are in purple. Production of $CH_3I$, $CH_3Br$, and $CH_3Cl$ are shown. Genes are rank ordered by $CH_3I$ activity. FIG. 10B, assay of methyl halide activity for a subset of MHT library. Measurements were performed in triplicate and standard deviations are shown.

FIG. 11A-D: Methyl iodide production in recombinant *S. cerevisiae*. FIG. 11A. $CH_3I$ production pathway. The *B. maritima* MHT is expressed with a N-terminal vacuole targeting tag. The ATP-dependent MHT methylates iodide ions using SAM as a methyl donor. FIG. 11B, $CH_3I$ measured in culture headspace over time. Activity on glucose-grown cells is shown. FIG. 11C, $CH_3I$ yields in grams per liter of culture per day. Values for the culturable red algae *E. muricata* are taken from the literature. Yields from *B. maritime* MHT-expressing *E. coli* and *S. cerevisiae* are calculated by comparison to standard curves. FIG. 11D, $CH_3I$ toxicity in yeast. Exponential phase cultures were diluted to an $OD_{600}$ of 0.05 and commercially available $CH_3I$ was added. $OD_{600}$ was measured at 24 hours of growth. The W303a lab strain is shown in filled boxes, the DNA methylation-sensitive RAD50Δ mutant is shown in open boxes.

DETAILED DESCRIPTION

1. Introduction

Figure 1:
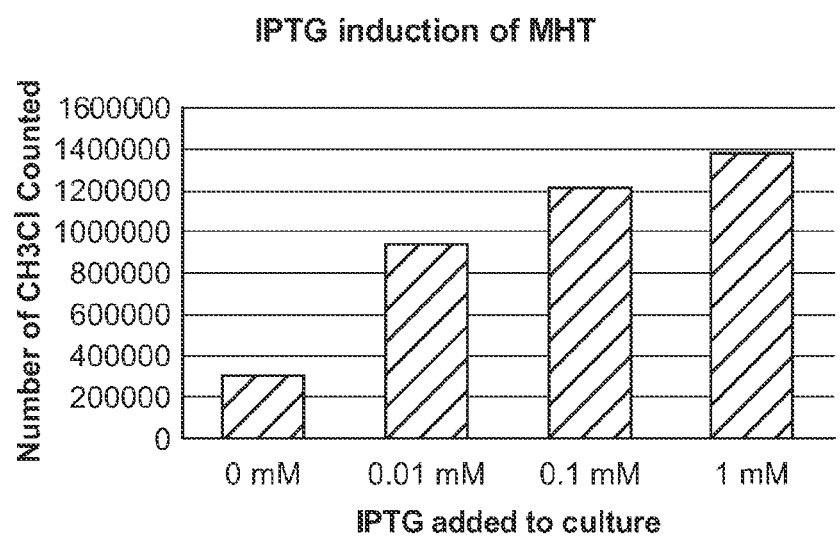
FIG. 1: Methyl halide production by bacteria containing a recombinant methyl halide transferase (MHT) gene expressed from an IPTG-inducible promoter.

Methyl halides can be converted to commodity chemicals and liquid fuels—including gasoline—using zeolite catalysts prevalent in the petrochemical industry. The methyl halide transferase (MHT) enzyme transfers the methyl group from the ubiquitous metabolite S-adenoyl methionine (SAM) to a halide ion in an ATP-dependent manner. Using bioinformatics and mail-order DNA synthesis, we identified and cloned a library of 89 putative MHT genes from plants, fungi, bacteria, and unidentified organisms. The library was screened in *Escherichia coli* to identify the rates of $CH_3Cl$, $CH_3Br$, and $CH_3I$ production, with 56% of the library active on chloride, 85% on bromide, and 69% on iodide. Expression of the highest activity MHT and subsequent engineering in *Saccharomyces cerevisiae* resulted in product yields of 4.5 g/L-day from glucose and sucrose, four orders of magnitude over culturable naturally occurring sources. Using a symbiotic co-culture of the engineered yeast and the cellulolytic bacterium *Actinotalea fermentans*, we were able to achieve methyl halide production from unprocessed switchgrass (*Panicum virgatum*), corn stover, and poplar. Methyl halides produced from various biorenewable resources can to be used as 1-carbon precursors for the production of alkanes, aromatics, olefins, and alcohols in the chemical industry.

In one aspect the invention provides methods for production of commodity chemical and fuels. The invention provides methods for production of biofuels and other commercially valuable organic products. In one aspect, recombinant bacteria, fungi or plant cells expressing a methyl halide transferase enzyme (MHT) are cultivated in the presence of a carbon source (e.g., agricultural or waste biomass, cultivation media, petroleum, natural gas application methane) under conditions in which methyl halide gas is produced. In one embodiment the MHT is heterologous. The methyl halide is converted to non-halogenated organic compounds such as long-chain alkanes, olefins, alcohols, ethers, and aldehydes. In one embodiment the organic compounds are suitable for use as biofuel. Conversion of methyl halide to other organic molecules can be achieved by any means and is not limited to a specific mechanism. In one embodiment the MHT-expressing organism also expresses enzymes (endogenous or heterologous) that convert the methyl halide to another organic molecule, such as methanol. In one embodiment the MHT-expressing organism releases methyl halide which is then converted by a different organism (natural or recombinant) to another organic molecule. In one embodiment methyl halide is collected and converted by well-known chemical synthetic methods (e.g., catalytic condensation). Following conversion of the methyl halide into a non-halogenated organic molecule or a mixture of non-halogenated organic molecules, the non-halogenated organic molecule(s) may be collected and/or packaged for subsequent use.

The invention also includes organisms expressing a heterologous methyl halide transferase enzyme and having at least one other genetic modification that causes the organism to produce more methyl halide than an organism lacking the at least one other genetic modification. An increase in yield of methyl halide in a MHT-expressing cell can be facilitated in various ways, for example by engineered SAM overproduction, increase in concentration and/or availability of ATP, expression of halide ion importers. Manipulation of genes in various metabolic pathways allows creation of organisms able to efficiently convert the carbon from cellulose, sugar, waste materials, or $CO_2$ to methyl halide gas.

The invention also provides co-culture systems in which a cellulolytic bacterium and a yeast cell expressing a heterologous protein are cultured together. In this system, the bacterium metabolizes cellulose to produce a product that serves as a carbon source for the yeast. In some examples, accumulation of the product in culture medium is toxic to the bacterial. Consumption of the product by the yeast cells serves to remove the product, so that the bacteria and yeast have a symbiotic relationship.

2. Methyl Halide Transferase-Expressing Cells

A variety of types of cells or organisms can be used in the practice of the invention, including cells that express an endogenous methyl-halide transferase (MHT), and cells modified to express an heterologous MHT. Preferably the organism is capable of producing about 1-1000 mg/L of methyl halide per day, often about 10-100 mg/L, such as about 20-60 mg/L, for example about 30-50 mg/L, or about 40 mg/L per day. As used herein, the term "heterologous" refers to a gene not normally in the cell genome, such as a gene from a different species or not found in nature, or a protein encoded by the heterologous gene. A gene found in the wild-type cell genome, or protein normally expressed in the cell, can be referred to as "endogenous." Additional copies of an endogenous gene (under the control of a constitutive or inducible promoter) can be introduced into a host organisms to increase levels of an endogenous enzyme.

In principal almost any cell type can be modified for use in the methods of the invention, although in practice, the cells or organism should be suitable for commercial scale bioproduction, e.g., typically unicellular and/or fast-growing. For simplicity, the term "cells" is used herein to encompass both MHT-expressing unicellular organisms, and MHT-expressing cells of multicellular organisms. Suitable cells may be eukaryotic or prokaryotic. Examples include bacterial, fungi, algae and higher plant cells.

Cells expressing endogenous MHT may be used. In such cases the cell is usually selected or modified to express endogenous MHT at high levels and/or is selected or modified at other loci that affect methyl halide production, as is discussed below. Although selection, with or without antecedent mutagenesis, may be used, recombinant techniques are usually preferred because they allow greater control over the final cell phenotype.

When recombinant cells are used, they may express a heterologous MHT, express a modified endogenous MHT, express an endogenous MHT at levels higher than wild-type cells, be modified at one or more loci other than the MHT gene (discussed below), or combinations of these modifications. Most preferably the cell expresses a heterologous MHT and is modified at at least one other locus that affects methyl halide production.

In one aspect, the recombinant organism is not *E. Coli*. In another aspect, the heterologous enzyme is not *Batis* MHT. In another aspect, the recombinant organism is not *E. coli* containing a *Batis* MHT.

2.1 Cells Expressing Endogenous MHT

A wide variety of plants, fungi and bacteria express endogenous MHT and can be used according to the method of the invention. In addition, MHT-expressing cells are a source of MHT genes that can be transferred to a heterologous host, such as *E. coli*. Organisms expressing MHTs include prokaryotes, e.g., bacteria or achaea. Examples of bacteria that can be used to produce MHT according to the invention include soil bacteria, and Proteobacteria, *Methylobacterium chloromethanicum*, and *Hyphomicrobium chloromethanicum*). The Proteobacteria phylum include genuses such as *Pseudomonas* and *Burkholderia*. Examples of *Burkholderia* include *Burkholderia xenovorans* (previously named *Pseudomonas cepacia* then *B. cepacia* and *B. fungorum*), known for the ability to degrade chlororganic pesticides and polychlorinated biphenyls (PCBs). Other *Burkholderia* species include *B. mallei, B. pseudomallei* and *B. cepacia*. Besides bacteria, other prokaryotes such as Archaea can be used to produce MHT with or without modification. Examples of Archaea include *Sulfolobuses* such as *S. acidocaldarius, S. islandicus, S. metallicus, S. neozealandicus, S. shibatae, S. solfataricus*, or S. sp. AMP12/99.

Other especially useful types of organisms include marine algae (e.g., phytoplankton, giant kelp and seaweed), higher plants (e.g., halophytic plants, *Brassicaceae* such as *Brassica oleracea* (TM1 or TM2), and *Arabidopsis Thaliana* (TM1 or TM2)) and fungi (e.g., yeast). Particular species include *Batis maritima, Burkholderia phymatum* STM815, *Synechococcus elongatus* PCC 6301, *Brassica rapa* subsp. *chinensis; Leptospirillum* sp. Group II UBA; *Cryptococcus neoformans* var. *neoformans* JEC21; *Oryza sativa* (japonica cultivar-group); *Ostreococcus tauri; Dechloromonas aromatica* RCB; *Coprinopsis cinerea okayama; Robiginitalea bofirmata* HTCC2501; *Maricaulis maris* MCS10; *Flavobacteria bacterium* BBFL7; *Vitis vinifera; halorhodospira halophila* SL1; *Phellinus pomaceus* (a white rot fungus), *Endocladia muricata* (a marine red algae), *Mesembryanthemum crystallium, Pavlova* species such as *P. pinguis* and *P. gyrans, Papenfusiella kuromo, Sargassum horneri*, and *Laminaria digitata*. See, e.g., Wuosmaa et al., 1990, *Science* 249:160-2; Nagatoshi et al., 2007, *Plant Biotechnology* 24, 503-506. Yet other species are disclosed herein.

2.2 Cells Expressing Heterologous MHT

In some embodiments, cells used in the invention do not express an endogenous MHT, but are modified to express a heterologous MHT. Alternatively, cells may be used that are modified to express a heterologous MHT and also express an endogenous MHT. The use of cells expressing a heterologous MHT has several advantages. First, it is possible, using the methods described herein, to combine desirable properties of an organism (ease of culture, ability to metabolize a particular feedstocks, suitability for recombinant manipulation of other loci) with desirable properties of an MHT gene (e.g., high enzymatic activity).

Cells that can be genetically modified to express heterologous MHT Include prokaryotes and eukaryotes such as plants, fungi and others. Exemplary prokaryotes include gram-negative bacteria such as *E. Coli* (e.g., MC1061, BL21 and DH10B), *Salmonella* (e.g., SL1344), *Rhodobacter, Synechtocystis, Rickettsia,* and *Erwinia* and gram-positive bacteria such as *B. subtilis* and *Clostridium*. Exemplary plants include algae (e.g., *Chlamydomonas, Chlorella* and *Prototheca*). Exemplary fungi include *Trichoderma reesei, Aspergillus* and yeast (e.g., *Saccharomyces cerevisae* and *Pichia*). Other cell types are disclosed herein and are known in the art. Other exemplary bacteria include *Sulfobolus sulfaticaricus,* and *Caulobacter* species such as *Maricaulis marls*.

An organism that efficiently metabolizes a particular carbon source can be selected to match an available feedstock. For example, when cellulosic materials are used as carbon sources, organisms such as *Erwinia, E. coli, Pichia, Clostridium,* and *Aspergillus Niger* can be used. *E. coli* and *Saccharomyces* are examples of organisms that can be used to metabolize starches and sugarcane. Similarly, photosynthetic organisms such as algae (e.g., *Chlorella* and *Prototheca*) can metabolize carbon sources such as $CO_2$.

2.3 Methyl Halide Transferases

In the context of this invention, a "methyl halide transferase (MHT)" is a protein that transfers a methyl group from S-adenosylmethionine to a halide. As noted above, methyl halide transferases are ubiquitous in nature. Exemplary naturally occurring methyl halide transferases include, but are not limited to, those disclosed herein. Other naturally occurring methyl halide transferase can be identified by referring to a protein database (for example, the NCBI protein sequence database, at http://www. followed by ncbi.nlm.nih.gov/sites/entrez?db=protein) and scientific literature.

Table 1 below lists some of the organisms known to have MHTs. Also see Figures, Tables 4 and 6 and Examples 8 and 9.

TABLE 1

| Organism |
| --- |
| *Batis maritima* |
| *Burkholderia phymatum* STM815 |
| *Synechococcus elongatus* PCC 6301 |
| *Brassica rapa* subsp. *chinensis* |
| *Brassica oleracea* TM1 |
| *Brassica oleracea* TM2 |
| *Arabidopsis thaliana* TM1 |
| *Arabidopsis thaliana* TM2 |
| *Leptospirillum* sp. Group II UBA |
| *Cryptococcus neoformans* var. *neoformans* JEC21 |
| *Oryza sativa* (*japonica* cultivar-group) |
| *Ostreococcus tauri* |
| *Dechlommonas aromatica* RCB |
| *Coprinopsis cinerea okayama* |
| *Robiginitalea bofirmata* HTCC2501 |
| *Maricaulis maris* MCS10 |
| *Flavobacteria bacterium* BBFL7 |
| *Vitis vinifera* |
| *Halorhodospira halophila* SL1 |

MHT genes can be cloned and introduced into a host organism under control of a promoter suitable for use in the host. Alternatively, genes encoding a desired MHT sequence can be synthesized, which allows codon usage in the gene to be optimized for the host. The promoter can be inducible or constitutive. The heterologous MHT gene can be integrated into the host chromosome (e.g., stable transfection) or can be maintained episomally.

Suitable MHTs are not limited to proteins encoded by naturally occurring genes. For example, techniques of directed evolution can be used to produce new or hybrid gene products with methyl transferase activity. In addition, catalytically active fragments and variants of naturally occurring MHTs can be used. Partially or wholly synthetic MHTs, such as enzymes designed in silico or produced by using art-known techniques for directed evolution including gene shuffling, family shuffling, staggered extension process (StEP), random chimeragenesis on transient templates (RACHITT), iterative truncation for the creation of hybrid enzymes (ITCHY), recombined extension on truncated templates (RETT), and the like (see Crameri et al., 1998, "DNA shuffling of a family of genes from diverse species accelerates directed evolution" *Nature* 391:288-91; Rubin-Pitel et al., 2006, "Recent advances in biocatalysis by directed enzyme evolution" *Comb Chem High Throughput Screen* 9:247-57; Johannes and Zhao, 2006, "Directed evolution of enzymes and biosynthetic pathways" *Curr Opin Microbiol.* 9:261-7; Bornscheuer and Pohl, 2001, "Improved biocatalysts by directed evolution and rational protein design" *Curr Opin Chem. Biol.* 5:137-43).

It will be clear that a variety of naturally and non-naturally occurring methyl halide transferases can be used in the methods of the invention, provided the MHT can effect the transfer of a methyl group from S-adenosylmethionine to a halide (i.e., chlorine, iodine and/or bromine) in the host organism. MHT enzyme activity can be measured using various assays known in the art. Assays can measure activity of purified or partially purified protein. See, e.g., Ni and Hager, 1999, *Proc. Natl. Acad. Sci. USA* 96:3611-15 and Nagatoshi and Nakamura, 2007, Plant Biotechnology 24:503-506. Alternatively, a protein can be expressed a cell that does otherwise express MHT and methyl halide production measured is described in the Examples, infra, and other art-know assays. In one assay an expression vector with a sequence encoding the MHT protein is introduced into a bacterial (e.g., *E. coli*) host cell and transformants selected. Clones are incubated in growth media in a tube or flask (e.g., LB media containing NaCl, NaI or NaBr and incubated at 37° C. for 4-22 hours with shaking. If the MHT encoding sequence is under control of an inducible promoter the inducing agent is included. The tube or flask is sealed (e.g., with parafilm and aluminum foil cinched with a rubber band). At the end of the incubation period the level of MeX in the headspace gas is determined, e.g., by gas chromatography.

As is demonstrated in Example 8, infra, there is considerable variability in MHT sequences that may be used in the practice of the invention. Sequences with as little as 29% sequence identity with each other have been used to produce methyl halide when heterologously expressed in bacterial or fungal cells. Moreover, as shown in Example 8, diverse methyl halide transferases can function in *E. coli*.

In certain embodiments the invention includes the use of enzymatically active polypeptides with at least about 25%, 30%, 40%, 50%, 60%, 70%, 80%, 90%, 95% or at least 99% identity with a known SAM-dependent methyhalide transferase (such as a MHT described herein) in the invention. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity.

3. Other Genetic Modifications that Affect Methyl Halide Production

In addition to introduction and manipulation of MHT genes, other genetic modifications can be made to increase the efficiency of methyl halide production, or increase the amount of methyl halide produced. These changes include increasing the intracellular concentration of reaction substrates such as halides and S-adenosylmethionine (also called "SAM" or "AdoMet"). Intracellular levels of SAM can be increased by changing the rate of SAM biosynthesis (e.g., by raising levels of SAM precursors), reducing SAM consumption, and the like. Intracellular levels of halide can be increased by stimulating transport of halides into the cell, adding halides to the extracellular environment, and the like. In general, techniques of metabolic engineering can be used to maximize production of methyl halides.

3.1 SAM Metabolic Pathways

Methyl halide production can be increased by manipulating flux though metabolic pathways that affect SAM levels, such as SAM biosynthetic pathways, methionine biosynthetic pathways, SAM utilization or degradation pathways, and SAM recycling pathways. S-adenosylmethionine is a ubiquitous metabolite involved in multiple metabolic pathways that entail methyl transfer. One such pathway is indicated below:

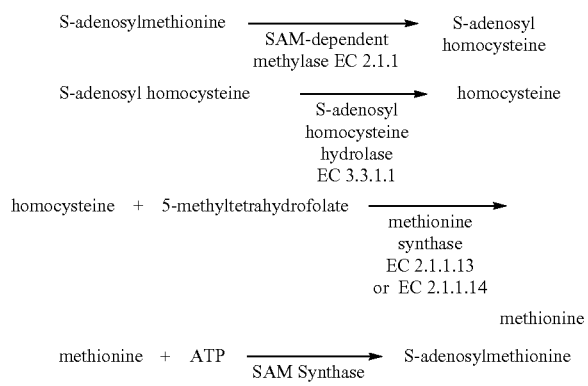

3.1.1 Overexpression of Sam Synthetase

SAM is synthesized from ATP and methionine, a reaction catalyzed by the enzyme S-adenosylmethionine synthetase (SAM synthetase, EC 2.5.1.6; Cantano, 1953, *J. Biol. Chem.* 1953, 204:403-16. In one aspect of the invention, a MHT-expressing cell is modified to increase SAM synthase activity by overexpression of endogenous SAM synthetase or introduction of a heterologous SAM synthase. SAM synthetase (SAMS) genes include metK in prokaryotes such as *E. Coli* (Acc. No. NP_289514.1), and sam1p (Acc. No. NP_010790.1) or sam2p in *S. Cerevisiae*, or MTO3 in *Arabidopsis* (Acc. No. NP_188365.1). SAMS can be overexpressed in a cell by introducing a heterologous SAMS gene or introducing additional copies of the SAMS genes of the host organisms, under the control of a constitutive or inducible promoter. For example, Yu et al., 2003, Sheng Wu Hua Xue Yu Sheng Wu Wu Li Xue Bao (Shanghai) 35:127-32, described enhanced production of SAM by overexpression in *Pichia pastoris* of an *S. cerevisiae* SAM synthetase 2 gene. As discussed below (Section 3.8) reference to particular genes is for illustration and not limitation. It is understood that gene names vary from organism to organism and reference above to a gene name is not intended to be limiting, but is intended to encompass homologs, orthologs and variants with the same enzymatic activity.

3.1.2 Increasing SAM Recycling

As shown above, methyl halide transferase catalyses conversion of SAM to S-adenosyl-homocysteine. S-adenosyl-homocysteine is "recycled" back to SAM via SAM biosynthetic pathways. SAM production or levels can thus be increased by increasing the level and/or activity of enzymes in the pathways. Examples of such enzymes include SAM-dependent methylase (EC 2.1.1), methionine synthase (EC 2.1.1.13 or EC 2.1.1.14), and $N^5$-methyl-tetrahydropteroyl-triglutamate-homocysteine methyltransferase (e.g., yeast MET6). S-adenosyl-L-homocysteine hydrolase (SAH1), a key enzyme of methylation metabolism, catabolizes S-adenosyl-L-homocysteine which acts as strong competitive inhibitor of all AdoMet-dependent methyltransferases.

It is understood that gene names vary from organism to organism and reference above to a gene name is not intended to be limiting, but is intended to encompass homologs with equivalent activity.

3.1.3 Impairment of SAM Utilization Pathways

Various metabolic pathways within the methyl halide producing organisms cause a decrease in intracellular levels of free SAM (SAM utilization pathways). The content and/or the biological activity of one or more enzymes involved in a SAM utilization pathway can be decreased in order to facilitate or increase methyl halide production.

Examples of genes that can be inhibited to reduce SAM utilization include S-adenosylmethionine decarboxylase (corresponding to *E. coli* gene speD). Further examples include cystathionine beta-synthetase, ribulose 5-phosphate 3-epimerase, glucose-6-phosphate dehydrogenase, L-alanine transaminase, 3',5'-bisphosphate nucleotidase, glycine hydroxymethyl transferase (reversible, mitochondrial), glycine hydroxymethyl transferase (reversible), corresponding to *S. cerevisae* genes CYS4, Rpe1, Zwf1, Alt, Met22, Shm 1-m, and Shm 2.

It is understood that gene names vary from organism to organism and reference above to a gene name is not intended to be limiting, but is intended to encompass homologs with equivalent activity.

3.1.4 Overexpression of SAM Transport Genes

In one approach, a SAM transport protein involved in the transport of SAM into a cell from the extracellular environment is expressed or over expressed in a cell. Examples include the Sam5p protein from yeast and homologs such as GenBank ID Nos. BC037142 (*Mus musculus*), AL355930 (*Neurospora crassa*), AE003753 (*Drosophila melanogaster*), Z68160 (*Caenorhabditis elegans*) and SLC25A26 (human). See Marrobio et al., 2003, *EMBO J.* 22:5975-82; and Agrimi et al., 2004, *Biochem. J.* 379:183-90.

It is understood that gene names vary from organism to organism and reference above to a gene name is not intended to be limiting, but is intended to encompass homologs with equivalent activity.

3.2. Methionine Biosynthetic Pathways

SAM biosynthesis, and in turn methyl halide production, can be increased by the use of microorganisms with increased efficiency for methionine synthesis. In general, the basic metabolic pathways leading to methionine synthesis are well known (see, e.g. Voet and Voet, 1995, *Biochemistry*, 2nd edition, Jon Wiley &Sons, Inc.; Rückert et al., 2003, *J. of Biotechnology* 104, 2 13-228; and Lee et al., 2003, *Appl. Microbiol. Biotechnol.*, 62:459-67). These pathways are generally under strict regulation by various mechanisms such as feedback control. (See, e.g., Neidhardt, 1996, *E. coli* and *S. lyphimurium*, ASM Press Washington). Accordingly, the expression or repression of relevant genes, or increase in the levels and/or activity of the corresponding gene products), can result in increased methionine production.

3.2.1 Methionine Biosynthetic Enzymes

Genes that can be expressed or upregulated include those involved in methionine biosynthesis. PCT Publication WO 02/10209, incorporated by reference in its entirety, describes the over-expression or repression of certain genes in order to increase the amount of methionine produced. Examples of methionine biosynthetic enzymes include O-acetyl-homoserine sulfhydrylase (metY) and O-succinyl-homoserine sulfhydrylase (metZ). Other genes include methylene tetrahydrofolate reductase (MetF); aspartate kinase (lysC); homoserine dehydrogenase (hom); homoserine acetyltransferase (metX); homoserine succinyltransferase (metA); cystathionine γ-synthetase (metB); cystathionine β-lyase (metC); Vitamin $B_{12}$-dependent methionine synthase (metH); Vitamin $B_{12}$-independent methionine synthase (metE); $N^{5,10}$-methylene-tetrahydrofolate reductase (metF) and S-adenosylmethionine synthase (metK).

Variants of these enzymes that are resistant to feedback inhibition by methionine can further increase methyl halide production. Some such variants are set forth in WO 07/011, 939, and Park et al., 2007, *Metab Eng.* 9:327-36, incorporated by reference in its entirety. By way of example, methyl halide production can be increased in prokaryotes such as *E. Coli* and *Corynebacterium* by overexpressing genes such as metY, metA, metB, metC, metE, and/or metH, or otherwise increasing the levels or activity of their gene products. Similarly, decreasing the levels or impairing the activity of the repressor proteins genes can increase methyl halide production (e.g., repressor encoded by the metJ or metD (McbR) genes, which repress methionine synthesis-related genes such as metB, metL and metF). See Rey et al., 2003, *J. Biotechnol.*, 103:1-65; Nakamori et al., 1999, *Applied Microbiology and Biotechnology* 52:179-85; WO 02/097096; each of which is incorporated by reference in its entirety).

It is understood that gene names vary from organism to organism and reference above to a gene name is not intended to be limiting, but is intended to encompass homologs with equivalent activity.

3.2.2 Methionine Biosynthesis Precursors

Methionine synthesis can also be increased by modifying the flux through those pathways that provide additional precursors, examples of which include sulfur atoms in different oxidative states, nitrogen in the reduced state such as ammonia, carbon precursors including C1-carbon sources such as serine, glycine and formate, precursors of methionine, and metabolites of tetrahydrofolate substituted with carbon at N5 and or N10. In addition energy e.g. in the form of reduction equivalents such as NADH, NADPH or FADH2 can be involved in the pathways leading to methionine.

For example, methyl halide production can be increased by increasing the level and/or activity of gene products involved in sulfate assimilation, cysteine biosynthesis and conversion of oxaloacetate to aspartate semialdehyde. Examples of genes include L-cysteine synthase (cysK), NADPH-dependent sulphite reductase (cysI) and alkane sulfonate monooxygenase (ssuD).

Increasing the levels of serine can also result in increased methionine production. Thus, the organism can be modified with respect to proteins involved in serine metabolism or transport. Enzymes involved in serine synthesis include D-3-phosphoglycerate dehydrogenase (SerA), phosphoserine phosphatase (Sera) and phosphoserine aminotransferase (SerC). See WO 07/135,188, incorporated by reference in its entirety. Enzymes involved in serine synthesis can be modified to reduce or prevent feedback inhibition by serine.

Similarly, the levels and/or the biological activity of one or more enzymes involved in the conversion of serine to methyltetrahydrofolate can be increased. Such genes include serine hydroxymethyltransferase (SHMT) and methylene tetrahydrofolate reductase (metF).

Similarly, the content and/or the biological activity of one or more enzymes involved in serine degradation to pyruvate (e.g., serine dehydratase, sdaA), or in serine export from the cell (e.g., ThrE) can be decreased.

It is understood that gene names vary from organism to organism and reference above to a gene name is not intended to be limiting, but is intended to encompass homologs with equivalent activity.

3.2.3 Methionine Uptake

Genes controlling methionine uptake in a cell can be modified to increase methyl halide production. For example, the MetD locus in *E. Coli* encodes an ATPase (metN), methionine permease (metI) and substrate binding protein (metQ). Expression of these genes is regulated by L-methionine and MetJ, a common repressor of the methionine regulon. Orthologs are known in many other species such as *Salmonella, Yersinia, Vibrio, Haemophilus, Agrobacterium, Rhizobium* and *Brucella*. See, e.g., Merlin et al., 2002, *J. Bacteriology* 184:5513-17. et al., 2003, *EMBO J.* 22:5975-82; and Agrimi et al., 2004, *Biochem. J.* 379:183-90.

It is understood that gene names vary from organism to organism and reference above to a gene name is not intended to be limiting, but is intended to encompass homologs with equivalent activity.

3.3 Increasing Intracellular Halide Concentration

Methyl halide production can also be increased by increasing the intracellular halide concentration in MHT-expressing cells. This can be accomplished in various ways, e.g., by introducing or increasing the levels and/or activity of one or more halide transporters, and/or increasing halide concentration in the medium. Examples include Gef1 of *Saccharomyces cerevisiae*, EriC of *E. coli* (P37019), and *Synechocystis* (P74477).

It is understood that gene names vary from organism to organism and reference above to a gene name is not intended to be limiting, but is intended to encompass homologs with equivalent activity.

3.4 Increasing ATP Levels

Methyl halide production can also be increased by methyl halide synthesis activity is increased by increasing the intracellular concentration and/or availability of ATP.

It is understood that gene names vary from organism to organism and reference above to a gene name is not intended to be limiting, but is intended to encompass homologs with equivalent activity.

3.5 Impairing Methyl Halide Utilization

The activity and/or level of methyl halide utilizing enzymes can be decreased. These include enzymes in the cmu gene cluster such as cmuC, cmuA, orf146, paaE and hutl. Other enzymes include bacterial 10-formyl-$H_4$ folate hydrolases, 5,10-methylene-$H_4$ folate reductase and purU and corrinoid enzymes such as halomethane: bisulfide/halide ion methyltransferase.

It is understood that gene names vary from organism to organism and reference above to a gene name is not intended to be limiting, but is intended to encompass homologs with equivalent activity.

3.6 Recombinant Yeast Expressing MHT

We have observed that use of yeast as the MHT expressing cell results in particularly high yield of methyl halide. See Example 10. In one aspect, the invention provides a recombinant yeast cell comprising a heterologous gene encoding S-adenosylmethionine (SAM)-dependent methyl halide transferase (MHT). Examples of MHT proteins that can be expressed in yeast include, as discussed elsewhere herein, those from *Batis maritima, Burkholderia phymatum, Synechococcus elongatus, Brassica rapa, Brassica oleracea, Arabidopsis thaliana, Arabidopsis thaliana, Leptospirillum, Cryptococcus neoformans, Oryza sativa, Ostreococcus tauri, Dechloromonas aromatica, Coprinopsis cinerea, Robiginitalea bofirmata, Maricaulis marls, Flavobacteria bacterium, Vitis vinifera* or *halorhodospira halophila*. Examples of suitable recombinant yeast cells include, as discussed elsewhere herein, *Saccharomyces cerevisiae, Pichia pastoris, Hansenula polymorpha, Kluyveromyces lactis, Yarrowia lipolytica, Trichoderma reesei, Scizosacchromyces pombe*, and others. Methods for culture and genetic manipulation of yeast are well known in the art.

3.7 Use of Targeting Domain to Increase Production in Yeast

Expression of heterologous methyl halide transferase (e.g., *Batis maritima* MCT) in *Saccharomyces cerevisiae* results in the production of methyl halide (e.g., methyl iodide). The yield is increased significantly by using a peptide signal to target the enzyme to vacuoles. See discussion below. Without intending to be limited to a particular mechanism, the increased production is believed to result from (i) the sequestration of the majority of the cell's SAM in the vacuole (Farooqui et al., 1983, Studies on compartmentation of S-adenosyl-L-methionine in *Saccharomyces cerevisiae* and isolated rat hepatocytes. *Biochim Biophys Acta* 757:342-51). and (ii) the sequestration of halide ions in the vacuole (Wada et al., 1994, *Chemiosmotic coupling of ion transport in the yeast vacuole: its role in acidification inside organelles. J Bioenerg Biomembr* 26: 631-7).

One peptide signal is the N-terminal peptide domain from carboxypeptidase Y known to target pendant proteins to the yeast vacuole, but other targeting peptides may be used. See, e.g., Valls et al., 1990, Yeast carboxypeptidase Y vacuolar targeting signal is defined by four propeptide amino acids. J Cell Biol 111:361-8; and Tague et al., 1987, "The Plant Vacuolar Protein, Phytohemagglutinin, Is Transported to the Vacuole of Transgenic Yeast", *J. Cell Biology,* 105: 1971-1979; Tague et al., 1990, "A Short Domain of the Plant Vacuolar Protein Phytohemagglutinin Targets Invertase to the Yeast Vacuole", *The Plant Cell,* 2:533-546 and U.S. Pat. No. 6,054,637, all of which are incorporated herein by reference.

In one approach, for illustration and not limitation, the coding sequence of *B. maritime* methylchloride transferase (MCT) is synthesized and cloned into a high copy vector under the control of a tet-repressible CYC promoter (plasmid pCM190, Gari et al, 1997, *Yeast* 13:837-48.). The MCT coding sequence is fused to a N-terminal peptide domain from carboxypeptidase Y known to target pendant proteins to the yeast vacuole (amino acid sequence: KAISLQRPLGLD-KDVL, SEQ ID NO:1, Valls et al., 1990, *J. Cell Biol.* 111: 361-8.) This expression system is transformed into *S. cerevisiae* strain W303a. Yeast carrying MCT expression vectors are streaked on uracil dropout plates from freezer stocks (15% glycerol) and grown for 48 hours. Individual colonies are inoculated into 2 mL of synthetic complete uracil dropout media and grown overnight at 30 degrees. Cultures are next inoculated into 100 mL fresh synthetic complete uracil dropout media and grown for 24 hours. Cells are spun down and concentrated to high cell density (OD 50) in fresh YP media with 2% glucose and 100 mM sodium iodide salt. 10 mL of this concentrated culture is aliquoted into 14 mL culture tubes and sealed with a rubber stopper. Cultures are grown at 30 degrees with 250 rpm shaking, and methyl iodide production assayed at specified intervals via GC-MS. The GC-MS system consists of a model 6850 Series II Network GC system (Agilent) and model 5973 Network mass selective system (Agilent). Oven temperature is programmed from 50 degrees (1 min) to 60 degrees (10 degrees/min). 100 microliters of culture headspace is withdrawn through the rubber stopper with a syringe and manually injected into the GC-MS and methyl iodide production measured.

Figure 9A:
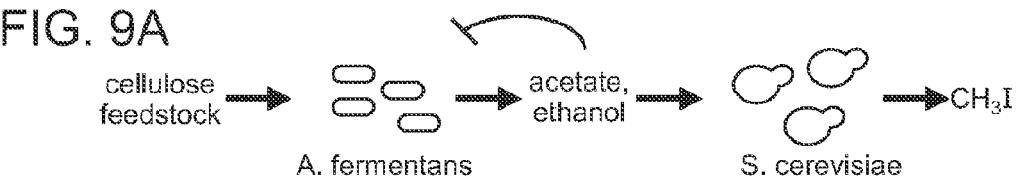
FIG. 9A-C: $CH_3I$ production from cellulosic feedstocks using a microbial co-culture.
Figure 9B:
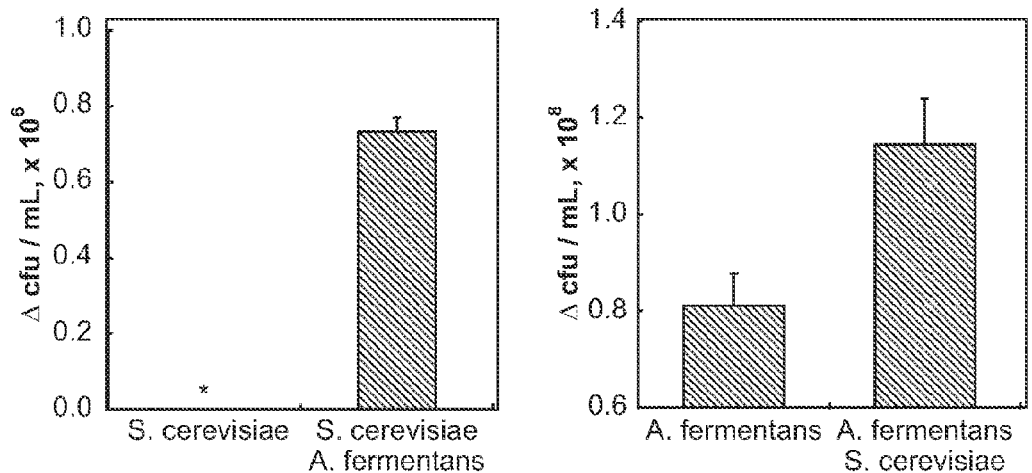
Figure 9C:
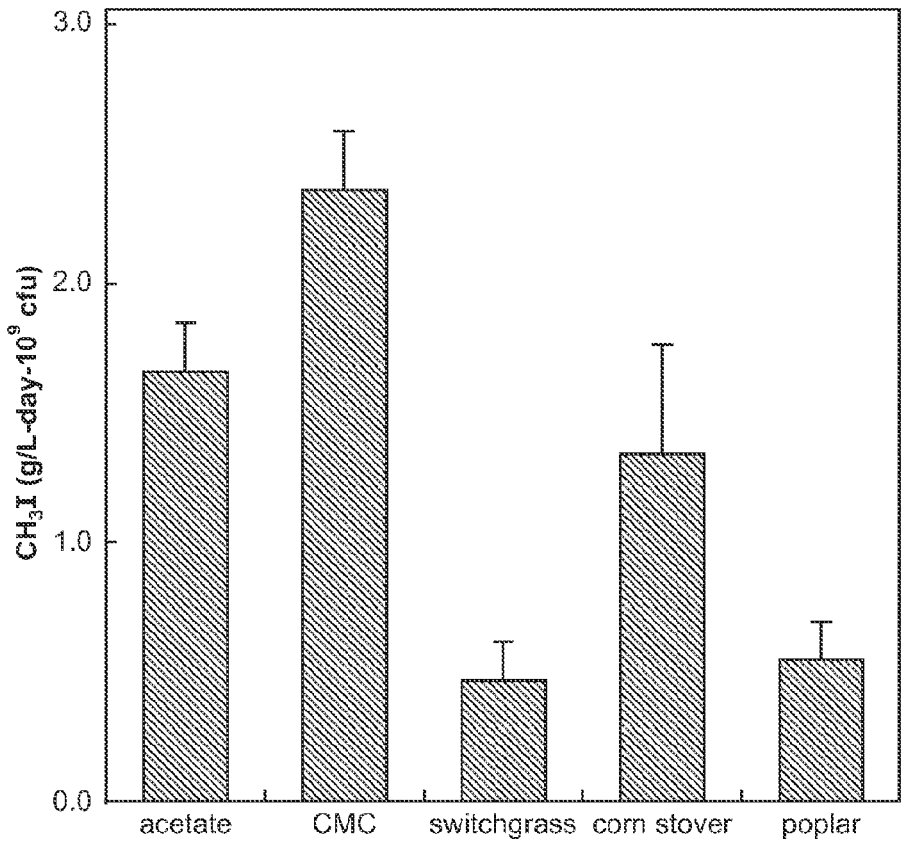

As is discussed below (Example 10), using the methods described above we targeted the *B. maritime* MHT to the *S. cerevisiae* strain W303a vacuole using the carboxypeptidase Y peptide, and assayed methyl iodide production from glucose (FIG. 9A). Yeast displayed high activity on glucose (FIG. 9B) and normal growth rates (approximately 90 min doubling time), compared to doubling times from natural sources of several days. Methyl iodide yield from glucose was measured at 4.5 g/L-day by comparison to standards, which is approximately 10,000 fold over the best natural sources (FIG. 9C).

It will be appreciated that, more generally, the targeting of other enzymes involved in metabolic processes to the vacuole can be used to increase production. In particular, yield from reactions in which a substrate(s) is SAM and/or a halide can be increased by such targeting. For example, ethylene may be produced by a metabolic pathway using SAM (see, e.g., U.S. Pat. No. 5,416,250, incorporated herein by reference). In a yeast (e.g., *S. cerevisiae*) expressing 1-aminocyclopropane-1 carboxylic acid (ACC) synthase (see Wilson et al., 1993, Apple ripening-related cDNA clone pAP4 confers ethylene-forming ability in transformed *Saccharomyces cerevisiae. Plant Physiol.* 102:783-8, incorporated herein by reference) and a ethylene forming enzyme (EFE, see McGarvey et al., 1992, Characterization and kinetic parameters of ethylene-forming enzyme from avocado fruit. *J Biol. Chem.* 267(9): 5964-7) ethylene production can be increased by targeting the enzymes to the vacuole.

3.7 Combinations

Generally, the process of the invention makes use of cells selected or modified at multiple (e.g., at least 2, sometimes at least 3, sometimes at least 4, and sometimes 5 or more than 5) different loci to increase methyl halide production. Cells may have additional genetic modifications to facilitate their growth on specific feedstocks, to provide antibiotic resistance and the like. In some embodiments strains developed for different purposes may be further modified to meet the needs of the current invention. See, for example, He et al., 2006, "A synergistic effect on the production of S-adenosyl-L-methionine in *Pichia pastoris* by knocking in of S-adenosyl-L-methionine synthase and knocking out of cystathionine-beta synthase" *J. Biotechnol.* 126:519-27. Park et al., 2007, "Characteristics of methionine production by an engineered *Corynebacterium glutamicum* strain" *Metab Eng.* 9:327-36 described genetic manipulation of a *C. glutamicum* strain to increase methionine production. The strain carries a deregulated horn gene to abolish feedback inhibition of homoserine dehydrogenase by threonine and a deletion of the thrB gene to abolish threonine synthesis. As also discussed, modified strains can be obtained by selection processes instead of recombinant technology, where organisms can be mutagenized and screened for methionine overproduction. High-producing strains have been isolated in many organisms including *E. coli* and yeast. See, e.g., Alvarez-Jacobs et al., 2005, *Biotechnology Letters*, 12:425-30; Dunyak et al., 1985, 21:182-85; Nakamori et al., 1999, *Applied Microbiology and Biotechnology* 52:179-85.

For illustration and not limitation, the following exemplary combinations may be used. Specifying specific modifications does not preclude the presence of additional modifications:

a) Expression of a heterologous MHT and a genetic modification to increase flux through a S-adenosyl-methionine (SAM) biosynthetic pathway. In one embodiment flux through a SAM biosynthetic pathway is increased by increasing expression of a SAM synthetase (which may be heterologous or endogenous). In one embodiment, the metK gene or a homolog is over expressed. In one embodiment, the sam1p and/or sam2p gene or a homolog is over expressed. See Section 3.1.1 above.

b) Expression of a heterologous MHT and a genetic modification to increase flux through a SAM "recycling" pathway. In one embodiment activity of SAM-dependent methylase, methionine synthase, S-adenosyl-L-homocysteine hydrolase (e.g., SAH1) and $N^5$-methyltetrahydropteroyl-triglutamate-homocysteine methyltransferase (e.g., MET6) is increased. See Section 3.1.2 above.

c) Expression of a heterologous MHT and a genetic modification to inhibit flux through a SAM utilization pathway. In one embodiment a coproporphyrinogen III oxidase, coproporphyrinogen III oxidase, S-adenosylmethionine decarboxylase, cystathionine beta-synthetase, ribulose 5-phosphate 3-epimerase, glucose-6-phosphate dehydrogenase, L-alanine transaminase, 3',5'-bisphosphate nucleotidase, glycine hydroxymethyltransferase or glycine hydroxymethyltransferase is inhibited. In one embodiment, the CYS4, Rpe1, Zwf1, Alt, Met22, Shm 1-m, Shm 2, HEM 13, or hemFgene is inhibited. See Section 3.1.3 above.

d) Expression of a heterologous MHT and a genetic modification to increase methionine biosynthesis. See Section 3.2.1 above.

e) Expression of a heterologous MHT and a genetic modification to increase activity of gene products involved in sulfate assimilation, cysteine biosynthesis and/or conversion of oxaloacetate to aspartate semialdehyde. In some embodiments, L-cysteine synthase (e.g., cysK), NADPH-dependent sulphite reductase (e.g., cysI) or alkane sulfonate monooxygenase (e.g., ssuD) is over expressed. See Section 3.2.2 above.

f) Expression of a heterologous MHT and a genetic modification to increase intracellular ATP levels. See Section 3.4 above.

g) Expression of a heterologous MHT and a genetic modification to increase levels of intracellular serine. See Section 3.2.2 above.

h) Expression of a heterologous MHT and a genetic modification to increase methionine uptake. See Section 3.2.3 above.

i) Expression of a heterologous MHT and a genetic modification to increase intracellular halide concentration. See Section 3.3 above.

j) Expression of a heterologous MHT and a genetic modification that reduces halide utilization other than for the synthesis of methyl halide. See Section 3.5 above.

k) Combinations of (a)-(j) such as a+b, a+c, a+d, a+e, a+f, a+g, a+h, a+i, a+j, b+c, b+d, b+e, b+f, b+g, b+h, b+i, b+j, c+d, c+e, c+f, c+g, c+h, c+i, c+j, d+e, d+f, d+g, d+h, d+i, d+j, e+f, e+g, e+h, e+i, e+j, f+g, f+h, f+i, f+j, g+h, g+i, g+j, h+i, or h+j.

l) Modifications presented in (a)-(k) above, except that the cell expresses or overexpresses an endogenous MHT rather than a heterologous MHT.

3.8 Homologs, Orthologs and Variants

It is understood that gene names vary from organism to organism and reference above to a gene name above is not intended to be limiting, but is intended to encompass homologs with equivalent activity. Moreover, where the method requires overexpression of an activity the encoded protein need not be identical to the naturally occurring version, so long as the overexpressed protein has the appropriate activity and can be expressed in the host. In certain embodiments the invention includes the use of enzymatically active polypeptides with at least 50%, at least 60%, at least 70%, at least 80%, at least 90%, at least 95% or at least 99% identity with a known protein described hereinabove.

4. Recombinant Techniques

Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of methyl halide within the organism or in the culture. Methods for genetic manipulation of procaryotes and eukaryotes are very well known in the art. Accordingly, methods are only very briefly described. Some culture and genetic engineering techniques are generally disclosed, for example, in Sambrook et al., 1989, MOLECULAR CLONING: A LABORATORY MANUAL, Cold Spring Harbor Laboratory Press; Sambrook and Russell, 2001, MOLECULAR CLONING: A LABORATORY MANUAL Cold Spring Harbor Laboratory Press; Ausubel, et al, 2002, SHORT PROTOCOLS IN MOLECULAR BIOLOGY, John Wiley & Sons; Tuan, R. S., 1997, RECOMBINANT GENE EXPRESSION PROTOCOLS Humana Press; Ball, A. S., 1997, BACTERIAL CELL CULTURE: ESSENTIAL DATA John Wiley & Sons; Richmond, A., 2003, HANDBOOK OF MICROALGAL CULTURE Wiley-Blackwell; Becker, E. W., 1994, MICROALGAE: BIOTECHNOLOGY AND MICROBIOLOGY Cambridge University Press; Guthrie and Fink, 2004, GUIDE TO YEAST GENETICS AND MOLECULAR BIOLOGY, Academic Press; and Walker, G. M., 1998, YEAST PHYSIOLOGY AND BIOTECHNOLOGY John Wiley & Sons, each of which is incorporated herein by reference for all purposes.

Expression and harvest of recombinant proteins or products produced by recombinant cells, on both laboratory and industrial scales, is well known and widely discussed in the literature. For production on an industrial level large bioreactors may be used (see, e.g., McKetta, J., CHEMICAL PROCESSING HANDBOOK, 1993, Marcel Dekker; Lee, S., ENCYCLOPEDIA OF CHEMICAL PROCESSING, 2006, Taylor and Francis Group; Asenjo, J., BIOREACTOR SYSTEM DESIGN, 1995, Marcel Dekker; Nielsen, J., BIOREACTION ENGINEERING PRINCIPLES, 2003, Kluwer Academics; Crow et al., "Process for manufacturing methyl chloride," U.S. Pat. No. 6,111,153; Van't Riet and Tramper, 1991, BASIC BIOREACTOR DESIGN, CRC Press; Asenjo and Merchuk, 1995, BIOREACTOR SYSTEM DESIGN, CRC Press).

4.1 Expression of Recombinant Genes

The expression of genes that contribute to methyl halide production, and/or the presence, levels, and/or activity of the corresponding gene products (mRNA and/or protein), can be achieved or increased. Overexpression can be accomplished by introducing a recombinant construct that directs expression of a gene product in a host cell, or by altering basal levels of expression of an endogenous gene product, for example by inducing or de-repressing its transcription, or enhancing the transport, stability and/or activity of gene products such as mRNA and/or protein. Codon optimization of non-endogenous nucleic acid sequences can also increase translation efficiency.

Stable introduction of cloned genes can be accomplished for example by maintaining the cloned gene(s) on replicating vectors or by integrating the cloned gene(s) into the genome of the production organism. Examples include multi-copy plasmids, transposons, viral vectors or YACs. The vector can contain an origin of replication such as PSC101, BAC, p15a or ColE1 (in prokaryotes) or ARS (yeast) or the SV40 origin (eukaryotes).

Expression vectors that can be used to produce a desired protein can comprise an operable linkage of (1) DNA elements coding for an origin for the maintenance of the expression vector in a host cell; (2) DNA elements that control initiation of transcription, such as a promoter; (3) DNA elements that control the processing of transcripts, such as a transcriptional terminator, and (4) optionally, a gene encoding a selectable marker, such as antibiotic resistance.

The sequence to be expressed can be placed under the control of a promoter that is functional in the desired prokaryotic or eukaryotic organism. An extremely wide variety of promoters are well known, and can be used, depending on the particular application. Inducible and constitutive promoters are both encompassed by the invention. Inducible promoters include those induced by arabinose (PBAD); IPTG (PTRC), halide salts (e.g., sodium chloride), osmolarity, sugar, starch, cellulose, or light.

As shown in Example 4, methyl halide production using an IPTG-inducible promoter in bacteria increases to peak levels within 1-2.5 hours after induction of expression.

The expression of genes can be increased by operatively linking the gene(s) to native or heterologous transcriptional control elements. This can be done by the use of synthetic operons, ribosome binding sites, transcription termination sites and the like. Various prokaryotic and eukaryotic expression control sequences are known in the art. See, e.g., WO 06/069220, incorporated by reference in its entirety. An example of a sequence encoding a recombinant ribosome binding site is ATTAAAGAGGAGAAATTAAGC (SEQ ID NO:2).

Recombinant sequences can be optimized for protein expression in a particular host species by changing any codons within a cloned gene that are not preferred by the organism's translation system to preferred codons without changing the amino acid sequence of the synthesized protein. Codon optimization can increase the translation of a recombinant gene. Optionally, the DNA sequence of a gene can be varied so as to maximize the difference with the wild-type DNA sequence, for example to avoid the possibility of regulation of the gene by the host cell's regulatory proteins.

4.2 Repression, Inhibition or Deletion of Genes

The expression of genes that tend to limit, regulate or decrease methyl halide production, or the presence, levels, and/or activity of the corresponding gene products (mRNA and/or protein), can be abolished or decreased. Genetic modifications that result in a decrease in expression and/or function of the gene and/or gene product can be through complete or partial inactivation, suppression, deletion, interruption, blockage or down-regulation of a gene. This can be accomplished for example by gene "knockout," inactivation, mutation, deletion, or antisense technology. Gene knockout can be accomplished using art-known methods including commercially available kits such as the "TargeTron gene knockout system" (Sigma-Aldrich). E. coil strains with individual gene knockouts can be obtained from the E. coli genome project (www.genome.wisc.edu). The invention includes multiple knockouts, e.g., 2-6 genes in same organism. The invention also includes any combination of gene introductions, deletions or modifications.

5. Cultivation/Fermentation Media and Conditions

The terms "cultivation" and "fermentation" are used interchangeably herein to refer to the culture of MHT-expressing cells in liquid media under conditions (either aerobic or anaerobic) in which methyl halides are produced. The growth medium used for production of methyl halides will depend largely on the host organism. Suitable growth conditions many procaryotes and eukaryotes commonly used in the laboratory or industrial settings are known and described in the scientific literature. See, e.g., Ball, A. S., 1997, BACTERIAL CELL CULTURE: ESSENTIAL DATA John Wiley & Sons; Richmond, A., 2003, HANDBOOK OF MICROALGAL CULTURE Wiley-Blackwell; Becker, E. W., 1994, MICROALGAE: BIOTECHNOLOGY AND MICROBIOLOGY Cambridge University Press; and Walker, G. M., 1998, YEAST PHYSIOLOGY AND BIOTECHNOLOGY John Wiley & Sons, each of which is incorporated herein by reference for all purposes. Methods of optimizing cultivation conditions may be determined using art known techniques.

A nutrient or cultivation media will include a carbon source, a halide source, as well as nutrients. The medium should also contain appropriate amounts of nitrogen and sulfur sources, e.g., in the form of one or more sulfates (such as ammonium sulfate) and/or thiosulfates. The medium can also contain vitamins such as vitamin B12. One suitable medium for bacteria such as E. coli is Luria-Bertani (LB) broth.

Carbon-containing substrates are metabolized to supply the methyl portion of methyl halides. Carbon compounds can also be metabolized to provide energy to drive methyl halide production. Substrates include carbon-containing compounds such as petroleum and/or natural gas, carbohydrates, in which carbon is present in a form that can be metabolized by the organism of choice. Examples of carbohydrates include monosaccharides, sugars such as glucose, fructose, or sucrose, oligosaccharides, polysaccharides such as starch or cellulose, and one-carbon substrates or mixtures thereof, for example presented in the form of feedstock. Carbon dioxide can also be used as a carbon source, especially when photosynthetic organisms such as algae are used. Common carbon-containing raw materials that can be used include but are not limited to wood chips, vegetables, biomass, excreta, animal wastes, oat, wheat, corn (e.g., corn stover), barley, milo, millet, rice, rye, sorghum, potato, sugar beets, taro, cassava, fruits, fruit juices, and sugar cane. Particularly useful are switchgrass (*Panicum virgatum*), elephant grass (Miscanthus giganteus), bagasse, poplar, corn stover and other dedicated energy crops. The optimal choice of substrate will vary according to choice of organism. As noted above, when cellulosic materials are used as carbon sources, organisms such as *Erwinia, E. coli, Pichia, Clostridium*, and *Aspergillus Niger* can be used. *E. coli* and *Saccharomyces* are examples of organisms that can be used to metabolize starches and sugarcane. Similarly, photosynthetic organisms such as algae (e.g., *Chlorella* and *Prototheca*) can metabolize carbon sources such as $CO_2$. See, Schmid, R. D., 2003, POCKET GUIDE TO BIOTECHNOLOGY AND GENETIC ENGINEERING John Wiley & Sons. Optionally cellulosic stocks may be blended or pulverized before addition to culture.

In addition to various genetic modifications, methyl halide production can be increased by optimizing the composition of the growth medium. As noted, the yield of methyl halides can also be increased by increasing the intracellular concentration of one or more reactants or precursors such as halides, methionine, SAM, and intermediates in SAM biosynthesis. Use of media rich in methionine, serine, and/or halide can increase methyl halide production. In certain embodiments the concentration of methionine in the medium is from about 0.5 gm/L to about 10 gm/L. In other embodiments the concentration of serine in the medium is from about 0.5 gm/L to about 10 gm/L.

Addition of halide salts to the medium can increase intracellular halide concentration. Halide salts include chlorides, iodides or bromides of sodium, potassium, magnesium, and the like. As shown below in Example 5, methyl halide production increases with atomic weight of the halide. Thus under certain circumstances, iodides can give better yield than bromides which in turn tend to given better yield than chlorides. As shown in Example 5, methyl halide production can be increased by adjusting the concentration of halides in the medium. The optimal osmolarity of a medium is often about 0.01 to 1 M, often about 0.05 to 0.3, such as about 0.1 M. The optimal concentration of a chosen halide salt can be determined empirically by one of skill guided by this disclosure. Using NaCl as an example, the invention contemplates the use of NaCl at about 0.01 to 0.1 M, often about 0.05 to 0.5 M, for example about 0.1 M, such as 0.085 M. Media such as Luria-Bertani (LB) broth (0.171 M of NaCl) are suitable. LB broth can also be prepared with various counter-ions made up to about 0.16 M. For example, an LB broth preparation of 5 g/L yeast extract, 10 g/L tryptone and 0.5 g/L NaCl can be supplemented with 16.7 g/L NaBr or 24.4 g/L NaI.

Increasing the levels of serine, for example by providing a serine-rich nutrient source can also result in increased methionine production. See, e.g., WO 07/135,188, incorporated by reference in its entirety).

The organisms can be maintained or cultivated under conditions that are conducive for methyl halide production. Many parameters such as headspace ratio, growth phase and oxygen levels can affect methyl halide production.

The invention contemplates culture conditions in which the organisms are in stationary phase or exponential (log) phase. Stationary phase is often suited for methyl halide production. Similarly, the invention also encompasses both aerobic and anaerobic growth of cultures. On occasion, aerobic growth is appropriate. Cell density can sometimes be increased (and nutrient concentrations can be also increased correspondingly) without impairing methyl halide production. Some host cells are maintained at elevated temperature (e.g., 37° C.) with agitation. In one approach, solid state fermentation is used (see, Mitchell et al., SOLID-STATE FERMENTATION BIOREACTORS, 2006, Springer). Aerobic or anaerobic conditions may be selected, depending in part on the organism and strain.

The ratio of headspace gas (air) per liquid culture volume can be optimized according to the invention using Henry's law. It has been determined that the optimum ratio is generally about 0.5:1 to 4:1, for example about 2:1.

Methyl halides and non-halogenated organic molecules produced using methods of the invention are usually produced at an industrial scale, for example for production of biofuels suitable as petroleum substitutes. Accordingly, organisms comprising a S-adenosylmethionine (SAM)-dependent methyl halide transferase (MHT) may in some embodiments be cultivated in bioreactors having a liquid capacity of at least 10 liters, at least 50 liters, at least 100 liters, or at least 500 liters. Often a bioreactor with a liquid capacity of at least 1000 liters, at least 5,000 liters, or at least 10,000 liters, for example. Often the volume of cultivation medium in cultures of the invention is at least 10 liters, at least 25 liters, at least 50 liters, at least 100 liters, at least 500 liters, at least 1,000 liters, or at least 5,000 liters. Culture may be carried out as a batch fermentation, in a continuous culture bioreactor, or using other methods known in the art.

5.1 Co-Culture of Yeast and Cellulolytic Bacteria

In another aspect, the invention provides a method for production of any of a variety of biological or organic products using cellulosic feedstocks as the sole or primary carbon source. According to the method, a co-culture comprising a mesophyllic cellulolytic bacterium (e.g., *Actinotalea fermentans*) and a recombinant yeast (e.g., *S. cerevisiae*) is prepared. Cellulose (e.g., cellulose, microcrystalline cellulose, Avicel, a cellulosic feedstock) is provided as an energy source to the co-culture. Where reference is made herein to cellulose, it is contemplated that hemicellulose and/or lignin (other biomass components) may be used in addition to or in place of cellulose in certain embodiments. Often, as described herein, raw or partially processed cellulosic feedstock is used. The cellulose is then metabolized by the bacterium to produce products which serve as a carbon source for the yeast. The recombinant yeast is thus able to carry out metabolic processes in a co-culture fed with cellulose. In some embodiments the bacteria-yeast co-culture is maintained under aerobic conditions. In some embodiments the bacteria-yeast co-culture is maintained under anaerobic conditions.

In some embodiments the co-culture is a symbiotic co-culture. A symbiotic co-culture is one in which the yeast is dependent on the bacterium for carbon (i.e., in the form of compounds that are waste products of bacteria metabolism), and the bacterium is dependent on the yeast for metabolism of toxic waste products. That is, the accumulation of bacterial waste products, in the absence of the yeast symbiant inhibits growth or viability of the bacteria. Thus, for example a cellulolytic bacterium that (a) metabolizes cellulose to produce ethanol and (b) is subject to growth inhibition by ethanol may be used in a symbiotic co-culture with a yeast that metabolizes ethanol. As another example, a cellulolytic bacterium that (a) metabolizes cellulose to produce acetate and (b) is subject to growth inhibition by acetate may be used in a symbiotic co-culture with a yeast that metabolizes acetate. As another example, a cellulolytic bacterium that (a) metabolizes cellulose to produce lactate and (b) is subject to growth inhibition by lactate may be used in a symbiotic co-culture with a yeast that metabolizes lactate. These examples are for illustration and not to limit the invention. Moreover, in this context the term "dependent" does not necessarily imply absolute dependency, but may mean that growth or viability of the organism is higher or more stable in co-culture. A symbiotic bacteria-yeast co-culture can be described as a mutually obligatory cooperative system, in which each organism is dependent upon the other for viability.

A large number of cellulolytic bacteria are suitable for use in co-culture. For a discussion of cellulolytic bacteria see, e.g., Lynd et al., 2002, Microbial cellulose utilization: fundamentals and biotechnology. *Microbiol. Mol Biol Rev.* 66:506-77. In some embodiments the cellulolytic bacterium is a *cellulomonas* or *actinotalea* species. For illustration and not limitation, exemplary celluolytic bacteria include *Trichoderma harzianum, Trichoderma reesei, Cellulomonas uda, Cellulomonas flavigena, Cellulomonas cellulolyticum, Pseudomonas* species and *Thermomonospora* species. Bacteria capable of aerobic fermentation of cellulose to ethanol, acetate, or lactate are well suited for co-culture. Also well suited for co-culture are bacteria capable of aerobic fermentation of cellulose to succinate, citrate, formate or malate. In some embodiments bacteria capable of anaerobic fermentation of cellulose to ethanol, acetate, lactate succinate, citrate, formate or malate are used. Cellulosic bacteria may be recombinantly modified (e.g., to incorporate drug resistance markers, modify a synthetic pathway in the cell, etc.). In some embodiments cellulolytic bacteria are selected based on growth inhibition by the product of the bacterial metabolism of cellulose (e.g., growth inhibition by ethanol, acetate, lactate succinate, citrate, formate or malate). It will be appreciated that bacteria exhibiting such growth inhibition are particularly useful for symbiotic co-cultures. Cellulolytic bacteria exhibiting such growth inhibition may be identified by reference to the scientific literature or may be identified or selected in the laboratory. In some embodiments, recombinant techniques are used to render a particular type or stain of bacterial susceptible to such inhibition. Other desirable properties include rapid growth, the ability to grow under either aerobic or anaerobic conditions, and the ability to secrete a significant portion of the carbon derived from cellulose (e.g., at least about 20%, preferably at least about 40%, most preferably at least about 50% under one or both of aerobic and anaerobic conditions). In some embodiments the bacteria is not a *Lactobacillus* species. In some embodiments the bacteria is not *Lactobacillus kefuranofaciens*.

In one embodiment the bacterium is *Actinotalea fermnentans*. *A. fermentans* is available from the American Type Culture Collection (ATCC 43279) and was previously referred to as *Cellulomonas fermentans* (see Yi et al., 2007, "Demequina aestuarii gen. nov., sp. nov., a novel actinomycete of the suborder Micrococcineae, and reclassification of *Cellulomonas fermentans* Bagnara et al. 1985 as *Actinotalea fermentans* gen. nov., comb. nov." *Int J Syst Evol Microbiol* 57(Pt 1):151-6; also see Bagnara et al., 1987, Physiological properties of *Cellulomonas fermentans*, a mesophilic cellulolytic bacterium. *Appl. Microbiol. Biotechnol.* 26:170-176, 1987). A. fermentans metabolizes cellulose to produce acetate and ethanol.

Similarly, a variety of yeast strains and species may be used. In one embodiment the yeast is *S. cerevisiae* (e.g., *S. cerevisiae* W303a). In other embodiments another yeast species is used (e.g., *Pichia pastoris, Hansenula polymorpha, Kluyveromyces lactis, Yarrowia lipolytica, Sacharomyces,* and *Scizosacchromyces pombe*).

The co-culture may comprise any combination of cellulolytic bacteria and yeast so long as the products of bacterial metabolism of cellulose can be used as a energy and carbon source by the yeast. In one embodiment the metabolism of cellulose by the bacterium produces secreted acetate and/or ethanol. Other end products of cellulosic bacteria include secreted lactate, succinate, citrate, malate, formate and other organic molecules (typically having 1-6 carbon atoms).

In one embodiment the cellulosic bacterium is *A. fermnentans* and the yeast is *S. cerevisiae.*

Usually the yeast is recombinantly engineered to produce a product of interest. For example, *S. cerevisiae* may be modified to express *Batis Maritima* MHT. Co-cultures with yeast engineered to express MHT may be used to produce may be methylhalide, as described in the examples. However, co-culture may be applied in many other applications. That is, given any yeast recombinantly modified to produce a product of interest, the product may be produced using a co-culture of the yeast and cellulosic bacterium in the presence of a cellulose source and any substrates required by the yeast to produce the product. The yeast product may be a drug, food product, amino acid, cofactor, hormone, proteins, vitamin, lipid, industrial enzyme or the like. Examples of products produced by recombinant yeast include small molecule drugs (see, e.g., Ro et al., 2006 "Production of the antimalarial drug precursor artemisinic acid in engineered yeast" *Nature* 440 (7086):940-3; petrochemical building blocks (see, e.g., Pirkov et al., 2008, "Ethylene production by metabolic engineering of the yeast *Saccharomyces cerevisiae*" *Metab Eng.* 10(5):276-80; commercially or medically useful proteins (see, e.g., Gerngross et al., 2004, "Advances in the production of human therapeutic proteins in yeasts and filamentous fungi" *Nat Biotechnol;* 22(11):1409-14). Exemplary medically useful proteins include insulin, hepatitis B antigen, desirudin, lepidurin, and glucagon. For other examples see Porro et al., 2005, "Recombinant protein production in yeasts" *Mol Biotechnol.* 31(3):245-59. Other examples of commercially valuable compounds that may be produced by the yeast in the co-cultures of the invention include, but are not limited to, 1,4 diacids (succinic, fumaric and malic); 2,5 furan dicarboxylic acid; 3 hydroxy propionic acid; aspartic acid; glucaric acid; glutamic acid; itaconic acid; levulinic acid; 3-hydroxybutyrolactone; Glycerol; Sorbitol; xylitol/arabinitol; gluconic acid; lactic acid; malonic acid; propionic acid; the triacids (citric and aconitic); xylonic acid; acetoin; furfural; levoglucosan; lysine; serine; threonine, valine and S-adenosylmethionine. Still others include 3 Glycerol, 3 hydroxypropionic acid, lactic acid, malonic acid, propionic acid, Serine; 4 Acetoin, aspartic acid, fumaric acid, 3-hydroxybutyrolactone, malic acid, succinic acid, threonine; 5 Arabinitol, furfural, glutamic acid, itaconic acid, levulinic acid, proline, xylitol, xylonic acid; Aconitic acid, citric acid, and 2,5 furan dicarboxylic acid. See Werpy et al., 2004, "TOP VALUE ADDED CHEMICALS FROM BIOMASS VOLUME I—RESULTS OF SCREENING FOR POTENTIAL CANDIDATES FROM SUGARS AND SYNTHESIS GAS" published by the Department of Energy Washington D.C. Also see the Biomass Document Database at http://www1. followed by eere.energy.gov/biomass/publications. Html, incorporated herein by reference in its entirety. Methods for genetically modifying yeast so that they produce desired products are known in the art or may be developed.

In one aspect the invention includes the further step of collecting or harvesting the product of interest produced by the yeast cells. In one embodiment the product of interest is a small molecule compound with a molecular weight less than 1000.

Typically and most conveniently, the bacteria and yeast components of the co-culture are grown together (comingled) in the liquid cultivation medium. In some embodiments, however, the co-cultured organisms can be, for example, maintained in separate compartments of a bioreactor, separated by a permeable membrane that allows metabolites and other molecules to diffuse between compartments. A wide variety of suitable bioreactors are known in the art.

In addition to cellulose, hemicellulose, lignin, biomass, feedstock or the like, which may be added, cultivation or growth media for use in coculture will include appropriate amounts of nitrogen and sulfur sources, e.g., in the form of one or more sulfates (such as ammonium sulfate) and/or thiosulfates. The medium can also contain vitamins such as vitamin B12. YP media may be used (Bacto-yeast extract (Difco) 10 gram, Bacto-peptone (Difco) 20 gram, ddH2O to 900 ml). Methods of optimizing cultivation conditions may be determined using art known techniques. See, e.g., Ball, A. S., 1997, BACTERIAL CELL CULTURE: ESSENTIAL DATA John Wiley & Sons; Richmond, A., 2003, HANDBOOK OF MICROALGAL CULTURE Wiley-Blackwell; Becker, E. W., 1994, MICROALGAE: BIOTECHNOLOGY AND MICROBIOLOGY Cambridge University Press; and Walker, G. M., 1998, YEAST PHYSIOLOGY AND BIOTECHNOLOGY John Wiley & Sons.

The invention provides a bacteria-yeast co-culture in which the bacteria metabolizes cellulose and produce one or more metabolic products, and the yeast uses the metabolic products of the bacterium as a carbon source. In some embodiments the microorganisms adapted to grow together while maintaining a relatively constant ratio of species populations such that neither microorganism overtakes the other. In bacteria-yeast co-cultures of the type described below in Section 5.1, we typically observed 100-fold excess of bacteria over yeast (approximately 1 million viable yeast cells and 100 million viable bacterial cells per milliliter).

5.1.1 Co-Culture of MHT-Expressing *S. Cerevisiae* and *Actinotalea fermentans*

Methyl iodide production in yeast offers several advantages over existing building block molecules, including compatibility with industrial processes. However, the production of biofuels and bio-based building blocks from food crop derived sugars (such as corn and sugarcane) may directly contribute to global food shortages. To mitigate these problems, methyl iodide (and other bio-based molecules) must be derived from cellulosic feedstocks, which include "energy crops" such as switchgrass (*Panicum virgatum*) and elephant grass (*Miscanthus giganteus*) as well as agricultural wastes such as corn stover. The conversion of these real-world biomass sources to fermentable sugars and products is problematic due to the recalcitrance of lignocellulosic materials to microbial digestion.

We constructed a co-culture of MHT-expressing yeast (as described above) with a mesophyllic cellulolytic bacterium, *Actinotalea fermentans*. *A. fermentans* ferments cellulose to acetate and ethanol aerobically, which *S. cerevisiae* are able to utilize as a carbon source. Importantly, *A. fermentans* growth is inhibited by accumulation of acetate and ethanol, creating a metabolic interdependence in the community, with *S. cerevisiae* dependent on *A. fermentans* for carbon, and *A. fermentans* dependent on *S. cerevisiae* for metabolism of toxic waste products (FIG. 9A). We inoculated *S. cerevisiae* with *A. fermentans* in media containing carboxymethylcellulose as the sole carbon source and measured the change in yeast and bacterium colony forming units (CFU) over time. Yeast grown in co-culture for 36 hours increase to $10^6$ cfu/ml, where yeast without the cellulolytic partner show little growth (FIG. 9B, left panel). The presence of yeast also increases the growth rate of the bacterium by consuming toxic components (FIG. 9B, right panel). This interaction demonstrates a symbiotic relationship.

We next tested the co-culture conversion of cellulosic feedstocks to methyl iodide. We inoculated the co-culture at low density on media containing pulverized dry switchgrass as the sole carbon source. At 36 hours after inoculation, sodium iodide was added to the medium to induce methyl iodide production. Methyl iodide yields on various cellulosic sources, including switchgrass, corn stover, and poplar are shown in FIG. 9C. Acetate is included as a non-fermentable carbon source reference and carboxymethylcellulose (CMC) is included as a cellulose standard. Energy crops such as switchgrass offer several advantages over conventional crops by requiring fewer agricultural inputs and by growing on marginal land, or by exhibiting extraordinary growth or genetic tractability (e.g., poplar). Agricultural residues such as corn (*Zea mays*) stover are another source of cellulosic carbon, with approximately 200 mg of stover produced in the United States each year. The results show that methyl iodide can be produced from a variety of cellulosic carbon sources.

Thus the invention provides a method for production of methyhalide comprising culturing a first microorganism which metabolizes cellulose and produces one or more metabolic products together with a second microorganism which does not metabolize cellulose and which is recombinantly modified to express a heterologous methyl halide transferase protein in a medium containing cellulose and a halide (e.g., chlorine, bromine and iodine) under conditions in which methyl halide is produced.

6. Collection and Purification of Methyl Halide

Methyl halides are volatile and escape into the vapor above the liquid culture. On a production scale this is advantageous over, for example, other biofuel intermediates because relatively little extra energy is required for purification of methyl halides, if so desired. In one embodiment, the methyl halide can be collected before conversion to one or more non-halogenated organic molecules. In another embodiment, the collection step is omitted, for example when the same organisms that produce methyl halide also convert the methyl halide to organic molecules.

Cultivation, collection of methyl halide, and/or conversion of methyl halide to organic compounds such as higher-molecular weight compounds (below) can be carried out in a reactor system. Methods for chemical processing and bioreactor systems are known in the art and can be readily adapted to the present invention. For illustration and not limitation, guidance is found in the scientific and engineering literature, e.g., McKetta, J., CHEMICAL PROCESSING HANDBOOK, 1993, Marcel Dekker; Lee, S., ENCYCLOPEDIA OF CHEMICAL PROCESSING, 2006, Taylor and Francis Group; Asenjo, J., BIOREACTOR SYSTEM DESIGN, 1995, Marcel Dekker; Nielsen, J., BIOREACTION ENGINEERING PRINCIPLES, 2003, Kluwer Academics; Crow et al., "Process for manufacturing methyl chloride," U.S. Pat. No. 6,111,153; Van 't Riet and Tramper, 1991, BASIC BIOREACTOR DESIGN, CRC Press; Asenjo and Merchuk, 1995, BIOREACTOR SYSTEM DESIGN, CRC Press; and Narita et al., "Preparation of methyl chloride," U.S. Pat. No. 5,917,099, each of which is incorporated herein by reference. For illustration and not limitation, one reactor system is shown in FIG. 9. Volatile methyl halide can be collected by any known method from the fermenter by transferring methyl halide that is produced in gaseous form to a condenser. In the condenser, the temperature of the gas comprising methyl halide can be lowered, for example resulting in the liquefaction of methyl halides but not other gaseous components, allowing for easy purification. Catalytic condensation or other reactions can take place in a reactor. Halide salts, generated as a by-product of the condensation reaction, can be recycled, e.g., by introducing back into the fermenter.

Gas phase production can be easily measured by, for example by gas chromatography mass spectroscopy, which determines the number of methyl halide molecules produced. The total amount of methyl halides produced can be calculated using Henry's Law.

7. Processing of Methyl Halides into Organic Molecules

The methyl halides can be converted to organic products such as alcohols, alkanes, (ethane-octane or longer), ethers, aldehydes, alkenes, olefins, and silicone polymers. These products in turn can be used to make a very wide range of petrochemical products, sometimes referred to as "biofuels." The use of alkyl halides, including methyl halides, in the production of more complex organic compounds is known in the conventional petrochemical industry. See, e.g., Osterwalder and Stark, 2007, Direct coupling of bromine-mediated methane activation and carbon-deposit gasification, *Chemp-*

*hyschem* 8: 297-303; Osterwalder and Stark, 2007, "Production of saturated C2 to C5 hydrocarbons" European patent application EP 1 837 320.

Conversion can be achieved by a variety of known methods, including biological conversion (e.g., through the use of biological organisms that can convert the methyl halide into non-halogenated organic molecules, for example through the action of one or more enzymes). If so desired, the conversion can be carried out in the same reactor or vessel in which the organism(s) that produce methyl halide are maintained. The conversion can be carried out by the same organisms that produce methyl halide or by different organisms, present within the same reactor or segregated in a different compartment or reactor. An organism can be modified to produce or convert (or both produce and convert) methyl halide to a greater rate or extent than an unmodified organism. When conversion is achieved by the same organisms that produce methyl halide, the collection of methyl halide can optionally be omitted. Both production and conversion can optionally be carried out in the same vessel or reactor.

The methyl halides can be converted to various organic molecules by the use of chemical catalysts. Depending on the choice of substrates (chemical catalyst used and/or methyl halide) as well as adjustment of different variables such as temperature, (partial) pressure and catalyst pre-treatment, various organic products can be obtained. For example, the use of a metal oxide catalyst can result in the production of higher alkanes. The use of an $AlBr_3$ catalyst can result in the production of propane. If the desired product is an alcohol, an ether or an aldehyde, the methyl halide can be passed over a specific metal oxide that is selected based upon its selectivity to produce the desired functionality (i.e. alcohol, ether or aldehyde). Should the desired product selectivity be affected by the amount of water present in the reaction between the alkyl monohalide and the metal oxide, water can be added to the alkyl monobromide feed to the appropriate level.

The use of a zeolite catalyst can result in the production of olefins. Examples of zeolites include naturally-occurring zeolites such as Amicite, Analcime, Barrerite, Bellbergite, Bikitaite, Boggsite, Brewsterite, Chabazite, Clinoptilolite, Cowlesite, Dachiardite, Edingtonite, Epistilbite, Erionite, Faujasite, Ferrierite, Garronite, Gismondine, Gmelinite, Gobbinsite, Gonnardite, Goosecreekite, Harmotome, Herschelite, Heulandite, Laumontite, Levyne, Maricopaite, Mazzite, Merlinoite, Mesolite, Montesommaite, Mordenite, Natrolite, Offretite, Paranatrolite, Paulingite, Pentasil, Perlialite, Phillipsite, Pollucite, Scolecite, Sodium Dachiardite, Stellerite, Stilbite, Tetranatrolite, Thomsonite, Tschernichite, Wairakite, Wellsite, Willhendersonite, and Yugawaralite. Synthetic zeolites can also be used. The use of zeolites to generate from methyl halides are well known in the art. See, e.g., Svelle et al., 2006, *Journal of Catalysis*, 241:243-54, and Millar et al., 1995, U.S. Pat. No. 5,397,560, both incorporated by reference in its entirety, discussing the use of a zeolite to produce hydrocarbon-type products, including alkenes such as ethene, propene and butenes, as well as ethylbenzenes and higher aromatics.

In addition to being a useful intermediate in the commercial manufacture of organic molecules, the methyl halide have various other uses, for example as a solvent in the manufacture of butyl rubber and in petroleum refining, as a methylating and/or halidating agent in organic chemistry, as an extractant for greases, oils and resins, as a propellant and blowing agent in polystyrene foam production, as a local anesthetic, as an intermediate in drug manufacturing, as a catalyst carrier in low temperature polymerization, as a fluid for thermometric and thermostatic equipment and as a herbicide.

8. Production of Methyl Formate

Methyl Formate (MF) is precursor for feedstock chemicals such as methanol and dimethyl ether (DME) and can be converted into esters, formamides, ethylene glycol, and other useful compounds. Methyl formate can be converted to methanol by art-known methods (e.g., copper catalysis). Methanol can be converted into DME which may then be converted to triptane (e.g., using H-BEA catalyst) or gasoline (e.g., using ZSM-5 catalyst).

Figure 13:
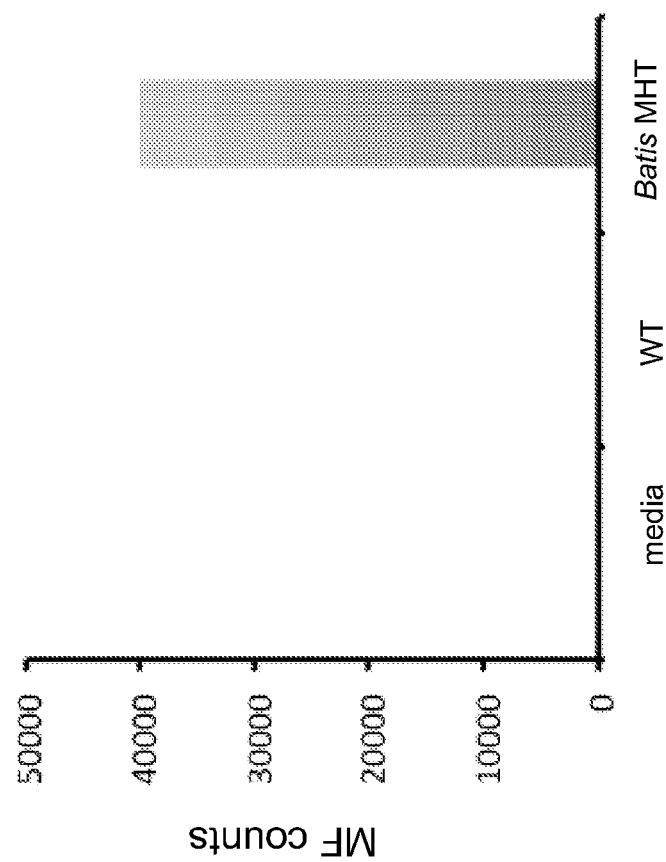
FIG. 13 shows production of methyl formate in yeast expressing *Batis methyl* halide transferase.
Figure 15:
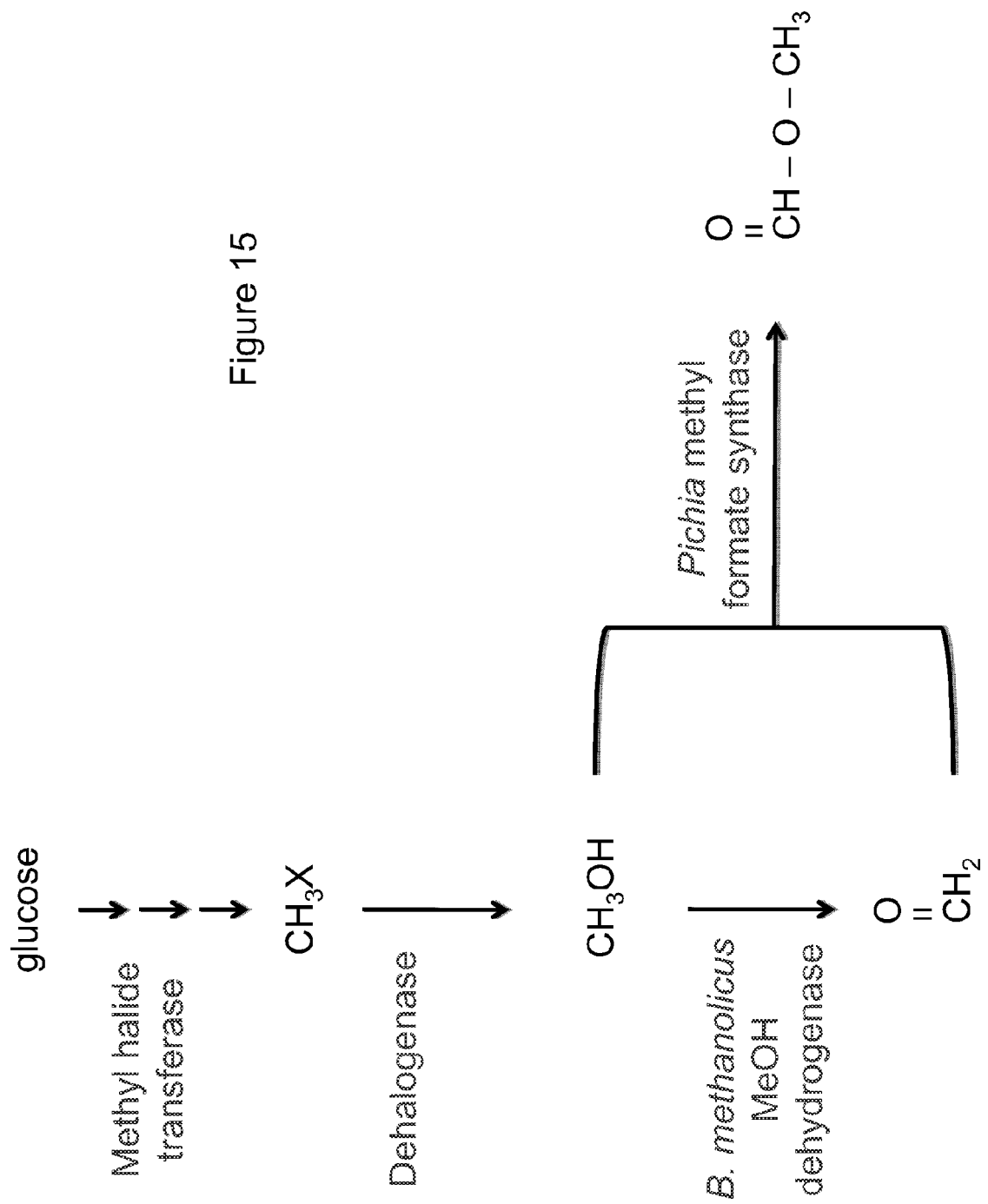
FIG. 15 shows an exemplary pathway for production of methylformate.
Figure 16:
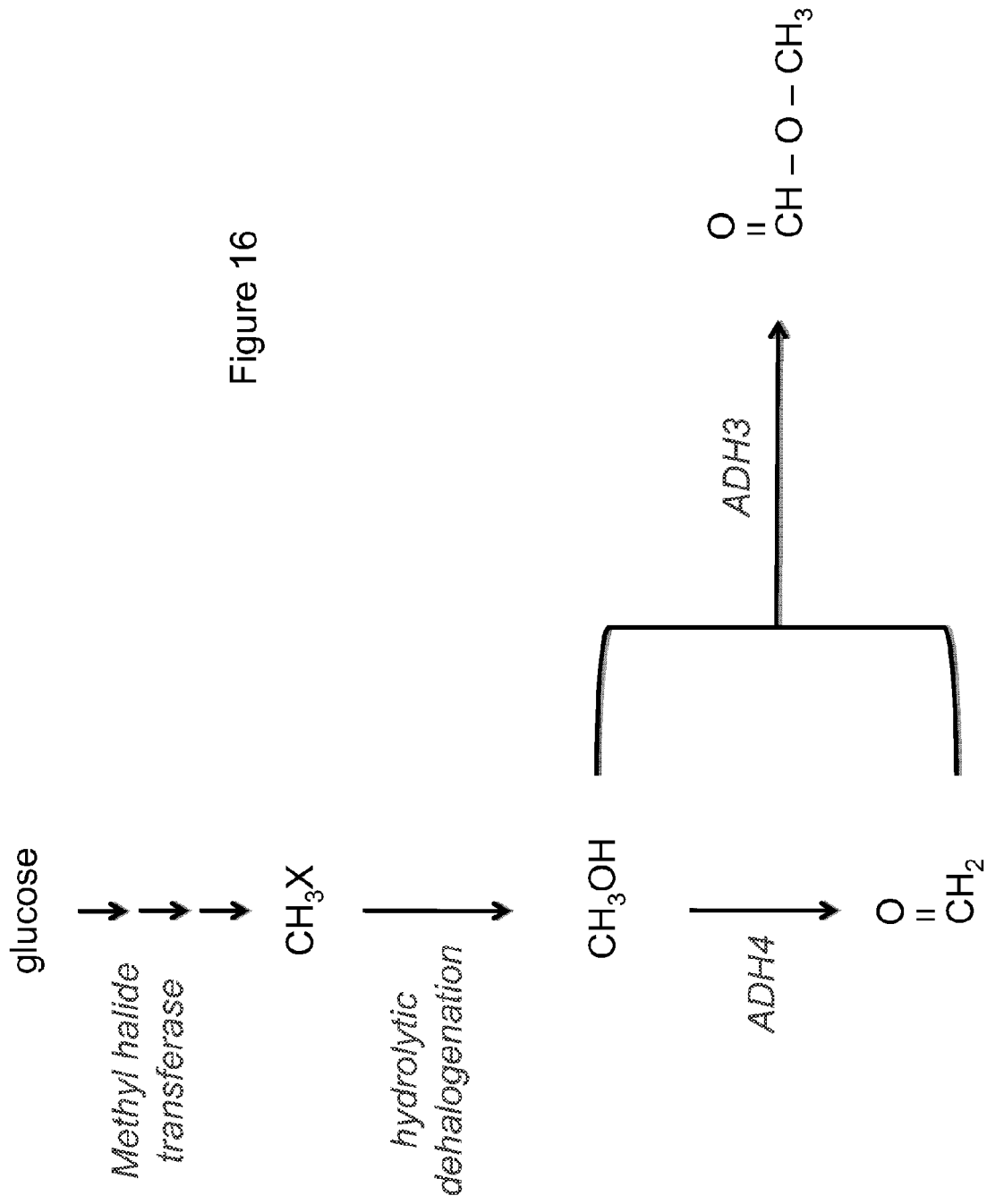
FIG. 16 shows an exemplary pathway for production of methylformate.

We have discovered that although methyl formate is not produced by wild type yeast grown on minimal media plus glucose and sodium iodide, it is produced by yeast expressing exogenous methyl halide transferase. See FIG. 13, comparing methyl formate production in yeast transformed with *Batis maritima* MHT to wild type production. Without intending to be bound by a specific mechanism, it is believed that methyl halide may undergo hydrolytic dehalogenation in the cell to produce methanol. Methanol may be dehydrogenated to produce formaldehyde (methanal). Methyl formate synthase may then act on methanol and formaldehyde produce methyl formate. This is as illustrated schematically in FIG. 15 (showing *B. methanolicus* methanol dehydrogenase and *Pichia* methyl formate synthase) and FIG. 16 (showing *Saccharomyces* genes). It will be appreciated that FIGS. 15 and 16 are for illustration, and are not intended to limit the invention.

Thus, in one aspect the invention provides a method for production of methyl formate by a recombinant organism (e.g., yeast) that expresses a heterologous MHT. The organism may be any organism described hereinabove and/or in PCT application No. PCT/US08/85019 published as WO 2009/073560 on Jun. 11, 2009 and/or in PCT application No. PCT/US2008/085013 published as WO 2009/073557 on Jun. 11, 2009, the entire disclosures of which are incorporated by reference herein. Thus, for example, the organism may be engineered to increase flux through the SAM biosynthetic pathway, or have any other modifications described hereinabove and in the cited references. Similarly, useful MHT proteins include those described hereinabove and in the cited references. Similarly, suitable culture conditions include those described hereinabove and in the cited references, including bacteria-yeast co-culture systems. In short, any modifications or conditions described herein for production of methyl halide may be used for production of methyl formate.

In some embodiments the organism is a yeast. In some embodiments the yeast is a methylotrophic yeast. In some embodiments the yeast is not a methylotrophic yeast. In some embodiments the yeast is of genus *Saccharomyces*, e.g., *Saccharomyces cerevisiae*.

In one embodiment, the recombinant organism does not generate any, or does not generate a significant quantity of methyl halide. As used in this context, "generate" means to release a compound (e.g., methyl halide and/or methyl formate) into the extracellular environment, e.g., as gas or vapor. In one embodiment the amount of methyl formate generated by the organism in culture (e.g., under conditions described herein) is at least 10-fold greater than the amount of methyl halide generated, often at least 100-fold greater, very often at least 1000-fold greater and sometimes at least 10.000-fold greater, measured as moles methyl formate and moles methyl halide. In one embodiment the amount of methyl formate generated by the organism in culture (e.g., under conditions described herein) is at least 10-fold greater than the amount of methyl halide generated, often at least 100-fold greater, very often at least 1000-fold greater and sometimes at least 10.000-fold greater, measured as grams methyl formate and grams methyl halide. Methyl formate production may be assayed under a variety of conditions, such as amount produced during a two hour period by a 1 liter stable culture in minimal medium plus halide and glucose.

The invention further provides further processing steps including removing methyl halide from the methyl formate that is collected, optionally, converting the collected methyl formate into methanol, and optionally converting the methanol to dimethyl ether. Methyl formate can be converted into methanol by art known methods.

In some embodiments the organism (e.g., yeast) is modified to increase the production of methyl formate. Without intending to be bound by a particular mechanism, such modifications include adopting culture conditions and/or introducing genetic changes (e.g., introducing modified or heterologous genes, increasing gene copy number, gene knock out, or up-regulation of gene expression) to (1) increase the conversion of methanol to formaldehyde, (2) increase the conversion of methanol and formaldehyde to methyl formate, and/or (3) increase the dehalogenation of methyl halide (e.g., methyl iodide) to methanol.

Methanol Dehydrogenases

For example and not limitation the rate of conversion of methanol to formaldehyde can be increased by expressing a heterologous methanol dehydrogenase or over-expressing an endogenous methanol dehydrogenase (e.g., by introducing a gene under control of a constitutive or inducible promoter). Methods for such expression are well within the ability of molecular biologists and other scientists.

An exemplary methanol dehydrogenase is described in de Vries et al., "Cloning, expression, and sequence analysis of the *Bacillus methanolicus* C1 methanol dehydrogenase gene" *J. Bacteriol.* 1992 August; 174(16):5346-53. [Accession A42952]. The sequence of the *B. methanolicus* protein is:

```
                                              (SEQ ID NO: 101)
MTNFFIPPAS VIGRGAVKEV GTRLKQIGAK KALIVTDAFL

HSTGLSEEVA KNIREAGLDV AIFPKAQPDP ADTQVHEGVD

VFKQENCDAL VSIGGGSSHD TAKAIGLVAA NGGRINDYQG

VNSVEKPVVP VVAITTTAGT GSETTSLAVI TDSARKVKMP

VIDEKITPTV AIVDPELMVK KPAGLTIATG MDALSHAIEA

YVAKGATPVT DAFAIQAMKL INEYLPKAVA NGEDIEAREA

MAYAQYMAGV AFNNGGLGLV HSISHQVGGV YKLQHGICNS

VNMPHVCAFN LIAKTERFAH IAELLGENVS GLSTAAAAER

AIVALERYNK NFGIPSGYAE MGVKEEDIEL LAKNAFEDVC

TQSNPRVATV QDIAQIIKNA L.
```

Other suitable methanol dehydrogenases are known (EC 1.1.1.244) and can be used in this method.

In one embodiment, the ADH4 protein of *Saccharomyces cerevisiae* is used. See Coissac et al., Yeast 12 (15), 1555-62 (1996). In one embodiment the In one embodiment the ADH4 protein has the following sequence [Accession CAA64131]:

```
                                              (SEQ ID NO: 102)
MLGITYAVNS TKQLIFCCLK YLTLLGYILL SNRKKGQRTN

MYKRVISISG LLKTGVKRFS SVYCKTTINN KFTFATTNSQ

IRKMSSVTGF YIPPISFFGE GALEETADYI KNKDYKKALI

VTDPGIAAIG LSGRVQKMLE ERDLNVAIYD KTQPNPNIAN

VTAGLKVLKE QNSEIVVSIG GGSAHDNAKA IALLATNGGE

IGDYEGVNQS KKAALPLFAI NTTAGTASEM TRFTIISNEE

KKIKMAIIDN NVTPAVAVND PSTMFGLPPA LTAATGLDAL

THCIEAYVST ASNPITDACA LKGIDLINES LVAAYKDGKD

KKARTDMCYA EYLAGMAFNN ASLGYVHALA HQLGGFYHLP

HGVCNAVLLP HVQEANMQCP KAKKRLGEIA LHFGASQEDP

EETIKALHVL NRTMNIPRNL KELGVKTEDF EILAEHAMHD

ACHLTNPVQF TKEQVVAIIK KAYEY
```

In some embodiments, homologs of ADH4 are used (e.g., a homolog from a yeast described hereinabove).

Methyl Formate Synthase

For example and not limitation the rate of production of methyl formate can be increased by expressing a heterologous methyl formate synthase or over-expressing an endogenous methyl formate synthase. Methyl formate synthase catalyzes the combination of methanol and formaldehyde to produce methyl formate.

In one embodiment, the methyl halide transferase is from *Pichia pastoria*. The genomic sequence of *P. pastoria* is described in De Schutter et al., 2009, "Genome sequence of the recombinant protein production host *Pichia pastoris*" *Nat. Biotechnol.* 27(6):561-6. In one embodiment, *P. pastoria* cells expressing methyl halide transferase, as described hereinabove, and expressing an endogenous methyl formate synthase is used. Other useful synthases are from *Candida boidinii* and *Pichia methanolica* (See Murdanoto "Purification and properties of methyl formate synthase, a mitochondrial alcohol dehydrogenase, participating in formaldehyde oxidation in methylotrophic yeasts" *Appl. Environ. Microbiol.*, 1997, 63:1715-20. See, e.g., Yurimoto et al., "Alcohol dehydrogenases that catalyze methyl formate synthesis participate in formaldehyde detoxification in the methylotrophic yeast *Candida boidinii*" Yeast 21:341-350 (2004).

In one embodiment, the MHT protein has the following sequence from *Pichia pastoria*:

```
                                              (SEQ ID NO: 103)
MSPTIPTTQKAVIFETNGGPLEYKDIPVPKPKSNELLINVKYSGVCHT

DLHAWKGDWPLDNKLPLVGGHEGAGVVVAYGENVTGWEIGDYA

GIKWLNGSCLNCEYCIQGAESSCAKADLSGFTHDGSFQQYATAD

ATQAARIPKEADLAEVAPILCAGITVYKALKTADLRIGQWVAISGAGG

GLGSLAVQYAKALGLRVLGIDGGADKGEFVKSLGAEVFVDFTKTK

DVVAEVQKLTNGGPHGVINVSVSPHAINQSVQYVRTLGKVVLVGLP

SGAVVNSDVFWHVLKSIEIKGSYVGNREDSAEAIDLFTRGLVKAPI

KIIGLSELAKVYEQMEAGAIIGRYVVDTSK
```

Figure 14:
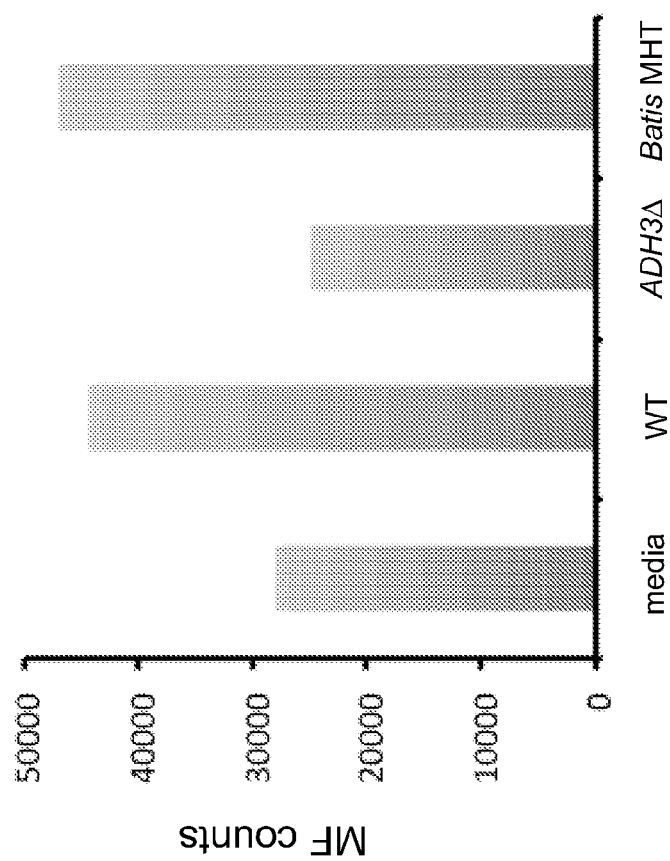
FIG. 14 shows the effect on production of methyl formate of knocking out ADH3 in yeast.

In one embodiment, the ADH3 protein of *Saccharomyces cerevisiae* [Swiss-Prot. Accession P07246] is used. FIG. 14 illustrates the effect on methyl formate production of knockout of the ADH3 gene in *S. cerevisiae* strain W303a. The figure shows methyl formate production in wild type (WT) cells, cells expressing *Batis* MHT, and ADH3 knockout (ADH3Δ) cells in medium containing methanol and formaldehyde. Methyl formate was produced in the WT and *Batis* MHT cultures, but was not observed in ADH3Δ cultures.

In some embodiments, other homologous alcohol dehydrogenaseses may be tested and used. Examples are: (showing Swiss-Prot accession numbers) *S. cerevisiae* Adh1p (cytosolic), P00330; *S. cerevisiae* Adh2p (cytosolic), P00331; P07246; *Kluyveromyces lactis* Adh1p (cytosolic), P20369; *K. lactis* Adh3p (mitochondrial), P49384; and *Candida albicans* Adhp, P43067.

Hydrolytic Dehalogenases

For example and not limitation the dehalogenation of methyl halide (e.g., MeI) can be increased by expressing a heterologous hydrolytic dehalogenase or over expressing an endogenous hydrolytic dehalogenase.

An exemplary hydrolytic dehalogenases is LinB from *Sphingomonas paucimobilis* (see Oakley et al., "Crystal structure of haloalkane dehalogenase LinB from *Sphingomonas paucimobilis* UT26 at 0.95 A resolution: dynamics of catalytic residues." *Biochemistry*. 2004 Feb. 3; 43(4):870-8. The sequence of the *S. paucimobilis* protein (Accession: AAR05978) is:

```
                                           (SEQ ID NO: 104)
MSLGAKPFGE KKFIEIKGRR MAYIDEGTGD PILFQHGNPT

SSYLWRNIMP HCAGLGRLIA CDLIGMGDSD KLDPSGPERY

TYAEHRDYLD ALWEALDLGD RVVLVVHDWG SVLGFDWARR

HRERVQGIAY MEAVTMPLEW ADFPEQDRDL FQAFRSQAGE

ELVLQDNVFV EQVLPGLILR PLSEAEMAAY REPFLAAGEA

RRPTLSWPRQ IPIAGTPADV VAIARDYAGW LSESPIPKLF

INAEPGHLTT GRIRDFCRTW PNQTEITVAG AHFIQEDSPD

EIGAAIAAFV RRLRPA
```

Other suitable dehalogenases are known (EC 3.8.1.5) and can be used in this method.

Exemplary Embodiments

In one embodiment a recombinant yeast (e.g., *S. cerevisiae*) comprising a heterologous gene encoding S-adenosyl-methionine (SAM)-dependent methyl halide transferase (e.g., *Batis maritime* MHT) is cultured in a medium containing a halide (e.g., chlorine, bromine or iodine) and carbon source under conditions in which methyl formate is produced; and methyl formate is collected from the culture.

In some embodiments the organism is a yeast expressing a heterologous methanol dehydrogenase (e.g., *Bacillus methanolicus* C1 methanol dehydrogenase) and/or a heterologous methyl formate synthase (e.g., *Pichia pastoria* methyl formate synthase) and/or a heterologous hydrolytic dehalogenase (e.g., *Sphingomonas paucimobilis* LinB protein).

In some embodiments the organism is a yeast expressing or over-expressing *S. cerevisia* ADH4 protein or a yeast homolog thereof and/or *S. cerevisia* ADH3 protein or a yeast homolog thereof.

In some embodiments methyl formate is produced using a bacteria-yeast co-culture comprising bacteria which metabolize cellulose and produce one or more metabolic products, and a genetically modified yeast as described hereinabove, where the yeast uses at least one metabolic product produced by the bacteria as a carbon source. In some embodiments the genetically modified yeast used in coculture is *Saccharomyces, Pichia, Hansenula, Kluyveromyces, Yarrowia, Trichoderma* or *Scizosacchromyces*. In on embodiment the yeast is *S. cerevisiae*. In come embodiments, the bacteria used in co-culture is a *Actinotalea* or *cellulomonas* species (such as *Actinotalea fermentans*).

9. Versatile Plasmid System for *Geobacillus* and Production Methyl Halide by *Geobacillus* Converting Hydrocarbon, Petroleum or Biomass

*Geobacillus* is thermophilic bacilli isolated from various terrestrial and marine environments including deep-subsurface and high temperature oil reservoirs. *Geobacillus* species have abilities to metabolize various saccharides and to use hydrocarbon in crude oil as a carbon and energy source. *Geobacillus* cells expressing methyl halide transferase may be used to convert hydrocarbon or petroleum to methyl halide.

A versatile plasmid expression system and a versatile super folder green fluorescent protein (sfGFP) expression plasmid have been developed for *Geobacillus* genus. *Geobacillus* may be engineered to produce methyl halide, using hydrocarbon or petroleum as the substrate. Production of methyl halide in this system has application for gasification of currently unrecoverable crude oil and for microbial enhanced oil recovery (MEOR).

A plasmid expression system for the genus *Geobacillus* has been constructed based on the *E. coli-Geobacillus* shuttle plasmid pNW33N. pNW33N was a plasmid for gene colony in *Geobacillus stearothermophilus* from *Bacillus* Genetic Strain Center. It is composed of the plasmid replicate origin and the multiple cloning sites of pUC18, the replicate origin and the repB *Geobacillus stearothermophilus* plasmid pTHT15, and a chloramphenicol acetyltransferase cat gene from *Staphylococcus aureus* plasmid pC194. Three genetic components, the promoter DNA fragment from *Bacillus* phage spo-1, a synthetic ribosome binding site for *Geobacillus* genus and a trpA terminator from *Bacillus subtils*, are integrated into this plasmid to construct gene expression unit.

A modified high osmolarity electroporation method from published *Bacillus* transformation method has been developed to transfer this plasmid to *Geobacillus* species with high transformation rate. This expression plasmid has been demonstrated to stably maintain in *Geobacillus* species from 40 to 60 degrees.

A super-folder green fluorescent protein (sfGFP) protein gene was inserted into the gene expression unit of this *Geobacillus* expression plasmid. This expression unit was further modularized at promoter, the ribosome binding site and the terminator fragments which made all these three elements replaceable by any DNA building block. Functional expression of a gene inserted into the plasmid expression unit has been demonstrated by expressing a super-folder green fluorescent protein (sfGFP) in *Geobacillus* species from 40 to 55 degrees.

The sfGFP expression plasmid was the first fluorescent protein expressing plasmid for *Geobacillus* which has been verify by the fluorescence microscopic observation and by flowmetry quantitative analysis. The On-Off ratio of fluorescence is more than 50 fold.

This sfGFP expression plasmid enables the localization of almost any protein expressed inside the *Geobacillus* cell and trace of the *Geobacillus* cell in any environments by fluorescence microscopy. The modularized sfGFP plasmid is a powerful tool to systematically analyze the function of *Geobacil-*

*lus* genetic elements such as the promoter, the ribosome binding site and the terminator.

Nine Methyl Halide Transferases from plant, bacteria and fungi were screened for the ability to produce Methyl halide in *Geobacillus*. The following are the list of the MHT primary sequences. The organism name and accession number are given.

```
> Oryza_sativa_2_EAY92545
                                        (SEQ ID NO: 26)
MASAIVDVAGGGRQQALDGSNPAVARLRQLIGGGQESSDGWS

RCWEEGVTPWDLGQPTPAVVELVHSGTLPAGDATTVLVPGCG

AGYDVVALSGPGRFVVGLDICDTAIQKAKQLSAAAAAAAD

GGDGSSSFFAFVADDFFTWEPPEPFHLIFDYTFFCALHP

SMRPAWAKRMADLLRPDGELITLMYLAEGQEAGPPFNTTV

LDYKEVLNPLGLVITSIEDNEVAVEPRKGMEKIARWKRMTKSD

> Vitis_vinifera_2_CAO46361
                                        (SEQ ID NO: 23)
MANDSTSIESNSELQKISQVIGSGFNGSWEEKWQQGLTPWDLGKATPII

EHLHQAGALPNGRTLIPGCGRGYDVVAIACPERFVVGLDISDSAIKKAK

ESSSSSWNASHFIFLKADFFTWNPTELFDLIIDYTFFCAIEPDMRPAWA

SRMQQLLKPDGELLTLMFPISDHTGGPPYKVSIADYEKVLHPMRFKAV

SIVDNEMAIGSRKGREKLGRWKRTDEPLL

> Oryza_sativa_japonica_1_ABF99844
                                        (SEQ ID NO: 27)
MASAIVDVAGGGRQQALDGSNPAVARLRQLIGGGQESSDGWSRCWE

EGVTPWDLGQRTPAVVELVHSGTLPAGDATTVLVPGCGAGYDVVALS

GPGRFVVGLDICDTAIQKAKQLSAAAAAAADGGDGSSSFFAFVADDF

FTWEPPEPFHLIFDYTFFCALHPSMRPAWAKRMADLLRPDGELITL

MYLVINRRYQHV

> Burkholderia_xenovorans_YP_557005
                                        (SEQ ID NO: 77)
MSDPTQPAVPDFETRDPNSPAFWDERFERRFTPWDQAGVPAAFQSF

AARHSGAAVLIPGCGSAYEAVWLAGQGNPVRAIDFSPAAVAAAHEQLG

AQHAQLVEQADFFTYEPPFTPAWIYERAFLCALPLARRADYAHRMADLL

PGGALLAGFFFLGATPKGPPFGIERAELDALLTPYFDLIEDEAVHDSIAV

FAGRERWLTWRRRA

> Burkholderia_pseudomallei_YP_332262
                                        (SEQ ID NO: 83)
MKDRLMSQGDGVTNEANQPEAAGQATGDAQPASPAGPAHIANPANP

ANPANPPALPSLSPPAAAPSSASSAAHFSSRDPGDASFWDERFEQG

VTPWDSARVPDAFAAFAARHARVPVLIPGCGSAYEARWLARAGWPV

RAIDFSAQAVAAARRELGEDAGLVEQADFFTYAPPFVPQWIYERAFLC

AIPRSRRADYARRMAELLPPGGFLAGFFFIGATPKGPPFGIERAELDAL

LCPHFALVEDEPVADSLPVFAGRERWLAWRRS

> Burkholderia_thailandensis_YP_441114
                                        (SEQ ID NO: 79)
MTSEANKGDAAVQAAGDAQPASPASPPSADVQPARAALAPSSVPPAP

SAANFASRDPGDASFWDERFERGVTPWDSARVPDAFAAFAARHPRCPVL

IPGCGSAYEARWLARAGWPVRAIDFSAQAVAAARRESGADAALVEQADFF

AYVPPFVPQWIYERAFLCAIPTSRRADYARRVAELLPAGGFLAGFFFIGA

TPKGPPFGIERAELDALLSPNFELVEDEPVADSLPVFAGRERWLAWRRS

> Aspergillus_clavatus_XP_001272206
                                        (SEQ ID NO: 39)
MSTPSLIPSGVHEVLAKYKDGNYVDGWAELWDKSKGDRLPWDRGFPN

PALEDTLIQKRAIIGGPLGQDAQGKTYRKKALVPGCGRGVDVLLLASFGY

DAYGLEYSATAVDVCQEEQAKNGDQYPVRDAEIGQGKITFVQGDFFED

TWLEKLNLTRNCFDVIYDYTFFCALNPSMRPQWALRHTQLLADSPRGHLI

CLEFPRHKDPSVQGPPWGSASEAYRAHLSHPGEEIPYDASRQCQFDS

SKAPSAQGLERVAYWQPERTHEVGKNEKGEVQDRVSIWQRPPQSSL

> Phaeosphaeria_nodorum_XP_001792029
                                        (SEQ ID NO: 32)
MANPNQDRLRSHFAALDPSTHASGWDSLWAEGTFIPWDRGYANPALID

LLANPSSPPTSSDANPTPGAPKPNTIDGQGVQLPAPLEGGVRRKALVP

GCGKGYDVALLASWGYDTWGLEVSRHAADAAKEYLKDAGEGALEGEY

KIKDAKIGKGREECVVADFFDDAWLKDVGAGEFDVIYDNTFLCALPPLL

RPKWAARMAQLLARDGVLICLEFPTHKPASSGGPPWSLPPTVHQELLK

RPGEDISYDEGGVVVATDRAESENALVRVAHWTPKRTHNIAVINGVVRD

CVSVWRHKKQS

> Kortia_algicida_ZP_02160755
                                        (SEQ ID NO: 70)
MNSDATKEYWSQRYKDNSTGWDIGSPSTPLKTYIDQLKDRNLKILIPGAG

NAYEAEYLLQQGFTNIYILDISEIPLQEFKQRNPEFPSDRLLCDDFFTHK

NTYDLIIEQTFFCSFPPLPETRAQYAKHMADLLNPNGKLVGLWFDFPLTD

DLEKRPFGGSKEEYLEYFKPYFDVKTFEKAYNSIAPRAGNELFGIFIKS
```

The genes encoding above selected MTH were chemically synthesized by DNA synthesis company and the DNA sequences have been optimized to be expressed in bacteria.

Production of methyl iodide by *Geobacillus thermoleovorans* DSM5366 bearing the selected nine MTH genes has been demonstrated in LB medium containing 100 mM NaI.

10. Methyl Halide Uses

Methyl halide transferases (MHTs) are produced naturally in a remarkable diversity of organisms from bacteria and Archaea to bok choy and pinot noir. In an application of synthetic metagenomics, we explored all available gene sequence databases to identify all the known genes that could possibly code for MHTs across all organisms and including genes with other putative functions, genes with no known function at all and genes from unknown organisms. We identified 89 sequences as candidate MHTs. The sequences for each of the 89 genes were chemically synthesized and expressed in *E. coli*, with appropriate minor modifications to optimize expression in the new host.

Each of the 89 MHTs thus produced were screened for their catalytic activity in producing the various methyl halides in different host species. The most active enzymes were from several plants including ice plants, rice and cabbage as well as soil bacteria and an unknown organism from a Sargasso Sea environmental metagenomic sample.

One approach is to engineer the metabolism of the yeast to divert more of the incoming carbon atoms from sugar through selected yeast metabolic pathways resulting in the overproduction of S-adenosyl methionine (SAM) to the exclusion of alternative metabolites. The MHT makes methyl halides from SAM and the corresponding halide ion. SAM is the standard carrier of methyl groups in the metabolism of all species and its production inside a cell is through well known pathways. The theoretical maximum metabolic yield of carbon from glucose to MeX is 53%, including the chemical energy required from ATP.

In addition to yeast and *E. coli*, the gene for the modified MHT can be transferred into other organisms with useful properties. Examples include an organism that would digest cellulose directly, or extremophile organisms that could directly consume cellulose, hydrocarbon tars or wastewater.

Figure 17:
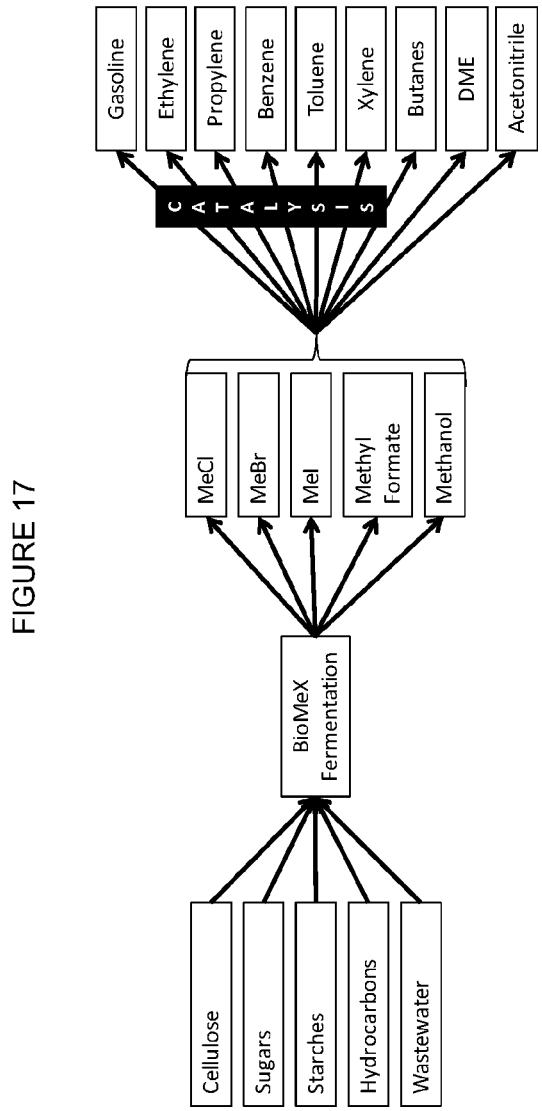
FIG. 17 shows exemplary products that can be made using organisms described herein.

Methyl halides may be used directly, or converted into a variety of important industrial chemicals. See FIG. 17, which is a non-comprehensive illustration of products. For example methyl chloride currently has a vast market as an industrial intermediate in the production of silicone polymers, quaternary ammonium surfactants and detergents. Methyl iodide is currently registered with the EPA as a soil fumigant replacing methyl bromide. Its major applications are in high value crops such as strawberries, peppers and cut flowers.

The conversion of compounds with just one carbon atom per molecule (like the methyl halides or methanol) into more complex chemicals has been studied for many years, and in some cases has been industrialized on a vast scale. The catalytic methods for the conversion of methanol into industrial chemicals are well understood and thoroughly described. Methanol has been converted into gasoline (a plant generating 570,000 tons per year of gasoline per day in a process known as methanol to gasoline (MTG) in New Zealand has been running since 1986). Similarly methanol to aromatics (MTX, producing BTX (butane, toluene and xylene)), methanol to olfefins (MTO, producing ethylene and propylene), methanol to the diesel fuel dimethyl ether (DME), and other similar processes are very well understood at large scale. The high upfront energy input to produce methanol (via syngas) from methane, and the relatively high temperatures required to convert it to products have limited some of these applications of methanol. Methyl formate could also be an input into these catalytic processes. The MTG product is put directly into the distribution chain for gasoline without any special accommodation.

Historically, methyl bromide has been less studied than methyl chloride as a feedstock for catalytic production of important chemicals. Methyl bromide has some advantages because the carbon-bromine bond is weaker than the carbon-chlorine bond in methyl chloride or the carbon-oxygen bond in methanol, so conditions for the catalytic conversion of methyl bromide can be milder than for the other compounds. The conversion of methyl bromide to ethylene and propylene has also been demonstrated.

Methyl iodide has also been catalytically converted into a variety of downstream products. The methods for converting methyl iodide have been studied mostly at bench scale, because inexpensive methods for the production of methyl iodide have been unavailable. Methyl iodide is even more reactive than methyl bromide, so milder catalytic conditions should suffice for its conversion. Olah and colleagues demonstrated the catalytic conversion of a combination of methanol and methyl iodide into a high octane gasoline with unusually high concentrations of the valuable fuel additive triptane. The special chemical properties of methyl iodide may prove attractive in a variety of applications where it is not used today.

The catalytic processes described above produce gasoline that is identical to that made from petroleum. As seen in the figure below, the distribution of products between C5 (pentanes) and 010 (decanes) is identical to that in gasoline produced from petroleum. This product will fit directly into the existing distribution infrastructure for gasoline, since it is chemically the same.

In many ways methyl halides are ideal chemical intermediates, and superior to many of the more traditional biochemical candidates. Their theoretical production limit from biomass is quite high. Unlike most other biochemical fermentation products, methyl halides are very easy to remove from the fermenter and inexpensive to purify. Methyl iodide should be easily swept out of the fermentation vessel on air that has been bubbled in to support fermentation and on the $CO_2$ produced by the fermenting organisms. Methyl chloride and methyl bromide are gases at fermentation temperatures, and methyl iodide is very near its boiling point. This continuous product removal prevents methyl halides from inhibiting the growth of the recombinant yeast, although we have found yeast in our laboratories to be surprisingly indifferent to relatively high concentrations of methyl iodide.

In these catalytic operations, the halide may be recycled in the plant and returned to the fermentation.

Engineered yeast's single carbon metabolic pathway may be diverted to make relatively large amounts of methyl formate. Methyl formate has been shown to be easily converted by catalytic or stoichiometric processes into a variety of downstream chemicals including methanol, ethylene, propylene, aromatics, and so on. Some catalysts are well optimized to convert oxygenated substrates such as methyl formate.

Methanol is another high value industrial chemical that can be produced directly by fermentation using our technology. Examples of this conversion have been demonstrated in recombinant organisms. Methanol can be converted to DME, an unusually clean diesel fuel.

We have designed a symbiotic relationship between its engineered yeast and a cellulose-degrading microorganism known as *A. fermentans*. *A. fermentans* was initially isolated from a landfill in France and was explored as a possible converter of cellulose into more useful chemicals. These efforts were frustrated by the bacterium's inability to grow in the presence of its own useful products, ethanol and acetate. We have demonstrated that *A. fermentans* in co-culture with engineered methyl iodide producing yeast grows well, since the yeast eats the ethanol and acetate, preventing their inhibition of *A. fermentans*. Interestingly, the co-culture of the yeast and the bacterium converges on a steady state mixed population of both organisms since each requires the other to thrive in the medium: yeast cannot eat cellulose, and without the yeast the accumulated ethanol stops the bacterium from growing. Optimal growth conditions for both yeast and *A. fermentans* are similar. The optimal growth temperature of both organisms is 30° C. and they share similar doubling times.

Microbes with the capability of metabolizing hydrocarbons may be engineered to include MHT pathways. An engineered organism capable of eating hydrocarbons and converting them into a halogenated hydrocarbons could have important implications. The low energy input liquefaction of tar sands and oil shales would render economically feasible the exploitation of important resources in North America and globally. The conversion of methane from natural gas into a methyl halide is energetically more challenging than the conversion of higher alkanes, but would also have important economic significance. An extremophilic organism engineered to incorporate an MHT pathway could also be useful in microbially enhanced oil recovery.

One application of our technology is the direct fermentation of biomass into industrial chemicals such as ethylene. Biosynthetic enzymes that produce ethylene are well known in nature, most prominently in ethylene's role as a plant hormone. The ethylene pathway involves much of the same single carbon metabolism required for methyl iodide fermentation, and thus would benefit from research synergy. The direct production of ethylene by fermentation could have major cost advantages over alternative routes.

11. Examples

The following examples are for illustrative purposes only and are not intended to be limiting.

Example 1

Expressing *Batis Maritima* MHT cDNA in *E. coli*

*Batis Maritima* MHT cDNA (Genbank Acc. No. AF109128 or AF084829) was artificially synthesized and cloned into an expression vector pTRC99a.

The resulting *E. coli*t (strain DH10B) comprising the expression construct encoding *Batis maritima* MHT under the control of an IPTG inducible promoter is referred to as the "*E. coli*-MHT$_{Batis}$" strain.

Example 2

Measuring Methyl Halide Production

Methyl halide production can be measured by gas chromatography. In the experiments described below an Agilent gas chromatography/mass spectrometry (GC/MS) system was used. Most often the "AIR.U" tune file, uses an ionization voltage of 1341. In some experiments an ionization voltage of about 1250 was used. A solvent delay of 0 was set and the scan parameters set to 15-100 MW. The injection port and column were preset to 50° C. The sample to be tested was mixed by shaking for a few seconds. 100 μL of the headspace gas was extracted with a gas-tight syringe. The sample gas was manually injected into the GCMS injection port. The GCMS program was started with the following settings: 1:00 at 50° C.; a ramp of 10° C. per min to 70° C. (the sample typically came off at ~52° C.); 1:00 at 70° C. The column was then cleaned (ramp to 240° C. for 2 minutes). The sample peak was identified by extracting the GC peak corresponding to 50MW (−0.3, +0.7). This peak was integrated to produce the "GC 50MW" data.

Example 3

Methyl Halide Production by Recombinant *E. Coli* Expressing *Batis maritima* Methyl Halide Transferase

*E. coli* (strains DH10B, BL21, or MC1061) and *Salmonella* (SL 1344) was transformed with a plasmid encoding a codon-optimized methyl chloride transferase gene MCT from *Batis Maritima* as described in Example 1. 10 mL of LB media with 1 mM IPTG was inoculated with a single colony of plated cells in a 16 mL culture tube. The tube was then sealed with parafilm and aluminum foil cinched with a rubber band. The cultures were incubated at 37° C. while shaking for 4-22 hours and methyl halide production measured. Each of the strains produced methylchloride.

In addition, the results were found to be highly reproducible. Repeat tests using 5 different clones of one *Batis maritima* MHT enzyme in *E. coli* (strain DH10B) resulted in methyl chloride production in each with a standard deviation of about 12% of the average methyl halide production.

Example 4

Production of Methyl Halide Follows an Induction Curve Seen with other IPTG-inducible Constructs

Figure 2:
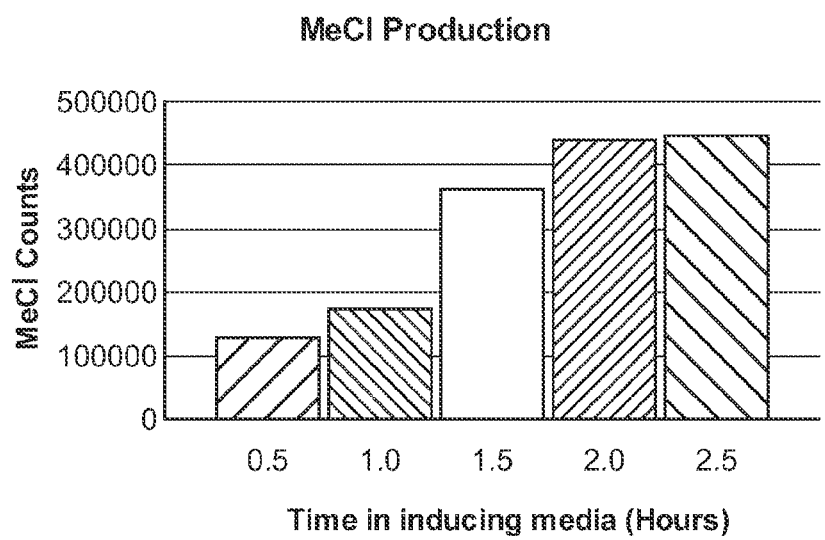
FIG. 2: Time-course of methyl halide production from bacteria containing a recombinant MHT gene expressed from an IPTG-inducible promoter, after addition of IPTG to the medium.

*E. coli* (strain DH10B) transformed with a plasmid encoding a codon-optimized methyl chloride transferase gene MCT from *Batis Maritima* as described in Example 1 was incubated in the presence of inducer (IPTG). As shown in FIG. 1, increasing IPTG levels resulted in increased methylchloride production As shown in FIG. 2, methyl halide production increased linearly with time in the inducing media up to about 1 to 2.5 hours after induction.

Figure 3:
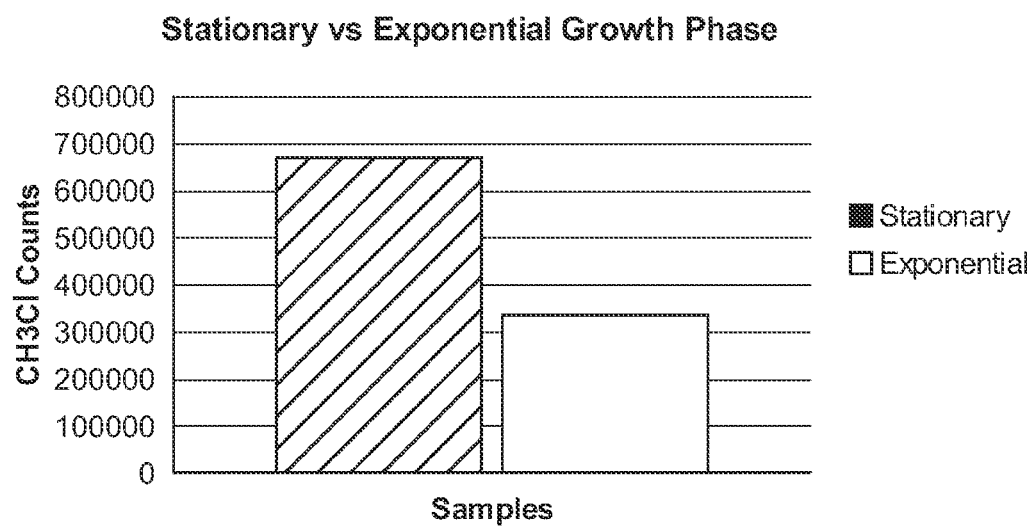
FIG. 3: Effect of bacterial growth phase on methyl halide production.

As shown in FIG. 3, cells at stationary phase produced more methyl halide than cells in growth phase. Artificially doubling the density of the culture did not increase production of methylhalide if the concentration of nutrients was not increased.

Methyl halide production was compared between aerobic and anaerobic culture conditions. Aerobic conditions resulted in higher levels of methyl halide cultures.

Example 5

Effect of Salt Concentration in the Cultivation Medium

Figure 4:
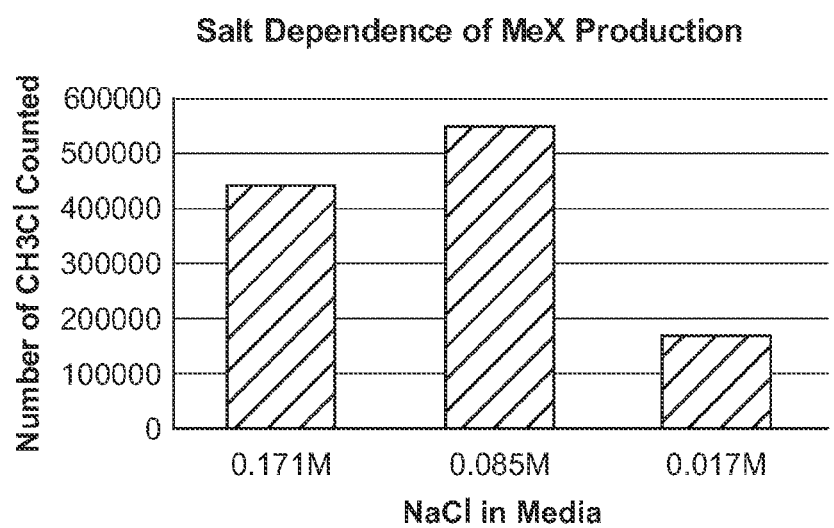
FIG. 4: Effect of halide salt concentration in the cultivation medium on methyl halide production.

*E. coli*-MHT$_{Batis}$ cells were grown in modified Luria-Bertani (LB) media in which the NaCl concentration was varied. Normal LB medium contains 5 g/L yeast extract, 10 g/L Tryptone, 10 g/L NaCl (0.171 M NaCl), at pH 7. Methyl chloride production in LB and modified LB containing 0.85 or 0.017 M NaCl was tested. Results are summarized in FIG. 4. 0.085 M NaCl produced the best results. However, normal LB was near optimal.

Modified Luria-Bertani media with bromine or iodine counter ions were at 0.16 M were made as shown in Table 3.

TABLE 3

|  | LB-NaBr | LB-NaI |
| --- | --- | --- |
| Yeast Extract | 5 g/L | 5 g/L |
| Tryptone | 10 g/L | 10 g/L |
| NaCl | 0.5 g/L | 0.5 g/L |
| NaBr | 16.7 g/L | 0 |
| NaI | 0 | 24.4 g/L |

Example 6

Effect of Different Halides

To compare methyl halide production using different salts halides, a standardized assay was devised. 20 mL of LB was inoculated with a single colony of plated cells, and was incubated at 37° C. while shaking for about 10-14 hours. The cells were pelleted and resuspended in LB. Equal aliquots were added to 10 mL LB, LB-Br or LB-I media with IPTG and incubated for 1.5 hours. 100 μL of headspace gas was taken and the amounts of methyl halide present measured as in Example 2.

Figure 5:
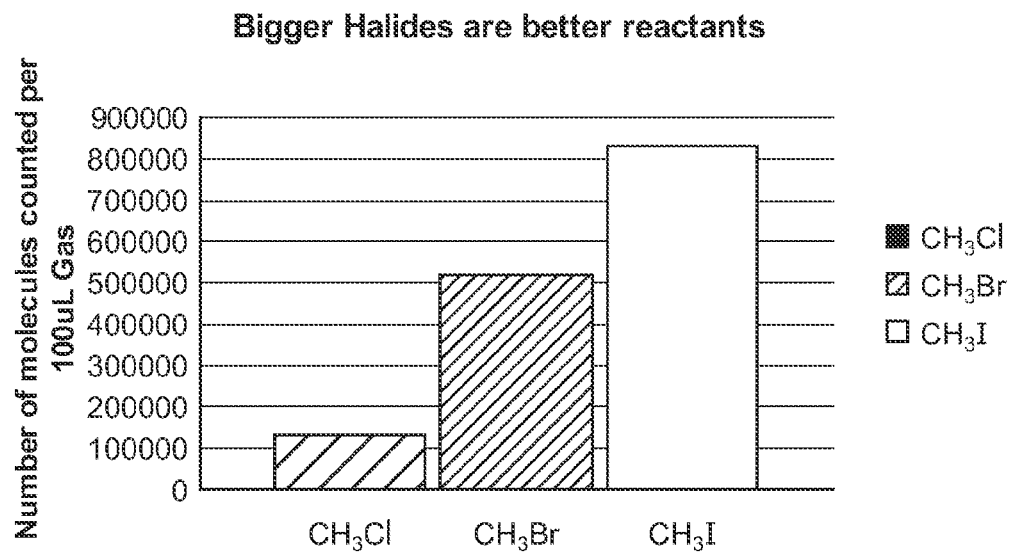
FIG. 5: Effect of different halides on methyl halide production.

As shown in FIG. 5 the higher molecular weight halides had higher methyl halide yield, with iodine ion giving the greatest yield, followed by bromine ion and chlorine ion. Using Henry's Law to calculate the total gas produced (dissolved in culture and present in the headspace), the production rate of methyl iodide was calculated to be about 40 (specifically, 43) mg/L per day.

Example 7

Figure 6:
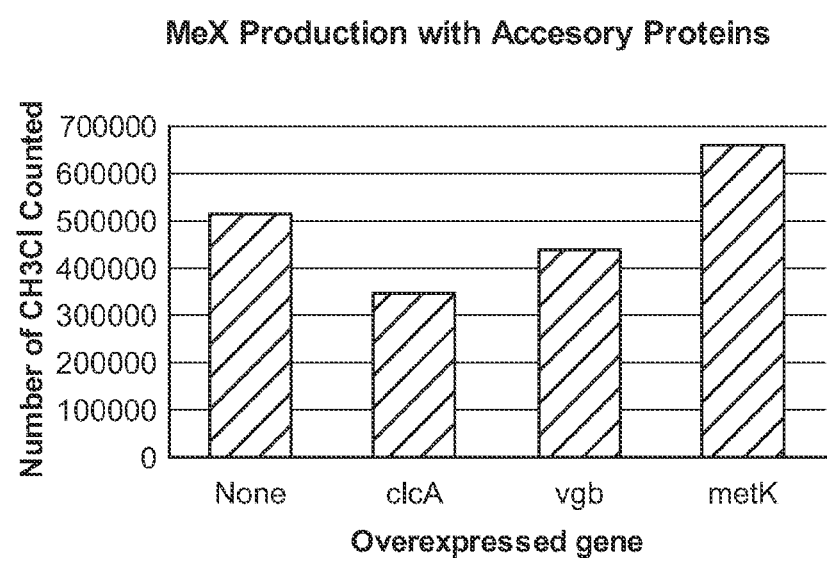
FIG. 6: Methyl halide production from bacteria overexpressing genes other than MHTs, e.g., metK.

Methyl Halide Production in *E. Coli* Cells Expressing Heterologous MHT and Overexpressing *E. Coli* metK The effect on methyl halide production by over-expression of certain accessory proteins was tested. The *E. coli*-MHT$_{Batis}$ strain was transformed with plasmids encoding *E. coli* metK, *E. coli* clcA, or *E. coli* vgb genes. Cells were cultured and methyl chloride production was measured. As shown in FIG. 6, overexpression of metK improved yield of methyl chloride. Under the conditions used, the expression of vgb and clcA caused general toxicity.

Example 8

Effect of Heterologous MHT Expression in *E. coli*

Nineteen methyl halide transferase genes from various organisms were codon-optimized and introduced into *E. Coli*. Production of methyl bromide and methyl iodide was determined for each. As shown in Table 5, the genes were from *Batis maritime, Burkholderia phymatum* STM815, *Synechococcus elongatus* PCC 6301, *Brassica raga* subsp. *chinensis; Brassica oleracea* TM1, *Brassica oleracea* TM2; *Arabidopsis thaliana* TM1; *Arabidopsis thaliana* TM2; *Leptospirillum* sp. Group II UBA; *Cryptococcus neoformans* var. *neoformans* JEC21; *Oryza sativa* (japonica cultivar-group); *Ostreococcus tauri; Dechloromonas aromatica* RCB; *Coprinopsis cinerea okayama; Robiginitalea bofirmata* HTCC2501; *Maricaulis maris* MCS10; *Flavobacteria bacterium* BBFL7; *Vitis vinifera* and; *halorhodospira halophila* SL1. The MHT sequences are shown in Table 4. Table 5 shows the level of amino acid identity with the *Batis maritima* protein.

TABLE 4

*BATIS MARITIMA*
MSTVANIAPVFTGDCKTIPTPEECATFLYKVVNSGGWEKCWV

EEVIPWDLGVPTPLVLHLVKNNALPNGKGLVPGCGGGYDVVA

MANPERFMVGLDISENALKKARETFSTMPNSSCFSFVKEDVF

TWRPEQPFDFIFDYVFFCAIDPKMRPAWGKAMYELLKPDGEL

ITLMYPITNHEGGPPFSVSESEYEKVLVPLGFKQLSLEDYSDLA

VEPRKGKEKLARWKKMNN (SEQ ID NO: 3)

*BURKHOLDERIA PHYMATUM* STM815
(29% IDENTICAL TO BATIS)
MSDKRPSVPPSAPDFENRDPNAPGFWDERFGRGFTPWDQAGV

PPAFKAFVERHSPVPVLIPGCGSAYEARWLAEKGWTVRAIDFA

PNAVEAARAQLGSHASLVHEADFFTYRPPFDPGWIYERAFLCA

TABLE 4-continued

LPPARRSDWVARMAQLLSPGGLLAGFFFIGATEKGPPFGI

ERAELDALMSPDFTLVEDEPVDDSIAVFAGRERWL

TWRRRGAARG (SEQ ID NO: 4)

*SYNECHOCOCCUS ELONGATUS* PCC 6301
MTNAVNQAQFWEQRYQEGSDRWDLGQAAPVWRSLLAGTNAPA

PGRIAVLGCGRGHDARLFAEQGFEVVGFDFAPSAIAAAQALAQG

TTAQFLQRDIFALPQEFAGQFDTVLEHTCFCAIDPDRRAEYVEVV

RQILKPKGCLLGLFWCHDRPSGPPYGCSLTELRDRFA

QGWQEEQLESVTESVEGRRGEEYLGRWRRLD (SEQ ID NO: 5)

*BRASSICA RAPA SUBSP. CHINENSIS*
MAEVQQNSAHINGENIIPPEDVAKFLPKTVEEGGWEKCWEDG

VTPWDQGRATPLVVHLVESSSLPLGRALVPGCGGGHDVVAMA

SPERYVVGLDISESALEKAAETYGSSPKAKYFTFVKEDFFTWRP

NELFDLIFDYVVFCAIEPETRPAWAKAMYELLKPDGELIT

LMYPITDHDGGPPYKVAFSTYEDVLVPVGFKAVSIEENPYSIA

TRKGKEKLARWKKIN (SEQ ID NO: 6)

*BRASSICA OLERACEA* (TM1)
MAEEQQKAGHSNGENIIPPEEVAKFLPETVEEGGWEKCW

EDGITPWDQGRATPLVVHLVDSSSLPLGRALVPGCGGGHD

VVAMASPERFVVGLDISESALEKAAETYGSSPKAKYFTFVK

EDFFTWRPNELFDLIFDYVVFCAIEPEMRPAWAKSMYELL

KPDGELITLMYPITDHDGGPPYKVAVSTYEDVLVPVGFKAV

SIEENPYSIATRKGKEKLGRWKKIN (SEQ ID NO: 7)

*BRASSICA OLERACEA* (TM2)
MAEVQQNSGNSNGENIIPPEDVAKFLPKTVDEGGWEKCW

EDGVTPWDQGRATPLVVHLVESSSLPLGRGLVPGCGGGH

DVVAMASPERYVVGLDISESALEKAAETYGSSPKAKYFTFV

KEDFFTWRPNELFDLIFDYVVFCAIEPETRPAWAKAMYELL

KPDGELITLMYPITDHDGGPPYKVAVSTYEDVLVPVGFKAV

SIEENPYSIATRKGKEKLARWKKIN (SEQ ID NO: 8)

*ARABIDOPSIS THALIANA* TM1
MAEEQQNSSYSIGGNILPTPEEAATFQPQVVAEGGWDKCW

EDGVTPWDQGRATPLILHLLDSSALPLGRTLVPGCGGGHDV

VAMASPERFVVGLDISDKALNKANETYGSSPKAEYFSFVKED

VFTWRPNELFDLIFDYVFFCAIEPEMRPAWGKSMHELLKP

DGELITLMYPMTDHEGGAPYKVALSSYEDVLVPVGFKAVS

VEENPDSIPTRKGKEKLARWKKIN (SEQ ID NO: 9)

*ARABIDOPSIS THALIANA* TM2
MAEEQQNSDQSNGGNVIPTPEEVATFLHKTVEEGGWEKCW

EEEITPWDQGRATPLIVHLVDTSSLPLGRALVPGCGGGHDVV

AMASPERFVVGLDISESALAKANETYGSSPKAEYFSFVKEDV

FTWRPTELFDLIFDYVFFCAIEPEMRPAWAKSMYELLKPDGELI

TLMYPITDHVGGPPYKVDVSTFEEVLVPIGFKAVSVEENPHA

TABLE 4-continued

IPTRQREAGKVEEDQLIPKKEILLFGKSVICVIYKE
(SEQ ID NO: 10)

*LEPTOSPIRILLUM* SP. GROUP II UBA
MPDKIFWNQRYLDKNTGWDLGQPAPPFVRLVEKGEFGPPGR

VLIPGAGRSYEGIFLASRGYDVTCVDFAPQAVREAREAARQAG

VKLTVVEEDFFRLDPRTIGVFDYLVEHTCFCAIDPPMRQAYVDQ

SHALLAPGGLLIGLFYAHGREGGPPWTTTEEEVRGLFGKK

FDLLSLGLTDWSVDSRKGEELLGLRRKNDRIE (SEQ ID NO: 11)

*CRYPTOCOCCUS NEOFORMANS* VAR. *NEOFORMANS* JEC21
(HYPOTHETICAL PROTEIN)
MAQASGDDNAWEERWAQGRTAFDQSAAHPVFVKFLKSDIAR

ELGVPKSGKALVPGCGRGYDVHLLASTGLDAIGLDLAPTGVEA

ARRWIGSQPSTSGKADILVQDFFTYDPLEKFDLIYDYTFLCALPP

SLRQEWARQTTHLANIAADTNPILITLMYPLPPSAKSGGPPFALS

EEIYQELLKEQGWKMVWSEDIEEPTRMVGAPGGEKLAVW

KRI (SEQ ID NO: 12)

*ORYZA SATIVA* (JAPONICA CULTIVAR-GROUP)
MASAIVDVAGGGRQQALDGSNPAVARLRQLIGGGQESSDGWSRC

WEEGVTPWDLGQRTPAVVELVHSGTLPAGDATTVLVPGCGAGYD

VVALSGPGRFVVGLDICDTAIQKAKQLSAAAAAAADGGDGSSSF

FAFVADDFFTWEPPEPFHLIFDYTFFCALHPSMRPAWAKRMADL

LRPDGELITLMYLAEGQEAGPPFNTTVLDYKEVLNPLGLVITS

IEDNEVAVEPRKGMEKIARWKRMTKSD (SEQ ID NO: 13)

*OSTREOCOCCUS TAURI* (UNNAMED PROTEIN PRODUCT)
MTTSSAPTRHTSMRVALAAPATVTRRLGTYKRVFDRRAMSTRAI

DGAVTSNAGDFARQDGSTDWEGMWSRGITKGAAFDCSRTEPAFQ

NALDAKEIAIGSGRALVPGCGRGYALASLARAGFGDVVGLEISE

TAKEACEEQLKAESIPETARVEVVVADFFAYDPKEAFDAAYDCT

FLCAIDPRRREEWARKHASLIKPGGTLVCLVFPVGDFEGGPPYA

LTPEIVRELLAPAGFEEIELRETPAEMYARGRLEYLFTWRRRS (SEQ ID NO: 14)

*DECHLOROMONAS AROMATICA* RCB
MSETIKPPEQRPEHPDFWCKRFGEGVTPWDAGKVPMAFVDFVGA

QTTPLNSLIPGCGSAWEAAHLAELGWPVTALDFSPLAIEKAREV

LGDSPVKLVCADFFTFAPRQPLDLIYERAFLCALPRKLWADWGK

QVAELLPSGARLAGFFFLCDQPKGPPFGILPAQLDELLRPNFEL

IEDQPVGDSVPVFAGRERWQVWRRR (SEQ ID NO: 15)

*COPRINOPSIS CINEREA OKAYAMA* (HYPOTHETICAL PROTEIN)
MADPNLAPEIRAKMQEIFKPDDRHSWDLLWKENITPWDAGDAQP

SLIELIEESGLDFARKGRALVPGCGTGYDAVYLASALGLQTIGM

DISESAVEAANRYRDSSGVQGADRAIFQKADFFTYKVPDEERF

DLIMDHTFFCAIHPSLRPEWGQRMSELIKPGGYLITICFPMIP

KVETGPPYYLRPEHYDEVLKETFEKVYDKVPTKSSENHKDKE

RMLVWKKK (SEQ ID NO: 16)

*ROBIGINITALEA BIFORMATA* HTCC2501
MTDLDRDFWEDRYRAGTDRWDLGGPSPPLTAYIDGLTDQELRI

LVPGAGRGYEAEYLYRAGFENLTIVDLARRPLDDLRRRLPELP

AAALQQTDFFSFRGGPFDLILEHTFFCALPPARRPDYVQAMHR

LLVPGGRLAGLFFDFPLTEDGPPFGGSETEYRNRFSSLF

HIRKLERARNSIPPRAGTELFFIFEKK (SEQ ID NO: 17)

*MARICAULIS MARIS* MCS10
MTHDENRSAFDWEARFIDGNTPWERGALHPAFEAWQHQSAFA

AGDRALIPGCGRSPELLALAQAGLAVTGADLSGTAMAWQRKL

FADAGQQVELITGDVFDWQPQQALDLVYEQTFLCAIHPRLRT

RYEEALARWLKPGGRLYALFMQKPERGGPPFDCALDAMRALF

PAERWTWPAEADIQPWPHPQLNGKAELGAVLIRR (SEQ ID NO: 18)

*FLAVOBACTERIA BACTERIUM* BBFL7
MPLNKQYWEDRYKNNSTGWDLGIISTPIKEYVNQLENKNSKIL

IPGAGNAHEATYLVKNGFKNIFILDIALSPLKFAKQRSKLPE

EHLIQQDFFDHKGSYDLIIEQTFFCALEPRFRESYVKKIHML

LRDQGCLIGVLFNFENNLSSPPFGGSINEYLNLFEPYFEIV

TMEPCNNSVIERQGKEIFIKLKKKK (SEQ ID NO: 19)

*VITIS VINIFERA*
MASPDNTKPKARSSESVTGQRRGRRPSDRHWPCVGEESGSF

YNTIADGERQYQHRIELRASKNKPSSWEEKWQQGLTPWDLG

KATPIIEHLHQAGALPNGRTLIPGCGRGYDVVAIACPERFV

VGLDISDSAIKKAKESSSSSWNASHFIFLKADFFTWNPTEL

FDLIIDYTFFCAIEPDMRPAWASRMQQLLKPDGELLTLMFP

ISDHTGGPPYKVSIADYEKVLHPMRFKAVSIVDNEMAIGSR

KKKYPLKPDLSLFGFVDRPKRAYEARSEEFRISDWVCGWMG

LCVPSGRISGGVCGLLSGRSLTWAKNLGVSTTQLRMSNNG

SSIESNPKVQKLNQIIGSDSAGGWEKSWQQGHTPWDLGKP

TPIIQHLHQTGTLPSGKTLVPGCGCGYDVVTIACPERFVV

GLDISDSAIKKAKEISDHAGGPPYKVSVADYEEVLHPMGFK

AVSIVDNKMAIGPRKGREKLGRWKRTPSKSLL (SEQ ID NO: 20)

*HALORHODOSPIRA HALOPHILA* SL1
MSGDPDPRRAPWEARWREGRTGWDRGGVSPTLEAWLSAGV

IPGRRVLVPGAGRGYEVEALARRGYKVTAVDIAAEACQQL

RDGLDAAGVEARVVQADLLAWQPDTPFDAVYEQTCLCALD

PADWPAYEQRLYGWLRPGGVLLALFMQTGASGGPPFHCAL

PEMATLFDSERWQWPAEPPRQWPHPSGRWEEAV

RLLRR (SEQ ID NO: 21)

TABLE 5

| Abbreviation | Name | % aa identity |
|---|---|---|
| Batis | *Batis maritima* | 100 |
| BP | *Burkholderia phymatum* STM815 | 29 |
| BR | *Brassica rapa* subsp. *chinensis* | 65 |
| SE | *Synechococcus elongatus* PCC 6301 | 30 |
| BO-1 | *Brassica oleracea* TM1 | 65 |
| BO-2 | *Brassica oleracea* TM2 | 64 |
| LS | *Leptospirillum* sp. Group II UBA | 34 |
| AT-1 | *Arabidopsis thaliana* TM1 | 69 |
| CN | *Cryptococcus neoformans* var. *neoformans* JEC21 | 33 |
| OS | *Oryza sativa* (*japonica* cultivar-group) | 58 |
| OT | *Ostreococcus tauri* | 33 |
| DA | *Dechloromonas aromatica* RCB | 30 |
| CC | *Coprinopsis cinerea okayama* | 36 |
| RB | *Robiginitalea bofirmata* HTCC2501 | 32 |
| MM | *Maricaulis maris* MCS10 | 30 |
| AT-2 | *Arabidopsis thaliana* TM2 | 67 |
| FB | *Flavobacteria bacterium* BBFL7 | 28 |
| VV | *Vitis vinifera* | 59 |
| HH | *Halorhodospira halophila* SL1 | 28 |

Cells were cultured as follows:

For each strain a single colony was picked and grown overnight (10-14 hrs) in 20 mL of LB miller in a 30 mL glass test tube with aeration (a loose cap) at 37 C and 250 rpm shaking. The culture was spun down in a swinging bucket centrifuge for 5 min @ 3000×g. The cells were resuspended in 20mL of appropriate media (10 g/L Tryptone, 5 g/L Yeast Extract, 165 mM NaX [where X=Cl, Br, I]) containing 100 uM IPTG inducer. The cells were sealed with rubber stoppers and parafilm and grown at 37 C with 250 rpm shaking for 1.5 hours. Cultures were taken to the GC/MS and 100 uL of headspace gas was sampled and loaded onto the column. The method run was VOIGT.m. The number of counts for the appropriate mass (MeCl, MeBr, MeI) were reported. Cells were always grown in the presence of 30 ug/mL chloramphenicol.

Figure 7:
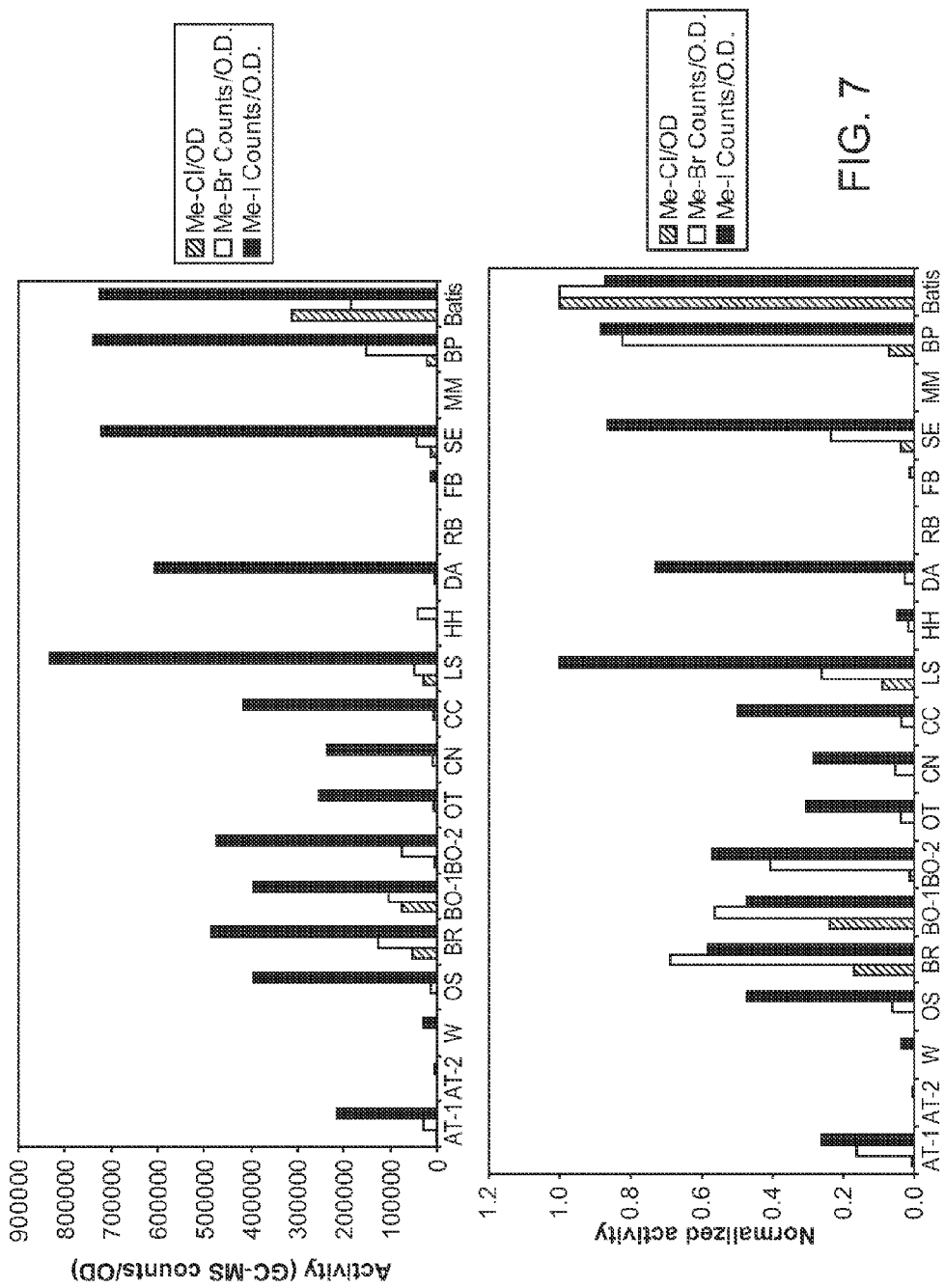
FIG. 7: Methyl halide production achieved by bacteria expressing various heterologous MHTs from various organisms.
Figure 8:
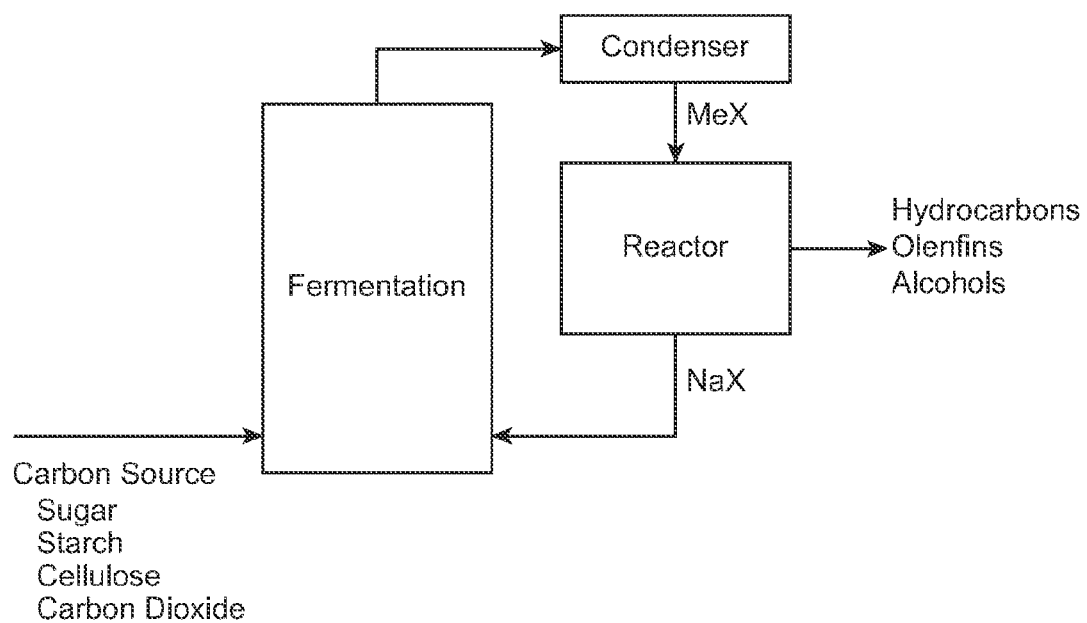
FIG. 8: A schematic of a bioreactor system for production of organic compounds.

Methyl halide production was measured as described in the previous Examples. The results are summarized in FIG. 7. The *B. maritima* transferase was found to give the best methyl bromide production, while the *B. phymatum* transferase gave the best methyl bromide production in bacteria. *C. neoformans* JEC21 gave the best methyl bromide and methyl iodide production. *Leptospirillum* gave the best methyl iodide production. Enzymes from *O. sativa, O. tauri; D. aromatica*, and *C. cinerea* showed significant specificity for methyl iodide production. *B. maritima, Brassica rapa* subsp. *chinensis* and *B. oleracea* show significant specificity for methyl bromide production. The enzymes RB, MM, AT-2, FB, VV and HH in Table 5 showed insignificant activity.

Example 9A

Identifying New Methyl Halide Transferases

Proteins with MHT activity (including proteins not previously known to have this activity) were identified through a BLAST protein-protein search for proteins having sequence identity with known MHTs such as from the MHT from *Batis maritima*. A cutoff of ~28% identity was assigned based on a 29% identity between *Batis maritima* and *Burkholderia phymatum* MHT sequences. Each identified sequence was BLASTed back to the database and a new list was generated. This was repeated until no additional sequences were found. Table 6 sets forth the sequences (and corresponding GenBank accession numbers) that have been identified as having MHT activity, including proteins that were hitherto not recognized to have MHT activity. Many of the newly identified proteins are thiopurine s-methyltransferases.

TABLE 6

```
> BATIS SEQ (Batas matitima)
MSTVANIAPVFTGDCKTIPTPEECATFLYKVVNSGGWEKCWVEEVIPWD

LGVPTPLVLHLVKNNALPNGKGLVPGCGGGYDVVAMANPERFMVGLDIS

ENALKKARETFSTMPNSSCFSFVKEDVFTWRPEQPFDFIFDYVFFCAID

PKMRPAWGKAMYELLKPDGELITLMYPITN

HEGGPPFSVSESEYEKVLVPLGFKQLSLEDYSDLAVEPRKGKEKLARW

KKMNN (SEQ ID NO: 3)

> GI|30689545|REF|
NP_850403.1| THIOL METHYLTRANSFERASE,
PUTATIVE [ARABIDOPSIS THALIANA]
MENAGKATSLQSSRDLFHRLMSENSSGGWEKSWEAGATPWDLGKPTPV

IAHLVETGSLPNGRALVPGCGTGYDVVAMASPDRHVVGLDISKTAVERS

TKKFSTLPNAKYFSFLSEDFFTWEPAEKFDLIFDYTFFCAFEPGVRPLW

AQRMEKLLKPGGELITLMFPIDERSGGPPYEVSVSEYEKVLIPLGFEAI

SIVDNELAVGPRKGMEKLGRWKKSSTFHSTL (SEQ ID NO: 22)

> GI|157353829|EMB|
CAO46361.1| UNNAMED PROTEIN PRODUCT
[VITIS VINIFERA]
MANDSTSIESNSELQKISQVIGSGFNGSWEEKWQQGLTPWDLGKATPII

EHLHQAGALPNGRTLIPGCGRGYDVVAIACPERFVVGLDISDSAIKKAK

ESSSSSWNASHFIFLKADFFTWNPTELFDLIIDYTFFCAIEPDMRPAWA

SRMQQLLKPDGELLTLMFPISDHTGGPPYKVSIADYEKVLHPMRFKAVS

IVDNEMAIGSRKGREKLGRWKRTDEPLL (SEQ ID NO: 23)

>GI|157353828|EMB|
CAO46360.1| UNNAMED PROTEIN PRODUCT
[VITIS VINIFERA]
MGLCVPSGRISGGVCGLLSGRSLTWAKNLGVSTTQLRMSNNGSSIESNP

KVQKLNQIIGSDSAGGWEKSWQQGHTPWDLGKPTPIIQHLHQTGTLPSG

KTLVPGCGCGYDVVTIACPERFVVGLDISDSAIKKAKELSSSLWNANHF

TFLKEDFFTWNPTELFDLIFDYTFFCAIEPDMRSVWAKRMRHLLKPDGE

LLTLMFPISDHAGGPPYKVSVADYEEVLHPMGFKAVSIVDNKMAIGPRK

GREKLGRWKRTPSKSLL (SEQ ID NO: 24)

>GI|125554131|GB|EAY99736.1|
 HYPOTHETICAL PROTEIN
OSI_020969 [ORYZA SATIVA
(INDICA CULTIVAR-GROUP)]
MDRALPLALSVSLWWLLVGDLGGRWTLEDDGGGGGVSRFGSWYRMCGW

WWVWADWIIELGASSWGNLFGLVLKRRKNEAVERDSSDGWEKSWEAAV

TPWDLGKPTPIIEHLVKSGTLPKGRALGYDVVALASPERFVVGLGISS

TAVEKAKQWSSSLPNADCFTFLADDFFKWKPSEQFDLIFDYTFFCALD

PSLRLAWAETVSGLLKPHGELITLIYLVTEESIYSFVYFSIEDVMVLI

ISYCAERISYYRSVTKKEDHHSIIQSPILLRCPFRNHSYQKVLEPLGF

KAILMEDNELAIKPRKAISAFRTSEQPSLAAQDVT

E (SEQ ID NO: 25)

>GI|125546406|GB|EAY92545.1|
HYPOTHETICAL PROTEIN OSI_013778 [ORYZA SATIVA
```

TABLE 6-continued (INDICA CULTIVAR-GROUP)]
MASAIVDVAGGGRQQALDGSNPAVARLRQLIGGGQESSDGWSRCWEEG

VTPWDLGQPTPAVVELVHSGTLPAGDATTVLVPGCGAGYDVVALSGPG

RFVVGLDICDTAIQKAKQLSAAAAAAADGGDGSSSFFAFVADDFFTWE

PPEPFHLIFDYTFFCALHPSMRPAWAKRMADLLRPDGELITLMYLAEG

QEAGPPENTTVLDYKEVLNPLGLVITSIEDNEVAVEPRKGMEKI

ARWKRMTKSD (SEQ ID NO: 26)

>GI|108712049|GB|ABF99844.1|
THIOPURINE S-METHYLTRANSFERASE
FAMILY PROTEIN, EXPRESSED [ORYZA SATIVA
(JAPONICA CULTIVAR-
GROUP)]
MASAIVDVAGGGRQQALDGSNPAVARLRQLIGGGQESSDGWSRCWEEG

VTPWDLGQRTPAVVELVHSGTLPAGDATTVLVPGCGAGYDVVALSGPG

RFVVGLDICDTAIQKAKQLSAAAAAAADGGDGSSSFFAEVADDFFTWE

PPEPFHLIFDYTFFCALHPSMRPAWAKRMADLLRPDGELITLMYLVIN

RRYQHV (SEQ ID NO: 27)

>GI|115466488|REF|
NP_001056843.1|OS06G0153900 [ORYZA
SATIVA (JAPONICA CULTIVAR-GROUP)]
MSSSAARVGGGGGRDPSNNPAVGRLRELVQRGDAADGWEKSWEAAVTP

WDLGKPTPIIEHLVKSGTLPKGRALVPGCGTGYDVVALASPERFVVGL

DISSTAVEKAKQWSSSLPNADCFTFLADDFFKWKPSEQFDLIFDYTFF

CALDPSLRLAWAETVSGLLKPHGELITLIYLISDQEGGPPFNNTVTDY

QKVLEPLGFKAILMEDNELAIKPRKGQEKLGRWKRFVPGSSL (SEQ ID NO: 28)

> COPRINOPSIS CINEREA OKAYAMA
(HYPOTHETICAL PROTEIN)
MADPNLAPEIRAKMQEIFKPDDRHSWDLLWKENITP

WDAGDAQPSLIELIEESGLDFAR

KGRALVPGCGTGYDAVYLASALGLQTIGMDISESAVEAANRYRDSSGV

QGADRAIFQKADFFTYKVPDEERFDLIMDHTFFCAIHPSLRPEWGQRM

SELIKPGGYLITICFPMIPKVETGPPYYLRPEHYDEVLKETFEKVYDKV

PTKSSENHKDKERMLVWKKK (SEQ ID NO: 16)

>GI|71024813|REF|
XP_762636.1|HYPOTHETICAL PROTEIN
UM06489.1 [USTILAGO MAYDIS 521]
MTSSLSKDDQIQNLRRLFADSGVPNDPKAWDQAWIDSTTPWDANRPQPA

LVELLEGAHDADAKVPDVDGNLIPVSQAIPKGDGTAVVPGCGRGYDARV

FAERGLTSYGVDISSNAVAAANKWLGDQDLPTELDDKVNFAEADFFTLGT

SKSLVLELSKPGQATLAYDYTFLCAIPPSLRTTWAETYTRLLAKHGVLIA

LVFPIHGDRPGGPPFSISPQLVRELLGSQKNADGSAAWTELVELKPGPE

TRPDVERMMVWRRS (SEQ ID NO: 30)

>GI|145230089|REF|
XP_001389353.1|HYPOTHETICAL PROTEIN
AN01G09330 [ASPERGILLUS NIGER]
MTDQSTLTAAQQSVHNTLAKYPGEKYVDGWAEIWNANPSPPWDKGAPNPA

LEDTLMQRR

GTIGNALATDAEGNRYRKKALVPGCGRGVDVLLLASFGYDAYGLEYSGA

AVQACRQEEKESTTSAKYPVRDEEGDFFKDDWLEELGLGLNCFDLIYDY

TFFCALSPSMRPDWALRHTQLLAPSPHGNLICLEYPRHKDPSLPGPPFG

LSSEAYMEHLSHPGEQVSYDAQGRCRGDPLREPSDRGLERVAYWQPART

HEVGKDANGEVQDRVSIWRRR (SEQ ID NO: 31)

>GI|111069917|GB|
EAT91037.1|HYPOTHETICAL PROTEIN
SNOG_01388 [PHAEOSPHAERIA
NODORUM SN15]
MANPNQDRLRSHFAALDPSTHASGWDSLWAEGTFIPWDRGYANPALID

LLANPSSPPTSSDANPTPGAPKPNTIDGQGVQLPAPLEGGVRRKALVP

GCGKGYDVALLASWGYDTWGLEVSRHAADAAKEYLKDAGEGALEGEYK

IKDAKIGKGREECVVADFFDDAWLKDVGAGEFDVIYDNTFLCALPPLL

RPKWAARMAQLLARDGVLICLEFPTHKPASSGGPPWSLPPTVHQELLK

RPGEDISYDEGGVVVATDRAESENALVRVAHWTPKRTHNIAVINGVVR

DCVSVWRHKKQS (SEQ ID NO: 32)

>GI|119195301|REF|
XP_001248254.1|HYPOTHETICAL PROTEIN
CIMG_02025 [COCCIDIOIDES IMMITIS RS]
MANEILRSAPNLSDRFKNLDGRNQGEVWDDLWKESRTPWDRGSHNPAL

EDALVEKRGFFGAPVFEDEPLRRKKALVPGCGRGVDVFLLASFGYDAY

GLEYSKTAVDVCLKEMEKYGEGGKVPPRDEKVGSGKVMFLEGDFFKDD

WVKEAGVEDGAFDLIYDYTFFCALNPALRPQWALRHRQLLAPSPRGNL

ICLEFPTTKDPAALGPPFASTPAMYMEHLSHPGEDIPYDDKGHV

KSNPLQQPSDKGLERVAHWQPKRTHTVGMDDKGNVLDWVSIWRRRD (SEQ ID NO: 33)

>GI|145234849|REF|
XP_001390073.1|HYPOTHETICAL PROTEIN
AN03G01710 [ASPERGILLUS NIGER]
MSEAPNPPVQGRLISHFADRRAEDQGSGWSALWDSNESVLWDRGSPSI

ALVDVVEQQQDVFFPYTRDGRRKKALVPGCGRGYDPVMLALHGFDVYG

LDISATGVSEATKYATSEMQSPQDVKFIAGDFFSSEWESQALQDGDKF

DLIYDYTFLCALHPDLRRKWAERMSQLLHPGGLLVCLEFPMYKDTSLP

GPPWGLNGVHWDLLARGGDGITNITKEEEDEDSGIQLSGQFRRA

QYFRPIRSYPSGKGTDMLSIYVRR (SEQ ID NO: 34)

>GI|119499868|REF|
XP_001266691.1|THIOL METHYLTRANSFERASE,
PUTATIVE [NEOSARTORYA FISCHERI NRRL 181]
MSNDPRLLSSIPEFIARYKENVEGWAELWNKSEGKPLPFDRGFPNPA

LEDTLIEKRDIIGGPIGRDAQGNTYRKKALVPGCGRGVDVLLLASFGY

DAYGLEYSDTAVQVCKEEQAKNGDKYPVRDAEIGQGKITFVQGDFFKD

TWLEKLQLPRNSFDLIYDYTFFCALDPSMRPQWALRHTQLLADSPRGH

LICLEFPRHKDTSLQGPPWASTSEAYMAHLNHPGEEIPYDANRQ

CSIDPSKAPSPQGLERVAYWQPARTHEVGIVEGEVQDRVSIWRRPN (SEQ ID NO: 35)

>GI|70993254|REF|
XP_751474.1|THIOL METHYLTRANSFERASE,
PUTATIVE [ASPERGILLUS FUMIGATUS AF293]
MSNDPRLVSSIPEFIARYKENVEGWAELWDSEGKPLPFDRGFPNPA

TABLE 6-continued

LEDTLIEKRDIIGDPIGRDAQGNTYRKKALVPGCGRGVDVLLLASFGY

DAYGLEYSATAVKVCKEEQAKNGDKYPVRDAEIGQGKITYVQGDFFKD

TWWEKLQLPRNSFDLIYDTFFCALDPSMRPQWALRHTQLLADSPRGH

LICLEFPRHKDTSLQGPPWASTSEAYMAHLNHPGEEIPYDANRQ

CSIDPSKAPSPQGLERVAYWQPARTHEVGIVEGEVQDRVSIWRRPN (SEQ ID NO: 36)

>GI|46137187|REF|
XP_390285.1|HYPOTHETICAL PROTEIN
FG10109.1 [GIBBERELLA ZEAE PH-1]
MATENPLEDRISSVPFAEQGPKWDSCWKDALTPWDRGTASIALHDLLA

QRPDLVPPSQHQDHRGHPLRDATGAIQKKTALVPGCGRGHDVLLLSSW

GYDVWGLDYSAAAKEEAIKNQKQAESEGLYMPVDGLDKGKIHWITGNF

FAQDWSKGAGDDGKFDLIYDYTFLCALPPDARPKWAKRMTELLSHDGR

LICLEFPSTKPMSANGPPWGVSPELYEALLAAPGEEIAYNDDGT

VHEDPCSKPWADALHRLSLLKPTRTHKAGMSPEGAVMDFLSVWSR (SEQ ID NO: 37)

>GI|145228457|REF|
XP_001388537.1|HYPOTHETICAL PROTEIN
AN01G00930 [ASPERGILLUS NIGER]
MTTPTDNKFKDAQAYLAKHQGDSYLKGWDLLWDKGDYLPWDRGFPNPA

LEDTLVERAGTIGGPIGPDGKRRKVLVPGCGRGVDVLLFASFGYDAYG

LECSAAAVEACKKEEEKVNNIQYRVRDEKVGKGKITFVQGDFFDDAWL

KEIGVPRNGFDVIYDYTFFCALNPELRPKWALRHTELLAPFPAGNLIC

LESPRHRDPLAPGPPFASPSEAYMEHLSHPGEEISYNDKGLVDA

DPLREPSKAGLERVAYWQPERTHTVGKDKNGVIQDRVSIWRRRD (SEQ ID NO: 38)

>GI|121708664|REF|
XP_001272206.1|THIOL METHYLTRANSFERASE,
PUTATIVE [ASPERGILLUS CLAVATUS NRRL 1]
MSTPSLIPSGVHEVLAKYKDGNYVDGWAELWDKSKGDRLPWDR

GFPNPALEDTLIQKRAIIGGPLGQDAQGKTYRKKALVPGCGRG

VDVLLLASEGYDAYGLEYSATAVDVCQEEQAKNGDQYPVRDAE

IGQGKITFVQGDFFEDTWLEKLNLTRNCFDVIYDYTFFCALNP

SMRPQWALRHTQLLADSPRGHLICLEFPRHKDPSVQGPPWGSA

SEAYRAHLSHPGEEIPYDASRQCQFDSSKAPSAQGLERVAYWQ

PERTHEVGKNEKGEVQDRVSIWQRPPQSSL (SEQ ID NO: 39)

>GI|67539848|REF|
XP_663698.1|HYPOTHETICAL PROTEIN AN6094.2
[ASPERGILLUS NIDULANS FGSC A4]
MSSPSQQPIKGRLISHFENRPTSHPKAWSDLWDSGKSSLWDR

GMPSPALIDLLESYQDTLLHPFEIDIEDEEDSSDAGKTRKRKR

ALVPGCGRGYDVITFALHGFDACGLEVSTTAVSEARAFAKKEL

CSPQSGNFGRRFDRERARHIGVGKAQFLQGDFFTDTWIENEST

GLDQGRTENGKFDLVYDYTFLCALHPAQRTRWAERMADLLRPG

GLLVCLEFPMYKDPALPGPPWGVNGIHWELLAGGDTGQGKFTR

KAYVQPERTFEVGRGTDMISVYERK (SEQ ID NO: 40)

>GI|121529427|REF|
ZP_01662039.1|CONSERVED HYPOTHETICAL
PROTEIN [RALSTONIA PICKETTII 12J]
MAQPPVFQSRDAADPAFWDERFTREHTPWDAAGVPAAFRQFCE

AQPAPLSTLIPGCGNAYEAGWLAERGWPVTAIDFAPSAVASAR

AVLGPHADVVQLADFFRFSPPRPVHWIYERAFLCAMPRRLWPD

YAAQVAKLLPPRGLLAGFFAVVEGREAMPKGPPFETTQPELD

ALLSPAFERISDMPIAETDSIPVFAGRERWQVWRRRAD (SEQ ID NO: 41)

>GI|17545181|REF|
NP_518583.1|HYPOTHETICAL PROTEIN RSC0462
[RALSTONIA SOLANACEARUM GMI1000]
MAQPPVFTTRDAAAPAFWDERFSRDHMPWDAHGVPPAFRQFCE

AQPAPLSTLIPGCGSAYEAGWLAERGWPVAAIDFAPSAVASAQ

AVLGPHAGVVELADFFRFTPRQPVQWIYERAFLCAMPRRLWAD

YATQVARLLPPGGLLAGFFVVVDGRAAAPSGPPFEITAQEQEA

LLSPAFERIADALVPENESIPVFAGRERWQVWRRRAD (SEQ ID NO: 42)

>GI|83644186|REF|
YP_432621.1|SAM-DEPENDENT
METHYLTRANSFERASE [HAHELLA CHEJUENSIS KCTC 2396]
MDANFWHERWAENSIAFHQCEANPLLVAHFNRLDLAKGSRVFV

PLCGKTLDISWLLSQGHRVVGCELSEMAIEQFFKELGVTPAIS

EIVAGKRYSAENLDIIVGDFFDLTVETLGHVDATYDRAALVALP

KPMRDSYAKHLMALTNNAPQLMLCYQYDQTQMEGPPFSISAEE

VQHHYADSYALTALATVGVEGGLRELNEVSETVWLLESR (SEQ ID NO: 43)

> LEPTOSPIRILLUM SP. GROUP II UBA
MPDKIEWNQRYLDKNTGWDLGQPAPPFVRLVEKGEFGRPGRVLI

PGAGRSYEGIFLASRGYDVTCVDFAPQAVREAREAARQAGVKLT

VVEEDFFRLDPRTIGVFDYLVEHTCFCAIDPPMRQAYVDQSHAL

LAPGGLLIGLFYAHGREGGPPWTTTEEEVRGLFGKKFDLLSLGLT

DWSVDSRKGEELLGRLRRKNDRIE (SEQ ID NO: 11)

>GI|37520387|REF|
NP_923764.1|SIMILAR TO THIOL
METHYLTRANSFERASE [GLOEOBACTER VIOLACEUS PCC 7421]
MPSEESSGVDQPAFWEYRYRGGQDRWDLGQPAPTFVHLLSGSE

APPLGTVAVPGCGRGHDALLFAARGYKVCGFDFAADAIADATR

LALRAGAAATFLQQDLFNLPRPFAGLFDLVVEHTCFCAIDPVRR

EEYVEIVHWLLKPGGELVAIFFAHPRPGGPPYRTDAGEIERLFSPRF

KITALLPAPMSVPSRRGEELFGRFVRA (SEQ ID NO: 44)

>GI|86130841|REF|
ZP_01049440.1|HYPOTHETICAL PROTEIN
MED134_07976 [CELLULOPHAGA SP. MED134]
MELTSTYWNNRYAEGSTGWDLKEVSPPIKAYLDQLENKELKILI

PGGGYSYEAQYCWEQGFKNVYVVDFSQLALENLKQRVPDEPSLQ

LIQEDFFTYDGQFDVIIEQTFFCALQPDLRPAYVAHMHTLLKAK

GKLVGLLFNFPLTEKGPPYGGSTTEYESLFSEHFDIQKMETAYNS

TABLE 6-continued

VAARAGKELFIKMVKK (SEQ ID NO: 45)

>GI|159875886|GB|
EDP69945.1|HYPOTHETICAL PROTEIN
FBALC1_10447 [FLAVOBACTERIALES BACTERIUM ALC-1]
MISMKKNKLDSDYWEDRYTKNSTSWDIGYPSTPIRTYIDQLKDK

SLKILIPGAGNSFEAEYLWNLGFKNIYILDFAKQPLENFKKRLP

DFPENQLLHIDFFKLDIHFDLILEQTFFCALNPSLREKYVEQMH

QLLKPKGKLVGLFFNFPLTKSGPPFGGSLTEYQFLFDKKFKIKIL

ETSINSIKEREGKELFFIFESP (SEQ ID NO: 46)

>GI|149199821|REF|
ZP_01876851.1|THIOL METHYLTRANSFERASE 1-
LIKE PROTEIN [LENTISPHAERA ARANEOSA HTCC2155]
MRTKGNEKAESWDKIYREGNPGWDIKKPA

PPFEDLFKQNPSWLKAGSLISFGCGGGHDA

NFFAQNDFNVTAVDFASEAVKLARSNYPQLNVIQKNILELSPE

YDEQFDYVLEHTCFCAVPLDHRRAYMESAHAILKAGAYLFGLF

YRFDPPDQDGPPYSLSLEDLEDAYSGLFTLEE

NAIPKRSHGRRTQRERFIVLKKI (SEQ ID NO: 47)

>GI|71066354|REF|
YP_265081.1|HYPOTHETICAL PROTEIN
PSYC_1799 [PSYCHROBACTER ARCTICUS 273-4]
MGNVNQAEFWQQRYEQDSIGWDMGQVSPPLKVYIDQLPEAAKE

QAVLVPGAGNAYEVGYLYEQGFTNITLVDFAPAPIKDFAERYP

DFPADKLICADFFDLLPKQHQFDWVLEQTFFCAINPARRDEYV

QQMARLLKPKGQLVGLLFDKDFGRNEPPFGGTKEEYQQRFSTH

FDTEIMEQSYNSHPARQGSELFIKMRVKD (SEQ ID NO: 48)

>GI|86135149|REF|
ZP_01053731.1|HYPOTHETICAL PROTEIN
MED152_10555 [TENACIBACULUM SP. MED152]
MIFDEQFWDNKYITNKTGWDLGQVSPPLKAYFDQLTNKDLKIL

IPGGGNSHEAEYLLENGFTNVYVIDISKLALTNLKNRVPGFPS

SNLIHQNFFELNQTFDLVIEQTFFCALNPNLREEYVSKMHSVL

NDNGKLVGLLFDAKLNEDHPPFGGSKKEYTSLFRNLFTIEVLE

ECYNSIENRKGMELFCKFVK (SEQ ID NO: 49)

>GI|93006905|REF|
YP_581342.1|THIOPURINE S-METHYLTRANSFERASE
[PSYCHROBACTER CRYOHALOLENTIS K5]
MENVNQAQFWQQRYEQDSIGWDMGQVSPPLKAYIDQLPEAAKN

QAVLVPGAGNAYEVGYLHEQGFTNVTLVDFAPAPIAAFAERYP

NFPAKHLICADFFELSPEQYQFDWVLEQTFFCAINPSRRDEYV

QQMASLVKPNGKLIGLLFDKDFGRDEPPFGGTKDEYQQRFAT

HFDIDIMEPSYNSHPARQGSELFIEMHVKD (SEQ ID NO: 50)

>GI|114778202|REF|
ZP_01453074.1|THIOL METHYLTRANSFERASE 1-
LIKE PROTEIN [MARIPROFUNDUS FERROOXYDANS PV-1]
MTVWEERYQRGETGWDRGGVSPALTQLVDHLHLEARVLIPGC

GRGHEVIELARLGFRVTAIDIAPSAIAHLSQQLEQEDLDAEL

VNGDLFAYAPDHCFDAVYEQTCLCAIEPEQRADYEQRLHGWL

KPEGVLYALFMQTGIRGGPPFHCDLLMMRELFDASRWQWPE

TABLE 6-continued

ETGAVLVPHKNGRFELGHMLRRTGR (SEQ ID NO: 51)

>GI|83855599|REF|
ZP_00949128.1|HYPOTHETICAL PROTEIN
CA2559_00890 [CROCEIBACTER ATLANTICUS HTCC2559]
MTSNFWEQRYANNNTGWDLNTVSPPLKHYIDTLSNKTLFILI

PGCGNAYEAEYLHNQGFENVFIVDLAEHPLLEFSKRVPDFPK

SHILHLDFFNLTQKFDLILEQTFFCALHPEQRLHYAHHTSKL

LNSNGCLVGLFFNKEFDKTGPPFGGNKKEYKNLFKNLFKIKK

LENCYNSIKPRQGSELFFIFEKK (SEQ ID NO: 52)

>GI|83858455|REF|
ZP_00951977.1|THIOPURINE S-
METHYLTRANSFERASE [OCEANICAULIS
ALEXANDRII HTCC2633]
MTQASSDTPRSEDRSGFDWESRFQSDDAPWERQGVHPAAQD

WVRNGEIKPGQAILTPGCGRSQEPAFLASRGEDVTATDIAP

TAIAWQKTRFQTLGVMAEAIETDALAWRPETGFDALYEQTFL

CAIHPKRRQDYEAMAHASLKSGGKLLALFMQKAEMGGPPY

GCGLDAMRELFADTRWVWPDGEARPYPHPGLNAKAELAMV

LIRR (SEQ ID NO: 53)

>GI|113866478|REF|
Y2_724967.1|THIOPURINE S-
METHYLTRANSFERASE (TPMT) [RALSTONIA EUTROPHA H16]
MSDPAKPVPTFATRNAADPAFWDERFEQGFTPWDQGGVPEE

FRQFIEGRAPCPTLVPGCGNGWEAAWLFERGWPVTAIDFSP

QAVASARQTLGPAGVVVQQGDFFAFTPQPPCELIYERAFLC

ALPPAMRADYAARVAQLLPPGGLLAGYFYLGENRGGPPFAM

PAEALDALLAPAFERLEDRPTAAPLPVFQGQERWQVWRRRS

G (SEQ ID NO: 54)

>GI|150025500|REF|
YP_001296326.1|HYPOTHETICAL PROTEIN
FP1441 [FLAVOBACTERIUM PSYCHROPHILUM JIP02/86]
MKKIDQKYWQNRYQTNDIAWDTGKITTPIKAYIDQIEDQSI

KILIPGCGNGYEYEYLIKKGFYNSFVADYAQTPIDNLKKRI

PNCNANQLLISDFFELEGSYDLIIEQTFFCALNPELRVKYA

QKMLSLLSPKGKIIGLLFQFPLTEAGPPFGGSKEEYLKLF

STNFNIKTIETAYNSIKPREGNELFFIFTKK (SEQ ID NO: 55)

>GI|124268594|REF|
YP_001022598.1|HYPOTHETICAL PROTEIN
MPE_A3410 [METHYLIBIUM PETROLEIPHILUM PM1]
MSGPDLNFWQQRFDTGQLPWDRGAPSPQLAAWLGDGSLAP

GRIAVPGCGSHEVVALARGGFSVTAIDYAPGAVRLTQGR

LAAAGLAAEVVQADVLTWQPTAPLDAVYEQTCLCALHPDH

WVAYAARLHAWLRPGGTLALLAMQALREGAGQGLIEGPPY

HVDVNALRALLPGDRWDWPRPPYARVPHPSSTWAELAIVL

TRR (SEQ ID NO: 56)

>GI|86141349|REF|
ZP_01059895.1|HYPOTHETICAL PROTEIN

TABLE 6-continued

MED217_05007 [*FLAVOBACTERIUM* SP. MED217]
MKTDLNKLYWEDRYQNQQTGWDIGSVSTPLKEYIDQIDDK

NIQILVPGAGYGHEVRYLAQQGFKNVDVIDLSVSALTQLK

KALPDTTAYQLIEGDFFEHHTSYDLILEQTFFCALEPD

KRPDYAAHAASLLKDSGKISGVLFNFPLTEKGPPFGGSS

EEYKKLFSEYFNIKTLEACYNSIKPRLGNELFFIFEKS

NQES (SEQ ID NO: 57)

>GI|124003356|REF|
ZP_01688206.1|THIOPURINE S-METHYLTRANSFERASE
(TPMT) SUPERFAMILY [*MICROSCILLA MARINA*
ATCC 23134]
MHTTLDKDFWSNRYQAQDTGWDAGSITTPIKAYVDQLED

KHLKILVPGAGNSHEAEYLHQQGFTNVTVIDIVQAPLDNL

KSRSPDFPEAHLLQGDFFELVGQYDLIIEQTFFCALNPS

LRESYVQKVKSLLKPEGKLVGVLFCNVFLDRTEPPFGA

TEQQHQEYFLPHFIAKHFASC

YNSIAPRQGAEWFICLIND (SEQ ID NO: 58)

>GI|151577463|GB|
EDN41864.1|THIOPURINE S-METHYLTRANSFERASE
[*RALSTONIA PICKETTII* 12D]
MAEPPVFQSRDAADPAFWDERFSREHTPWDAAGVPAAFQ

QFCESQPVPLSTLIPGCGSAYEAGWLAERGWPVTAIDFA

PSAVASARAVLGPHADVVEMADFFGFSPARSVQWIYERAF

LCAMPRRLWPDYAAQVAKLLPPGGLLAGFFAVVEGREAV

PKGPPFETTQPELDALLSPAFERISDIPIAEADSIPVFA

GRERWQVWRRRAD (SEQ ID NO: 59)

>GI|121303859|GB|
EAX44825.1|CONSERVED HYPOTHETICAL PROTEIN
[*RALSTONIA PICKETTII* 12J]
MAQPPVFQSRDAADPAFWDERFTREHTPWDAAGVPAAFR

QFCEAQPAPLSTLIPGCGNAYEAGWLAERGWPVTAIDFA

PSAVASARAVLGPHADVVQLADFFRFSPPRPVHWIYERAF

LCAMPRRLWPDYAAQVAKLLPPRGLLAGFFAVVE

GREAMPKGPPFETTQPELDALLSPAFERISDMPIA

ETDSIPVFAGRERWQVWRRRAD (SEQ ID NO: 41)

>GI|121583316|REF|
YP_973752.1|THIOPURINE S-METHYLTRANSFERASE
[*POLAROMONAS NAPHTHALENIVORANS* CJ2]
MAGPTTDFWQARFDNKETGWDRGAPGPQLLAWLESGAL

QPCRIAVPGCGSGWEVAELARRGFEVVGIDYTPAAVER

TRALLAAQGLAAEVVQADVLAYQPHKPFEAIYEQTCL

CALHPDHWVAYARQLQQWLKPQGSIWALFMQMVRPEAT

DEGLIQGPPYHCDINAMRALFPAQHWAWPRPPYAK

VPHPNVGHELGLRLMLRQGR (SEQ ID NO: 60)

>GI|88802008|REF|
ZP_01117536.1|HYPOTHETICAL PROTEIN
PI23P_05077 [*POLARIBACTER IRGENSII* 23-P]
MNLSADAWDERYTNNDIAWDLGEVSSPLKAYFDQLENK

EIKILIPGGGNSHEAAYLFENGFKNIWVVDLSETAIGN

IQKRIPEFPPSQLIQGDFFNMDDVFDLIIEQTFFCAIN

PNLRADYTTKMHHLLKSKGKLVGVLFNVPLNTNKFPFG

GDKSEYLEYFKPFFIIKKMEACYNSFGNRKGREL

FVILRSK (SEQ ID NO: 61)

>GI|126661882|REF|
ZP_01732881.1|THIOPURINE S-
METHYLTRANSFERASE [*FLAVOBACTERIA BACTERIUM* BAL38]
MNYWEERYKKGETGWDAGTITTPLKEYIDQLTDKNLTI

LIPGAGNGHEFDYLIDNGFKNVFVVDIAITPLENIKKR

KPKYSSHLINADFFSLTTTFDLILEQTFFCALPPEMRQ

RYVEKMTSLLNPNGKLAGLLFDFPLTSEGPPFGGSKSE

YITLFSNTFSIKTLERAYNSIKPRENKELFFIFE

TK (SEQ ID NO: 62)

>GI|149924142|REF|
ZP_01912520.1|HYPOTHETICAL PROTEIN
PPSIR1_29093
[*PLESIOCYSTIS PACIFICA* SIR-1]
MRVIVPGAGVGHDALAWAQAGHEVVALDFAPAAVARLR

ERAAEAGLTIEAHVADVTNPGPALNDGLGGRFDLVW

EQTCLCAITPELRGAYLAQARSWLTPDGSMLALLWNT

GNEGGPPYDMPPELVERLMTGLFVIDKFAPVTGSNPN

RREHLYWLRPEPT (SEQ ID NO: 63)

>GI|126647682|REF|
ZP_01720187.1|HYPOTHETICAL PROTEIN
ALPR1_06920 [*ALGORIPHAGUS* SP. PR1]
MAELDEKYWSERYKSGLTGWDIGFPSTPIVQYLDQIVN

KDVEILIPGAGNAYEAYYAFQSGFSNVHVLDISQEPLR

NFKDKFPNEPSSNLHHGDFFEHHGSYNLILEQTFFCAL

NPSLRPKYVKKMSELLLKGGKLVGLLFNKEFNSPGPPF

GGGIKEYQKLFHNSFEIDVMEECYNSIPARAGSE

AFIRLINSKG (SEQ ID NO: 64)

>GI|89900214|REF|
YP_522685.1|THIOPURINE S-METHYLTRANSFERASE
[*RHODOFERAX FERRIREDUCENS* T118]
MAGPTTEFWQERFEKKETGWDRGSPSPQLLAWLASGAL

RPCRIAVPGCGSGWEVAELAQRGFDVVGLDYTAAATTR

TRALCDARGLKAEVLQADVLSYQPEKKFAAIYEQTCL

CAIHPDHWIDYARQLHQWLEPQGSLWVLFMQMIRPAA

TEEGLIQGPPYHCDINAMRALFPQKDWVWPKPPYAR

VSHPNLSHELALQLVRR (SEQ ID NO: 65)

>GI|17545181|REF|
NP_518583.1|HYPOTHETICAL PROTEIN RSC0462
[*RALSTONIA SOLANACEARUM* GMI1000]
MAQPPVFTTRDAAAPAFWDERFSRDHMPWDAHGVPPA

FRQFCEAQPAPLSTLIPGCGSAYEAGWLAERGWPVAA

IDFAPSAVASAQAVLGPHAGVVELADFFRFTPRQPVQ

WIYERAFLCAMPRRLWADYATQVARLLPPGGLLAGFF

VVVDGRAAAPSGPPFEITAQEQEALLSPAFERIADALV

TABLE 6-continued

PENESIPVFAGRERWQVWRRRAD (SEQ ID NO: 42)

>GI|120436745|REF|
YP_862431.1|THIOPURINE S-METHYLTRANSFERASE
[*GRAMELLA FORSETII* KT0803]
MNKDFWSLRYQKGNTGWDIGNISTPLKEYIDHLHKKEL

KILIPGAGNSYEAEYLFEKGFKNIWICDIAKEPIENFK

KALPEFPESQILNRDFFELKDQFDLILEQTFFCALPVN

FRENYAKKVFELLKVNGKISGVLFDFPLTPDGPPFGGS

KEEYLAYESPYFKINTFERCYNSINPRQGKELFF

NFSKK (SEQ ID NO: 66)

>GI|86159623|REF|
YP_466408.1|METHYLTRANSFERASE TYPE 12
[*ANAEROMYXOBACTER DEHALOGENANS* 2CP-C]
MGTSYRLAYLIGFTPWEDQPLPPELSALVEGLRARPPGR

ALDLGCGRGAHAVYLASHGWKVTGVDLVPAALAKARQRA

TDAGVDVQFLDGDVTRLDTLGLSPGYDLLLDAGCFHGLS

DPERAAYARGVTALRAPRAAMLLFAFKPGWRGPAPRGAS

AEDLTSAFGPSWRLVRSERARESRLPLPLR

NADPRWHLLEAA (SEQ ID NO: 67)

>GI|118468119|REF|
YP_886428.1|METHYLTRANSFERASE TYPE 12
[*MYCOBACTERIUM SMEGMATIS* STR. MC2 155]
MDTTPTRELFDEAYESRTAPWVIGEPQPAVVELERAGL

IRSRVLDVGCGAGEHTILLTRLGYDVLGIDFSPQAIEM

ARENARGRGVDARFAVGDAMALGDLGDGAYDTILDSALF

HIFDDADRQTYVASLHAGCRPGGTVHILALSDAGRGFGP

EVSEEQIRKAFGDGWDLEALETTTYRGVVGPVHAEAIGL

PVGTQVDEPAWLARARRL (SEQ ID NO: 68)

>GI|119504877|REF|
ZP_01626954.1|THIOPURINE S-METHYLTRANSFERASE
[MARINE GAMMA PROTEOBACTERIUM HTCC2080]
MEKFGASAMEPVLDWEARYQESSVPWERTGLNPAFVAW

QSWLRDHQGGTVVVPGCGRSPELQAFADMGFNVIGVDL

SPSAAQFQETVLAAKGLDGKLVVSNLFDWSPDTPVDF

VYEQTCLCALKPDHWRAYENLLTRWLRPGGTLLALFMQ

TGESGGPPFHCGKAAMEQLFSEQRWIWDETSVRSE

HPLGVHELGFRLTLR (SEQ ID NO: 69)

>Gi|161325846|GB|EDP97172.1|
HYPOTHETICAL PROTEIN KAOT1_18457
[*KORDIA ALGICIDA* OT-1]
MNSDATKEYWSQRYKDNSTGWDIGSPSTPLKTYIDQL

KDRNLKILIPGAGNAYEAEYLLQQGFTNIYILDISEI

PLQEFKQRNPEFPSDRLLCDDFFTHKNTYDLIIEQTF

FCSFPPLPETRAQYAKHMADLLNPNGKLVGLWFDFPL

TDDLEKRPFGGSKEEYLEYFKPYFDVKTFEKAYNSIAP

RAGNELFGIFIKS (SEQ ID NO: 70)

>GI|150389542|REF|

YP_001319591.1|METHYLTRANSFERASE TYPE 11
[*ALKALIPHILUS METALLIREDIGENS* QYMF]
MNDKLDQEVILNQEDLLNMLDSLLEKWDEEWWNEFYSD

KGKPIPFFVNAPDENLVTYFDKYFDDIGRALDVGCGNG

RNSRFIASRGYDVEGLDFSKKSIEWAKEESKKTGDIAL

YVNDSFFNINRELSSYDLIYDSGCLHHIKPHRRSQYLE

KVHRLLKPGGYFGLVCFNLKGGANLSDHDVYKKS

SMAGGLGYSDIKLKKILGTYFEIVEFREMRECAD

NALYGKDICWSILMRRLAK (SEQ ID NO: 71)

>GI|71024813|REF|
XP_762636.1|HYPOTHETICAL PROTEIN UM06489.1
[*USTILAGO MAYDIS* 521]
MTSSLSKDDQIQNLRRLFADSGVPNDPKAWDQAWIDST

TPWDANRPQPALVELLEGAHDADAKVPDVDGNLIPVSQ

AIPKGDGTAVVPGCGRGYDARVFAERGLTSYGVDISSN

AVAAANKWLGDQDLPTELDDKVNFAEADFFTLGTSKSL

VLELSKPGQATLAYDYTFLCAIPPSLRTTWAETY

TRLLAKHGVLIALVFPIHGDRPGGPPFSISPQLVREL

LGSQKNADGSAAWTELVELKPKGPE

TRPDVERMMVWRRS (SEQ ID NO: 30)

>GI|20090980|REF|
NP_617055.1|HYPOTHETICAL PROTEIN MA2137
[*METHANOSARCINA ACETIVORANS* C2A]
MFWDEVYKGTPPWDIDHPQPAFQALIESGEIRPGRAL

DIGCGRGENAIMLAKNGCDVTGIDLAKDAISDAKAKA

IERHVKVNFIVGNVLEMDQLFTEDEFDIVIDSGLFHV

ITDEERLLFTRHVHKVLKEGGKYFMLCFSDKEPGEYEL

PRRASKAEIESTFSPLFNIIYIKDVIFDSLLNPGRRQ

AYLLSATKS (SEQ ID NO: 72)

>HALORHODOSPIRA HALOPHILA SL1
MSGDPDPRRAPWEARWREGRTGWDRGGVSPTLEAWLSA

GVIPGRRVLVPGAGRGYEVEALARRGYKVTAVDIAAEA

CQQLRDGLDAAGVEARVVQADLLAWQPDTPFDAVYEQT

CLCALDPADWPAYEQRLYGWLRPGGVLLALFMQTGASG

GPPFHCALPEMATLFDSERWQWPAEPPRQWPHPS

GRWEEAVRLLRR (SEQ ID NO: 21)

>GI|54295659|REF|
YP_128074.1|THIOPURINE S-METHYLTRANSFERASE
[*LEGIONELLA PNEUMOPHILA* STR. LENS]
MNKGQYFWNELWCEGRISPHKKEVNPDLIAYVSSLNIP

AKGRVLVPLCGKSVDMLWLVRQGYHVVGIELVEKAILQ

FVQEHQITVRENTIGQAKQYFTDNLNLWVTDIFALNSA

LIEPVDAIYDRAALVALPKKLRPAYVDICLKWLKPGGS

ILLKTLQYNQEKVQGPPYSVSPEEIALSYQQCAK

IKLLKSQKRIQEPNDHLFNFGISEVNDSVWCIRK

G (SEQ ID NO: 73)

TABLE 6-continued

>GI|116187307|REF|
ZP_01477195.1|HYPOTHETICAL PROTEIN
VEX2W_02000031 [*VIBRIO SP.* EX25]
MKQAPTINQQFWDNLFTQGTMRWDAKTTPQELKAYLENALHSGQSVF

IPGCGAAYELSSFIQYGHDVIAMDYSEQAVKMAQSTLGKHKDKVVLG

DVFNADSTHSFDVIYERAFLAALPRDQWPEYFAMVDKLLPRGGLLIG

YFVIDDDYHSREPPFCLRSGELEGYLEPVFKLVESSVVANSVEVF

KGRERWMVWQKSCRI (SEQ ID NO: 74)

>GI|120402886|REF|
YP_952715.1|METHYLTRANSFERASE TYPE 11
[*MYCOBACTERIUM VANBAALENII* PYR-1]
MDLTPRLSREDEFYKNQTPPWVIGEPQQAIVELEQAGLIGGRVLDV

GCGTGEHTILLARAGYDVLGIDGAPTAVEQARRNAEAQGVDARFEL

ADALHLGPDPTYDTIVDSALFHIFDDADRATYVRSLHAATRPGSVV

HLLALSDSGRGFGPEVSEHTIRAAFGAGWEVEALTETTYRGVVID

AHTEALNLPAGTVVDEPAWSARIRRL (SEQ ID NO: 75)

>GI|134101246|REF|
YP_001106907.1|6-O-METHYLGUANINE DNA
METHYLTRANSFERASE
[*SACCHAROPOLYSPORA ERYTHRAEA* NRRL 2338]
MDDELAESQRAHWQDTYSAHPGMYGEEPSAPAVHAAGVFRAAGAR

DVLELGAGHGRDALHFAREGFTVQALDFSSSGLQQLRDAARAQQV

EQRVTTAVHDVRHPLPSADASVDAVFAHMLLCMALSTEEIHALVG

EIHRVLRPGGVLVYTVRHTGDAHHGTGVAHGDDIFEHDGFAVHFF

PRGLVDSLADGWTLDEVHAFEEGDLPRRLWRVTQTLPR (SEQ ID NO: 76)

>*BURKHOLDERIA PHYMATUM* STM815 (29% IDENTICAL TO
BATIS)MSDKRPSVPPSAPDFENRDPNAPGFWDERFGRGFTP

WDQAGVPPAFKAFVERHSPV

PVLIPGCGSAYEARWLAEKGWTVRAIDFAPNAVEAARAQLGSHASLVH

EADFFTYRPPFDPGWIYERAFLCALPPARRSDWVARMAQLLSPGGLLA

GFFFIGATEKGPPFGIERAELDALMSPDFTLVEDEPVDDSIAVFAGRE

RWLTWRRRGAARG (SEQ ID NO: 4)

>GI|91781799|REF|
YP_557005.1|HYPOTHETICAL PROTEIN BXE_A4046
[*BURKHOLDERIA XENOVORANS* LB400]
MSDPTQPAVPDFETRDPNSPAFWDERFERRFTPWDQAGVPAAFQSFAA

RHSGAAVLIPGCGSAYEAVWLAGQGNPVRAIDFSPAAVAAAHEQLGAQ

HAQLVEQADFFTYEPPFTPAWIYERAFLCALPLARRADYAHRMADLLP

GGALLAGFFFLGATPKGPPFGIERAELDALLTPYFDLIEDEA

VHDSIAVFAGRERWLTWRRRA (SEQ ID NO: 77)

>GI|118038664|REF|
ZP_01510068.1|THIOPURINE S-
METHYLTRANSFERASE [*BURKHOLDERIA PHYTOFIRMANS* PSJN]
MSDPTQPSAPEFESRDPNSPEFWDERFERGFMPWDQAGVPSAFESFA

ARHAGAAVLIPGCGSAYEAVWLAGEGYPVRAIDFSPAAVAAAHEQLG

AQHADLVEQADFFTYELPFTPAWIYERAFLCALPLARRADYARRMADL

LPGGALLAGFFFIGATPKGPPFGIERAELDGLLKPYFELIEDEP

VHDSIAVFAGRERWLTWRRRV (SEQ ID NO: 78)

>GI|83719252|REF|
YP_441114.1|THIOPURINE S-METHYLTRANSFERASE
FAMILY PROTEIN [*BURKHOLDERIA THAILANDENSIS* E264]
MTSEANKGDAAVQAAGDAQPASPASPPSADVQPARAALAPSSVPPAPS

AANFASRDPGDASFWDERFERGVTPWDSARVPDAFAAFAARHPRCPVL

IPGCGSAYEARWLARAGWPVRAIDFSAQAVAAARRESGADAALVEQAD

FFAYVPPFVPQWIYERAFLCAIPTSRRADYARRVAELLPAGGFLAGFF

FIGATPKGPPFGIERAELDALLSPNFELVEDEPVADSLPVFAGRERW

LAWRRS (SEQ ID NO: 79)

>GI|134296925|REF|YP_001120660.1|THIOPURINE S-
METHYLTRANSFERASE [*BURKHOLDERIA VIETNAMIENSIS* G4]
MSNPTQPPPPSAADFATRDPANASFWDERF

ARGVTPWEFGGVPDGFRAFAQRRAPCTVLIPG

CGSAQEAGWLAQAGWPVRAIDFAEQAVVAAKATLGA

HADVVEQADFFAYQPPFVVQWVYERA

FLCALPPSLRAGYAARMAELLPAGGLLAGYFFVMKKP

KGPPFGIERAELDALLAPSFELIED

LPVTDSLAVFDGHERWLTWRRR (SEQ ID NO: 80)

>GI|118707586|REF|
ZP_01560172.1|THIOPURINE S-
METHYLTRANSFERASE [*BURKHOLDERIA CENOCEPACIA* MCO-3]
MSDPKQPAAPSAAEFATRDPGSASFWDERFA

RGVTPWEFGGVPDGFRAFAQRHEPCAVLIPG

CGSAQEAGWLAQAGWPVRAIDFAAQAVAAAK

VQLGAHADVVEQADFFQYRPPFDVQWVYERA

FLCALPPSLRADYAARMAELLPTGGLLAGYFFVV

AKPKGPPFGIERAELDALLAPHFELLED

LPVTDSLAVFDGHERWLTWRRR (SEQ ID NO: 81)

>GI|53724994|REF|
YP_102027.1|THIOPURINE S-METHYLTRANSFERASE
FAMILY PROTEIN [*BURKHOLDERIA MALLEI* ATCC
23344]
MKDRLMSQGDGVTNEANQPEAAGQAAGDAQPASPAGPAHIANPANPAN

PPALPSFSPPAAASSSASSAAPFSSRDPGDASFWDERFEQGVTPWDSA

RVPDAFAARHARVPVLIPGCGSAYEARWLARAGWPVRAIDFSAQAVAA

ARRELGEDAGLVEQADFFTYAPPFVPQWIYERAFLCAIPRSR

RADYARRMAELLPPGGFLAGFFFIGATPKGPPFGIERAELDALLCPHF

ALVEDEPVADSLPVFAGRERWLAWRRS (SEQ ID NO: 82)

>GI|76808612|REF|
YP_332262.1|THIOPURINE S-METHYLTRANSFERASE
FAMILY PROTEIN [*BURKHOLDERIA PSEUDOMALLEI* 1710B]
MKDRLMSQGDGVTNEANQPEAAGQATGDAQPASPAGPAHIANPANPA

NPANPPALPSLSPPAAAPSSASSAAHFSSRDPGDASFWDERFEQGVT

PWDSARVPDAFAAFAARHARVPVLIPGCGSAYEARWLARAGWPVRAI

DFSAQAVAAARRELGEDAGLVEQADFFTYAPPFVPQWIYERAFLC

AIPRSRRADYARRMAELLPPGGFLAGFFFIGATPKGPPFGIERAE

LDALLCPHFALVEDEPVADSLPVFAGRERWLAWRRS

TABLE 6-continued (SEQ ID NO: 83)

>GI|107023663|REF|
YP_621990.1|THIOPURINE S-METHYLTRANSFERASE
[BURKHOLDERIA CENOCEPACIA AU 1054]
MSDPKQPAAPSAADFATRDPGSASFWDERFARGVTPWEFGGVPDGFRV

FAQRREPCAVLIPGCGSAQEAGWLAQAGWPVRAIDFAAQAVAAAKAQL

GAHADVVEQADFFQYRPPFDVQWVYERAFLCALPPGLRAGYAARMAEL

LPTGGLLAGYFFVVAKPKGPRFGIERAELDALLAPHFELLED

LPVTDSLAVFDGHERWLTWRRR (SEQ ID NO: 84)

>GI|84362923|REF|
ZP_00987534.1|COG0500: SAM-DEPENDENT
METHYLTRANSFERASES [BURKHOLDERIA DOLOSA AUO158]
MTGRSFAMSDPKQPGTPTAADFATRDPGDASFWDERFARGVTPWEFG

GVPDGFRAFAQRLERCAVLIPGCGSAQEAGWLADAGWPVRAIDFAAQ

AVATAKAQLGAHADVVELADFFTYRPPFDVRWIYERAFLCALPPARR

ADYAAQMAALLPAGGLLAGYFFVTAKPKGPPFGIERAELDALLAP

QFDLIDDWPVTDSLPVFEGHERWLTWRRR (SEQ ID NO: 85)

>GI|115352830|REF|
YP_774669.1|THIOPURINE S-METHYLTRANSFERASE
[BURKHOLDERIA AMBIFARIA AMMD]
MSEPKQPSTPGAADFATRDPGDASFWDERFARGVTPWEFGGVPEGFRA

FAQRLGPCAVLIPGCGSAQEAGWLAQAGWPVRAIDFAAQAVAAAKAQL

GAHADVVEQADFFMYRPPFDVQWVYERAFLCALPPSLRAGYAARMAEL

LPAGALLAGYFFVTKKPKGPPFGIERAELDALLAPHFELIDD

LPVTDSLAVFEGHERWLTWRRR (SEQ ID NO: 86)

>GI|78067524|REF|
YP_370293.1|THIOPURINE S-METHYLTRANSFERASE
[BURKHOLDERIA SP. 383]
MSDPKQPKPNAPAAADFTTRDPGNASFWNERFERGVTPWEFGGVPEGF

SVFAHRLELCAVLIPGCGSAQEAGWLAEAGWPVRAIDFAAQAVAAAKA

QLGAHAGVVEQADFFAYRPPFDVQWVYERAFLCALPPAMRADYAARMA

ELLPADGLLAGYFFLMAKPKGPPFGIERAELDALLTPHFELI

EDLPVTDSLAVFEGHERWLTWRRR (SEQ ID NO: 87)

>GI|161523751|REF|
YP_001578763.1|THIOPURINE S-
METHYLTRANSFERASE [BURKHOLDERIA MULTIVORANS
ATCC 17616]
MSDPKHAAAPAAASFETRDPGDASFWDERFARGMTPWEFGGVPAGFRA

FASARPPCAVLIPGCGSAREAGWLAQAGWPVRAIDFSAQAVAAAKAQL

GAHADVVEQADFFAYRPPFDVQWIYERAFLCALPPARRADYAATMAAL

LPAQGLLAGYFFVADKQKGPPFGITRGELDALLGAHFELIDD

APVSDSLPVFEGHERWLAWRRR (SEQ ID NO: 88)

>GI|84355663|REF|
ZP_00980538.1|COG0500: SAM-DEPENDENT
METHYLTRANSFERASES [BURKHOLDERIA
CENOCEPACIA PC184]
MLIPGCGSAQEAGWLAQAGWPVRAIDFAAQAVAAAKAQLGAHADVVE

QADFFAYRPPFDVQWVYERAFLCALPPSLRAGYAARMAELLPTGGLLA

GYFFVVAKPKGPPFGIEPAELDALLAPHFALLEDLPVTDSLAVFDGHE

RWLTWRRR (SEQ ID NO: 89)

>GI|116187307|REF|ZP_01477195.1|
HYPOTHETICAL PROTEIN
VEX2W_02000031 [VIBRIO SP. EX25]
MKQAPTINQQFWDNLFTQGTMPWDAKTTPQELKAYLENALHSGQSVF

IPGCGAAYELSSFIQYGHDVIAMDYSEQAVKMAQSTLGKHKDKVVLG

DVFNADSTHSFDVIYERAFLAALPRDQWPEYFAMVDKLLPAGGLLIG

YFVIDDDYHSRFPPFCLRSGELEGYLEPVFKLVESSVVANSVEVF

KGRERWMVWQKSCRI (SEQ ID NO: 74)

>GI|28901001|REF|NP_800656.1|
HYPOTHETICAL PROTEIN VPA1146
[VIBRIO PARAHAEMOLYTICUS RIMD 2210633]
MKSKDSPIINEQFWDALFFNGTMPWDRSQTPNELKHYLKRIADKTHSV

FIPGCGAAYEVSHFVDCGHDVIAMDYSAEAVNLAKSQLGQHQDKVMLG

DVFNADFSREFDVIYERAFLAALPREIWGDYFAMIERLLPSNGLLVGY

FVISDDYRSRFPPPFCLRSGEIEQKLEANFHLIESTPVIDSVD

VFKGKEQWMVWQKK (SEQ ID NO: 90)

>GI|91224783|REF|
ZP_01260043.1|HYPOTHETICAL PROTEIN
V12G01_01280 [VIBRIO
ALGINOLYTICUS 12G01]
MKQAPMINTQFWDDLFIRGTMPWDAQSTPQELKD

YLDNSLHVGQSVFIPGCGAAYELSTFIQ

YGHDVIAMDYSQEAVKMAQSALGNYKDKVVLGDVFNADFSHSFDVIYE

RAFLAALPRDMWSEYESTVDKLLPSGGFLIGFFVIDDDYCSRFPPFCL

RSGELASFLEPTFELVKSSVVANSVEVF

KGREQWMVWQKR (SEQ ID NO: 91)

> SYNECHOCOCCUS ELONGATUS PCC
6301MTNAVNQAQFWEQRYQEGSDRWDLGQAAPVWRSLLAGTNAPAPG

RIAVLGCGRGHDARLFAEQGFEVVGFDFAPSAIAAAQALAQGTTAQFL

QRDIFALPQEFAGQFDTVLEHTCFCAIDPDRRAEYVEVVRQILKPKGC

LLGLFWCHDRPSGPPYGCSLTELRDRFAQGWQEEQLESVTES

VEGRRGEEYLGRWRRLD (SEQ ID NO: 5)

>GI|148239221|REF|
YP_001224608.1|POSSIBLE THIOPURINE S-
METHYLTRANSFERASE [SYNECHOCOCCUS SP. WH 7803]
MTNVHLPQAWDARYQHGTDGWELGKAAPPLQAFLEHHPRAPQPEGTVL

VPGCGRGHEAALLARLGFEVIGLDFSSEAIREARRLHGEHPRLRWLQA

DLFDADALSGAGLASGSLSGVLEHTCFCAIDPSQRAHYRSTVDRLLRA

EGWLLGLFFCHPRPGGPPFGSDPEQLAASWAQIGFYPLIWEP

ARGSVAGRSEEWLGFWRKPEQRSA (SEQ ID NO: 92)

>GI|87124194|REF|
ZP_01080043.1|THIOL
METHYLTRANSFERASE 1-LIKE
PROTEIN [SYNECHOCOCCUS SP. RS9917]
MQLDGASSAPTLTARDWDARYRQGTDRWELGMAAPPLQAFLEQHPLAP

KPTGTVLVPGCGRGHEAALLARLGFDVVGLDFSVEAIREARRLQGEHE

NLRWLQADLFNGAALDRAGLGAHSLSGVVEHTCFCAIDPSQRDHYRST

VDRLLEPGGWLLGVFFCHDRPGGPPYGSDAEQLAASWSQIGFTGVIWE

PAQGSVAQRSDEWLGLWRKPSQADNEAIPAGSR (SEQ ID NO: 93)

TABLE 6-continued

>GI|111027025|REF|YP_709003.1|
POSSIBLE 3-DEMETHYLUBIQUINONE-9
3-METHYLTRANSFERASE [*RHODOCOCCUS SP.* RHA1]
MVDAPRFPYPGSPPVHGPDDLYVTPPPWDIGRAQPVFVALAEGGAIRG

RVLDCGCGTGEHVLLAAGLGLDATGVDLAATALRIAEQKARDRGLTAR

FLHHDARRLAELGERFDTVLDCGLFHIFDPDDRAAYVDSLRDVLVPGG

RYLMLGFSDQQPGDWGPHRLIRDEITTAFDDGWTIDSLESAT

LEVTLDPAGMRAWQLAATRTWPHPIERECSAPC (SEQ ID NO: 94)

>GI|118038664|REF|
ZP_01510068.11|THIOPURINE S-
METHYLTRANSFERASE [*BURKHOLDERIA PHYTOFIRMANS* PSJN]
MSDPTQPSAPEFESRDPNSPEFWDERFERGFMPWDQAGVPSAFESFAA

RHAGAAVLIPGCGSAYEAVWLAGHGYPVRAIDFSPAAVAAAHEQLGAQ

HADLVEQADFFTYELPFTPAWIYERAFLCALPLARRADYARRMADLLP

GGALLAGFFFIGATPKGPPFGIERAELDGLLKPYFELIEDEP

VHDSIAVFAGRERWLTWRRRV (SEQ ID NO: 78)

>GI|91685753|GB|ABE28953.1|
CONSERVED HYPOTHETICAL PROTEIN
[*BURKHOLDERIA XENOVORANS* LB400]
MSDPTQPAVPDFETRDPNSPAFWDERFERRFTPWDQAGVPAAFQSFAA

RHSGAAVLIPGCGSAYEAVWLAGQGNPVRAIDFSPAAVAAAHEQLGAQ

HAQLVEQADFFTYEPPFTPAWIYERAFLCALPLARRADYAHRMADLLP

GGALLAGFFFLGATPKGPPFGIERAELDALLTPYFDLIEDEA

VHDSIAVFAGRERWLTWRRRA (SEQ ID NO: 77)

>GI|118655249|GB|EAV62028.1|
THIOPURINE S-METHYLTRANSFERASE
[*BURKHOLDERIA CENOCEPACIA* MC0-3]
MSDPKQPAAPSAAEFATRDPGSASFWDERFARGVTPWEFGGVPDGFRA

FAQRHEPCAVLIPGCGSAQEAGWLAQAGWPVRAIDFAAQAVAAAKVQL

GAHADVVEQADFFQYRPPFDVQWVYERAFLCALPPSLRADYAARMAEL

LPTGGLLAGYFFVVAKPKGPPFGIERAELDALLAPHFELLED

LPVTDSLAVFDGHERWLTWRRR (SEQ ID NO: 81)

>GI|134140082|GB|ABO55825.1|
THIOPURINE S-METHYLTRANSFERASE
[*BURKHOLDERIA VIETNAMIENSIS* G4]
MSNPTQPPPPSAADFATRDPANASFWDERFARGVTPWEFGGVPDGFRA

FAQRRAPCTVLIPGCGSAQEAGWLAQAGWPVRAIDFAEQAVVAAKATL

GAHADVVEQADFFAYQPPFVVQWVYERAFLCALPPSLRAGYAARMAEL

LPAGGLLAGYFFVMKKPKGPPFGIERAELDALLAPSFELIED

LPVTDSLAVFDGHERWLTWRRR (SEQ ID NO: 80)

>GI|83653077|GB|ABC37140.1|
THIOPURINE S-METHYLTRANSFERASE
FAMILY PROTEIN [*BURKHOLDERIA THAILANDENSIS* E264]
MTSEANKGDAAVQAAGDAQPASPASPPSADVQPARAALAPSSVPPAPS

AANFASRDPGDASFWDERFERGVTPWDSARVPDAFAAFAARHPRCPVL

IPGCGSAYEARWLARAGWPVRAIDFSAQAVAAARRESGADAALVEQAD

FFAYVPPFVPQWIYERAFLCAIPTSRRADYARRVAELEPAGG

FLAGFFFIGATPKGPPFGIERAELDALLSPNFELVEDEPVADSLPVF

AGRERWLAWARS (SEQ ID NO: 79)

>GI|148029498|GB|EDK87403.1|
THIOPURINE S-METHYLTRANSFERASE
FAMILY PROTEIN [*BURKHOLDERIA MALLEI* 2002721280]
MKDRLMSQGDGVTNEANQPEAAGQAAGDAQPASPAGPAHIANPANPAN

PPALPSFSPPAAASSSASSAAPFSSRDPGDASFWDERFEQGVTPWDSA

RVPDAFAARHARVPVLIPGCGSAYEARWLARAGWPVRAIDFSAQAVA

AARRELGEDAGLVEQADFFTYAPPFVPQWIYERAFLCAIPRSR

RADYARRMAELLPPGGELAGFFFIGATPKGPPFGIERAELDALLCPH

FALVEDEPVADSLPVFAGRERWLAWRRS (SEQ ID NO: 82)

>GI|116648837|GB|ABK09478.1|
THIOPURINE S-METHYLTRANSFERASE
[*BURKHOLDERIA CENOCEPACIA* HI2424]
MSDPKQPAAPSAADFATRDPGSASFWDERFARGVTPWEFGGVPDGFR

VFAQRREPCAVLIPGCGSAQEAGWLAQAGWPVRAIDFAAQAVAAAKA

QLGAHADVVEQADFFQYRPPFDVQWVYERAFLCALPPGLRAGYAARMA

ELLPTGGLLAGYFFVVAKPKGPPFGIERAELDALLAPHFELLED

LPVTDSLAVFDGHERWLTWRRR (SEQ ID NO: 84)

>GI|124292927|GB|ABN02196.1|
THIOPURINE S-METHYLTRANSFERASE
FAMILY PROTEIN [*BURKHOLDERIA MALLEI* NCTC 10229]
MSQGDGVTNEANQPEAAGQAAGDAQPASPAGPAHIANPANPANPPALP

SFSPPAAASSSASSAAPFSSRDPGDASFWDERFEQGVTPWDSARVPDA

FAARHARVPVLIPGCGSAYEARWLARAGWPVRAIDFSAQAVAAARREL

GEDAGLVEQADFFTYAPPFVPQWIYERAFLCAIPRSRRADYA

RRMAELLPPGGFLAGFFFIGATPKGPPFGIERAELDALLCPHFALVED

EPVADSLPVFAGRERWLAWRRS (SEQ ID NO: 95)

>GI|84362923|REF|ZP_00987534.1|
COG0500: SAM-DEPENDENT
METHYLTRANSFERASES [*BURKHOLDERIA DOLOSA* AUO158]
MTGRSFAMSDPKQPGTPTAADFATRDPGDASFWDERFARGVTPWEFGG

VPDGFRAFAQRLERCAVLIPGCGSAQEAGWLADAGWPVRAIDFAAQAV

ATAKAQLGAHADVVELADFFTYRPPFDVRWIYERAFLCALPPARRADY

AAQMAALLPAGGLLAGYFFVTAKPKGPPFGIERAELDALLAP

QFDLIDDWPVTDSLPVFEGHERWLTWRRR (SEQ ID NO: 85)

>GI|147750562|GB|EDK57631.1|
THIOPURINE S-METHYLTRANSFERASE
FAMILY PROTEIN [*BURKHOLDERIA MALLET* JHU]
MTNEANQPEAAGQAAGDAQPASPAGPAHIANPANPANPPALPSFSPPA

AASSSASSAAPFSSRDPGDASFWDERFEQGVTPWDSARVPDAFAARHA

RVPVLIPGCGSAYEARWLARAGWPVRAIDFSAQAVAAARRELGEDAGL

VEQADFFTYAPPFVPQWIYERAFLCAIPRSRRADYARRMAEL

LPPGGFLAGFFFIGATPKGPPFGIERAELDALLCPHFALVEDEPVAD

SLPVFAGRERWLAWRRS (SEQ ID NO: 96)

>GI|126220666|GB|ABN84172.1|
PUTATIVE THIOPURINE S-
METHYLTRANSFERASE [*BURKHOLDERIA PSEUDOMALLEI* 668]
MKDRLMSQGDGVTNEANQPEAAGQAAGDAQPASPAGPAHIANPANPAN

PANPPALPSLSPPAAAPSSASSAAHFSSRDPGDASFWDERFEQGVTPW

DSARVPDAFAAFAARHARVPVLIPGCGSAYEARWLARAGWLVRAIDFS

TABLE 6-continued

AQAVAAARRELGEDARLVEQADFFTYAPPFVPQWIYERAFLCAIPRSR

RADYARRMAELLPPGGFLAGFFFIGATPKGPPEGIERAELDALLCPRF

ALVEDEPVADSLPVFAGRERWLAWRRS (SEQ ID NO: 97)

>GI|77968269|GB|ABB09649.1|
THIOPURINE S-METHYLTRANSFERASE
[BURKHOLDERIA SP. 383]
MSDPKQPKPNAPAAADFTTRDPGNASFWNERFERGVTPWEFGGVPEGF

SVFAHRLELCAVLIPGCGSAQEAGWLAEAGWPVRAIDFAAQAVAAAKA

QLGAHAGVVEQADFFAYRPPFDVQWVYERAFLCALPPAMRADYAARM

AELLPADGLLAGYFFLMAKPKGPPFGIERAELDALLTPHFELI

EDLPVTDSLAVFEGHERWLTWRRR (SEQ ID NO: 87)

>GI|115282818|GB|ABI88335.1|
THIOPURINE S-METHYLTRANSFERASE
[BURKHOLDERIA AMBIFARIA AMMD]
MSEPKQPSTPGAADFATRDPGDASFWDERFARGVTPWEFGGVPEGFRA

FAQRLGPCAVLIPGCGSAQEAGWLAQAGWPVRAIDFAAQAVAAANAQL

GAHADVVEQADFFMYRPPFDVQWVYERAFLCALPPSLRAGYAARMAEL

LPAGALLAGYFFVTKKPKGPPEGIERAELDALLAPHFELIDD

LPVTDSLAVFEGHERWLTWRRR (SEQ ID NO: 86)

>GI|118659542|GB|EAV66286.1|
THIOPURINE S-METHYLTRANSFERASE
[BURKHOLDERIA MULTIVORANS ATCC 17616]
MSDPKHAAAPAAASFETRDPGDASFWDERFARGMTPWEFGGVPAGFRA

FASARPPCAVLIPGCGSAREAGWLAQAGWPVRAIDFSAQAVAAAKAQL

GAHADVVEQADFFAYRPPFDVQWIYERAFLCALPPARRADYAATMAAL

LPAQGLLAGYFFVADKQKGPPFGITRGELDALLGAHFELIDD

APVSDSLPVFEGHERWLAWRRR (SEQ ID NO: 88)

>GI|113866478|REF|YP_724967.1|
THIOPURINE S-METHYLTRANSFERASE
(TPMT) [RALSTONIA EUTROPHA H16]
MSDPAKPVPTFATRNAADPAFWDERFEQGFTPWDQGGVPEEFRQFIEG

RAPCPTLVPGCGNGWEAAWLFERGWPVTAIDFSPQAVASARQTLGPAG

VVVQQGDFFAFTPQPPCELIYERAFLCALPPAMRADYAARVAQLLPPG

GLLAGYFYLGENRGGPPFAMPAEALDALLAPAFERLEDRPTA

APLPVFQGQERWQVWRRRSG (SEQ ID NO: 54)

>GI|151577463|GB|EDN41864.1|
THIOPURINE S-METHYLTRANSFERASE
[RALSTONIA PICKETTII 12D]
MAEPPVFQSRDAADPAFWDERFSREHTPWDAAGVPAAFQQFCESQPVP

LSTLIPGCGSAYEAGWLAERGWPVTAIDFAPSAVASARAVLGPHADVV

EMADFFGESPARSVQWIYERAFLCAMPRRLWPDYAAQVAKLLPPGGLL

AGFFAVVEGREAVPKGPPFETTQPELDALLSPAFERISDIPI

AEADSIPVFAGRERWQVWRRRAD (SEQ ID NO: 59)

>GI|34102667|GB|AAQ59032.1|
CONSERVED HYPOTHETICAL PROTEIN
[CHROMOBACTERIUM VIOLACEUM ATCC 12472]
MADSSRADFWEQRYREGVTPWEGGQLPPRARAFFAAQRPLRVLMPGCG

SAADLPPLLAMGHDVLAVDFSEAAIELAARQWPEAAGRLLLADFFQLQ

MPAFDCLFERAFLCALPVGMRSQYAERVAALIAPGGALAGVFFVADTE

RGPPFGMQAEALRELLSPWFELEEDLALDESVAVFRNRERWM

VWRRRGFDLGQVSEHESTGNCGAHRKE (SEQ ID NO: 98)

>GI|157353828|EMB|CAO46360.1|UNNAMED
PROTEIN PRODUCT [VITIS
VINIFERA]
MGLCVPSGRISGGVCGLLSGRSLTWAKNLGVSTTQLRMSNNGSSIESN

PKVQKLNQIIGSDSAGGWEKSWQQGHTPWDLGKPTPIIQHLHQTGTLP

SGKTLVPGCGCGYDVVTIACPERFVVGLDISDSAIKKAKELSSSLWNA

NHFTFLKEDFFTWNPTELFDLIFDYTFFCAIEPDMRSVWAKRMRHLLK

PDGELLTLMFPISDHAGGPPYKVSVADYEEVLHPMGFKAVSIVDNKMA

IGPRKGREKLGRWKRTPSKSLL (SEQ ID NO: 24)

>GI|46102042|GB|EAK87275.1|
HYPOTHETICAL PROTEIN UM06489.1
[USTILAGO MAYDIS 521]
MTSSLSKDDQIQNLRRLFADSGVPNDPKAWDQAWIDSTTPWDANRPQP

ALVELLEGAHDADAKVPDVDGNLIPVSQAIPKGDGTAVVPGCGRGYD

ARVFAERGLTSYGVDISSNAVAAANKWLGDQDLPTELDDKVNFAEADF

FTLGTSKSLVLELSKPGQATLAYDYTFLCAIPPSLRTTWAETY

TRLLAKHGVLIALVFPIHGDRPGGPPFSISPQLVRELLGSQKNADGSA

AWTELVELKPKGPETRPDVERMMVWRRS (SEQ ID NO: 30)

>GI|134057747|EMB|CAK38144.1|UNNAMED
PROTEIN PRODUCT [ASPERGILLUS NIGER]
MSEAPNPPVQGRLISHFADRRAEDQGSGWSALWDSNESVLWDRGSPSI

ALVDVVEQQQDVFFPYTRDGRRKKALVPGCGRGYDPVMLALHGEDVYG

LDISATGVSEATKYATSEMQSPQDVKFIAGDFFSSEWESQALQDGDKF

DLIYDYTFLCALHPDLRRKWAERMSQLLHPGGLLVCLEFPMY

KDTSLPGPPWGLNGVHWDLLARGGDGITNITKEEEDEDSGIQLSGQFR

RAQYFRPIRSYPSGKGTDMLSIYVRR (SEQ ID NO: 34)

>GI|46137187|REF|XP_390285.1|
HYPOTHETICAL PROTEIN FG10109.1
[GIBBERELLA ZEAE PH-1]
MATENPLEDRISSVPFAEQGPKWDSCWKDALTPWDRGTASIALHDLLA

QRPDLVPPSQHQDHRGHPLRDATGAIQKKTALVPGCGRGHDVLLLSSW

GYDVWGLDYSAAAKEEAIKNQKQAESEGLYMPVDGLDKGKIHWITGNF

FAQDWSKGAGDDGKFDLIYDYTFLCALPPDARPKWAKRMTELLSHDGR

LICLEFPSTKPMSANGPPWGVSPELYEAL

LAAPGEEIAYNDDGTVHEDPCSKPWAD

ALHRLSLLKPTRTHKAGMSPEGAVMDFLSVWSR (SEQ ID NO: 37)

>GI|88184126|GB|EAQ91594.1|
HYPOTHETICAL PROTEIN CHGG_03529
[CHAETOMIUM GLOBOSUM CBS 148.51]
MAHPKSDPPGRLITHFANRDRQSQKAGWSELWDSDQTDLWDRGMPSPA

LIDFITTRRDIIGRLGGGRRRPRALVPGCGRGYDVVMLAFHGEDAIGL

EVSQTAVNSARAYAEVELSDPSAYNFATEDDEKRRATCQPGTVSFVC

GDFFQREWETSCFAPGDDGGEDLIYDYTFLCALLPEMRKDWAQQMREL

IRPTGVLVCLEFPLYKDVTADGPPWGLQGIYWNLLAEGGNGRMDGPAA

TDGGRGPFSRVAYIKPSRSYEMGRGTDMLSVWAPQEPSGDRKRPATAA

TABLE 6-continued

TPIPWCAHYLLNDTPAPFPLAYTTSIVVNRVCVRPSSQKQLAEARVAV

PVAGARSYMKGRLARVVRLPARRSHFQKGLGGWVKLELYCALEIRPG

CVAGLHLSYRAPLDMRCARNLEPAASPSELD (SEQ ID NO: 99)

>GI|119414856|GB|EAW24794.1|THIOL
METHYLTRANSFERASE, PUTATIVE
[NEOSARTORYA FISCHERI NRRL 181]
MSNDPRLLSSIPEFIARYKENYVEGWAELWNKSEGKPLPFDRGFPNPA

LEDTLIEKRDIIGGPIGRDAQGNTYRKKALVPGCGRGVDVLLLASFGY

DAYGLEYSDTAVQVCKEEQAKNGDKYPVRDAEIGQGKITFVQGDFFKD

TWLEKLQLPRNSFDLIYDYTFFCALDPSMRPQWALRHTQLLADSPRGH

LICLEFPRHKDTSLQGPPWASTSEAYMAHLNHPGEEIPYDANRQCSID

PSKAPSPQGLERVAYWQPARTHEVGIVEGEVQDRVSIWRRPN (SEQ ID NO: 35)

>GI|90307040|GB|EAS36671.1|
HYPOTHETICAL PROTEIN CIMG_02025
[COCCIDIOIDES IMMITIS RS]
MANEILRSAPNLSDRFKNLDGRNQGEVWDDLWKESRTPWDRGSHNPA

LEDALVEKRGFFGAPVFEDEPLRRKKALVPGCGRGVDVFLLASFGYDA

YGLEYSKTAVDVCLKEMEKYGEGGKVPPRDEKVGSGKVMFLEGDFFKD

DWVKEAGVEDGAFDLIYDYTFFCALNPALRPQWALRHRQLLAPSPRGN

LICLEEPTTKDPAALGPPFASTPAMYMEHLSHPGEDIPYDDKGHVKSN

PLQQPSDKGLERVAHWQPKRTHTVGMDDKGNVLDWVSIWRRRD (SEQ ID NO: 33)

>GI|145018369|GB|
EDK02648.1|THIOL METHYLTRANSFERASE 1,
PUTATIVE [MAGNAPORTHE GRISEA 70-15]
MGTPEQTNKLSNLFLDQPLSEHGKRWDGLWKEDYTPWDRAGPSMALYD

VLTGRPDLVPPPTGGQKKRALVPGCGRGYDVLLLSRLGYDVWGLDYSE

EATKQSIIYEKKVEQGDDGTYAELEREGVKKGKVTWLTGDFFSDEWVN

KAGVQQFDLTYDYTFLCALPISARPAWARRMADLLAHEGRLVCLQWPT

AKPWSGGGPPWGVLPEHYIAQLARPGEKVEYESDGKIPAQAMPKVVEQ

GGLRRLELVVPSRTHNSGIADGVLHDRIAVFAH (SEQ ID NO: 100)

>GI|111069917|GB|EAT91037.1|
HYPOTHETICAL PROTEIN SNOG_01388
[PHAEOSPHAERIA NODORUM SN15]
MANPNQDRLRSHFAALDPSTHASGWDSLWAEGTFIPWDRGYANPALI

DLLANPSSPPTSSDANPTPGAPKPNTIDGQGVQLPAPLEGGVRRKAL

VPGCGKGYDVALLASWGYDTWGLEVSRHAADAAKEYLKDAGEGALEG

EYKIKDAKIGKGREECVVADFFDDAWLKDVGAGEFDVIYDNTFLC

ALPPLLRPKWAARMAQLLARDGVLICLEFPTHKPASSGGPPWSLPPT

VHQELLKRPGEDISYDEGGVVVATDRAESENALVRVAHWTPKRTHN

IAVINGVVRDCVSVWRHKKQS (SEQ ID NO: 32)

>GI|39577142|EMB|CAE80965.1|
CONSERVED HYPOTHETICAL PROTEIN
[BDELLOVIBRIO BACTERIOVORUS HD100]
MAIPTNFIQIDEEGFALSREVRIQDPIVGQEILQNLKIHEGGTLLSTF

GDVPVIVEAFDEPYVAAQVNLKEDKTWEILLPYGVHYAFELESLSLD

EWDRFHGYAANKIPFVMSRKAQATFFNLLEEFGDDFIEFDGKTYDIP

TABLE 6-continued

AYWPPHKDVEKETYWSQIYQQEENPGWNLGEPAEALKDMIPRLK

ISRSRVLVLGCGEGHDAALFAAAGHFVTAVDISPLALERAKKLYGHL

PTLTFVEADLFKLPQDFDQSFDVVFEHTCYCAINPERRQELVKVWNR

VLVQGGHLMGVFFTFEKRQGPPYGGTEWELRQRLKNHYHPIFWGRW

QKSIPRRQGKELFIYTKKK (SEQ ID NO: 29)

>GI|35211380|DBJ|BAC88759.1|
GLL0818 [GLOEOBACTER VIOLACEUS PCC 7421]
MPSEESSGVDQPAFWEYRYRGGQDRWDLGQPAPTFVELLSGSEAPPL

GTVAVPGCGRGHDALLFAARGYKVCGFDFAADAIADATRLALRAGAAA

TFLQQDLENLPRPFAGLFDLVVEHTCFCAIDPVRREEYVEIVHWLLKP

GGELVAIFFAHPRPGGPPYRTDAGEIERLFSPRFKITALLPAP

MSVPSRRGEELFGRFVRA (SEQ ID NO: 44)

>GI|85818252|GB|EAQ39412.1|
HYPOTHETICAL PROTEIN MED134_07976
[DOKDONIA DONGHAENSIS MED134]
MELTSTYWNNRYAEGSTGWDLKEVSPPIKAYLDQLENKELKILIPGGG

YSYEAQYCWEQGFKNVYVVDFSQLALENLKQRVPDFPSLQLIQEDFFT

YDGQFDVIIEQTFFCALQPDLRPAYVAHMHTLLKAKGKLVGLLFNFPL

TEKGPPYGGSTTEYESLFSEHFDIQKMETAYNSVAARAGKEL

FIKMVKK (SEQ ID NO: 45)

>GI|151939691|GB|EDN58518.1|
THIOPURINE S-METHYLTRANSFERASE
(TPMT) SUPERFAMILY [VIBRIO SP. EX25]
MKQAPTINQQFWDNLFTQGTMPWDAKTTPQELKAYLENALHSGQSVF

IPGCGAAYELSSFIQYGHDVIAMDYSEQAVKMAQSTLGKHKDKVVLGD

VFNADSTHSEDVIYERAFLAALPRDQMPEYFAMVDKLLPRGGLLIGYF

VIDDDYHSRFPPFCLRSGELEGYLEPVFKLVESSVVANSVEVF

KGRERWMVWQKSCRI (SEQ ID NO: 74)

>GI|124261369|GB|ABM96363.1|
HYPOTHETICAL PROTEIN MPE_A3410
[METHYLIBIUM PETROLEIPHILUM PM1]
MSGPDLNFWQQRFDTGQLPWDRGAPSPQLAAWLGDGSLAPGRIAVPGC

GSGHEVVALARGGFSVTAIDYAPGAVRLTQGRLAAAGLAAEVVQADVL

TWQPTAPLDAVYEQTCLCALHPDHWVAYAARLHAWLRPGGTLALLAMQ

ALREGAGQGLIEGPPYHVDVNALRALLPGDRWDWPRPPYARV

PHPSSTWAELAIVLTRR (SEQ ID NO: 56)

>GI|114551449|GB|EAU54004.1|
THIOL METHYLTRANSFERASE 1-LIKE
PROTEIN [MARIPROFUNDUS FERROOXYDANS PV-1]
MTVWEERYQRGETGWDRGGVSPALTQLVDHLHLEARVLIPGCGRGHEV

IELARLGERVTAIDIAPSAIAHLSQQLEQEDLDAELVNGDLFAYAPDH

CFDAVYEQTCLCAIEPEQRADYEQRLHGWLKPEGVLYALFMQTGIRGG

PPFHCDLLMMRELFDASRWQWPEETGAVLVPHKNGRFELGHM

LRRTGR (SEQ ID NO: 51)

>GI|92394583|GB|ABE75856.1|
THIOPURINE S-METHYLTRANSFERASE
[PSYCHROBACTER CRYOHALOLENTIS K5]
MENVNQAQFWQQRYEQDSIGWDMGQVSPPLKAYIDQLPEAAKNQAVLV

TABLE 6-continued

```
PGAGNAYEVGYLHEQGFTNVTLVDFAPAPIAAFAERYPNFPAKHLICA

DFFELSPEQYQFDWVLEQTFFCAINPSRRDEYVQQMASLVKPNGKLIG

LLFDKDFGRDEPPFGGTKDEYQQRFATHEDIDIMEPSYNSHP

ARQGSELFIEMHVKD (SEQ ID NO: 50)

>GI|83849399|GB|EAP87267.1|
HYPOTHETICAL PROTEIN CA2559_00890
[CROCEIBACTER ATLANTICUS HTCC2559]
MTSNEWEQRYANNNTGWDLNTVSPPLKHYIDELSNKTLFILIPGCGNA

YEAEYLHNQGFENVFIVDLAEHPLLEFSKRVPDFPKSHILHLDFFNLT

QKFDLILEQTFFCALHPEQRLHYAHHTSKLLNSNGCLVGLFFNKEFDK

TGPPFGGNKKEYKNLFKNLFKIKKLENCYNSIKPRQGSELFF

IFEKK (SEQ ID NO: 52)

>GI|120596574|GB|ABM40010.1|
THIOPURINE S-METHYLTRANSFERASE
[POLAROMONAS NAPHTHALENIVORANS CJ2]
MAGPTTDFWQARFDNKETGWDRGAPGPQLLAWLESGALQPCRIAVPGC

GSGWEVAELARRGFEVVGIDYTPAAVERTRALLAAQGLAAEVVQADVL

AYQPHKPFEAIYEQTCLCALHPDHWVAYARQLQQWLKPQGSIWALFM

QMVRPEATDEGLIQGPPYHCDINAMRALFPAQHWAWPRPPYAK

VPHPNVGHELGLRLMLRQGR (SEQ ID NO: 60)
```

Codon-optimized nucleic acids encoding the sequences above are synthesized and inserted into expression vectors active in *E. coli, S. cervisiae*, and other host cells. The cells are cultured in the presence of carbon and halide sources and under conditions in which the methylhalide transferase is expressed un under conditions in which methyl halide is produced. The methyl halide is optionally collected and converted into non-halogenated organic molecules.

Example 9B

Identifying New Methyl Halide Transferases

As described in Example 9A, to screen for MHTs with high activity in a recombinant host, we synthesized all putative MHTs from the NCBI sequence database and assayed methyl halide production in *E. coli*t. We first identified a self-consistent set of 89 genes with similarity to known MHTs (Rhew et al., 2003, "Genetic control of methyl halide production in *Arabidopsis*," *Curr Biol* 13:1809-13; Attieh et al., 1995, "Purification and characterization of a novel methyltransferase responsible for biosynthesis of halomethanes and methanethiol in *Brassica oleracea*," *J Biol Chem* 270:9250-7; Ni and Hager, 1999, "Expression of *Batis maritima* methyl chloride transferase in *Escherichia coli*". *Proc Natl Acad Sci USA* 96:3611-5) The library contains a remarkable degree of sequence diversity, with an average of 26% amino acid identity between sequences. The library includes putative, hypothetical, and misannotated genes, as well as genes from uncharacterized organisms and environmental samples. These genes were computationally codon optimized for *E. coli* and yeast expression and constructed using automated whole gene DNA synthesis. This is an example of information-based cloning, where genetic data was retrieved from databases, the genes chemically synthesized, and function assayed, without contact with the source organisms.

Figure 10A:
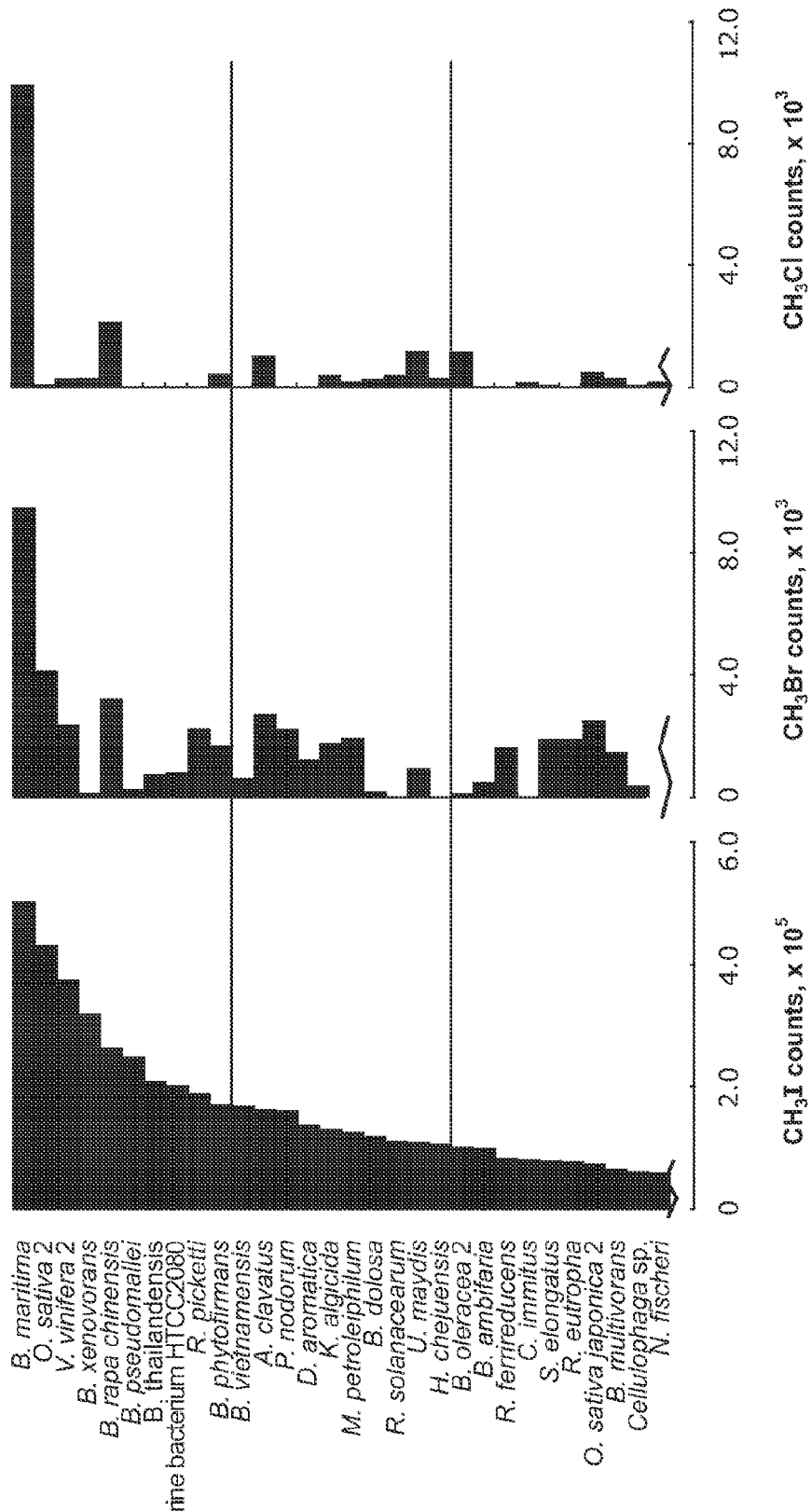
FIG. 10A-B: Screening the MHT library for methyl halide activity.
Figure 10A:
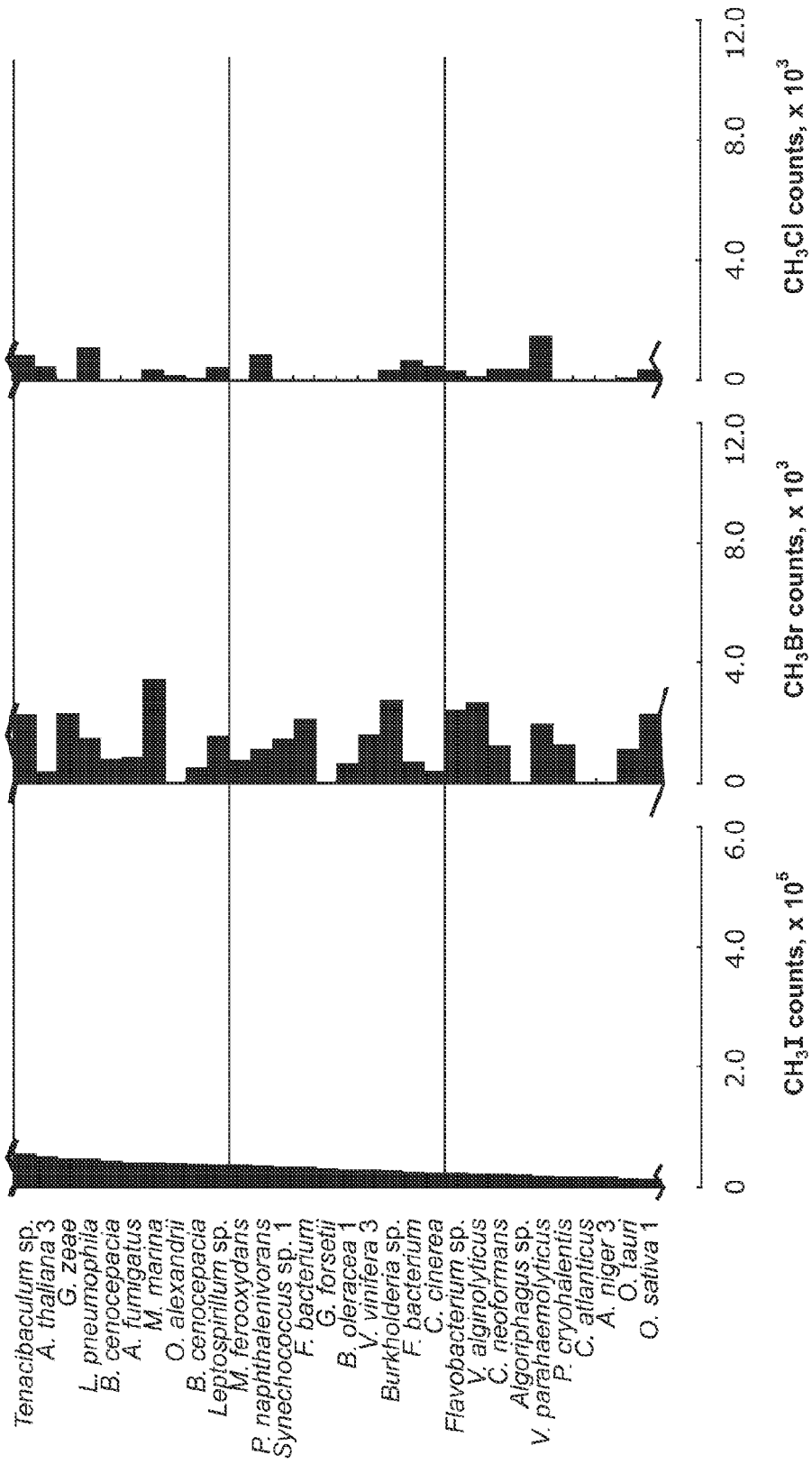
Figure 10A:
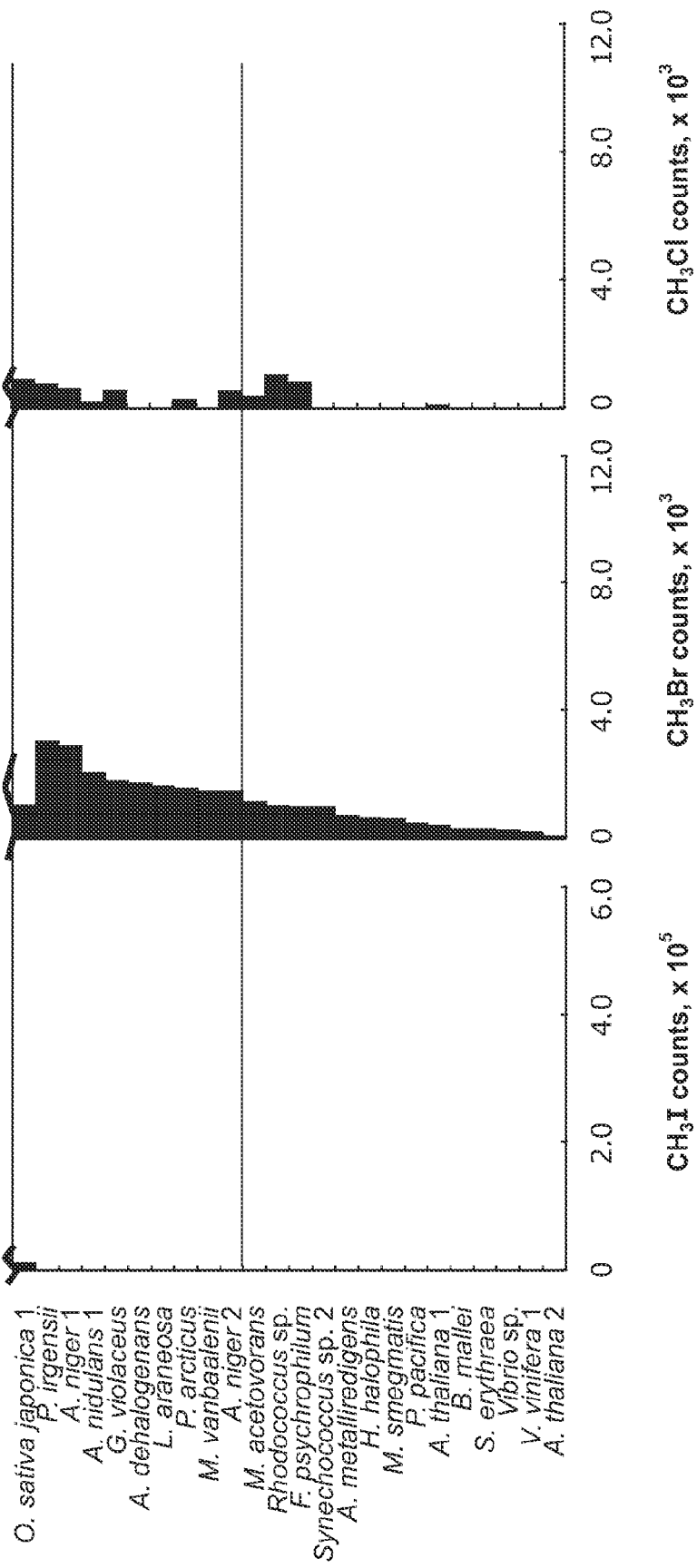
Figure 10B:
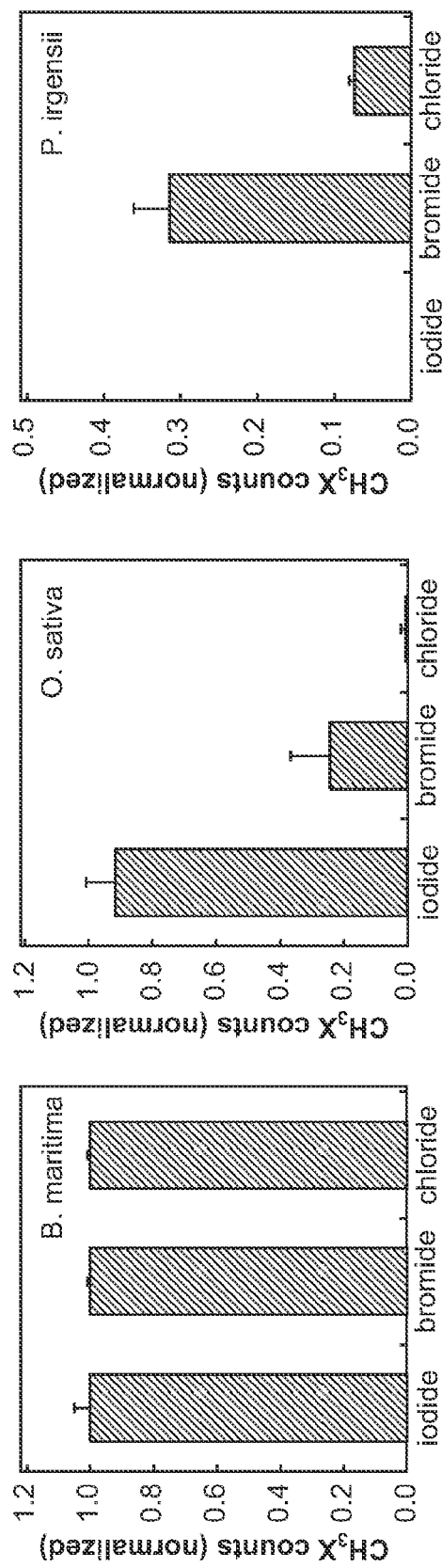
Figure 10B:
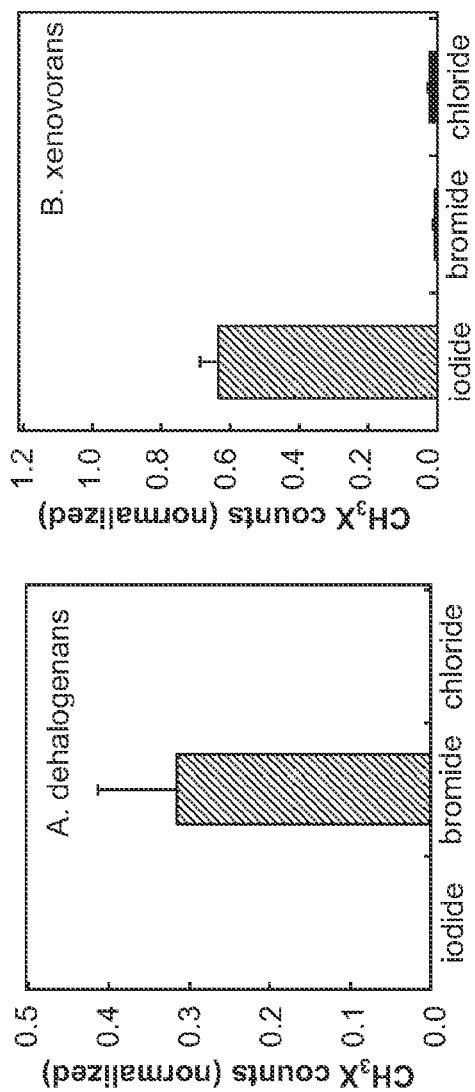

Methyl halide activity was assayed on three ions (chloride, bromide, and iodide) by adding the appropriate halide salt to the growth media. Methyl halide production was sampled by analyzing the headspace gas using GC-MS (Supplementary Information). We found a wide distribution of activities on each ion, with 51% of genes showing activity on chloride, 85% of genes showing activity on bromide, and 69% of genes showing activity on iodide (FIG. 10A). In particular, the MHT from *Batis maritima*, a halophytic plant, displayed the highest activity of all genes on each ion. Several genes showed unique specificities for given ions (FIG. 10B), a phenomenon that has also been observed on the organism level (Rhew et al., 2003, supra). The highest yield of methyl iodide is about 10-fold higher than methyl bromide, which is 10-fold higher then methyl chloride. This is consistent with the measured $K_M$ of these enzymes: I$^-$ (8.5 mM), Br$^-$ (18.5 mM), and Cl$^-$ (155 mM) (Attieh et al., 1995, supra, Ni and Hager, 1999, supra).

Example 10

Expression of *B. maritima* MHT in *Saccharomyces cerevisia*

We transferred the *B. maritima* MHT gene to the yeast *Saccharomyces cerevisia* (FIG. 11A). One advantage to metabolic engineering in a eukaryotic host is the ability to target gene products to specific cellular compartments that may be more favorable environments for enzyme function. We hypothesized that targeting the *B. maritima* MHT to the yeast vacuole could increase methyl iodide yield: the majority of SAM is sequestered in the vacuole (Farooqui et al., 1983, "Studies on compartmentation of S-adenosyl-L-methionine in *Saccharomyces cerevisiae* and isolated rat hepatocytes," *Biochim Biophys Acta* 757:342-51) and halide ions are sequestered there as well (Wada and Anraku, 1994 "Chemiosmotic coupling of ion transport in the yeast vacuole: its role in acidification inside organelles," *J Bioenerg Biomembr* 26: 631-7). We targeted the *B. maritima* MHT to the yeast vacuole using a sixteen amino acid N-terminal tag from Carboxypeptidase Y as discussed above.

Figure 11C:
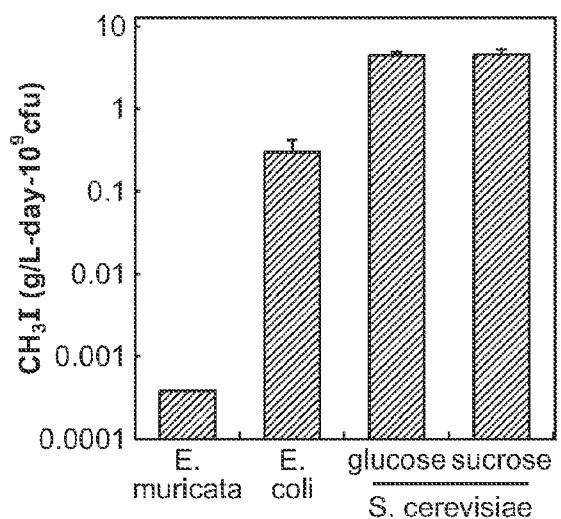

Yeast displayed high production rate from glucose or sucrose (FIGS. 11B and 11C) and normal growth rates. Methyl iodide yield from glucose was measured at 4.5 g/L-day, which is 10-fold higher than that obtained from *E. coli* and approximately 12.000-fold over the best natural source (FIG. 11C). In addition to rate, the carbon conversion efficiency of glucose to methyl iodide is an important parameter in determining process viability. For yeast, we determined the maximum theoretical yield of methyl iodide as 0.66 (mole fraction) from the balanced equation:

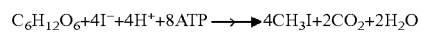
$$C_6H_{12}O_6 + 4I^- + 4H^+ + 8ATP \longrightarrow 4CH_3I + 2CO_2 + 2H_2O$$

The maximum efficiency of carbon liberation from glucose is identical to the maximum efficiency of ethanol from glucose. The measured carbon conversion efficiency of glucose to methyl iodide is 2.5%, indicating room for yield improvement by redirecting carbon flux to SAM.

Figure 11D:
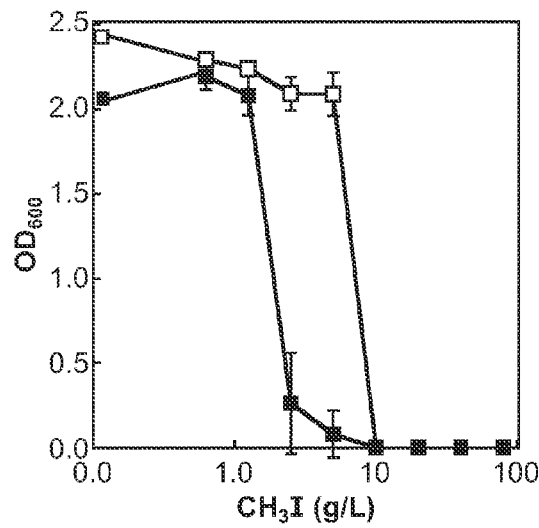

The response of the host organism to toxic effects of an overproduced metabolite is important for development of an integrated industrial process. Methyl halides are $S_N2$ methylating agents known to cause cytotoxic lesions in ssDNA and RNA. We found that yeast were resistant to deleterious methylating effects of methyl iodide up to high levels (>5 g/L, FIG. 11D). Because the fermentation is aerobic and methyl iodide has a large Henry's constant (see Moore et al., 1995, *Chemosphere* 30:1183-91), it can be recovered from the offgas of the fermentor. A mutant strain deficient in a DNA-repair gene (RAD50ΔSynnington et al., 2002, *Microbiol Mol Biol Rev* 66:630-70) showed increased sensitivity to methyl iodide, confirming the role of methylation stress in cellular toxicity.

Example 11

Methyl Iodide Production by Vacuole-targeted MHT

Figure 12:
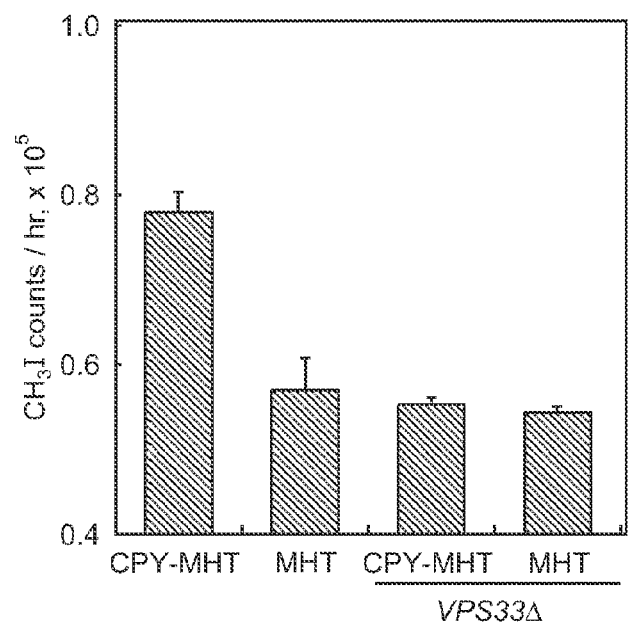
FIG. 12: Methyl iodide production improvement by targeting the *B. maritime* MHT to the yeast vacuole using a N-terminus fused CPY signal. Methyl iodide counts per hour are shown for each culture. The vacuole targeted (CPY-MHT) and cytoplasmic MHT were expressed in the W303 strain and in a W303 strain harboring a VPS33 deletion, which abolishes vacuole formation.

We fused a 16 amino acid vacuolar targeting tag (KAISLQRPLGLDKDVL, SEQ ID NO:1) from yeast carboxypeptidase Y to the N-terminus of the *B. maritima* MCT and expressed the enzyme from the vector pCM190. Assays of methyl iodide production indicated that targeting the MCT to the vacuole resulted in a 50% increase in production rate (FIG. 12). We next expressed the cytosolic and vacuolar targeted enzymes in a VPS33Δ background, which is unable to form functional vacuoles. The difference in production rate was abolished in the VPS33D strain, indicating that MCT targeting to fully formed vacuoles is necessary for enhancing the rate of methyl iodide formation.

Example 12

Materials and Methods

This example describes materials and methods used in the examples discussed above.
Strains and Plasmids
Cloning was performed using standard procedures in *E. coli* TOP10 cells (Invitrogen). Primers are listed below. The MHT coding regions were synthesized by DNA 2.0 (Menlo Park, Calif.) in the pTRC99a inducible expression vector carrying a gene for chloramphenicol resistance. Constructs were transformed into DH10B strain for methyl halide production assays. For yeast expression, the *B. maritima* MHT coding region was cloned into vector pCM190.

Cloning was performed using standard procedures in *E. coli* TOP10 cells (Invitrogen). The *B. maritima* MCT coding region was synthesized by DNA 2.0 (Menlo Park, Calif.) and amplified using specified primers with PfuUltra II (Stratagene) according to manufacturer's instructions. PCR products were purified using a Zymo Gel Extraction kit according to manufacturer's instructions. Purified expression vector (pCM190) and coding region insert were digested with restriction enzymes NotI and PstI overnight at 37 degrees and gel purified on a 1% agarose gel and extracted using a Promega Wizard SV Gel kit according to manufacturer's instructions. Vector and insert were quantitated and ligated (10 fmol vector to 30 fmol insert) with T4 ligase (Invitrogen) for 15 minutes at room temperature and transformed into chemically competent *E. coli* TOP10 cells (Invitrogen). Transformants were screened and plasmids were sequenced using specified primers to confirm cloning.

Constructs were transformed into the *S. cerevisiae* W303a background using standard lithium acetate technique and plated on selective media. Briefly, competent W303a cells were prepared by sequential washes with water and 100 mM lithium acetate in Tris-EDTA buffer. 1 □g of plasmid was incubated for 30 minutes at 30 degrees with 50 □L of competent cells along with 300 □L of PEG 4000 and 5 Dg of boiled salmon sperm DNA as a carrier. Cells were then heat-shocked at 42 degrees for 20 minutes. Cells were spun down and resuspended in 100 □L water and plated on synthetic complete uracil dropout plates. Plates were incubated at 30 degrees for 48 hours and positive transformants were confirmed by streaking on uracil dropout plates.
Media and Growth Conditions
Bacteria carrying MHT expression vectors were inoculated from freshly streaked plates and grown overnight. Cells were diluted 100-fold into media containing 1 mM IPTG and 100 mM appropriate sodium halide salt. Culture tubes were sealed with a rubber stopper and grown at 37 degrees for 3 hours. Yeast carrying MHT expression vectors were streaked on uracil dropout plates from freezer stocks (15% glycerol) and grown for 48 hours. Individual colonies were inoculated into 2 mL of synthetic complete uracil dropout media and grown overnight at 30 degrees. Cultures were next inoculated into 100 mL fresh synthetic complete uracil dropout media and grown for 24 hours. Cells were spun down and concentrated to high cell density (OD 50) in fresh YP media with 2% glucose and 100 mM sodium iodide salt. 10 mL of this concentrated culture was aliquoted into 14 mL culture tubes and sealed with a rubber stopper. Cultures were grown at 30 degrees with 250 rpm shaking.
Gas Chromatography-Mass Spectrometry
The GC-MS system consisted of a model 6850 Series II Network GC system (Agilent) and model 5973 Network mass selective system (Agilent). Oven temperature was programmed from 50 degrees (1 min) to 70 degrees (10 degrees/min). 100 □L of culture headspace was withdrawn through the rubber stopper with a syringe and manually injected into the GC-MS. Samples were confirmed as methyl iodide by comparison with commercially obtained methyl iodide (Sigma), which had a retention time of 1.50 minutes and molecular weight of 142. Methyl iodide production was compared to a standard curve of commercially available methyl iodide in YPD. Standards were prepared at 0.1 g/L, 0.5 g/L 1.0 g/L, and 10 g/L in 10 mL YP media plus 2% glucose, aliquoted into 14 mL culture tubes and sealed with rubber stoppers. Standards were incubated at 30 degrees for 1 hour and methyl iodide in the headspace was measured as above. A standard curve was fit to the data to relate headspace counts with methyl iodide.
Methyl Iodide Toxicity Assay
Individual colonies were inoculated in YP media with 2% glucose and grown overnight. Cultures were diluted to an $OD_{600}$ of 0.05 and methyl iodide was added to the specified amount. Cultures were grown at 30 degrees with 250 rpm shaking for 24 hours. $OD_{600}$ was measured by spectrometry with YP media used as a blank. Each data point was performed in triplicate. The RAD50Δ mutant was obtained from the *Saccharomyces* Genome Deletion Project (Invitrogen).
Efficiency of Glucose to Methyl Iodide Conversion
Efficiency was measured as grams of high energy carbon produced per grams of glucose consumed. Methyl iodide production was measured by GC-MS of the culture headspace and the fraction of methyl iodide in the liquid phase was calculated using a standard curve. Grams of high energy carbon (—$CH_3$) are calculated by subtracting the molecular weight of the halide ion to give a comparison with other hydrocarbon production technologies. Amount of glucose consumed was calculated by measuring glucose in the growth media before and after a defined amount of time (90 min) with a hexokinase kit (Sigma) as per manufacturer's instructions and was quantitated using a standard glucose curve.
Cumulative Methyl Iodide Production Assay
Long-term (>2 hour) methyl iodide production was measured by inducing cultures as above, assaying methyl iodide at 1 hour, and venting the culture to simulate product extraction. Cultures were then re-sealed and methyl iodide was measured again to determine how much methyl iodide had been vented. Cultures were again grown for 1 hour, measured, and vented. Data is displayed in the main text by summing the production each hour.

Growth and Methyl Iodide Production on Cellulosic Stocks

Actinotalea fermentans was obtained from ATCC (43279). A. fermentans and S. cerevisiae cells were inoculated in either YP media+2% glucose (for S. cerevisiae) or BH media+2% glucose (for A. fermentans) and grown overnight. Cultures were diluted to $OD_{600}=0.05$ in 50 mL of YP media with 20 g/L of cellulosic stock as the sole carbon source. Corn stover and poplar were pulverized using a commercially available blender with a 1 HP, 1000 W motor. Bagasse was aliquoted into the appropriate dry weight, then washed 3 times with hot water to remove soil and residual sugar. Cultures were incubated at 30 degrees with 250 rpm agitation for 36 hours. 9 mL aliquots of cultures were placed in 14 mL tubes with 1 mL of 1M sodium chloride and sealed with a rubber stopper. Headspace samples were assayed for GC-MS production as above. A. fermentans and S. cerevisiae were quantitated as described below.

Yeast and Bacteria Quantitation

S. cerevisiae and A. fermentans were quantitated from cultures grown on cellulosic stocks by plating on selective media. Cultures were diluted in sterile water and 100 uL was plated on either YPD agar+ampicillin (to quantitate S. cerevisiae) or brain-heart agar (to quantitate A. fermentans). Plates were incubated at 30 degrees for either 48 hours (for YPD) or 16 hours (for BH). Colonies were counted by hand and counts from at least 4 plates were averaged. In the switchgrass and corn stover grown cultures some unidentified background cultures were apparent but showed distinguishable morphology from A. fermentans.

Strains

E. coli (Invitrogen TOP10)

[F⁻ mcrA (mrr-hsdRMS-mcrBC) 80lacZM15 lacX74 recA1 ara139 (ara-leu)7697 galU galK rpsL ($Str^R$) endA1 nupG]

S. cerevisiae W303a (MATa leu2-3,112 trp1-1 cant-100 ura3-1 ade2-1 his3-11, 15)

A. fermentans (ATCC 43279)

* * *

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments.

The disclosures of all references and publications cited above are expressly incorporated by reference in their entireties to the same extent as if each were incorporated by reference individually.

---

The invention claimed is:

1. A method of producing methyl formate comprising
   a) combining
      i) a recombinant yeast comprising a heterologous gene encoding S-adenosylmethionine (SAM)-dependent methyl halide transferase (MHT),
      ii) a halide selected from the group consisting of chlorine, bromine and iodine; and
      iii) a carbon source;
   in a cultivation medium under conditions in which methyl formate is produced; and
   b) collecting methyl formate.

2. The method of claim 1 in which methyl halide is not collected, or the amount of methyl formate collected is at least 10-fold greater than the amount of methyl halide collected.

3. The method of claim 2 further comprising removing methyl halide from the methyl formate that is collected.

4. The method of claim 1 further comprising the step of converting the collected methyl formate into methanol.

5. The method of claim 1 wherein the organism is a yeast that is from a genus selected from the group consisting of *Saccharomyces, Pichia, Hansenula, Kluyveromyces, Yarrowia, Trichoderma* and *Scizosacchromyces*.

6. The method of claim 1 wherein the organism is a yeast that is not a methylotrophic yeast.

7. The method of claim 1 wherein MHT is from *Batis maritima*.

8. The method of claim 1 wherein the organism is a yeast genetically modified to increase flux through a S-adenosylmethionine (SAM) biosynthetic pathway.

9. The method of claim 1 wherein the organism is a yeast genetically modified to express a heterologous or modified methanol dehydrogenase.

10. The method of claim 1 wherein the organism is a yeast genetically modified to express a heterologous or modified methyl formate synthase.

11. The method of claim 1 wherein the organism is a yeast genetically modified to express a heterologous or modified hydrolytic dehalogenase.

12. The method of claim 11 wherein the yeast is genetically modified to express *Sphingomonas paucimobilis* LinB protein.

13. The method of claim 9 wherein the organism is a yeast genetically modified to express or over-express *S. cerevisia* ADH4 protein and/or *S. cerevisia* ADH3 protein.

14. The method of claim 13 wherein the yeast is *S. cerevisia* modified to over-express *S. cerevisia* ADH4 protein and/or *S. cerevisia* ADH3 protein.

15. A genetically engineered yeast cell expressing a heterologous S adenosylmethionine (SAM)-dependent methyl halide transferase (MHT) and expressing one, two or three of:
 a) a heterologous methyl formate synthase,
 b) a heterologous methanol dehydrogenase,
 c) a heterologous hydrolytic dehalogenase.

16. A genetically engineered yeast cell expressing a heterologous S adenosylmethionine (SAM)-dependent methyl halide transferase (MHT) and over-expressing one or more of a methyl formate synthase, a methanol dehydrogenase, and a hydrolytic dehydrogenase.

17. A bacteria-yeast co-culture comprising:
 (i) bacteria which metabolize cellulose and produce one or more metabolic products, and
 (ii) a yeast according to claim 15, wherein the yeast uses at least one metabolic product produced by the bacteria as a carbon source.

18. The co-culture system of claim 17 wherein the yeast is selected from the group consisting of *Saccharomyces, Pichia, Hansenula, Kluyveromyces, Yarrowia, Trichoderma* and *Scizosacchromyces*.

19. The co-culture of claim 17 in which the yeast is *S. cerevisiae* and the bacterium is *Actinotalea fermentans*.

* * * * *

SEQUENCE LISTING

```
<160> NUMBER OF SEQ ID NOS: 104

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide of N-terminal domain from
      carboxypeptidase Y

<400> SEQUENCE: 1

Lys Ala Ile Ser Leu Gln Arg Pro Leu Gly Leu Asp Lys Asp Val Leu
1               5                   10                  15

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA of recombinant ribosome binding
      site

<400> SEQUENCE: 2
attaaagagg agaaattaag c                                                   21

<210> SEQ ID NO 3
<211> LENGTH: 230
<212> TYPE: PRT
<213> ORGANISM: Batis maritima

<400> SEQUENCE: 3

Met Ser Thr Val Ala Asn Ile Ala Pro Val Phe Thr Gly Asp Cys Lys
1               5                   10                  15

Thr Ile Pro Thr Pro Glu Glu Cys Ala Thr Phe Leu Tyr Lys Val Val
                20                  25                  30
```

Asn Ser Gly Gly Trp Glu Lys Cys Trp Val Glu Glu Val Ile Pro Trp
            35                  40                  45

Asp Leu Gly Val Pro Thr Pro Leu Val Leu His Leu Val Lys Asn Asn
 50                  55                  60

Ala Leu Pro Asn Gly Lys Gly Leu Val Pro Gly Cys Gly Gly Gly Tyr
 65                  70                  75                  80

Asp Val Val Ala Met Ala Asn Pro Glu Arg Phe Met Val Gly Leu Asp
                 85                  90                  95

Ile Ser Glu Asn Ala Leu Lys Lys Ala Arg Glu Thr Phe Ser Thr Met
             100                 105                 110

Pro Asn Ser Ser Cys Phe Ser Phe Val Lys Glu Asp Val Phe Thr Trp
         115                 120                 125

Arg Pro Glu Gln Pro Phe Asp Phe Ile Phe Asp Tyr Val Phe Phe Cys
 130                 135                 140

Ala Ile Asp Pro Lys Met Arg Pro Ala Trp Gly Lys Ala Met Tyr Glu
145                 150                 155                 160

Leu Leu Lys Pro Asp Gly Glu Leu Ile Thr Leu Met Tyr Pro Ile Thr
                165                 170                 175

Asn His Glu Gly Gly Pro Pro Phe Ser Val Ser Glu Ser Glu Tyr Glu
            180                 185                 190

Lys Val Leu Val Pro Leu Gly Phe Lys Gln Leu Ser Leu Glu Asp Tyr
        195                 200                 205

Ser Asp Leu Ala Val Glu Pro Arg Lys Gly Lys Glu Lys Leu Ala Arg
    210                 215                 220

Trp Lys Lys Met Asn Asn
225                 230

<210> SEQ ID NO 4
<211> LENGTH: 213
<212> TYPE: PRT
<213> ORGANISM: Burkholderia phymatum

<400> SEQUENCE: 4

Met Ser Asp Lys Arg Pro Ser Val Pro Pro Ser Ala Pro Asp Phe Glu
1               5                   10                  15

Asn Arg Asp Pro Asn Ala Pro Gly Phe Trp Asp Glu Arg Phe Gly Arg
             20                  25                  30

Gly Phe Thr Pro Trp Asp Gln Ala Gly Val Pro Pro Ala Phe Lys Ala
         35                  40                  45

Phe Val Glu Arg His Ser Pro Val Pro Val Leu Ile Pro Gly Cys Gly
 50                  55                  60

Ser Ala Tyr Glu Ala Arg Trp Leu Ala Glu Lys Gly Trp Thr Val Arg
 65                  70                  75                  80

Ala Ile Asp Phe Ala Pro Asn Ala Val Glu Ala Ala Arg Ala Gln Leu
                 85                  90                  95

Gly Ser His Ala Ser Leu Val His Glu Ala Asp Phe Phe Thr Tyr Arg
            100                 105                 110

Pro Pro Phe Asp Pro Gly Trp Ile Tyr Glu Arg Ala Phe Leu Cys Ala
        115                 120                 125

Leu Pro Pro Ala Arg Arg Ser Asp Trp Val Ala Arg Met Ala Gln Leu
    130                 135                 140

Leu Ser Pro Gly Gly Leu Leu Ala Gly Phe Phe Ile Gly Ala Thr
145                 150                 155                 160

Glu Lys Gly Pro Pro Phe Gly Ile Glu Arg Ala Glu Leu Asp Ala Leu

```
                        165                 170                 175
Met Ser Pro Asp Phe Thr Leu Val Glu Asp Glu Pro Val Asp Asp Ser
                    180                 185                 190

Ile Ala Val Phe Ala Gly Arg Glu Arg Trp Leu Thr Trp Arg Arg Arg
                195                 200                 205

Gly Ala Ala Arg Gly
            210

<210> SEQ ID NO 5
<211> LENGTH: 199
<212> TYPE: PRT
<213> ORGANISM: Synechococcus elongatus

<400> SEQUENCE: 5

Met Thr Asn Ala Val Asn Gln Ala Gln Phe Trp Glu Gln Arg Tyr Gln
1               5                   10                  15

Glu Gly Ser Asp Arg Trp Asp Leu Gly Gln Ala Ala Pro Val Trp Arg
                20                  25                  30

Ser Leu Leu Ala Gly Thr Asn Ala Pro Ala Pro Gly Arg Ile Ala Val
            35                  40                  45

Leu Gly Cys Gly Arg Gly His Asp Ala Arg Leu Phe Ala Glu Gln Gly
        50                  55                  60

Phe Glu Val Val Gly Phe Asp Phe Ala Pro Ser Ala Ile Ala Ala Ala
65                  70                  75                  80

Gln Ala Leu Ala Gln Gly Thr Thr Ala Gln Phe Leu Gln Arg Asp Ile
                85                  90                  95

Phe Ala Leu Pro Gln Glu Phe Ala Gly Gln Phe Asp Thr Val Leu Glu
            100                 105                 110

His Thr Cys Phe Cys Ala Ile Asp Pro Asp Arg Arg Ala Glu Tyr Val
        115                 120                 125

Glu Val Val Arg Gln Ile Leu Lys Pro Lys Gly Cys Leu Leu Gly Leu
    130                 135                 140

Phe Trp Cys His Asp Arg Pro Ser Gly Pro Pro Tyr Gly Cys Ser Leu
145                 150                 155                 160

Thr Glu Leu Arg Asp Arg Phe Ala Gln Gly Trp Gln Glu Glu Gln Leu
                165                 170                 175

Glu Ser Val Thr Glu Ser Val Glu Gly Arg Arg Gly Glu Glu Tyr Leu
            180                 185                 190

Gly Arg Trp Arg Arg Leu Asp
        195

<210> SEQ ID NO 6
<211> LENGTH: 226
<212> TYPE: PRT
<213> ORGANISM: Brassica rapa

<400> SEQUENCE: 6

Met Ala Glu Val Gln Gln Asn Ser Ala His Ile Asn Gly Glu Asn Ile
1               5                   10                  15

Ile Pro Pro Glu Asp Val Ala Lys Phe Leu Pro Lys Thr Val Glu Glu
                20                  25                  30

Gly Gly Trp Glu Lys Cys Trp Glu Asp Gly Val Thr Pro Trp Asp Gln
            35                  40                  45

Gly Arg Ala Thr Pro Leu Val Val His Leu Val Glu Ser Ser Ser Leu
        50                  55                  60

Pro Leu Gly Arg Ala Leu Val Pro Gly Cys Gly Gly Gly His Asp Val
```

```
                65                  70                  75                  80
Val Ala Met Ala Ser Pro Glu Arg Tyr Val Val Gly Leu Asp Ile Ser
                    85                  90                  95

Glu Ser Ala Leu Glu Lys Ala Ala Glu Thr Tyr Gly Ser Ser Pro Lys
                100                 105                 110

Ala Lys Tyr Phe Thr Phe Val Lys Glu Asp Phe Phe Thr Trp Arg Pro
                115                 120                 125

Asn Glu Leu Phe Asp Leu Ile Phe Asp Tyr Val Val Phe Cys Ala Ile
            130                 135                 140

Glu Pro Glu Thr Arg Pro Ala Trp Ala Lys Ala Met Tyr Glu Leu Leu
145                 150                 155                 160

Lys Pro Asp Gly Glu Leu Ile Thr Leu Met Tyr Pro Ile Thr Asp His
                    165                 170                 175

Asp Gly Gly Pro Pro Tyr Lys Val Ala Phe Ser Thr Tyr Glu Asp Val
                180                 185                 190

Leu Val Pro Val Gly Phe Lys Ala Val Ser Ile Glu Glu Asn Pro Tyr
                195                 200                 205

Ser Ile Ala Thr Arg Lys Gly Lys Glu Lys Leu Ala Arg Trp Lys Lys
            210                 215                 220

Ile Asn
225

<210> SEQ ID NO 7
<211> LENGTH: 226
<212> TYPE: PRT
<213> ORGANISM: Brassica oleracea

<400> SEQUENCE: 7

Met Ala Glu Glu Gln Gln Lys Ala Gly His Ser Asn Gly Glu Asn Ile
1               5                   10                  15

Ile Pro Pro Glu Glu Val Ala Lys Phe Leu Pro Glu Thr Val Glu Glu
                20                  25                  30

Gly Gly Trp Glu Lys Cys Trp Glu Asp Gly Ile Thr Pro Trp Asp Gln
            35                  40                  45

Gly Arg Ala Thr Pro Leu Val Val His Leu Val Asp Ser Ser Ser Leu
        50                  55                  60

Pro Leu Gly Arg Ala Leu Val Pro Gly Cys Gly Gly His Asp Val
65                  70                  75                  80

Val Ala Met Ala Ser Pro Glu Arg Phe Val Val Gly Leu Asp Ile Ser
                    85                  90                  95

Glu Ser Ala Leu Glu Lys Ala Ala Glu Thr Tyr Gly Ser Ser Pro Lys
                100                 105                 110

Ala Lys Tyr Phe Thr Phe Val Lys Glu Asp Phe Phe Thr Trp Arg Pro
                115                 120                 125

Asn Glu Leu Phe Asp Leu Ile Phe Asp Tyr Val Val Phe Cys Ala Ile
            130                 135                 140

Glu Pro Glu Met Arg Pro Ala Trp Ala Lys Ser Met Tyr Glu Leu Leu
145                 150                 155                 160

Lys Pro Asp Gly Glu Leu Ile Thr Leu Met Tyr Pro Ile Thr Asp His
                    165                 170                 175

Asp Gly Gly Pro Pro Tyr Lys Val Ala Val Ser Thr Tyr Glu Asp Val
                180                 185                 190

Leu Val Pro Val Gly Phe Lys Ala Val Ser Ile Glu Glu Asn Pro Tyr
                195                 200                 205
```

Ser Ile Ala Thr Arg Lys Gly Lys Glu Lys Leu Gly Arg Trp Lys Lys
                210                 215                 220

Ile Asn
225

<210> SEQ ID NO 8
<211> LENGTH: 226
<212> TYPE: PRT
<213> ORGANISM: Brassica oleracea

<400> SEQUENCE: 8

Met Ala Glu Val Gln Gln Asn Ser Gly Asn Ser Asn Gly Glu Asn Ile
1               5                   10                  15

Ile Pro Pro Glu Asp Val Ala Lys Phe Leu Pro Lys Thr Val Asp Glu
            20                  25                  30

Gly Gly Trp Glu Lys Cys Trp Glu Asp Gly Val Thr Pro Trp Asp Gln
        35                  40                  45

Gly Arg Ala Thr Pro Leu Val Val His Leu Val Glu Ser Ser Ser Leu
50                  55                  60

Pro Leu Gly Arg Gly Leu Val Pro Gly Cys Gly Gly His Asp Val
65                  70                  75                  80

Val Ala Met Ala Ser Pro Glu Arg Tyr Val Val Gly Leu Asp Ile Ser
                85                  90                  95

Glu Ser Ala Leu Glu Lys Ala Ala Glu Thr Tyr Gly Ser Ser Pro Lys
            100                 105                 110

Ala Lys Tyr Phe Thr Phe Val Lys Glu Asp Phe Phe Thr Trp Arg Pro
        115                 120                 125

Asn Glu Leu Phe Asp Leu Ile Phe Asp Tyr Val Val Phe Cys Ala Ile
    130                 135                 140

Glu Pro Glu Thr Arg Pro Ala Trp Ala Lys Ala Met Tyr Glu Leu Leu
145                 150                 155                 160

Lys Pro Asp Gly Glu Leu Ile Thr Leu Met Tyr Pro Ile Thr Asp His
                165                 170                 175

Asp Gly Gly Pro Pro Tyr Lys Val Ala Val Ser Thr Tyr Glu Asp Val
            180                 185                 190

Leu Val Pro Val Gly Phe Lys Ala Val Ser Ile Glu Glu Asn Pro Tyr
        195                 200                 205

Ser Ile Ala Thr Arg Lys Gly Lys Glu Lys Leu Ala Arg Trp Lys Lys
    210                 215                 220

Ile Asn
225

<210> SEQ ID NO 9
<211> LENGTH: 227
<212> TYPE: PRT
<213> ORGANISM: Arabidopsis thaliana

<400> SEQUENCE: 9

Met Ala Glu Glu Gln Gln Asn Ser Ser Tyr Ser Ile Gly Gly Asn Ile
1               5                   10                  15

Leu Pro Thr Pro Glu Glu Ala Thr Phe Gln Pro Gln Val Val Ala
            20                  25                  30

Glu Gly Gly Trp Asp Lys Cys Trp Glu Asp Gly Val Thr Pro Trp Asp
        35                  40                  45

Gln Gly Arg Ala Thr Pro Leu Ile Leu His Leu Leu Asp Ser Ser Ala
50                  55                  60

```
Leu Pro Leu Gly Arg Thr Leu Val Pro Gly Cys Gly Gly His Asp
 65                  70                  75                  80

Val Val Ala Met Ala Ser Pro Glu Arg Phe Val Val Gly Leu Asp Ile
                 85                  90                  95

Ser Asp Lys Ala Leu Asn Lys Ala Asn Glu Thr Tyr Gly Ser Ser Pro
            100                 105                 110

Lys Ala Glu Tyr Phe Ser Phe Val Lys Glu Asp Val Phe Thr Trp Arg
        115                 120                 125

Pro Asn Glu Leu Phe Asp Leu Ile Phe Asp Tyr Val Phe Phe Cys Ala
    130                 135                 140

Ile Glu Pro Glu Met Arg Pro Ala Trp Gly Lys Ser Met His Glu Leu
145                 150                 155                 160

Leu Lys Pro Asp Gly Glu Leu Ile Thr Leu Met Tyr Pro Met Thr Asp
                165                 170                 175

His Glu Gly Gly Ala Pro Tyr Lys Val Ala Leu Ser Ser Tyr Glu Asp
            180                 185                 190

Val Leu Val Pro Val Gly Phe Lys Ala Val Ser Val Glu Glu Asn Pro
        195                 200                 205

Asp Ser Ile Pro Thr Arg Lys Gly Lys Glu Lys Leu Ala Arg Trp Lys
    210                 215                 220

Lys Ile Asn
225

<210> SEQ ID NO 10
<211> LENGTH: 246
<212> TYPE: PRT
<213> ORGANISM: Arabidopsis thaliana

<400> SEQUENCE: 10

Met Ala Glu Glu Gln Gln Asn Ser Asp Gln Ser Asn Gly Gly Asn Val
  1               5                  10                  15

Ile Pro Thr Pro Glu Glu Val Ala Thr Phe Leu His Lys Thr Val Glu
                 20                  25                  30

Glu Gly Gly Trp Glu Lys Cys Trp Glu Glu Ile Thr Pro Trp Asp
             35                  40                  45

Gln Gly Arg Ala Thr Pro Leu Ile Val His Leu Val Asp Thr Ser Ser
     50                  55                  60

Leu Pro Leu Gly Arg Ala Leu Val Pro Gly Cys Gly Gly His Asp
 65                  70                  75                  80

Val Val Ala Met Ala Ser Pro Glu Arg Phe Val Val Gly Leu Asp Ile
                 85                  90                  95

Ser Glu Ser Ala Leu Ala Lys Ala Asn Glu Thr Tyr Gly Ser Ser Pro
            100                 105                 110

Lys Ala Glu Tyr Phe Ser Phe Val Lys Glu Asp Val Phe Thr Trp Arg
        115                 120                 125

Pro Thr Glu Leu Phe Asp Leu Ile Phe Asp Tyr Val Phe Phe Cys Ala
    130                 135                 140

Ile Glu Pro Glu Met Arg Pro Ala Trp Ala Lys Ser Met Tyr Glu Leu
145                 150                 155                 160

Leu Lys Pro Asp Gly Glu Leu Ile Thr Leu Met Tyr Pro Ile Thr Asp
                165                 170                 175

His Val Gly Gly Pro Pro Tyr Lys Val Asp Val Ser Thr Phe Glu Glu
            180                 185                 190

Val Leu Val Pro Ile Gly Phe Lys Ala Val Ser Val Glu Glu Asn Pro
        195                 200                 205
```

```
His Ala Ile Pro Thr Arg Gln Arg Glu Ala Gly Lys Val Glu Glu Asp
    210                 215                 220

Gln Leu Ile Pro Lys Lys Glu Ile Leu Leu Phe Gly Lys Ser Val Ile
225                 230                 235                 240

Cys Val Ile Tyr Lys Glu
                245

<210> SEQ ID NO 11
<211> LENGTH: 201
<212> TYPE: PRT
<213> ORGANISM: Unknown
<220> FEATURE:
<223> OTHER INFORMATION: Leptospirillum species, synthetic polypeptide
      of methyl halide transferase thereof

<400> SEQUENCE: 11

Met Pro Asp Lys Ile Phe Trp Asn Gln Arg Tyr Leu Asp Lys Asn Thr
1               5                   10                  15

Gly Trp Asp Leu Gly Gln Pro Ala Pro Phe Val Arg Leu Val Glu
            20                  25                  30

Lys Gly Glu Phe Gly Pro Pro Gly Arg Val Leu Ile Pro Gly Ala Gly
                35                  40                  45

Arg Ser Tyr Glu Gly Ile Phe Leu Ala Ser Arg Gly Tyr Asp Val Thr
    50                  55                  60

Cys Val Asp Phe Ala Pro Gln Ala Val Arg Glu Ala Arg Glu Ala Ala
65                  70                  75                  80

Arg Gln Ala Gly Val Lys Leu Thr Val Val Glu Glu Asp Phe Phe Arg
                85                  90                  95

Leu Asp Pro Arg Thr Ile Gly Val Phe Asp Tyr Leu Val Glu His Thr
            100                 105                 110

Cys Phe Cys Ala Ile Asp Pro Pro Met Arg Gln Ala Tyr Val Asp Gln
        115                 120                 125

Ser His Ala Leu Leu Ala Pro Gly Gly Leu Leu Ile Gly Leu Phe Tyr
    130                 135                 140

Ala His Gly Arg Glu Gly Gly Pro Pro Trp Thr Thr Thr Glu Glu Glu
145                 150                 155                 160

Val Arg Gly Leu Phe Gly Lys Lys Phe Asp Leu Leu Ser Leu Gly Leu
                165                 170                 175

Thr Asp Trp Ser Val Asp Ser Arg Lys Gly Glu Leu Leu Gly Arg
            180                 185                 190

Leu Arg Arg Lys Asn Asp Arg Ile Glu
        195                 200

<210> SEQ ID NO 12
<211> LENGTH: 216
<212> TYPE: PRT
<213> ORGANISM: Cryptococcus neoformans

<400> SEQUENCE: 12

Met Ala Gln Ala Ser Gly Asp Asp Asn Ala Trp Glu Arg Trp Ala
1               5                   10                  15

Gln Gly Arg Thr Ala Phe Asp Gln Ser Ala Ala His Pro Val Phe Val
            20                  25                  30

Lys Phe Leu Lys Ser Asp Ile Ala Arg Glu Leu Gly Val Pro Lys Ser
        35                  40                  45

Gly Lys Ala Leu Val Pro Gly Cys Gly Arg Gly Tyr Asp Val His Leu
    50                  55                  60
```

```
Leu Ala Ser Thr Gly Leu Asp Ala Ile Gly Leu Asp Leu Ala Pro Thr
 65                  70                  75                  80

Gly Val Glu Ala Ala Arg Arg Trp Ile Gly Ser Gln Pro Ser Thr Ser
                 85                  90                  95

Gly Lys Ala Asp Ile Leu Val Gln Asp Phe Phe Thr Tyr Asp Pro Leu
            100                 105                 110

Glu Lys Phe Asp Leu Ile Tyr Asp Tyr Thr Phe Leu Cys Ala Leu Pro
        115                 120                 125

Pro Ser Leu Arg Gln Glu Trp Ala Arg Gln Thr Thr His Leu Ala Asn
    130                 135                 140

Ile Ala Ala Asp Thr Asn Pro Ile Leu Ile Thr Leu Met Tyr Pro Leu
145                 150                 155                 160

Pro Pro Ser Ala Lys Ser Gly Gly Pro Pro Phe Ala Leu Ser Glu Glu
                165                 170                 175

Ile Tyr Gln Glu Leu Leu Lys Glu Gln Gly Trp Lys Met Val Trp Ser
            180                 185                 190

Glu Asp Ile Glu Glu Pro Thr Arg Met Val Gly Ala Pro Gly Gly Glu
        195                 200                 205

Lys Leu Ala Val Trp Lys Arg Ile
    210                 215

<210> SEQ ID NO 13
<211> LENGTH: 246
<212> TYPE: PRT
<213> ORGANISM: Oryza sativa

<400> SEQUENCE: 13

Met Ala Ser Ala Ile Val Asp Val Ala Gly Gly Gly Arg Gln Gln Ala
1               5                   10                  15

Leu Asp Gly Ser Asn Pro Ala Val Ala Arg Leu Arg Gln Leu Ile Gly
            20                  25                  30

Gly Gly Gln Glu Ser Ser Asp Gly Trp Ser Arg Cys Trp Glu Glu Gly
        35                  40                  45

Val Thr Pro Trp Asp Leu Gly Gln Arg Thr Pro Ala Val Val Glu Leu
    50                  55                  60

Val His Ser Gly Thr Leu Pro Ala Gly Asp Ala Thr Val Leu Val
 65                  70                  75                  80

Pro Gly Cys Gly Ala Gly Tyr Asp Val Val Ala Leu Ser Gly Pro Gly
                 85                  90                  95

Arg Phe Val Val Gly Leu Asp Ile Cys Asp Thr Ala Ile Gln Lys Ala
            100                 105                 110

Lys Gln Leu Ser Ala Ala Ala Ala Ala Asp Gly Gly Asp Gly
        115                 120                 125

Ser Ser Ser Phe Phe Ala Phe Val Ala Asp Asp Phe Phe Thr Trp Glu
    130                 135                 140

Pro Pro Glu Pro Phe His Leu Ile Phe Asp Tyr Thr Phe Phe Cys Ala
145                 150                 155                 160

Leu His Pro Ser Met Arg Pro Ala Trp Ala Lys Arg Met Ala Asp Leu
                165                 170                 175

Leu Arg Pro Asp Gly Glu Leu Ile Thr Leu Met Tyr Leu Ala Glu Gly
            180                 185                 190

Gln Glu Ala Gly Pro Pro Phe Asn Thr Thr Val Leu Asp Tyr Lys Glu
        195                 200                 205

Val Leu Asn Pro Leu Gly Leu Val Ile Thr Ser Ile Glu Asp Asn Glu
```

```
                210               215               220
Val Ala Val Glu Pro Arg Lys Gly Met Glu Lys Ile Ala Arg Trp Lys
225                 230                 235                 240

Arg Met Thr Lys Ser Asp
                245

<210> SEQ ID NO 14
<211> LENGTH: 263
<212> TYPE: PRT
<213> ORGANISM: Ostreococcus tauri

<400> SEQUENCE: 14

Met Thr Thr Ser Ser Ala Pro Thr Arg His Thr Ser Met Arg Val Ala
1               5                   10                  15

Leu Ala Ala Pro Ala Thr Val Thr Arg Arg Leu Gly Thr Tyr Lys Arg
            20                  25                  30

Val Phe Asp Arg Arg Ala Met Ser Thr Arg Ala Ile Asp Gly Ala Val
        35                  40                  45

Thr Ser Asn Ala Gly Asp Phe Ala Arg Gln Asp Gly Ser Thr Asp Trp
    50                  55                  60

Glu Gly Met Trp Ser Arg Gly Ile Thr Lys Gly Ala Ala Phe Asp Cys
65                  70                  75                  80

Ser Arg Thr Glu Pro Ala Phe Gln Asn Ala Leu Asp Ala Lys Glu Ile
                85                  90                  95

Ala Ile Gly Ser Gly Arg Ala Leu Val Pro Gly Cys Gly Arg Gly Tyr
            100                 105                 110

Ala Leu Ala Ser Leu Ala Arg Ala Gly Phe Gly Asp Val Val Gly Leu
        115                 120                 125

Glu Ile Ser Glu Thr Ala Lys Glu Ala Cys Glu Glu Gln Leu Lys Ala
    130                 135                 140

Glu Ser Ile Pro Glu Thr Ala Arg Val Glu Val Val Ala Asp Phe
145                 150                 155                 160

Phe Ala Tyr Asp Pro Lys Glu Ala Phe Asp Ala Ala Tyr Asp Cys Thr
                165                 170                 175

Phe Leu Cys Ala Ile Asp Pro Arg Arg Glu Glu Trp Ala Arg Lys
            180                 185                 190

His Ala Ser Leu Ile Lys Pro Gly Gly Thr Leu Val Cys Leu Val Phe
        195                 200                 205

Pro Val Gly Asp Phe Glu Gly Gly Pro Pro Tyr Ala Leu Thr Pro Glu
    210                 215                 220

Ile Val Arg Glu Leu Leu Ala Pro Ala Gly Phe Glu Glu Ile Glu Leu
225                 230                 235                 240

Arg Glu Thr Pro Ala Glu Met Tyr Ala Arg Gly Arg Leu Glu Tyr Leu
                245                 250                 255

Phe Thr Trp Arg Arg Arg Ser
            260

<210> SEQ ID NO 15
<211> LENGTH: 201
<212> TYPE: PRT
<213> ORGANISM: Dechloromonas aromatica

<400> SEQUENCE: 15

Met Ser Glu Thr Ile Lys Pro Pro Glu Gln Arg Pro Glu His Pro Asp
1               5                   10                  15

Phe Trp Cys Lys Arg Phe Gly Glu Gly Val Thr Pro Trp Asp Ala Gly
```

```
                20                  25                  30
Lys Val Pro Met Ala Phe Val Asp Phe Val Gly Ala Gln Thr Thr Pro
                35                  40                  45
Leu Asn Ser Leu Ile Pro Gly Cys Gly Ser Ala Trp Glu Ala Ala His
 50                  55                  60
Leu Ala Glu Leu Gly Trp Pro Val Thr Ala Leu Asp Phe Ser Pro Leu
 65                  70                  75                  80
Ala Ile Glu Lys Ala Arg Glu Val Leu Gly Asp Ser Pro Val Lys Leu
                85                  90                  95
Val Cys Ala Asp Phe Phe Thr Phe Ala Pro Arg Gln Pro Leu Asp Leu
                100                 105                 110
Ile Tyr Glu Arg Ala Phe Leu Cys Ala Leu Pro Arg Lys Leu Trp Ala
                115                 120                 125
Asp Trp Gly Lys Gln Val Ala Glu Leu Leu Pro Ser Gly Ala Arg Leu
                130                 135                 140
Ala Gly Phe Phe Phe Leu Cys Asp Gln Pro Lys Gly Pro Pro Phe Gly
145                 150                 155                 160
Ile Leu Pro Ala Gln Leu Asp Glu Leu Leu Arg Pro Asn Phe Glu Leu
                165                 170                 175
Ile Glu Asp Gln Pro Val Gly Asp Ser Val Pro Val Phe Ala Gly Arg
                180                 185                 190
Glu Arg Trp Gln Val Trp Arg Arg Arg
                195                 200

<210> SEQ ID NO 16
<211> LENGTH: 224
<212> TYPE: PRT
<213> ORGANISM: Artificial Sequence
<220> FEATURE:
<223> OTHER INFORMATION: Synthetic polypeptide of hypothetical protein
      of coprinopsis cinerea.

<400> SEQUENCE: 16

Met Ala Asp Pro Asn Leu Ala Pro Glu Ile Arg Ala Lys Met Gln Glu
1               5                   10                  15
Ile Phe Lys Pro Asp Asp Arg His Ser Trp Asp Leu Leu Trp Lys Glu
                20                  25                  30
Asn Ile Thr Pro Trp Asp Ala Gly Asp Ala Gln Pro Ser Leu Ile Glu
                35                  40                  45
Leu Ile Glu Glu Ser Gly Leu Asp Phe Ala Arg Lys Gly Arg Ala Leu
 50                  55                  60
Val Pro Gly Cys Gly Thr Gly Tyr Asp Ala Val Tyr Leu Ala Ser Ala
 65                  70                  75                  80
Leu Gly Leu Gln Thr Ile Gly Met Asp Ile Ser Glu Ser Ala Val Glu
                85                  90                  95
Ala Ala Asn Arg Tyr Arg Asp Ser Ser Gly Val Gln Gly Ala Asp Arg
                100                 105                 110
Ala Ile Phe Gln Lys Ala Asp Phe Phe Thr Tyr Lys Val Pro Asp Glu
                115                 120                 125
Glu Arg Phe Asp Leu Ile Met Asp His Thr Phe Phe Cys Ala Ile His
                130                 135                 140
Pro Ser Leu Arg Pro Glu Trp Gly Gln Arg Met Ser Glu Leu Ile Lys
145                 150                 155                 160
Pro Gly Gly Tyr Leu Ile Thr Ile Cys Phe Pro Met Ile Pro Lys Val
                165                 170                 175
```

Glu Thr Gly Pro Pro Tyr Tyr Leu Arg Pro His Tyr Asp Glu Val
            180                 185                 190

Leu Lys Glu Thr Phe Gly Lys Val Tyr Asp Lys Val Pro Thr Lys Ser
        195                 200                 205

Ser Glu Asn His Lys Asp Lys Glu Arg Met Leu Val Trp Lys Lys Lys
210                 215                 220

<210> SEQ ID NO 17
<211> LENGTH: 195
<212> TYPE: PRT
<213> ORGANISM: Robiginitalea biformata

<400> SEQUENCE: 17

Met Thr Asp Leu Asp Arg Asp Phe Trp Glu Asp Arg Tyr Arg Ala Gly
1               5                   10                  15

Thr Asp Arg Trp Asp Leu Gly Gly Pro Ser Pro Leu Thr Ala Tyr
            20                  25                  30

Ile Asp Gly Leu Thr Asp Gln Glu Leu Arg Ile Leu Val Pro Gly Ala
        35                  40                  45

Gly Arg Gly Tyr Glu Ala Glu Tyr Leu Tyr Arg Ala Gly Phe Glu Asn
    50                  55                  60

Leu Thr Ile Val Asp Leu Ala Arg Arg Pro Leu Asp Asp Leu Arg Arg
65                  70                  75                  80

Arg Leu Pro Glu Leu Pro Ala Ala Ala Leu Gln Gln Thr Asp Phe Phe
                85                  90                  95

Ser Phe Arg Gly Gly Pro Phe Asp Leu Ile Leu Glu His Thr Phe Phe
            100                 105                 110

Cys Ala Leu Pro Pro Ala Arg Arg Pro Asp Tyr Val Gln Ala Met His
        115                 120                 125

Arg Leu Leu Val Pro Gly Gly Arg Leu Ala Gly Leu Phe Phe Asp Phe
    130                 135                 140

Pro Leu Thr Glu Asp Gly Pro Pro Phe Gly Gly Ser Glu Thr Glu Tyr
145                 150                 155                 160

Arg Asn Arg Phe Ser Ser Leu Phe His Ile Arg Lys Leu Glu Arg Ala
                165                 170                 175

Arg Asn Ser Ile Pro Pro Arg Ala Gly Thr Glu Leu Phe Phe Ile Phe
            180                 185                 190

Glu Lys Lys
        195

<210> SEQ ID NO 18
<211> LENGTH: 202
<212> TYPE: PRT
<213> ORGANISM: Maricaulis maris

<400> SEQUENCE: 18

Met Thr His Asp Glu Asn Arg Ser Ala Phe Asp Trp Glu Ala Arg Phe
1               5                   10                  15

Ile Asp Gly Asn Thr Pro Trp Glu Arg Gly Ala Leu His Pro Ala Phe
            20                  25                  30

Glu Ala Trp Gln His Gln Ser Ala Phe Ala Ala Gly Asp Arg Ala Leu
        35                  40                  45

Ile Pro Gly Cys Gly Arg Ser Pro Glu Leu Leu Ala Leu Ala Gln Ala
    50                  55                  60

Gly Leu Ala Val Thr Gly Ala Asp Leu Ser Gly Thr Ala Met Ala Trp
65                  70                  75                  80

```
Gln Arg Lys Leu Phe Ala Asp Ala Gly Gln Val Glu Leu Ile Thr
                85                  90                  95

Gly Asp Val Phe Asp Trp Gln Pro Gln Ala Leu Asp Leu Val Tyr
            100                 105                 110

Glu Gln Thr Phe Leu Cys Ala Ile His Pro Arg Leu Arg Thr Arg Tyr
            115                 120                 125

Glu Glu Ala Leu Ala Arg Trp Leu Lys Pro Gly Gly Arg Leu Tyr Ala
            130                 135                 140

Leu Phe Met Gln Lys Pro Gly Arg Gly Pro Phe Asp Cys Ala
145                 150                 155                 160

Leu Asp Ala Met Arg Ala Leu Phe Pro Ala Glu Arg Trp Thr Trp Pro
                165                 170                 175

Ala Glu Ala Asp Ile Gln Pro Trp Pro His Pro Gln Leu Asn Gly Lys
            180                 185                 190

Ala Glu Leu Gly Ala Val Leu Ile Arg Arg
            195                 200

<210> SEQ ID NO 19
<211> LENGTH: 193
<212> TYPE: PRT
<213> ORGANISM: Flavobacteria bacterium

<400> SEQUENCE: 19

Met Pro Leu Asn Lys Gln Tyr Trp Glu Asp Arg Tyr Lys Asn Asn Ser
1               5                   10                  15

Thr Gly Trp Asp Leu Gly Ile Ile Ser Thr Pro Ile Lys Glu Tyr Val
            20                  25                  30

Asn Gln Leu Glu Asn Lys Asn Ser Lys Ile Leu Ile Pro Gly Ala Gly
            35                  40                  45

Asn Ala His Glu Ala Thr Tyr Leu Val Lys Asn Gly Phe Lys Asn Ile
        50                  55                  60

Phe Ile Leu Asp Ile Ala Leu Ser Pro Leu Lys Phe Ala Lys Gln Arg
65                  70                  75                  80

Ser Lys Leu Pro Glu Glu His Leu Ile Gln Gln Asp Phe Phe Asp His
                85                  90                  95

Lys Gly Ser Tyr Asp Leu Ile Ile Glu Gln Thr Phe Phe Cys Ala Leu
            100                 105                 110

Glu Pro Arg Phe Arg Glu Ser Tyr Val Lys Lys Ile His Met Leu Leu
            115                 120                 125

Arg Asp Gln Gly Cys Leu Ile Gly Val Leu Phe Asn Phe Glu Asn Asn
        130                 135                 140

Leu Ser Ser Pro Pro Phe Gly Ser Ile Asn Glu Tyr Leu Asn Leu
145                 150                 155                 160

Phe Glu Pro Tyr Phe Glu Ile Val Thr Met Glu Pro Cys Asn Asn Ser
                165                 170                 175

Val Ile Glu Arg Gln Gly Lys Gly Ile Phe Ile Lys Leu Lys Lys Lys
            180                 185                 190

Lys

<210> SEQ ID NO 20
<211> LENGTH: 480
<212> TYPE: PRT
<213> ORGANISM: Vitis vinifera

<400> SEQUENCE: 20

Met Ala Ser Pro Asp Asn Thr Lys Pro Lys Ala Arg Ser Ser Glu Ser
```

```
  1               5                   10                  15
Val Thr Gly Gln Arg Gly Arg Arg Pro Ser Asp Arg His Trp Pro
                20                  25                  30
Cys Val Gly Glu Glu Ser Gly Ser Phe Tyr Asn Thr Ile Ala Asp Gly
                35                  40                  45
Glu Arg Gln Tyr Gln His Arg Ile Glu Leu Arg Ala Ser Lys Asn Lys
 50                  55                  60
Pro Ser Ser Trp Glu Glu Lys Trp Gln Gln Gly Leu Thr Pro Trp Asp
 65                  70                  75                  80
Leu Gly Lys Ala Thr Pro Ile Ile Glu His Leu His Gln Ala Gly Ala
                85                  90                  95
Leu Pro Asn Gly Arg Thr Leu Ile Pro Gly Cys Gly Arg Gly Tyr Asp
                100                 105                 110
Val Val Ala Ile Ala Cys Pro Glu Arg Phe Val Val Gly Leu Asp Ile
                115                 120                 125
Ser Asp Ser Ala Ile Lys Lys Ala Lys Glu Ser Ser Ser Ser Ser Trp
                130                 135                 140
Asn Ala Ser His Phe Ile Phe Leu Lys Ala Asp Phe Phe Thr Trp Asn
 145                 150                 155                 160
Pro Thr Glu Leu Phe Asp Leu Ile Ile Asp Tyr Thr Phe Phe Cys Ala
                165                 170                 175
Ile Glu Pro Asp Met Arg Pro Ala Trp Ala Ser Arg Met Gln Gln Leu
                180                 185                 190
Leu Lys Pro Asp Gly Glu Leu Leu Thr Leu Met Phe Pro Ile Ser Asp
                195                 200                 205
His Thr Gly Gly Pro Pro Tyr Lys Val Ser Ile Ala Asp Tyr Glu Lys
                210                 215                 220
Val Leu His Pro Met Arg Phe Lys Ala Val Ser Ile Val Asp Asn Glu
 225                 230                 235                 240
Met Ala Ile Gly Ser Arg Lys Lys Lys Tyr Pro Leu Lys Pro Asp Leu
                245                 250                 255
Ser Leu Phe Gly Phe Val Asp Arg Pro Lys Arg Ala Tyr Glu Ala Arg
                260                 265                 270
Ser Glu Glu Phe Arg Ile Ser Asp Trp Val Cys Gly Trp Met Gly Leu
                275                 280                 285
Cys Val Pro Ser Gly Arg Ile Ser Gly Gly Val Cys Gly Leu Leu Ser
                290                 295                 300
Gly Arg Ser Leu Thr Trp Ala Lys Asn Leu Gly Val Ser Thr Thr Gln
 305                 310                 315                 320
Leu Arg Met Ser Asn Asn Gly Ser Ser Ile Glu Ser Asn Pro Lys Val
                325                 330                 335
Gln Lys Leu Asn Gln Ile Ile Gly Ser Asp Ser Ala Gly Gly Trp Glu
                340                 345                 350
Lys Ser Trp Gln Gln Gly His Thr Pro Trp Asp Leu Gly Lys Pro Thr
                355                 360                 365
Pro Ile Ile Gln His Leu His Gln Thr Gly Thr Leu Pro Ser Gly Lys
                370                 375                 380
Thr Leu Val Pro Gly Cys Gly Cys Gly Tyr Asp Val Val Thr Ile Ala
 385                 390                 395                 400
Cys Pro Glu Arg Phe Val Val Gly Leu Asp Ile Ser Asp Ser Ala Ile
                405                 410                 415
Lys Lys Ala Lys Glu Ile Ser Asp His Ala Gly Gly Pro Pro Tyr Lys
                420                 425                 430
```

```
Val Ser Val Ala Asp Tyr Glu Glu Val Leu His Pro Met Gly Phe Lys
        435                 440                 445

Ala Val Ser Ile Val Asp Asn Lys Met Ala Ile Gly Pro Arg Lys Gly
        450                 455                 460

Arg Glu Lys Leu Gly Arg Trp Lys Arg Thr Pro Ser Lys Ser Leu Leu
465                 470                 475                 480

<210> SEQ ID NO 21
<211> LENGTH: 198
<212> TYPE: PRT
<213> ORGANISM: Halorhodospira halophila

<400> SEQUENCE: 21

Met Ser Gly Asp Pro Asp Pro Arg Arg Ala Pro Trp Glu Ala Arg Trp
1               5                   10                  15

Arg Glu Gly Arg Thr Gly Trp Asp Arg Gly Gly Val Ser Pro Thr Leu
                20                  25                  30

Glu Ala Trp Leu Ser Ala Gly Val Ile Pro Gly Arg Arg Val Leu Val
            35                  40                  45

Pro Gly Ala Gly Arg Gly Tyr Glu Val Glu Ala Leu Ala Arg Arg Gly
        50                  55                  60

Tyr Lys Val Thr Ala Val Asp Ile Ala Ala Glu Ala Cys Gln Gln Leu
65                  70                  75                  80

Arg Asp Gly Leu Asp Ala Ala Gly Val Glu Ala Arg Val Val Gln Ala
                85                  90                  95

Asp Leu Leu Ala Trp Gln Pro Asp Thr Pro Phe Asp Ala Val Tyr Glu
            100                 105                 110

Gln Thr Cys Leu Cys Ala Leu Asp Pro Ala Asp Trp Pro Ala Tyr Glu
        115                 120                 125

Gln Arg Leu Tyr Gly Trp Leu Arg Pro Gly Gly Val Leu Leu Ala Leu
    130                 135                 140

Phe Met Gln Thr Gly Ala Ser Gly Gly Pro Pro Phe His Cys Ala Leu
145                 150                 155                 160

Pro Glu Met Ala Thr Leu Phe Asp Ser Glu Arg Trp Gln Trp Pro Ala
                165                 170                 175

Glu Pro Pro Arg Gln Trp Pro His Pro Ser Gly Arg Trp Glu Glu Ala
            180                 185                 190

Val Arg Leu Leu Arg Arg
        195

<210> SEQ ID NO 22
<211> LENGTH: 226
<212> TYPE: PRT
<213> ORGANISM: Arabidopsis thaliana

<400> SEQUENCE: 22

Met Glu Asn Ala Gly Lys Ala Thr Ser Leu Gln Ser Ser Arg Asp Leu
1               5                   10                  15

Phe His Arg Leu Met Ser Glu Asn Ser Ser Gly Gly Trp Glu Lys Ser
                20                  25                  30

Trp Glu Ala Gly Ala Thr Pro Trp Asp Leu Gly Lys Pro Thr Pro Val
            35                  40                  45

Ile Ala His Leu Val Glu Thr Gly Ser Leu Pro Asn Gly Arg Ala Leu
        50                  55                  60

Val Pro Gly Cys Gly Thr Gly Tyr Asp Val Val Ala Met Ala Ser Pro
65                  70                  75                  80
```

```
Asp Arg His Val Val Gly Leu Asp Ile Ser Lys Thr Ala Val Glu Arg
                85                  90                  95

Ser Thr Lys Lys Phe Ser Thr Leu Pro Asn Ala Lys Tyr Phe Ser Phe
               100                 105                 110

Leu Ser Glu Asp Phe Phe Thr Trp Glu Pro Ala Glu Lys Phe Asp Leu
           115                 120                 125

Ile Phe Asp Tyr Thr Phe Phe Cys Ala Phe Glu Pro Gly Val Arg Pro
130             135                 140

Leu Trp Ala Gln Arg Met Glu Lys Leu Leu Lys Pro Gly Gly Glu Leu
145                 150                 155                 160

Ile Thr Leu Met Phe Pro Ile Asp Glu Arg Ser Gly Gly Pro Pro Tyr
                165                 170                 175

Glu Val Ser Val Ser Glu Tyr Glu Lys Val Leu Ile Pro Leu Gly Phe
                180                 185                 190

Glu Ala Ile Ser Ile Val Asp Asn Glu Leu Ala Val Gly Pro Arg Lys
                195                 200                 205

Gly Met Glu Lys Leu Gly Arg Trp Lys Lys Ser Ser Thr Phe His Ser
210                 215                 220

Thr Leu
225

<210> SEQ ID NO 23
<211> LENGTH: 224
<212> TYPE: PRT
<213> ORGANISM: Vitis vinifera

<400> SEQUENCE: 23

Met Ala Asn Asp Ser Thr Ser Ile Glu Ser Asn Ser Glu Leu Gln Lys
1               5                   10                  15

Ile Ser Gln Val Ile Gly Ser Gly Phe Asn Gly Ser Trp Glu Glu Lys
                20                  25                  30

Trp Gln Gln Gly Leu Thr Pro Trp Asp Leu Gly Lys Ala Thr Pro Ile
            35                  40                  45

Ile Glu His Leu His Gln Ala Gly Ala Leu Pro Asn Gly Arg Thr Leu
50                  55                  60

Ile Pro Gly Cys Gly Arg Gly Tyr Asp Val Val Ala Ile Ala Cys Pro
65                  70                  75                  80

Glu Arg Phe Val Val Gly Leu Asp Ile Ser Asp Ser Ala Ile Lys Lys
                85                  90                  95

Ala Lys Glu Ser Ser Ser Ser Trp Asn Ala Ser His Phe Ile Phe
               100                 105                 110

Leu Lys Ala Asp Phe Phe Thr Trp Asn Pro Thr Glu Leu Phe Asp Leu
           115                 120                 125

Ile Ile Asp Tyr Thr Phe Phe Cys Ala Ile Glu Pro Asp Met Arg Pro
130             135                 140

Ala Trp Ala Ser Arg Met Gln Gln Leu Leu Lys Pro Asp Gly Glu Leu
145                 150                 155                 160

Leu Thr Leu Met Phe Pro Ile Ser Asp His Thr Gly Pro Pro Tyr
                165                 170                 175

Lys Val Ser Ile Ala Asp Tyr Glu Lys Val Leu His Pro Met Arg Phe
                180                 185                 190

Lys Ala Val Ser Ile Val Asp Asn Glu Met Ala Ile Gly Ser Arg Lys
                195                 200                 205

Gly Arg Glu Lys Leu Gly Arg Trp Lys Arg Thr Asp Glu Pro Leu Leu
```

<210> SEQ ID NO 24
<211> LENGTH: 262
<212> TYPE: PRT
<213> ORGANISM: Vitis vinifera

<400> SEQUENCE: 24

Met Gly Leu Cys Val Pro Ser Gly Arg Ile Ser Gly Val Cys Gly
1               5                   10                  15

Leu Leu Ser Gly Arg Ser Leu Thr Trp Ala Lys Asn Leu Gly Val Ser
            20                  25                  30

Thr Thr Gln Leu Arg Met Ser Asn Asn Gly Ser Ser Ile Glu Ser Asn
                35                  40                  45

Pro Lys Val Gln Lys Leu Asn Gln Ile Ile Gly Ser Asp Ser Ala Gly
        50                  55                  60

Gly Trp Glu Lys Ser Trp Gln Gln Gly His Thr Pro Trp Asp Leu Gly
65                  70                  75                  80

Lys Pro Thr Pro Ile Ile Gln His Leu His Gln Thr Gly Thr Leu Pro
                85                  90                  95

Ser Gly Lys Thr Leu Val Pro Gly Cys Gly Cys Gly Tyr Asp Val Val
            100                 105                 110

Thr Ile Ala Cys Pro Glu Arg Phe Val Val Gly Leu Asp Ile Ser Asp
        115                 120                 125

Ser Ala Ile Lys Lys Ala Lys Glu Leu Ser Ser Ser Leu Trp Asn Ala
130                 135                 140

Asn His Phe Thr Phe Leu Lys Glu Asp Phe Phe Thr Trp Asn Pro Thr
145                 150                 155                 160

Glu Leu Phe Asp Leu Ile Phe Asp Tyr Thr Phe Phe Cys Ala Ile Glu
                165                 170                 175

Pro Asp Met Arg Ser Val Trp Ala Lys Arg Met Arg His Leu Leu Lys
            180                 185                 190

Pro Asp Gly Glu Leu Leu Thr Leu Met Phe Pro Ile Ser Asp His Ala
        195                 200                 205

Gly Gly Pro Pro Tyr Lys Val Ser Val Ala Asp Tyr Glu Glu Val Leu
    210                 215                 220

His Pro Met Gly Phe Lys Ala Val Ser Ile Val Asp Asn Lys Met Ala
225                 230                 235                 240

Ile Gly Pro Arg Lys Gly Arg Glu Lys Leu Gly Arg Trp Lys Arg Thr
                245                 250                 255

Pro Ser Lys Ser Leu Leu
            260

<210> SEQ ID NO 25
<211> LENGTH: 324
<212> TYPE: PRT
<213> ORGANISM: Artificial Sequence
<220> FEATURE:
<223> OTHER INFORMATION: Synthetic polypeptide of hypothetical protein
      OSI_020969 from Oryza sativa

<400> SEQUENCE: 25

Met Asp Arg Ala Leu Pro Leu Ala Leu Ser Val Ser Leu Trp Trp Leu
1               5                   10                  15

Leu Val Gly Asp Leu Gly Gly Arg Trp Thr Leu Glu Asp Asp Gly Gly
            20                  25                  30

Gly Gly Gly Val Ser Arg Phe Gly Ser Trp Tyr Arg Met Cys Gly Trp

```
              35                  40                  45
Trp Trp Val Trp Ala Asp Trp Ile Ile Glu Leu Gly Ala Ser Ser Trp
 50                  55                  60

Gly Asn Leu Phe Gly Leu Val Leu Lys Arg Arg Lys Asn Glu Ala Val
 65                  70                  75                  80

Glu Arg Asp Ser Ser Asp Gly Trp Glu Lys Ser Trp Glu Ala Ala Val
                 85                  90                  95

Thr Pro Trp Asp Leu Gly Lys Pro Thr Pro Ile Ile Glu His Leu Val
                100                 105                 110

Lys Ser Gly Thr Leu Pro Lys Gly Arg Ala Leu Gly Tyr Asp Val Val
                115                 120                 125

Ala Leu Ala Ser Pro Glu Arg Phe Val Val Gly Leu Gly Ile Ser Ser
            130                 135                 140

Thr Ala Val Glu Lys Ala Lys Gln Trp Ser Ser Ser Leu Pro Asn Ala
145                 150                 155                 160

Asp Cys Phe Thr Phe Leu Ala Asp Asp Phe Phe Lys Trp Lys Pro Ser
                165                 170                 175

Glu Gln Phe Asp Leu Ile Phe Asp Tyr Thr Phe Phe Cys Ala Leu Asp
                180                 185                 190

Pro Ser Leu Arg Leu Ala Trp Ala Glu Thr Val Ser Gly Leu Leu Lys
            195                 200                 205

Pro His Gly Glu Leu Ile Thr Leu Ile Tyr Leu Val Thr Glu Glu Ser
210                 215                 220

Ile Tyr Ser Phe Val Tyr Phe Ser Ile Glu Asp Val Met Val Leu Ile
225                 230                 235                 240

Ile Ser Tyr Cys Ala Glu Arg Ile Ser Tyr Tyr Arg Ser Val Thr Lys
                245                 250                 255

Lys Glu Asp His His Ser Ile Ile Gln Ser Pro Ile Leu Leu Arg Cys
                260                 265                 270

Pro Phe Arg Asn His Ser Tyr Gln Lys Val Leu Glu Pro Leu Gly Phe
            275                 280                 285

Lys Ala Ile Leu Met Glu Asp Asn Glu Leu Ala Ile Lys Pro Arg Lys
290                 295                 300

Ala Ile Ser Ala Phe Arg Thr Ser Glu Gln Pro Ser Leu Ala Ala Gln
305                 310                 315                 320

Asp Val Thr Glu

<210> SEQ ID NO 26
<211> LENGTH: 246
<212> TYPE: PRT
<213> ORGANISM: Artificial Sequence
<220> FEATURE:
<223> OTHER INFORMATION: Synthetic polypeptide of hypothetical protein
      OSI_013778 from Oryza sativa

<400> SEQUENCE: 26

Met Ala Ser Ala Ile Val Asp Val Ala Gly Gly Gly Arg Gln Gln Ala
 1               5                  10                  15

Leu Asp Gly Ser Asn Pro Ala Val Ala Arg Leu Arg Gln Leu Ile Gly
                20                  25                  30

Gly Gly Gln Glu Ser Ser Asp Gly Trp Ser Arg Cys Trp Glu Glu Gly
                35                  40                  45

Val Thr Pro Trp Asp Leu Gly Gln Pro Thr Pro Ala Val Val Glu Leu
 50                  55                  60

Val His Ser Gly Thr Leu Pro Ala Gly Asp Ala Thr Thr Val Leu Val
```

```
                65                  70                  75                  80
Pro Gly Cys Gly Ala Gly Tyr Asp Val Val Ala Leu Ser Gly Pro Gly
                    85                  90                  95
Arg Phe Val Val Gly Leu Asp Ile Cys Asp Thr Ala Ile Gln Lys Ala
                100                 105                 110
Lys Gln Leu Ser Ala Ala Ala Ala Ala Ala Asp Gly Gly Asp Gly
            115                 120                 125
Ser Ser Ser Phe Phe Ala Phe Val Ala Asp Asp Phe Phe Thr Trp Glu
            130                 135                 140
Pro Pro Glu Pro Phe His Leu Ile Phe Asp Tyr Thr Phe Phe Cys Ala
145                 150                 155                 160
Leu His Pro Ser Met Arg Pro Ala Trp Ala Lys Arg Met Ala Asp Leu
                165                 170                 175
Leu Arg Pro Asp Gly Glu Leu Ile Thr Leu Met Tyr Leu Ala Glu Gly
                180                 185                 190
Gln Glu Ala Gly Pro Pro Phe Asn Thr Thr Val Leu Asp Tyr Lys Glu
            195                 200                 205
Val Leu Asn Pro Leu Gly Leu Val Ile Thr Ser Ile Glu Asp Asn Glu
    210                 215                 220
Val Ala Val Glu Pro Arg Lys Gly Met Glu Lys Ile Ala Arg Trp Lys
225                 230                 235                 240
Arg Met Thr Lys Ser Asp
                245

<210> SEQ ID NO 27
<211> LENGTH: 198
<212> TYPE: PRT
<213> ORGANISM: Oryza sativa

<400> SEQUENCE: 27

Met Ala Ser Ala Ile Val Asp Val Ala Gly Gly Gly Arg Gln Gln Ala
1               5                   10                  15
Leu Asp Gly Ser Asn Pro Ala Val Ala Arg Leu Arg Gln Leu Ile Gly
                20                  25                  30
Gly Gly Gln Glu Ser Ser Asp Gly Trp Ser Arg Cys Trp Glu Glu Gly
            35                  40                  45
Val Thr Pro Trp Asp Leu Gly Gln Arg Thr Pro Ala Val Val Glu Leu
    50                  55                  60
Val His Ser Gly Thr Leu Pro Ala Gly Asp Ala Thr Thr Val Leu Val
65                  70                  75                  80
Pro Gly Cys Gly Ala Gly Tyr Asp Val Val Ala Leu Ser Gly Pro Gly
                    85                  90                  95
Arg Phe Val Val Gly Leu Asp Ile Cys Asp Thr Ala Ile Gln Lys Ala
                100                 105                 110
Lys Gln Leu Ser Ala Ala Ala Ala Ala Ala Asp Gly Gly Asp Gly
            115                 120                 125
Ser Ser Ser Phe Phe Ala Phe Val Ala Asp Asp Phe Phe Thr Trp Glu
            130                 135                 140
Pro Pro Glu Pro Phe His Leu Ile Phe Asp Tyr Thr Phe Phe Cys Ala
145                 150                 155                 160
Leu His Pro Ser Met Arg Pro Ala Trp Ala Lys Arg Met Ala Asp Leu
                165                 170                 175
Leu Arg Pro Asp Gly Glu Leu Ile Thr Leu Met Tyr Leu Val Ile Asn
                180                 185                 190
```

```
Arg Arg Tyr Gln His Val
        195

<210> SEQ ID NO 28
<211> LENGTH: 234
<212> TYPE: PRT
<213> ORGANISM: Oryza sativa

<400> SEQUENCE: 28

Met Ser Ser Ala Ala Arg Val Gly Gly Gly Gly Arg Asp Pro
1               5                   10                  15

Ser Asn Asn Pro Ala Val Gly Arg Leu Arg Glu Leu Val Gln Arg Gly
            20                  25                  30

Asp Ala Ala Asp Gly Trp Glu Lys Ser Trp Glu Ala Ala Val Thr Pro
        35                  40                  45

Trp Asp Leu Gly Lys Pro Thr Pro Ile Ile Glu His Leu Val Lys Ser
    50                  55                  60

Gly Thr Leu Pro Lys Gly Arg Ala Leu Val Pro Gly Cys Gly Thr Gly
65                  70                  75                  80

Tyr Asp Val Val Ala Leu Ala Ser Pro Glu Arg Phe Val Val Gly Leu
                85                  90                  95

Asp Ile Ser Ser Thr Ala Val Glu Lys Ala Lys Gln Trp Ser Ser Ser
            100                 105                 110

Leu Pro Asn Ala Asp Cys Phe Thr Phe Leu Ala Asp Asp Phe Phe Lys
        115                 120                 125

Trp Lys Pro Ser Glu Gln Phe Asp Leu Ile Phe Asp Tyr Thr Phe Phe
    130                 135                 140

Cys Ala Leu Asp Pro Ser Leu Arg Leu Ala Trp Ala Glu Thr Val Ser
145                 150                 155                 160

Gly Leu Leu Lys Pro His Gly Glu Leu Ile Thr Leu Ile Tyr Leu Ile
                165                 170                 175

Ser Asp Gln Glu Gly Gly Pro Pro Phe Asn Asn Thr Val Thr Asp Tyr
            180                 185                 190

Gln Lys Val Leu Glu Pro Leu Gly Phe Lys Ala Ile Leu Met Glu Asp
        195                 200                 205

Asn Glu Leu Ala Ile Lys Pro Arg Lys Gly Gln Glu Lys Leu Gly Arg
    210                 215                 220

Trp Lys Arg Phe Val Pro Gly Ser Ser Leu
225                 230

<210> SEQ ID NO 29
<211> LENGTH: 345
<212> TYPE: PRT
<213> ORGANISM: Artificial Sequence
<220> FEATURE:
<223> OTHER INFORMATION: Synthetic polypeptide of conserved hypothetical
      protein from Bdellovibrio bacteriovorus

<400> SEQUENCE: 29

Met Ala Ile Pro Thr Asn Phe Ile Gln Ile Asp Glu Glu Gly Phe Ala
1               5                   10                  15

Leu Ser Arg Glu Val Arg Ile Gln Asp Pro Ile Val Gly Gln Glu Ile
            20                  25                  30

Leu Gln Asn Leu Lys Ile His Glu Gly Gly Thr Leu Leu Ser Thr Phe
        35                  40                  45

Gly Asp Val Pro Val Ile Val Glu Ala Phe Asp Glu Pro Tyr Val Ala
    50                  55                  60
```

```
Ala Gln Val Asn Leu Lys Glu Asp Lys Thr Trp Glu Ile Leu Leu Pro
 65                  70                  75                  80

Tyr Gly Val His Tyr Ala Phe Glu Leu Glu Ser Leu Ser Leu Asp Glu
                 85                  90                  95

Trp Asp Arg Phe His Gly Tyr Ala Ala Asn Lys Ile Pro Phe Val Met
            100                 105                 110

Ser Arg Lys Ala Gln Ala Thr Phe Phe Asn Leu Leu Glu Glu Phe Gly
        115                 120                 125

Asp Asp Phe Ile Glu Phe Asp Gly Lys Thr Tyr Asp Ile Pro Ala Tyr
130                 135                 140

Trp Pro Pro His Lys Asp Val Glu Lys Glu Thr Tyr Trp Ser Gln Ile
145                 150                 155                 160

Tyr Gln Gln Glu Glu Asn Pro Gly Trp Asn Leu Gly Glu Pro Ala Glu
                165                 170                 175

Ala Leu Lys Asp Met Ile Pro Arg Leu Lys Ile Ser Arg Ser Arg Val
            180                 185                 190

Leu Val Leu Gly Cys Gly Glu Gly His Asp Ala Ala Leu Phe Ala Ala
        195                 200                 205

Ala Gly His Phe Val Thr Ala Val Asp Ile Ser Pro Leu Ala Leu Glu
210                 215                 220

Arg Ala Lys Lys Leu Tyr Gly His Leu Pro Thr Leu Thr Phe Val Glu
225                 230                 235                 240

Ala Asp Leu Phe Lys Leu Pro Gln Asp Phe Asp Gln Ser Phe Asp Val
                245                 250                 255

Val Phe Glu His Thr Cys Tyr Cys Ala Ile Asn Pro Gly Arg Arg Gln
            260                 265                 270

Glu Leu Val Lys Val Trp Asn Arg Val Leu Val Gln Gly Gly His Leu
        275                 280                 285

Met Gly Val Phe Phe Thr Phe Glu Lys Arg Gln Gly Pro Pro Tyr Gly
290                 295                 300

Gly Thr Glu Trp Glu Leu Arg Gln Arg Leu Lys Asn His Tyr His Pro
305                 310                 315                 320

Ile Phe Trp Gly Arg Trp Gln Lys Ser Ile Pro Arg Arg Gln Gly Lys
                325                 330                 335

Glu Leu Phe Ile Tyr Thr Lys Lys Lys
            340                 345

<210> SEQ ID NO 30
<211> LENGTH: 262
<212> TYPE: PRT
<213> ORGANISM: Artificial Sequence
<220> FEATURE:
<223> OTHER INFORMATION: Synthetic polypeptide of hypothetical protein
      UM06489.1 from Ustilago maydis

<400> SEQUENCE: 30

Met Thr Ser Ser Leu Ser Lys Asp Asp Gln Ile Gln Asn Leu Arg Arg
1               5                   10                  15

Leu Phe Ala Asp Ser Gly Val Pro Asn Asp Pro Lys Ala Trp Asp Gln
            20                  25                  30

Ala Trp Ile Asp Ser Thr Thr Pro Trp Asp Ala Asn Arg Pro Gln Pro
        35                  40                  45

Ala Leu Val Glu Leu Leu Glu Gly Ala His Asp Ala Asp Ala Lys Val
    50                  55                  60

Pro Asp Val Asp Gly Asn Leu Ile Pro Val Ser Gln Ala Ile Pro Lys
65                  70                  75                  80
```

```
Gly Asp Gly Thr Ala Val Val Pro Gly Cys Gly Arg Gly Tyr Asp Ala
                85                  90                  95

Arg Val Phe Ala Glu Arg Gly Leu Thr Ser Tyr Gly Val Asp Ile Ser
            100                 105                 110

Ser Asn Ala Val Ala Ala Asn Lys Trp Leu Gly Asp Gln Asp Leu
            115                 120                 125

Pro Thr Glu Leu Asp Asp Lys Val Asn Phe Ala Glu Ala Asp Phe Phe
130                 135                 140

Thr Leu Gly Thr Ser Lys Ser Leu Val Leu Glu Leu Ser Lys Pro Gly
145                 150                 155                 160

Gln Ala Thr Leu Ala Tyr Asp Tyr Thr Phe Leu Cys Ala Ile Pro Pro
                165                 170                 175

Ser Leu Arg Thr Thr Trp Ala Glu Thr Tyr Thr Arg Leu Leu Ala Lys
            180                 185                 190

His Gly Val Leu Ile Ala Leu Val Phe Pro Ile His Gly Asp Arg Pro
            195                 200                 205

Gly Gly Pro Pro Phe Ser Ile Ser Pro Gln Leu Val Arg Glu Leu Leu
        210                 215                 220

Gly Ser Gln Lys Asn Ala Asp Gly Ser Ala Ala Trp Thr Glu Leu Val
225                 230                 235                 240

Glu Leu Lys Pro Lys Gly Pro Glu Thr Arg Pro Asp Val Glu Arg Met
                245                 250                 255

Met Val Trp Arg Arg Ser
                260

<210> SEQ ID NO 31
<211> LENGTH: 276
<212> TYPE: PRT
<213> ORGANISM: Artificial Sequence
<220> FEATURE:
<223> OTHER INFORMATION: Synthetic polypeptide of hypothetical protein
      An01g09330 from Aspergillus niger

<400> SEQUENCE: 31

Met Thr Asp Gln Ser Thr Leu Thr Ala Ala Gln Gln Ser Val His Asn
1               5                   10                  15

Thr Leu Ala Lys Tyr Pro Gly Glu Lys Tyr Val Asp Gly Trp Ala Glu
            20                  25                  30

Ile Trp Asn Ala Asn Pro Ser Pro Pro Trp Asp Lys Gly Ala Pro Asn
            35                  40                  45

Pro Ala Leu Glu Asp Thr Leu Met Gln Arg Arg Gly Thr Ile Gly Asn
    50                  55                  60

Ala Leu Ala Thr Asp Ala Glu Gly Asn Arg Tyr Arg Lys Lys Ala Leu
65                  70                  75                  80

Val Pro Gly Cys Gly Arg Gly Val Asp Val Leu Leu Leu Ala Ser Phe
                85                  90                  95

Gly Tyr Asp Ala Tyr Gly Leu Glu Tyr Ser Gly Ala Ala Val Gln Ala
            100                 105                 110

Cys Arg Gln Glu Glu Lys Glu Ser Thr Thr Ser Ala Lys Tyr Pro Val
            115                 120                 125

Arg Asp Glu Glu Gly Asp Phe Phe Lys Asp Asp Trp Leu Glu Glu Leu
130                 135                 140

Gly Leu Gly Leu Asn Cys Phe Asp Leu Ile Tyr Asp Tyr Thr Phe Phe
145                 150                 155                 160

Cys Ala Leu Ser Pro Ser Met Arg Pro Asp Trp Ala Leu Arg His Thr
```

```
                165                 170                 175
Gln Leu Leu Ala Pro Ser Pro His Gly Asn Leu Ile Cys Leu Glu Tyr
            180                 185                 190

Pro Arg His Lys Asp Pro Ser Leu Pro Gly Pro Pro Phe Gly Leu Ser
        195                 200                 205

Ser Glu Ala Tyr Met Glu His Leu Ser His Pro Gly Glu Gln Val Ser
    210                 215                 220

Tyr Asp Ala Gln Gly Arg Cys Arg Gly Asp Pro Leu Arg Glu Pro Ser
225                 230                 235                 240

Asp Arg Gly Leu Glu Arg Val Ala Tyr Trp Gln Pro Ala Arg Thr His
                245                 250                 255

Glu Val Gly Lys Asp Ala Asn Gly Glu Val Gln Asp Arg Val Ser Ile
            260                 265                 270

Trp Arg Arg Arg
        275

<210> SEQ ID NO 32
<211> LENGTH: 300
<212> TYPE: PRT
<213> ORGANISM: Artificial Sequence
<220> FEATURE:
<223> OTHER INFORMATION: Synthetic polypeptide of hypothetical protein
      SNOG_01388 from Phaeosphaeria nodorum

<400> SEQUENCE: 32

Met Ala Asn Pro Asn Gln Asp Arg Leu Arg Ser His Phe Ala Ala Leu
1               5                   10                  15

Asp Pro Ser Thr His Ala Ser Gly Trp Asp Ser Leu Trp Ala Glu Gly
            20                  25                  30

Thr Phe Ile Pro Trp Asp Arg Gly Tyr Ala Asn Pro Ala Leu Ile Asp
        35                  40                  45

Leu Leu Ala Asn Pro Ser Ser Pro Pro Thr Ser Ser Asp Ala Asn Pro
    50                  55                  60

Thr Pro Gly Ala Pro Lys Pro Asn Thr Ile Asp Gly Gln Gly Val Gln
65                  70                  75                  80

Leu Pro Ala Pro Leu Glu Gly Gly Val Arg Arg Lys Ala Leu Val Pro
                85                  90                  95

Gly Cys Gly Lys Gly Tyr Asp Val Ala Leu Leu Ala Ser Trp Gly Tyr
            100                 105                 110

Asp Thr Trp Gly Leu Glu Val Ser Arg His Ala Ala Asp Ala Ala Lys
        115                 120                 125

Glu Tyr Leu Lys Asp Ala Gly Glu Gly Ala Leu Glu Gly Glu Tyr Lys
    130                 135                 140

Ile Lys Asp Ala Lys Ile Gly Lys Gly Arg Glu Glu Cys Val Val Ala
145                 150                 155                 160

Asp Phe Phe Asp Asp Ala Trp Leu Lys Asp Val Gly Ala Gly Glu Phe
                165                 170                 175

Asp Val Ile Tyr Asp Asn Thr Phe Leu Cys Ala Leu Pro Pro Leu Leu
            180                 185                 190

Arg Pro Lys Trp Ala Ala Arg Met Ala Gln Leu Leu Ala Arg Asp Gly
        195                 200                 205

Val Leu Ile Cys Leu Glu Phe Pro Thr His Lys Pro Ala Ser Ser Gly
    210                 215                 220

Gly Pro Pro Trp Ser Leu Pro Pro Thr Val His Gln Glu Leu Leu Lys
225                 230                 235                 240
```

```
Arg Pro Gly Glu Asp Ile Ser Tyr Asp Glu Gly Gly Val Val Val Ala
            245                 250                 255

Thr Asp Arg Ala Glu Ser Glu Asn Ala Leu Val Arg Val Ala His Trp
        260                 265                 270

Thr Pro Lys Arg Thr His Asn Ile Ala Val Ile Asn Gly Val Val Arg
    275                 280                 285

Asp Cys Val Ser Val Trp Arg His Lys Lys Gln Ser
290                 295                 300

<210> SEQ ID NO 33
<211> LENGTH: 282
<212> TYPE: PRT
<213> ORGANISM: Artificial Sequence
<220> FEATURE:
<223> OTHER INFORMATION: Synthetic polypeptide of hypothetical protein
      CIMG_02025 from Coccidioides immitis

<400> SEQUENCE: 33

Met Ala Asn Glu Ile Leu Arg Ser Ala Pro Asn Leu Ser Asp Arg Phe
1               5                   10                  15

Lys Asn Leu Asp Gly Arg Asn Gln Gly Glu Val Trp Asp Asp Leu Trp
            20                  25                  30

Lys Glu Ser Arg Thr Pro Trp Asp Arg Gly Ser His Asn Pro Ala Leu
        35                  40                  45

Glu Asp Ala Leu Val Glu Lys Arg Gly Phe Phe Gly Ala Pro Val Phe
    50                  55                  60

Glu Asp Glu Pro Leu Arg Arg Lys Lys Ala Leu Val Pro Gly Cys Gly
65                  70                  75                  80

Arg Gly Val Asp Val Phe Leu Leu Ala Ser Phe Gly Tyr Asp Ala Tyr
                85                  90                  95

Gly Leu Glu Tyr Ser Lys Thr Ala Val Asp Val Cys Leu Lys Glu Met
            100                 105                 110

Glu Lys Tyr Gly Glu Gly Gly Lys Val Pro Pro Arg Asp Glu Lys Val
        115                 120                 125

Gly Ser Gly Lys Val Met Phe Leu Glu Gly Asp Phe Phe Lys Asp Asp
    130                 135                 140

Trp Val Lys Glu Ala Gly Val Glu Asp Gly Ala Phe Asp Leu Ile Tyr
145                 150                 155                 160

Asp Tyr Thr Phe Phe Cys Ala Leu Asn Pro Ala Leu Arg Pro Gln Trp
                165                 170                 175

Ala Leu Arg His Arg Gln Leu Leu Ala Pro Ser Pro Arg Gly Asn Leu
            180                 185                 190

Ile Cys Leu Glu Phe Pro Thr Thr Lys Asp Pro Ala Ala Leu Gly Pro
        195                 200                 205

Pro Phe Ala Ser Thr Pro Ala Met Tyr Met Glu His Leu Ser His Pro
    210                 215                 220

Gly Glu Asp Ile Pro Tyr Asp Asp Lys Gly His Val Lys Ser Asn Pro
225                 230                 235                 240

Leu Gln Gln Pro Ser Asp Lys Gly Leu Glu Arg Val Ala His Trp Gln
                245                 250                 255

Pro Lys Arg Thr His Thr Val Gly Met Asp Asp Lys Gly Asn Val Leu
            260                 265                 270

Asp Trp Val Ser Ile Trp Arg Arg Asp
        275                 280

<210> SEQ ID NO 34
```

<211> LENGTH: 260
<212> TYPE: PRT
<213> ORGANISM: Artificial Sequence
<220> FEATURE:
<223> OTHER INFORMATION: Synthetic polypeptide of hypothetical protein
      An03g01710 from Aspergillus niger

<400> SEQUENCE: 34

Met Ser Glu Ala Pro Asn Pro Val Gln Gly Arg Leu Ile Ser His
1               5                   10                  15

Phe Ala Asp Arg Arg Ala Glu Asp Gln Gly Ser Gly Trp Ser Ala Leu
            20                  25                  30

Trp Asp Ser Asn Glu Ser Val Leu Trp Asp Arg Gly Ser Pro Ser Ile
        35                  40                  45

Ala Leu Val Asp Val Val Glu Gln Gln Gln Asp Val Phe Phe Pro Tyr
    50                  55                  60

Thr Arg Asp Gly Arg Arg Lys Lys Ala Leu Val Pro Gly Cys Gly Arg
65                  70                  75                  80

Gly Tyr Asp Pro Val Met Leu Ala Leu His Gly Phe Asp Val Tyr Gly
                85                  90                  95

Leu Asp Ile Ser Ala Thr Gly Val Ser Glu Ala Thr Lys Tyr Ala Thr
            100                 105                 110

Ser Glu Met Gln Ser Pro Gln Asp Val Lys Phe Ile Ala Gly Asp Phe
        115                 120                 125

Phe Ser Ser Glu Trp Glu Ser Gln Ala Leu Gln Asp Gly Asp Lys Phe
    130                 135                 140

Asp Leu Ile Tyr Asp Tyr Thr Phe Leu Cys Ala Leu His Pro Asp Leu
145                 150                 155                 160

Arg Arg Lys Trp Ala Glu Arg Met Ser Gln Leu Leu His Pro Gly Gly
                165                 170                 175

Leu Leu Val Cys Leu Glu Phe Pro Met Tyr Lys Asp Thr Ser Leu Pro
            180                 185                 190

Gly Pro Pro Trp Gly Leu Asn Gly Val His Trp Asp Leu Leu Ala Arg
        195                 200                 205

Gly Gly Asp Gly Ile Thr Asn Ile Thr Lys Glu Glu Glu Asp Glu Asp
    210                 215                 220

Ser Gly Ile Gln Leu Ser Gly Gln Phe Arg Arg Ala Gln Tyr Phe Arg
225                 230                 235                 240

Pro Ile Arg Ser Tyr Pro Ser Gly Lys Gly Thr Asp Met Leu Ser Ile
                245                 250                 255

Tyr Val Arg Arg
            260

<210> SEQ ID NO 35
<211> LENGTH: 282
<212> TYPE: PRT
<213> ORGANISM: Neosartorya fischeri

<400> SEQUENCE: 35

Met Ser Asn Asp Pro Arg Leu Leu Ser Ser Ile Pro Glu Phe Ile Ala
1               5                   10                  15

Arg Tyr Lys Glu Asn Tyr Val Glu Gly Trp Ala Glu Leu Trp Asn Lys
            20                  25                  30

Ser Glu Gly Lys Pro Leu Pro Phe Asp Arg Gly Phe Pro Asn Pro Ala
        35                  40                  45

Leu Glu Asp Thr Leu Ile Glu Lys Arg Asp Ile Ile Gly Gly Pro Ile
    50                  55                  60

```
Gly Arg Asp Ala Gln Gly Asn Thr Tyr Arg Lys Lys Ala Leu Val Pro
 65                  70                  75                  80

Gly Cys Gly Arg Gly Val Asp Val Leu Leu Leu Ala Ser Phe Gly Tyr
                 85                  90                  95

Asp Ala Tyr Gly Leu Glu Tyr Ser Asp Thr Ala Val Gln Val Cys Lys
            100                 105                 110

Glu Glu Gln Ala Lys Asn Gly Asp Lys Tyr Pro Val Arg Asp Ala Glu
        115                 120                 125

Ile Gly Gln Gly Lys Ile Thr Phe Val Gln Gly Asp Phe Phe Lys Asp
130                 135                 140

Thr Trp Leu Glu Lys Leu Gln Leu Pro Arg Asn Ser Phe Asp Leu Ile
145                 150                 155                 160

Tyr Asp Tyr Thr Phe Phe Cys Ala Leu Asp Pro Ser Met Arg Pro Gln
                165                 170                 175

Trp Ala Leu Arg His Thr Gln Leu Leu Ala Asp Ser Pro Arg Gly His
            180                 185                 190

Leu Ile Cys Leu Glu Phe Pro Arg His Lys Asp Thr Ser Leu Gln Gly
        195                 200                 205

Pro Pro Trp Ala Ser Thr Ser Glu Ala Tyr Met Ala His Leu Asn His
210                 215                 220

Pro Gly Glu Glu Ile Pro Tyr Asp Ala Asn Arg Gln Cys Ser Ile Asp
225                 230                 235                 240

Pro Ser Lys Ala Pro Ser Pro Gln Gly Leu Glu Arg Val Ala Tyr Trp
                245                 250                 255

Gln Pro Ala Arg Thr His Glu Val Gly Ile Val Glu Gly Glu Val Gln
            260                 265                 270

Asp Arg Val Ser Ile Trp Arg Arg Pro Asn
        275                 280

<210> SEQ ID NO 36
<211> LENGTH: 282
<212> TYPE: PRT
<213> ORGANISM: Aspergillus fumigatus

<400> SEQUENCE: 36

Met Ser Asn Asp Pro Arg Leu Val Ser Ser Ile Pro Glu Phe Ile Ala
 1               5                  10                  15

Arg Tyr Lys Glu Asn Tyr Val Glu Gly Trp Ala Glu Leu Trp Asp Lys
                20                  25                  30

Ser Glu Gly Lys Pro Leu Pro Phe Asp Arg Gly Phe Pro Asn Pro Ala
            35                  40                  45

Leu Glu Asp Thr Leu Ile Glu Lys Arg Asp Ile Ile Gly Asp Pro Ile
        50                  55                  60

Gly Arg Asp Ala Gln Gly Asn Thr Tyr Arg Lys Lys Ala Leu Val Pro
 65                  70                  75                  80

Gly Cys Gly Arg Gly Val Asp Val Leu Leu Leu Ala Ser Phe Gly Tyr
                 85                  90                  95

Asp Ala Tyr Gly Leu Glu Tyr Ser Ala Thr Ala Val Lys Val Cys Lys
            100                 105                 110

Glu Glu Gln Ala Lys Asn Gly Asp Lys Tyr Pro Val Arg Asp Ala Glu
        115                 120                 125

Ile Gly Gln Gly Lys Ile Thr Tyr Val Gln Gly Asp Phe Phe Lys Asp
130                 135                 140

Thr Trp Trp Glu Lys Leu Gln Leu Pro Arg Asn Ser Phe Asp Leu Ile
```

```
145                 150                 155                 160

Tyr Asp Tyr Thr Phe Phe Cys Ala Leu Asp Pro Ser Met Arg Pro Gln
                165                 170                 175

Trp Ala Leu Arg His Thr Gln Leu Leu Ala Asp Ser Pro Arg Gly His
            180                 185                 190

Leu Ile Cys Leu Glu Phe Pro Arg His Lys Asp Thr Ser Leu Gln Gly
        195                 200                 205

Pro Pro Trp Ala Ser Thr Ser Glu Ala Tyr Met Ala His Leu Asn His
    210                 215                 220

Pro Gly Glu Glu Ile Pro Tyr Asp Ala Asn Arg Gln Cys Ser Ile Asp
225                 230                 235                 240

Pro Ser Lys Ala Pro Ser Pro Gln Gly Leu Glu Arg Val Ala Tyr Trp
                245                 250                 255

Gln Pro Ala Arg Thr His Glu Val Gly Ile Val Glu Gly Glu Val Gln
            260                 265                 270

Asp Arg Val Ser Ile Trp Arg Arg Pro Asn
        275                 280

<210> SEQ ID NO 37
<211> LENGTH: 281
<212> TYPE: PRT
<213> ORGANISM: Artificial Sequence
<220> FEATURE:
<223> OTHER INFORMATION: Synthetic polypeptide of hypothetical protein
      FG10109.1 from Gibberella zeae

<400> SEQUENCE: 37

Met Ala Thr Glu Asn Pro Leu Glu Asp Arg Ile Ser Ser Val Pro Phe
1               5                   10                  15

Ala Glu Gln Gly Pro Lys Trp Asp Ser Cys Trp Lys Asp Ala Leu Thr
            20                  25                  30

Pro Trp Asp Arg Gly Thr Ala Ser Ile Ala Leu His Asp Leu Leu Ala
        35                  40                  45

Gln Arg Pro Asp Leu Val Pro Pro Ser Gln His Gln Asp His Arg Gly
    50                  55                  60

His Pro Leu Arg Asp Ala Thr Gly Ala Ile Gln Lys Lys Thr Ala Leu
65                  70                  75                  80

Val Pro Gly Cys Gly Arg Gly His Asp Val Leu Leu Leu Ser Ser Trp
                85                  90                  95

Gly Tyr Asp Val Trp Gly Leu Asp Tyr Ser Ala Ala Ala Lys Glu Glu
            100                 105                 110

Ala Ile Lys Asn Gln Lys Gln Ala Glu Ser Glu Gly Leu Tyr Met Pro
        115                 120                 125

Val Asp Gly Leu Asp Lys Gly Lys Ile His Trp Ile Thr Gly Asn Phe
    130                 135                 140

Phe Ala Gln Asp Trp Ser Lys Gly Ala Gly Asp Asp Gly Lys Phe Asp
145                 150                 155                 160

Leu Ile Tyr Asp Tyr Thr Phe Leu Cys Ala Leu Pro Pro Asp Ala Arg
                165                 170                 175

Pro Lys Trp Ala Lys Arg Met Thr Glu Leu Leu Ser His Asp Gly Arg
            180                 185                 190

Leu Ile Cys Leu Glu Phe Pro Ser Thr Lys Pro Met Ser Ala Asn Gly
        195                 200                 205

Pro Pro Trp Gly Val Ser Pro Glu Leu Tyr Glu Ala Leu Leu Ala Ala
    210                 215                 220
```

```
Pro Gly Glu Glu Ile Ala Tyr Asn Asp Asp Gly Thr Val His Glu Asp
225                 230                 235                 240

Pro Cys Ser Lys Pro Trp Ala Asp Ala Leu His Arg Leu Ser Leu Leu
                245                 250                 255

Lys Pro Thr Arg Thr His Lys Ala Gly Met Ser Pro Glu Gly Ala Val
            260                 265                 270

Met Asp Phe Leu Ser Val Trp Ser Arg
        275                 280
```

<210> SEQ ID NO 38
<211> LENGTH: 280
<212> TYPE: PRT
<213> ORGANISM: Artificial Sequence
<220> FEATURE:
<223> OTHER INFORMATION: Synthetic polypeptide of hypothetical protein
      An01g00930 from Aspergillus niger

<400> SEQUENCE: 38

```
Met Thr Thr Pro Thr Asp Asn Lys Phe Lys Asp Ala Gln Ala Tyr Leu
1               5                   10                  15

Ala Lys His Gln Gly Asp Ser Tyr Leu Lys Gly Trp Asp Leu Leu Trp
            20                  25                  30

Asp Lys Gly Asp Tyr Leu Pro Trp Asp Arg Gly Phe Pro Asn Pro Ala
        35                  40                  45

Leu Glu Asp Thr Leu Val Glu Arg Ala Gly Thr Ile Gly Gly Pro Ile
50                  55                  60

Gly Pro Asp Gly Lys Arg Arg Lys Val Leu Val Pro Gly Cys Gly Arg
65                  70                  75                  80

Gly Val Asp Val Leu Leu Phe Ala Ser Phe Gly Tyr Asp Ala Tyr Gly
                85                  90                  95

Leu Glu Cys Ser Ala Ala Ala Val Glu Ala Cys Lys Lys Glu Glu Glu
            100                 105                 110

Lys Val Asn Asn Ile Gln Tyr Arg Val Arg Asp Glu Lys Val Gly Lys
        115                 120                 125

Gly Lys Ile Thr Phe Val Gln Gly Asp Phe Phe Asp Asp Ala Trp Leu
130                 135                 140

Lys Glu Ile Gly Val Pro Arg Asn Gly Phe Asp Val Ile Tyr Asp Tyr
145                 150                 155                 160

Thr Phe Phe Cys Ala Leu Asn Pro Glu Leu Arg Pro Lys Trp Ala Leu
                165                 170                 175

Arg His Thr Glu Leu Leu Ala Pro Phe Pro Ala Gly Asn Leu Ile Cys
            180                 185                 190

Leu Glu Ser Pro Arg His Arg Asp Pro Leu Ala Pro Gly Pro Pro Phe
        195                 200                 205

Ala Ser Pro Ser Glu Ala Tyr Met Glu His Leu Ser His Pro Gly Glu
210                 215                 220

Glu Ile Ser Tyr Asn Asp Lys Gly Leu Val Asp Ala Asp Pro Leu Arg
225                 230                 235                 240

Glu Pro Ser Lys Ala Gly Leu Glu Arg Val Ala Tyr Trp Gln Pro Glu
                245                 250                 255

Arg Thr His Thr Val Gly Lys Asp Lys Asn Gly Val Ile Gln Asp Arg
            260                 265                 270

Val Ser Ile Trp Arg Arg Asp
        275                 280
```

<210> SEQ ID NO 39

<211> LENGTH: 288
<212> TYPE: PRT
<213> ORGANISM: Aspergillus clavatus

<400> SEQUENCE: 39

```
Met Ser Thr Pro Ser Leu Ile Pro Ser Gly Val His Glu Val Leu Ala
1               5                   10                  15
Lys Tyr Lys Asp Gly Asn Tyr Val Asp Gly Trp Ala Glu Leu Trp Asp
            20                  25                  30
Lys Ser Lys Gly Asp Arg Leu Pro Trp Asp Arg Gly Phe Pro Asn Pro
        35                  40                  45
Ala Leu Glu Asp Thr Leu Ile Gln Lys Arg Ala Ile Ile Gly Gly Pro
    50                  55                  60
Leu Gly Gln Asp Ala Gln Gly Lys Thr Tyr Arg Lys Lys Ala Leu Val
65                  70                  75                  80
Pro Gly Cys Gly Arg Gly Val Asp Val Leu Leu Ala Ser Phe Gly
            85                  90                  95
Tyr Asp Ala Tyr Gly Leu Glu Tyr Ser Ala Thr Ala Val Asp Val Cys
                100                 105                 110
Gln Glu Glu Gln Ala Lys Asn Gly Asp Gln Tyr Pro Val Arg Asp Ala
            115                 120                 125
Glu Ile Gly Gln Gly Lys Ile Thr Phe Val Gln Gly Asp Phe Phe Glu
        130                 135                 140
Asp Thr Trp Leu Glu Lys Leu Asn Leu Thr Arg Asn Cys Phe Asp Val
145                 150                 155                 160
Ile Tyr Asp Tyr Thr Phe Phe Cys Ala Leu Asn Pro Ser Met Arg Pro
                165                 170                 175
Gln Trp Ala Leu Arg His Thr Gln Leu Leu Ala Asp Ser Pro Arg Gly
            180                 185                 190
His Leu Ile Cys Leu Glu Phe Pro Arg His Lys Asp Pro Ser Val Gln
        195                 200                 205
Gly Pro Pro Trp Gly Ser Ala Ser Glu Ala Tyr Arg Ala His Leu Ser
    210                 215                 220
His Pro Gly Glu Glu Ile Pro Tyr Asp Ala Ser Arg Gln Cys Gln Phe
225                 230                 235                 240
Asp Ser Ser Lys Ala Pro Ser Ala Gln Gly Leu Glu Arg Val Ala Tyr
                245                 250                 255
Trp Gln Pro Glu Arg Thr His Glu Val Gly Lys Asn Glu Lys Gly Glu
            260                 265                 270
Val Gln Asp Arg Val Ser Ile Trp Gln Arg Pro Pro Gln Ser Ser Leu
        275                 280                 285
```

<210> SEQ ID NO 40
<211> LENGTH: 283
<212> TYPE: PRT
<213> ORGANISM: Artificial Sequence
<220> FEATURE:
<223> OTHER INFORMATION: Synthetic polypeptide of hypothetical protein AN6094.2 from Aspergillus nidulans

<400> SEQUENCE: 40

```
Met Ser Ser Pro Ser Gln Gln Pro Ile Lys Gly Arg Leu Ile Ser His
1               5                   10                  15
Phe Glu Asn Arg Pro Thr Pro Ser His Pro Lys Ala Trp Ser Asp Leu
            20                  25                  30
Trp Asp Ser Gly Lys Ser Ser Leu Trp Asp Arg Gly Met Pro Ser Pro
        35                  40                  45
```

```
Ala Leu Ile Asp Leu Leu Glu Ser Tyr Gln Asp Thr Leu Leu His Pro
         50                  55                  60

Phe Glu Ile Asp Ile Glu Asp Glu Glu Asp Ser Ser Asp Ala Gly Lys
 65                  70                  75                  80

Thr Arg Lys Arg Lys Arg Ala Leu Val Pro Gly Cys Gly Arg Gly Tyr
                 85                  90                  95

Asp Val Ile Thr Phe Ala Leu His Gly Phe Asp Ala Cys Gly Leu Glu
            100                 105                 110

Val Ser Thr Thr Ala Val Ser Glu Ala Arg Ala Phe Ala Lys Lys Glu
        115                 120                 125

Leu Cys Ser Pro Gln Ser Gly Asn Phe Gly Arg Arg Phe Asp Arg Glu
130                 135                 140

Arg Ala Arg His Ile Gly Val Gly Lys Ala Gln Phe Leu Gln Gly Asp
145                 150                 155                 160

Phe Phe Thr Asp Thr Trp Ile Glu Asn Glu Ser Thr Gly Leu Asp Gln
                165                 170                 175

Gly Arg Thr Glu Asn Gly Lys Phe Asp Leu Val Tyr Asp Tyr Thr Phe
            180                 185                 190

Leu Cys Ala Leu His Pro Ala Gln Arg Thr Arg Trp Ala Glu Arg Met
        195                 200                 205

Ala Asp Leu Leu Arg Pro Gly Gly Leu Leu Val Cys Leu Glu Phe Pro
210                 215                 220

Met Tyr Lys Asp Pro Ala Leu Pro Gly Pro Pro Trp Gly Val Asn Gly
225                 230                 235                 240

Ile His Trp Glu Leu Leu Ala Gly Gly Asp Thr Gly Gln Gly Lys Phe
                245                 250                 255

Thr Arg Lys Ala Tyr Val Gln Pro Glu Arg Thr Phe Glu Val Gly Arg
            260                 265                 270

Gly Thr Asp Met Ile Ser Val Tyr Glu Arg Lys
        275                 280

<210> SEQ ID NO 41
<211> LENGTH: 209
<212> TYPE: PRT
<213> ORGANISM: Artificial Sequence
<220> FEATURE:
<223> OTHER INFORMATION: Synthetic polypeptide of conserved hypothetical
      protein from Ralstonia pickettii

<400> SEQUENCE: 41

Met Ala Gln Pro Pro Val Phe Gln Ser Arg Asp Ala Ala Asp Pro Ala
 1               5                  10                  15

Phe Trp Asp Glu Arg Phe Thr Arg Glu His Thr Pro Trp Asp Ala Ala
                20                  25                  30

Gly Val Pro Ala Ala Phe Arg Gln Phe Cys Glu Ala Gln Pro Ala Pro
            35                  40                  45

Leu Ser Thr Leu Ile Pro Gly Cys Gly Asn Ala Tyr Glu Ala Gly Trp
        50                  55                  60

Leu Ala Glu Arg Gly Trp Pro Val Thr Ala Ile Asp Phe Ala Pro Ser
 65                  70                  75                  80

Ala Val Ala Ser Ala Arg Ala Val Leu Gly Pro His Ala Asp Val Val
                 85                  90                  95

Gln Leu Ala Asp Phe Phe Arg Phe Ser Pro Pro Arg Pro Val His Trp
            100                 105                 110

Ile Tyr Glu Arg Ala Phe Leu Cys Ala Met Pro Arg Arg Leu Trp Pro
```

```
            115                 120                 125
Asp Tyr Ala Ala Gln Val Ala Lys Leu Leu Pro Pro Arg Gly Leu Leu
    130                 135                 140

Ala Gly Phe Phe Ala Val Val Glu Gly Arg Glu Ala Met Pro Lys Gly
145                 150                 155                 160

Pro Pro Phe Glu Thr Thr Gln Pro Glu Leu Asp Ala Leu Leu Ser Pro
                165                 170                 175

Ala Phe Glu Arg Ile Ser Asp Met Pro Ile Ala Glu Thr Asp Ser Ile
                180                 185                 190

Pro Val Phe Ala Gly Arg Glu Arg Trp Gln Val Trp Arg Arg Arg Ala
                195                 200                 205

Asp

<210> SEQ ID NO 42
<211> LENGTH: 209
<212> TYPE: PRT
<213> ORGANISM: Artificial Sequence
<220> FEATURE:
<223> OTHER INFORMATION: Synthetic polypeptide of hypothetical protein
      RSc0462 from Ralstonia solanacearum

<400> SEQUENCE:

Met Asp Ala Asn Phe Trp His Glu Arg Trp Ala Glu Asn Ser Ile Ala
1               5                   10                  15

Phe His Gln Cys Glu Ala Asn Pro Leu Leu Val Ala His Phe Asn Arg
            20                  25                  30

Leu Asp Leu Ala Lys Gly Ser Arg Val Phe Val Pro Leu Cys Gly Lys
        35                  40                  45

Thr Leu Asp Ile Ser Trp Leu Leu Ser Gln Gly His Arg Val Val Gly
50                  55                  60

Cys Glu Leu Ser Glu Met Ala Ile Glu Gln Phe Lys Glu Leu Gly
65              70                  75                  80

Val Thr Pro Ala Ile Ser Glu Ile Val Ala Gly Lys Arg Tyr Ser Ala
                85                  90                  95

Glu Asn Leu Asp Ile Ile Val Gly Asp Phe Phe Asp Leu Thr Val Glu
            100                 105                 110

Thr Leu Gly His Val Asp Ala Thr Tyr Asp Arg Ala Ala Leu Val Ala
        115                 120                 125

Leu Pro Lys Pro Met Arg Asp Ser Tyr Ala Lys His Leu Met Ala Leu
    130                 135                 140

Thr Asn Asn Ala Pro Gln Leu Met Leu Cys Tyr Gln Tyr Asp Gln Thr
145                 150                 155                 160

Gln Met Glu Gly Pro Pro Phe Ser Ile Ser Ala Glu Glu Val Gln His
                165                 170                 175

His Tyr Ala Asp Ser Tyr Ala Leu Thr Ala Leu Ala Thr Val Gly Val
            180                 185                 190

Glu Gly Gly Leu Arg Glu Leu Asn Glu Val Ser Glu Thr Val Trp Leu
        195                 200                 205

Leu Glu Ser Arg
    210

<210> SEQ ID NO 44
<211> LENGTH: 204
<212> TYPE: PRT
<213> ORGANISM: Gloeobacter violaceus

<400> SEQUENCE: 44

Met Pro Ser Glu Glu Ser Ser Gly Val Asp Gln Pro Ala Phe Trp Glu
1               5                   10                  15

Tyr Arg Tyr Arg Gly Gly Gln Asp Arg Trp Asp Leu Gly Gln Pro Ala
            20                  25                  30

Pro Thr Phe Val His Leu Leu Ser Gly Ser Glu Ala Pro Pro Leu Gly
        35                  40                  45

Thr Val Ala Val Pro Gly Cys Gly Arg Gly His Asp Ala Leu Leu Phe
50                  55                  60

Ala Ala Arg Gly Tyr Lys Val Cys Gly Phe Asp Phe Ala Ala Asp Ala
65                  70                  75                  80

Ile Ala Asp Ala Thr Arg Leu Ala Leu Arg Ala Gly Ala Ala Ala Thr
                85                  90                  95

Phe Leu Gln Gln Asp Leu Phe Asn Leu Pro Arg Pro Phe Ala Gly Leu
            100                 105                 110

Phe Asp Leu Val Val Glu His Thr Cys Phe Cys Ala Ile Asp Pro Val
        115                 120                 125

Arg Arg Glu Glu Tyr Val Glu Ile Val His Trp Leu Leu Lys Pro Gly
    130                 135                 140

Gly Glu Leu Val Ala Ile Phe Phe Ala His Pro Arg Pro Gly Gly Pro
145                 150                 155                 160

```
Pro Tyr Arg Thr Asp Ala Gly Glu Ile Glu Arg Leu Phe Ser Pro Arg
            165                 170                 175

Phe Lys Ile Thr Ala Leu Leu Pro Ala Pro Met Ser Val Pro Ser Arg
            180                 185                 190

Arg Gly Glu Glu Leu Phe Gly Arg Phe Val Arg Ala
            195                 200

<210> SEQ ID NO 45
<211> LENGTH: 193
<212> TYPE: PRT
<213> ORGANISM: Unknown
<220> FEATURE:
<223> OTHER INFORMATION: Cellulophaga species, synthetic polypeptide of
      hypothetical protein MED134_07976 thereof

<400> SEQUENCE: 45

Met Glu Leu Thr Ser Thr Tyr Trp Asn Asn Arg Tyr Ala Glu Gly Ser
1               5                   10                  15

Thr Gly Trp Asp Leu Lys Glu Val Ser Pro Ile Lys Ala Tyr Leu
            20                  25                  30

Asp Gln Leu Glu Asn Lys Glu Leu Lys Ile Leu Ile Pro Gly Gly Gly
            35                  40                  45

Tyr Ser Tyr Glu Ala Gln Tyr Cys Trp Glu Gln Gly Phe Lys Asn Val
        50                  55                  60

Tyr Val Val Asp Phe Ser Gln Leu Ala Leu Glu Asn Leu Lys Gln Arg
65                  70                  75                  80

Val Pro Asp Phe Pro Ser Leu Gln Leu Ile Gln Glu Asp Phe Phe Thr
                85                  90                  95

Tyr Asp Gly Gln Phe Asp Val Ile Ile Glu Gln Thr Phe Phe Cys Ala
            100                 105                 110

Leu Gln Pro Asp Leu Arg Pro Ala Tyr Val Ala His Met His Thr Leu
        115                 120                 125

Leu Lys Ala Lys Gly Lys Leu Val Gly Leu Leu Phe Asn Phe Pro Leu
    130                 135                 140

Thr Glu Lys Gly Pro Pro Tyr Gly Gly Ser Thr Thr Glu Tyr Glu Ser
145                 150                 155                 160

Leu Phe Ser Glu His Phe Asp Ile Gln Lys Met Glu Thr Ala Tyr Asn
                165                 170                 175

Ser Val Ala Ala Arg Ala Gly Lys Glu Leu Phe Ile Lys Met Val Lys
            180                 185                 190

Lys

<210> SEQ ID NO 46
<211> LENGTH: 199
<212> TYPE: PRT
<213> ORGANISM: Artificial Sequence
<220> FEATURE:
<223> OTHER INFORMATION: Synthetic polypeptide of hypothetical protein
      FBALC1_10447 from Flavobacteriales bacterium

<400> SEQUENCE: 46

Met Ile Ser Met Lys Lys Asn Lys Leu Asp Ser Asp Tyr Trp Glu Asp
1               5                   10                  15

Arg Tyr Thr Lys Asn Ser Thr Ser Trp Asp Ile Gly Tyr Pro Ser Thr
            20                  25                  30

Pro Ile Arg Thr Tyr Ile Asp Gln Leu Lys Asp Lys Ser Leu Lys Ile
        35                  40                  45
```

```
Leu Ile Pro Gly Ala Gly Asn Ser Phe Glu Ala Glu Tyr Leu Trp Asn
 50                  55                  60

Leu Gly Phe Lys Asn Ile Tyr Ile Leu Asp Phe Ala Lys Gln Pro Leu
 65                  70                  75                  80

Glu Asn Phe Lys Lys Arg Leu Pro Asp Phe Pro Glu Asn Gln Leu Leu
                 85                  90                  95

His Ile Asp Phe Phe Lys Leu Asp Ile His Phe Asp Leu Ile Leu Glu
            100                 105                 110

Gln Thr Phe Cys Ala Leu Asn Pro Ser Leu Arg Glu Lys Tyr Val
        115                 120                 125

Glu Gln Met His Gln Leu Leu Lys Pro Lys Gly Lys Leu Val Gly Leu
    130                 135                 140

Phe Phe Asn Phe Pro Leu Thr Lys Ser Gly Pro Pro Phe Gly Gly Ser
145                 150                 155                 160

Leu Thr Glu Tyr Gln Phe Leu Phe Asp Lys Lys Phe Lys Ile Lys Ile
                165                 170                 175

Leu Glu Thr Ser Ile Asn Ser Ile Lys Glu Arg Glu Gly Lys Glu Leu
            180                 185                 190

Phe Phe Ile Phe Glu Ser Pro
        195

<210> SEQ ID NO 47
<211> LENGTH: 200
<212> TYPE: PRT
<213> ORGANISM: Lentisphaera araneosa

<400> SEQUENCE: 47

Met Arg Thr Lys Gly Asn Glu Lys Ala Glu Ser Trp Asp Lys Ile Tyr
 1               5                   10                  15

Arg Glu Gly Asn Pro Gly Trp Asp Ile Lys Lys Pro Ala Pro Pro Phe
                20                  25                  30

Glu Asp Leu Phe Lys Gln Asn Pro Ser Trp Leu Lys Ala Gly Ser Leu
            35                  40                  45

Ile Ser Phe Gly Cys Gly Gly Gly His Asp Ala Asn Phe Phe Ala Gln
 50                  55                  60

Asn Asp Phe Asn Val Thr Ala Val Asp Phe Ala Ser Glu Ala Val Lys
 65                  70                  75                  80

Leu Ala Arg Ser Asn Tyr Pro Gln Leu Asn Val Ile Gln Lys Asn Ile
                85                  90                  95

Leu Glu Leu Ser Pro Glu Tyr Asp Glu Gln Phe Asp Tyr Val Leu Glu
            100                 105                 110

His Thr Cys Phe Cys Ala Val Pro Leu Asp His Arg Arg Ala Tyr Met
        115                 120                 125

Glu Ser Ala His Ala Ile Leu Lys Ala Gly Ala Tyr Leu Phe Gly Leu
    130                 135                 140

Phe Tyr Arg Phe Asp Pro Pro Asp Gln Asp Gly Pro Pro Tyr Ser Leu
145                 150                 155                 160

Ser Leu Glu Asp Leu Glu Asp Ala Tyr Ser Gly Leu Phe Thr Leu Glu
                165                 170                 175

Glu Asn Ala Ile Pro Lys Arg Ser His Gly Arg Arg Thr Gln Arg Glu
            180                 185                 190

Arg Phe Ile Val Leu Lys Lys Ile
        195                 200

<210> SEQ ID NO 48
```

```
<211> LENGTH: 201
<212> TYPE: PRT
<213> ORGANISM: Artificial Sequence
<220> FEATURE:
<223> OTHER INFORMATION: Synthetic polypeptide of hypothetical protein
      Psyc_1799 from Psychrobacter arcticus

<400> SEQUENCE: 48

Met Gly Asn Val Asn Gln Ala Glu Phe Trp Gln Gln Arg Tyr Glu Gln
1               5                   10                  15

Asp Ser Ile Gly Trp Asp Met Gly Gln Val Ser Pro Pro Leu Lys Val
            20                  25                  30

Tyr Ile Asp Gln Leu Pro Glu Ala Ala Lys Glu Gln Ala Val Leu Val
        35                  40                  45

Pro Gly Ala Gly Asn Ala Tyr Glu Val Gly Tyr Leu Tyr Glu Gln Gly
    50                  55                  60

Phe Thr Asn Ile Thr Leu Val Asp Phe Ala Pro Ala Pro Ile Lys Asp
65                  70                  75                  80

Phe Ala Glu Arg Tyr Pro Asp Phe Pro Ala Asp Lys Leu Ile Cys Ala
                85                  90                  95

Asp Phe Phe Asp Leu Leu Pro Lys Gln His Gln Phe Asp Trp Val Leu
            100                 105                 110

Glu Gln Thr Phe Phe Cys Ala Ile Asn Pro Ala Arg Arg Asp Glu Tyr
        115                 120                 125

Val Gln Gln Met Ala Arg Leu Leu Lys Pro Lys Gly Gln Leu Val Gly
    130                 135                 140

Leu Leu Phe Asp Lys Asp Phe Gly Arg Asn Glu Pro Pro Phe Gly Gly
145                 150                 155                 160

Thr Lys Glu Glu Tyr Gln Gln Arg Phe Ser Thr His Phe Asp Thr Glu
                165                 170                 175

Ile Met Glu Gln Ser Tyr Asn Ser His Pro Ala Arg Gln Gly Ser Glu
            180                 185                 190

Leu Phe Ile Lys Met Arg Val Lys Asp
        195                 200

<210> SEQ ID NO 49
<211> LENGTH: 192
<212> TYPE: PRT
<213> ORGANISM: Unknown
<220> FEATURE:
<223> OTHER INFORMATION: Tenacibaculum species, synthetic polypeptide
      of hypothetical protein MED152_10555 thereof

<400> SEQUENCE: 49

Met Ile Phe Asp Glu Gln Phe Trp Asp Asn Lys Tyr Ile Thr Asn Lys
1               5                   10                  15

Thr Gly Trp Asp Leu Gly Gln Val Ser Pro Leu Lys Ala Tyr Phe
            20                  25                  30

Asp Gln Leu Thr Asn Lys Asp Leu Lys Ile Leu Ile Pro Gly Gly Gly
        35                  40                  45

Asn Ser His Glu Ala Glu Tyr Leu Leu Glu Asn Gly Phe Thr Asn Val
    50                  55                  60

Tyr Val Ile Asp Ile Ser Lys Leu Ala Leu Thr Asn Leu Lys Asn Arg
65                  70                  75                  80

Val Pro Gly Phe Pro Ser Ser Asn Leu Ile His Gln Asn Phe Phe Glu
                85                  90                  95

Leu Asn Gln Thr Phe Asp Leu Val Ile Glu Gln Thr Phe Phe Cys Ala
            100                 105                 110
```

```
Leu Asn Pro Asn Leu Arg Glu Glu Tyr Val Ser Lys Met His Ser Val
            115                 120                 125

Leu Asn Asp Asn Gly Lys Leu Val Gly Leu Leu Phe Asp Ala Lys Leu
130                 135                 140

Asn Glu Asp His Pro Pro Phe Gly Gly Ser Lys Lys Glu Tyr Thr Ser
145                 150                 155                 160

Leu Phe Arg Asn Leu Phe Thr Ile Glu Val Leu Glu Glu Cys Tyr Asn
            165                 170                 175

Ser Ile Glu Asn Arg Lys Gly Met Glu Leu Phe Cys Lys Phe Val Lys
            180                 185                 190
```

<210> SEQ ID NO 50
<211> LENGTH: 201
<212> TYPE: PRT
<213> ORGANISM: Psychrobacter cryohalolentis

<400> SEQUENCE: 50

```
Met Glu Asn Val Asn Gln Ala Gln Phe Trp Gln Gln Arg Tyr Glu Gln
1               5                   10                  15

Asp Ser Ile Gly Trp Asp Met Gly Gln Val Ser Pro Pro Leu Lys Ala
            20                  25                  30

Tyr Ile Asp Gln Leu Pro Glu Ala Ala Lys Asn Gln Ala Val Leu Val
        35                  40                  45

Pro Gly Ala Gly Asn Ala Tyr Glu Val Gly Tyr Leu His Glu Gln Gly
    50                  55                  60

Phe Thr Asn Val Thr Leu Val Asp Phe Ala Pro Ala Pro Ile Ala Ala
65                  70                  75                  80

Phe Ala Glu Arg Tyr Pro Asn Phe Pro Ala Lys His Leu Ile Cys Ala
                85                  90                  95

Asp Phe Phe Glu Leu Ser Pro Glu Gln Tyr Gln Phe Asp Trp Val Leu
            100                 105                 110

Glu Gln Thr Phe Phe Cys Ala Ile Asn Pro Ser Arg Arg Asp Glu Tyr
        115                 120                 125

Val Gln Gln Met Ala Ser Leu Val Lys Pro Asn Gly Lys Leu Ile Gly
    130                 135                 140

Leu Leu Phe Asp Lys Asp Phe Gly Arg Asp Glu Pro Pro Phe Gly Gly
145                 150                 155                 160

Thr Lys Asp Glu Tyr Gln Gln Arg Phe Ala Thr His Phe Asp Ile Asp
                165                 170                 175

Ile Met Glu Pro Ser Tyr Asn Ser His Pro Ala Arg Gln Gly Ser Glu
            180                 185                 190

Leu Phe Ile Glu Met His Val Lys Asp
        195                 200
```

<210> SEQ ID NO 51
<211> LENGTH: 192
<212> TYPE: PRT
<213> ORGANISM: Mariprofundus ferrooxydans

<400> SEQUENCE: 51

```
Met Thr Val Trp Glu Glu Arg Tyr Gln Arg Gly Glu Thr Gly Trp Asp
1               5                   10                  15

Arg Gly Gly Val Ser Pro Ala Leu Thr Gln Leu Val Asp His Leu His
            20                  25                  30

Leu Glu Ala Arg Val Leu Ile Pro Gly Cys Gly Arg Gly His Glu Val
        35                  40                  45
```

Ile Glu Leu Ala Arg Leu Gly Phe Arg Val Thr Ala Ile Asp Ile Ala
 50                  55                  60

Pro Ser Ala Ile Ala His Leu Ser Gln Gln Leu Glu Gln Glu Asp Leu
 65                  70                  75                  80

Asp Ala Glu Leu Val Asn Gly Asp Leu Phe Ala Tyr Ala Pro Asp His
                 85                  90                  95

Cys Phe Asp Ala Val Tyr Glu Gln Thr Cys Leu Cys Ala Ile Glu Pro
                100                 105                 110

Glu Gln Arg Ala Asp Tyr Glu Gln Arg Leu His Gly Trp Leu Lys Pro
                115                 120                 125

Glu Gly Val Leu Tyr Ala Leu Phe Met Gln Thr Gly Ile Arg Gly Gly
                130                 135                 140

Pro Pro Phe His Cys Asp Leu Leu Met Met Arg Glu Leu Phe Asp Ala
145                 150                 155                 160

Ser Arg Trp Gln Trp Pro Glu Glu Thr Gly Ala Val Leu Val Pro His
                165                 170                 175

Lys Asn Gly Arg Phe Glu Leu Gly His Met Leu Arg Arg Thr Gly Arg
                180                 185                 190

<210> SEQ ID NO 52
<211> LENGTH: 191
<212> TYPE: PRT
<213> ORGANISM: Artificial Sequence
<220> FEATURE:
<223> OTHER INFORMATION: Synthetic polypeptide of hypothetical protein
      CA2559_00890 from Croceibacter atlanticus

<400> SEQUENCE: 52

Met Thr Ser Asn Phe Trp Glu Gln Arg Tyr Ala Asn Asn Thr Gly
1                5                  10                  15

Trp Asp Leu Asn Thr Val Ser Pro Pro Leu Lys His Tyr Ile Asp Thr
                 20                  25                  30

Leu Ser Asn Lys Thr Leu Phe Ile Leu Ile Pro Gly Cys Gly Asn Ala
                 35                  40                  45

Tyr Glu Ala Glu Tyr Leu His Asn Gln Gly Phe Glu Asn Val Phe Ile
 50                  55                  60

Val Asp Leu Ala Glu His Pro Leu Leu Glu Phe Ser Lys Arg Val Pro
 65                  70                  75                  80

Asp Phe Pro Lys Ser His Ile Leu His Leu Asp Phe Phe Asn Leu Thr
                 85                  90                  95

Gln Lys Phe Asp Leu Ile Leu Gly Gln Thr Phe Phe Cys Ala Leu His
                100                 105                 110

Pro Glu Gln Arg Leu His Tyr Ala His His Thr Ser Lys Leu Leu Asn
                115                 120                 125

Ser Asn Gly Cys Leu Val Gly Leu Phe Phe Ala Asn Lys Glu Phe Asp Lys
130                 135                 140

Thr Gly Pro Pro Phe Gly Gly Asn Lys Lys Glu Tyr Lys Asn Leu Phe
145                 150                 155                 160

Lys Asn Leu Phe Lys Ile Lys Lys Leu Glu Asn Cys Tyr Asn Ser Ile
                165                 170                 175

Lys Pro Arg Gln Gly Ser Glu Leu Phe Phe Ile Phe Glu Lys Lys
                180                 185                 190

<210> SEQ ID NO 53
<211> LENGTH: 208
<212> TYPE: PRT

<213> ORGANISM: Oceanicaulis alexandrii

<400> SEQUENCE: 53

Met Thr Gln Ala Ser Ser Asp Thr Pro Arg Ser Glu Asp Arg Ser Gly
1               5                   10                  15

Phe Asp Trp Glu Ser Arg Phe Gln Ser Asp Asp Ala Pro Trp Glu Arg
            20                  25                  30

Gln Gly Val His Pro Ala Ala Gln Asp Trp Val Arg Asn Gly Glu Ile
        35                  40                  45

Lys Pro Gly Gln Ala Ile Leu Thr Pro Gly Cys Gly Arg Ser Gln Glu
    50                  55                  60

Pro Ala Phe Leu Ala Ser Arg Gly Phe Asp Val Thr Ala Thr Asp Ile
65                  70                  75                  80

Ala Pro Thr Ala Ile Ala Trp Gln Lys Thr Arg Phe Gln Thr Leu Gly
                85                  90                  95

Val Met Ala Glu Ala Ile Glu Thr Asp Ala Leu Ala Trp Arg Pro Glu
            100                 105                 110

Thr Gly Phe Asp Ala Leu Tyr Glu Gln Thr Phe Leu Cys Ala Ile His
        115                 120                 125

Pro Lys Arg Arg Gln Asp Tyr Glu Ala Met Ala His Ala Ser Leu Lys
    130                 135                 140

Ser Gly Gly Lys Leu Leu Ala Leu Phe Met Gln Lys Ala Glu Met Gly
145                 150                 155                 160

Gly Pro Pro Tyr Gly Cys Gly Leu Asp Ala Met Arg Glu Leu Phe Ala
                165                 170                 175

Asp Thr Arg Trp Val Trp Pro Asp Gly Glu Ala Arg Pro Tyr Pro His
            180                 185                 190

Pro Gly Leu Asn Ala Lys Ala Glu Leu Ala Met Val Leu Ile Arg Arg
        195                 200                 205

<210> SEQ ID NO 54
<211> LENGTH: 206
<212> TYPE: PRT
<213> ORGANISM: Ralstonia eutropha

<400> SEQUENCE: 54

Met Ser Asp Pro Ala Lys Pro Val Pro Thr Phe Ala Thr Arg Asn Ala
1               5                   10                  15

Ala Asp Pro Ala Phe Trp Asp Glu Arg Phe Glu Gln Gly Phe Thr Pro
            20                  25                  30

Trp Asp Gln Gly Gly Val Pro Glu Glu Phe Arg Gln Phe Ile Glu Gly
        35                  40                  45

Arg Ala Pro Cys Pro Thr Leu Val Pro Gly Cys Gly Asn Gly Trp Glu
    50                  55                  60

Ala Ala Trp Leu Phe Glu Arg Gly Trp Pro Val Thr Ala Ile Asp Phe
65                  70                  75                  80

Ser Pro Gln Ala Val Ala Ser Ala Arg Gln Thr Leu Gly Pro Ala Gly
                85                  90                  95

Val Val Val Gln Gln Gly Asp Phe Phe Ala Phe Thr Pro Gln Pro Pro
            100                 105                 110

Cys Glu Leu Ile Tyr Glu Arg Ala Phe Leu Cys Ala Leu Pro Pro Ala
        115                 120                 125

Met Arg Ala Asp Tyr Ala Ala Arg Val Ala Gln Leu Leu Pro Pro Gly
    130                 135                 140

Gly Leu Leu Ala Gly Tyr Phe Tyr Leu Gly Glu Asn Arg Gly Gly Pro

```
                145                 150                 155                 160
Pro Phe Ala Met Pro Ala Glu Ala Leu Asp Ala Leu Ala Pro Ala
                165                 170                 175

Phe Glu Arg Leu Glu Asp Arg Pro Thr Ala Ala Pro Leu Pro Val Phe
                180                 185                 190

Gln Gly Gln Glu Arg Trp Gln Val Trp Arg Arg Arg Ser Gly
                195                 200                 205

<210> SEQ ID NO 55
<211> LENGTH: 194
<212> TYPE: PRT
<213> ORGANISM: Artificial Sequence
<220> FEATURE:
<223> OTHER INFORMATION: Synthetic polypeptide of hypothetical protein
      FP1441 from Flavobacterium psychrophilum

<400> SEQUENCE: 55

Met Lys Lys Ile Asp Gln Lys Tyr Trp Gln Asn Arg Tyr Gln Thr Asn
1               5                   10                  15

Asp Ile Ala Trp Asp Thr Gly Lys Ile Thr Thr Pro Ile Lys Ala Tyr
                20                  25                  30

Ile Asp Gln Ile Glu Asp Gln Ser Ile Lys Ile Leu Ile Pro Gly Cys
            35                  40                  45

Gly Asn Gly Tyr Glu Tyr Glu Tyr Leu Ile Lys Lys Gly Phe Tyr Asn
        50                  55                  60

Ser Phe Val Ala Asp Tyr Ala Gln Thr Pro Ile Asp Asn Leu Lys Lys
65                  70                  75                  80

Arg Ile Pro Asn Cys Asn Ala Asn Gln Leu Leu Ile Ser Asp Phe Phe
                85                  90                  95

Glu Leu Glu Gly Ser Tyr Asp Leu Ile Ile Glu Gln Thr Phe Phe Cys
                100                 105                 110

Ala Leu Asn Pro Glu Leu Arg Val Lys Tyr Ala Gln Lys Met Leu Ser
            115                 120                 125

Leu Leu Ser Pro Lys Gly Lys Ile Ile Gly Leu Leu Phe Gln Phe Pro
        130                 135                 140

Leu Thr Glu Ala Gly Pro Pro Phe Gly Gly Ser Lys Glu Glu Tyr Leu
145                 150                 155                 160

Lys Leu Phe Ser Thr Asn Phe Asn Ile Lys Thr Ile Glu Thr Ala Tyr
                165                 170                 175

Asn Ser Ile Lys Pro Arg Glu Gly Asn Glu Leu Phe Phe Ile Phe Thr
            180                 185                 190

Lys Lys

<210> SEQ ID NO 56
<211> LENGTH: 203
<212> TYPE: PRT
<213> ORGANISM: Artificial Sequence
<220> FEATURE:
<223> OTHER INFORMATION: Synthetic polypeptide of hypothetical protein
      Mpe_A3410 from Methylibium petroleiphilum

<400> SEQUENCE: 56

Met Ser Gly Pro Asp Leu Asn Phe Trp Gln Gln Arg Phe Asp Thr Gly
1               5                   10                  15

Gln Leu Pro Trp Asp Arg Gly Ala Pro Ser Pro Gln Leu Ala Ala Trp
                20                  25                  30

Leu Gly Asp Gly Ser Leu Ala Pro Gly Arg Ile Ala Val Pro Gly Cys
            35                  40                  45
```

Gly Ser Gly His Glu Val Val Ala Leu Ala Arg Gly Gly Phe Ser Val
        50                  55                  60

Thr Ala Ile Asp Tyr Ala Pro Gly Ala Val Arg Leu Thr Gln Gly Arg
 65                  70                  75                  80

Leu Ala Ala Ala Gly Leu Ala Ala Glu Val Val Gln Ala Asp Val Leu
                85                  90                  95

Thr Trp Gln Pro Thr Ala Pro Leu Asp Ala Val Tyr Glu Gln Thr Cys
                100                 105                 110

Leu Cys Ala Leu His Pro Asp His Trp Val Ala Tyr Ala Ala Arg Leu
            115                 120                 125

His Ala Trp Leu Arg Pro Gly Gly Thr Leu Ala Leu Ala Met Gln
        130                 135                 140

Ala Leu Arg Glu Gly Ala Gly Gln Gly Leu Ile Glu Gly Pro Pro Tyr
145                 150                 155                 160

His Val Asp Val Asn Ala Leu Arg Ala Leu Leu Pro Gly Asp Arg Trp
                165                 170                 175

Asp Trp Pro Arg Pro Pro Tyr Ala Arg Val Pro His Pro Ser Ser Thr
                180                 185                 190

Trp Ala Glu Leu Ala Ile Val Leu Thr Arg Arg
            195                 200

<210> SEQ ID NO 57
<211> LENGTH: 199
<212> TYPE: PRT
<213> ORGANISM: Unknown
<220> FEATURE:
<223> OTHER INFORMATION: Flavobacterium species, synthetic polypeptide
      of hypothetical protein MED217_05007 thereof

<400> SEQUENCE: 57

Met Lys Thr Asp Leu Asn Lys Leu Tyr Trp Glu Asp Arg Tyr Gln Asn
 1               5                  10                  15

Gln Gln Thr Gly Trp Asp Ile Gly Ser Val Ser Thr Pro Leu Lys Glu
                20                  25                  30

Tyr Ile Asp Gln Ile Asp Asp Lys Asn Ile Gln Ile Leu Val Pro Gly
            35                  40                  45

Ala Gly Tyr Gly His Glu Val Arg Tyr Leu Ala Gln Gln Gly Phe Lys
        50                  55                  60

Asn Val Asp Val Ile Asp Leu Ser Val Ser Ala Leu Thr Gln Leu Lys
 65                  70                  75                  80

Lys Ala Leu Pro Asp Thr Thr Ala Tyr Gln Leu Ile Glu Gly Asp Phe
                85                  90                  95

Phe Glu His His Thr Ser Tyr Asp Leu Ile Leu Glu Gln Thr Phe Phe
                100                 105                 110

Cys Ala Leu Glu Pro Asp Lys Arg Pro Asp Tyr Ala Ala His Ala Ala
            115                 120                 125

Ser Leu Leu Lys Asp Ser Gly Lys Ile Ser Gly Val Leu Phe Asn Phe
        130                 135                 140

Pro Leu Thr Glu Lys Gly Pro Pro Phe Gly Gly Ser Ser Glu Tyr
145                 150                 155                 160

Lys Lys Leu Phe Ser Glu Tyr Phe Asn Ile Lys Thr Leu Glu Ala Cys
                165                 170                 175

Tyr Asn Ser Ile Lys Pro Arg Leu Gly Asn Glu Leu Phe Phe Ile Phe
            180                 185                 190

Glu Lys Ser Asn Gln Glu Ser

<210> SEQ ID NO 58
<211> LENGTH: 196
<212> TYPE: PRT
<213> ORGANISM: Microscilla marina

<400> SEQUENCE: 58

Met His Thr Thr Leu Asp Lys Asp Phe Trp Ser Asn Arg Tyr Gln Ala
1               5                   10                  15

Gln Asp Thr Gly Trp Asp Ala Gly Ser Ile Thr Pro Ile Lys Ala
            20                  25                  30

Tyr Val Asp Gln Leu Glu Asp Lys His Leu Lys Ile Leu Val Pro Gly
        35                  40                  45

Ala Gly Asn Ser His Glu Ala Glu Tyr Leu His Gln Gln Gly Phe Thr
    50                  55                  60

Asn Val Thr Val Ile Asp Ile Val Gln Ala Pro Leu Asp Asn Leu Lys
65                  70                  75                  80

Ser Arg Ser Pro Asp Phe Pro Glu Ala His Leu Leu Gln Gly Asp Phe
                85                  90                  95

Phe Glu Leu Val Gly Gln Tyr Asp Leu Ile Ile Glu Gln Thr Phe Phe
            100                 105                 110

Cys Ala Leu Asn Pro Ser Leu Arg Glu Ser Tyr Val Gln Lys Val Lys
        115                 120                 125

Ser Leu Leu Lys Pro Glu Gly Lys Leu Val Gly Val Leu Phe Cys Asn
    130                 135                 140

Val Phe Leu Asp Arg Thr Glu Pro Pro Phe Gly Ala Thr Glu Gln Gln
145                 150                 155                 160

His Gln Glu Tyr Phe Leu Pro His Phe Ile Ala Lys His Phe Ala Ser
                165                 170                 175

Cys Tyr Asn Ser Ile Ala Pro Arg Gln Gly Ala Glu Trp Phe Ile Cys
            180                 185                 190

Leu Ile Asn Asp
        195

<210> SEQ ID NO 59
<211> LENGTH: 209
<212> TYPE: PRT
<213> ORGANISM: Ralstonia pickettii

<400> SEQUENCE: 59

Met Ala Glu Pro Pro Val Phe Gln Ser Arg Asp Ala Ala Asp Pro Ala
1               5                   10                  15

Phe Trp Asp Glu Arg Phe Ser Arg Glu His Thr Pro Trp Asp Ala Ala
            20                  25                  30

Gly Val Pro Ala Ala Phe Gln Gln Phe Cys Glu Ser Gln Pro Val Pro
        35                  40                  45

Leu Ser Thr Leu Ile Pro Gly Cys Gly Ser Ala Tyr Glu Ala Gly Trp
    50                  55                  60

Leu Ala Glu Arg Gly Trp Pro Val Thr Ala Ile Asp Phe Ala Pro Ser
65                  70                  75                  80

Ala Val Ala Ser Ala Arg Ala Val Leu Gly Pro His Ala Asp Val Val
                85                  90                  95

Glu Met Ala Asp Phe Phe Gly Phe Ser Pro Ala Arg Ser Val Gln Trp
            100                 105                 110

Ile Tyr Glu Arg Ala Phe Leu Cys Ala Met Pro Arg Arg Leu Trp Pro

```
                115                 120                 125
Asp Tyr Ala Ala Gln Val Ala Lys Leu Leu Pro Pro Gly Gly Leu Leu
    130                 135                 140

Ala Gly Phe Phe Ala Val Val Glu Gly Arg Glu Ala Val Pro Lys Gly
145                 150                 155                 160

Pro Pro Phe Glu Thr Thr Gln Pro Glu Leu Asp Ala Leu Leu Ser Pro
                165                 170                 175

Ala Phe Glu Arg Ile Ser Asp Ile Pro Ile Ala Glu Ala Asp Ser Ile
            180                 185                 190

Pro Val Phe Ala Gly Arg Glu Arg Trp Gln Val Trp Arg Arg Arg Ala
        195                 200                 205

Asp

<210> SEQ ID NO 60
<211> LENGTH: 206
<212> TYPE: PRT
<213> ORGANISM: Polaromonas naphthalenivorans

<400> SEQUENCE: 60

Met Ala Gly Pro Thr Thr Asp Phe Trp Gln Ala Arg Phe Asp Asn Lys
1               5                   10                  15

Glu Thr Gly Trp Asp Arg Gly Ala Pro Gly Pro Gln Leu Leu Ala Trp
            20                  25                  30

Leu Glu Ser Gly Ala Leu Gln Pro Cys Arg Ile Ala Val Pro Gly Cys
        35                  40                  45

Gly Ser Gly Trp Glu Val Ala Glu Leu Ala Arg Arg Gly Phe Glu Val
    50                  55                  60

Val Gly Ile Asp Tyr Thr Pro Ala Ala Val Glu Arg Thr Arg Ala Leu
65                  70                  75                  80

Leu Ala Ala Gln Gly Leu Ala Ala Glu Val Val Gln Ala Asp Val Leu
                85                  90                  95

Ala Tyr Gln Pro His Lys Pro Phe Glu Ala Ile Tyr Glu Gln Thr Cys
            100                 105                 110

Leu Cys Ala Leu His Pro Asp His Trp Val Ala Tyr Ala Arg Gln Leu
        115                 120                 125

Gln Gln Trp Leu Lys Pro Gln Gly Ser Ile Trp Ala Leu Phe Met Gln
    130                 135                 140

Met Val Arg Pro Glu Ala Thr Asp Glu Gly Leu Ile Gln Gly Pro Pro
145                 150                 155                 160

Tyr His Cys Asp Ile Asn Ala Met Arg Ala Leu Phe Pro Ala Gln His
                165                 170                 175

Trp Ala Trp Pro Arg Pro Pro Tyr Ala Lys Val Pro His Pro Asn Val
            180                 185                 190

Gly His Glu Leu Gly Leu Arg Leu Met Leu Arg Gln Gly Arg
        195                 200                 205

<210> SEQ ID NO 61
<211> LENGTH: 193
<212> TYPE: PRT
<213> ORGANISM: Artificial Sequence
<220> FEATURE:
<223> OTHER INFORMATION: Synthetic polypeptide of hypothetical protein
      PI23P_05077 from Polaribacter irgensii

<400> SEQUENCE: 61

Met Asn Leu Ser Ala Asp Ala Trp Asp Glu Arg Tyr Thr Asn Asn Asp
1               5                   10                  15
```

```
Ile Ala Trp Asp Leu Gly Glu Val Ser Ser Pro Leu Lys Ala Tyr Phe
            20                  25                  30

Asp Gln Leu Glu Asn Lys Glu Ile Lys Ile Leu Ile Pro Gly Gly Gly
            35                  40                  45

Asn Ser His Glu Ala Ala Tyr Leu Phe Glu Asn Gly Phe Lys Asn Ile
 50                  55                  60

Trp Val Val Asp Leu Ser Glu Thr Ala Ile Gly Asn Ile Gln Lys Arg
 65                  70                  75                  80

Ile Pro Glu Phe Pro Pro Ser Gln Leu Ile Gln Gly Asp Phe Phe Asn
                    85                  90                  95

Met Asp Asp Val Phe Asp Leu Ile Ile Glu Gln Thr Phe Phe Cys Ala
                100                 105                 110

Ile Asn Pro Asn Leu Arg Ala Asp Tyr Thr Thr Lys Met His His Leu
            115                 120                 125

Leu Lys Ser Lys Gly Lys Leu Val Gly Val Leu Phe Asn Val Pro Leu
130                 135                 140

Asn Thr Asn Lys Pro Pro Phe Gly Gly Asp Lys Ser Glu Tyr Leu Glu
145                 150                 155                 160

Tyr Phe Lys Pro Phe Phe Ile Ile Lys Lys Met Glu Ala Cys Tyr Asn
                    165                 170                 175

Ser Phe Gly Asn Arg Lys Gly Arg Glu Leu Phe Val Ile Leu Arg Ser
            180                 185                 190

Lys

<210> SEQ ID NO 62
<211> LENGTH: 188
<212> TYPE: PRT
<213> ORGANISM: Flavobacteria bacterium

<400> SEQUENCE: 62

Met Asn Tyr Trp Glu Glu Arg Tyr Lys Lys Gly Glu Thr Gly Trp Asp
 1               5                  10                  15

Ala Gly Thr Ile Thr Thr Pro Leu Lys Glu Tyr Ile Asp Gln Leu Thr
            20                  25                  30

Asp Lys Asn Leu Thr Ile Leu Ile Pro Gly Ala Gly Asn Gly His Glu
            35                  40                  45

Phe Asp Tyr Leu Ile Asp Asn Gly Phe Lys Asn Val Phe Val Val Asp
 50                  55                  60

Ile Ala Ile Thr Pro Leu Glu Asn Ile Lys Lys Arg Lys Pro Lys Tyr
 65                  70                  75                  80

Ser Ser His Leu Ile Asn Ala Asp Phe Phe Ser Leu Thr Thr Thr Phe
                    85                  90                  95

Asp Leu Ile Leu Glu Gln Thr Phe Phe Cys Ala Leu Pro Pro Glu Met
                100                 105                 110

Arg Gln Arg Tyr Val Glu Lys Met Thr Ser Leu Leu Asn Pro Asn Gly
            115                 120                 125

Lys Leu Ala Gly Leu Leu Phe Asp Phe Pro Leu Thr Ser Glu Gly Pro
130                 135                 140

Pro Phe Gly Gly Ser Lys Ser Glu Tyr Ile Thr Leu Phe Ser Asn Thr
145                 150                 155                 160

Phe Ser Ile Lys Thr Leu Glu Arg Ala Tyr Asn Ser Ile Lys Pro Arg
                    165                 170                 175

Glu Asn Lys Glu Leu Phe Phe Ile Phe Glu Thr Lys
            180                 185
```

<210> SEQ ID NO 63
<211> LENGTH: 161
<212> TYPE: PRT
<213> ORGANISM: Artificial Sequence
<220> FEATURE:
<223> OTHER INFORMATION: Synthetic polypeptide of hypothetical protein
      PPSIR1_29093 from Plesiocystis pacifica

<400> SEQUENCE: 63

Met Arg Val Ile Val Pro Gly Ala Gly Val Gly His Asp Ala Leu Ala
1               5                   10                  15

Trp Ala Gln Ala Gly His Glu Val Val Ala Leu Asp Phe Ala Pro Ala
            20                  25                  30

Ala Val Ala Arg Leu Arg Glu Arg Ala Ala Glu Ala Gly Leu Thr Ile
        35                  40                  45

Glu Ala His Val Ala Asp Val Thr Asn Pro Gly Pro Ala Leu Asn Asp
    50                  55                  60

Gly Leu Gly Gly Arg Phe Asp Leu Val Trp Gln Thr Cys Leu Cys
65                  70                  75                  80

Ala Ile Thr Pro Glu Leu Arg Gly Ala Tyr Leu Ala Gln Ala Arg Ser
                85                  90                  95

Trp Leu Thr Pro Asp Gly Ser Met Leu Ala Leu Leu Trp Asn Thr Gly
            100                 105                 110

Asn Glu Gly Gly Pro Pro Tyr Asp Met Pro Pro Glu Leu Val Glu Arg
        115                 120                 125

Leu Met Thr Gly Leu Phe Val Ile Asp Lys Phe Ala Pro Val Thr Gly
    130                 135                 140

Ser Asn Pro Asn Arg Arg Glu His Leu Tyr Trp Leu Arg Pro Glu Pro
145                 150                 155                 160

Thr

<210> SEQ ID NO 64
<211> LENGTH: 196
<212> TYPE: PRT
<213> ORGANISM: Unknown
<220> FEATURE:
<223> OTHER INFORMATION: Algoriphagus species, synthetic polypeptide
      of hypothetical protein ALPR1_06920 thereof

<400> SEQUENCE: 64

Met Ala Glu Leu Asp Glu Lys Tyr Trp Ser Glu Arg Tyr Lys Ser Gly
1               5                   10                  15

Leu Thr Gly Trp Asp Ile Gly Phe Pro Ser Thr Pro Ile Val Gln Tyr
            20                  25                  30

Leu Asp Gln Ile Val Asn Lys Asp Val Glu Ile Leu Ile Pro Gly Ala
        35                  40                  45

Gly Asn Ala Tyr Glu Ala Tyr Tyr Ala Phe Gln Ser Gly Phe Ser Asn
    50                  55                  60

Val His Val Leu Asp Ile Ser Gln Glu Pro Leu Arg Asn Phe Lys Asp
65                  70                  75                  80

Lys Phe Pro Asn Phe Pro Ser Ser Asn Leu His His Gly Asp Phe Phe
                85                  90                  95

Glu His His Gly Ser Tyr Asn Leu Ile Leu Glu Gln Thr Phe Phe Cys
            100                 105                 110

Ala Leu Asn Pro Ser Leu Arg Pro Lys Tyr Val Lys Lys Met Ser Glu
        115                 120                 125

Leu Leu Leu Lys Gly Gly Lys Leu Val Gly Leu Leu Phe Asn Lys Glu
            130                 135                 140

Phe Asn Ser Pro Gly Pro Pro Phe Gly Gly Ile Lys Glu Tyr Gln
145                 150                 155                 160

Lys Leu Phe His Asn Ser Phe Glu Ile Asp Val Met Glu Glu Cys Tyr
                165                 170                 175

Asn Ser Ile Pro Ala Arg Ala Gly Ser Glu Ala Phe Ile Arg Leu Ile
            180                 185                 190

Asn Ser Lys Gly
        195

<210> SEQ ID NO 65
<211> LENGTH: 203
<212> TYPE: PRT
<213> ORGANISM: Rhodoferax ferrireducens

<400> SEQUENCE: 65

Met Ala Gly Pro Thr Thr Glu Phe Trp Gln Glu Arg Phe Glu Lys Lys
1               5                   10                  15

Glu Thr Gly Trp Asp Arg Gly Ser Pro Ser Pro Gln Leu Leu Ala Trp
            20                  25                  30

Leu Ala Ser Gly Ala Leu Arg Pro Cys Arg Ile Ala Val Pro Gly Cys
        35                  40                  45

Gly Ser Gly Trp Glu Val Ala Glu Leu Ala Gln Arg Gly Phe Asp Val
    50                  55                  60

Val Gly Leu Asp Tyr Thr Ala Ala Ala Thr Thr Arg Thr Arg Ala Leu
65                  70                  75                  80

Cys Asp Ala Arg Gly Leu Lys Ala Glu Val Leu Gln Ala Asp Val Leu
                85                  90                  95

Ser Tyr Gln Pro Glu Lys Lys Phe Ala Ala Ile Tyr Glu Gln Thr Cys
            100                 105                 110

Leu Cys Ala Ile His Pro Asp His Trp Ile Asp Tyr Ala Arg Gln Leu
        115                 120                 125

His Gln Trp Leu Glu Pro Gln Gly Ser Leu Trp Val Leu Phe Met Gln
    130                 135                 140

Met Ile Arg Pro Ala Ala Thr Glu Glu Gly Leu Ile Gln Gly Pro Pro
145                 150                 155                 160

Tyr His Cys Asp Ile Asn Ala Met Arg Ala Leu Phe Pro Gln Lys Asp
                165                 170                 175

Trp Val Trp Pro Lys Pro Pro Tyr Ala Arg Val Ser His Pro Asn Leu
            180                 185                 190

Ser His Glu Leu Ala Leu Gln Leu Val Arg Arg
        195                 200

<210> SEQ ID NO 66
<211> LENGTH: 191
<212> TYPE: PRT
<213> ORGANISM: Gramella forsetii

<400> SEQUENCE: 66

Met Asn Lys Asp Phe Trp Ser Leu Arg Tyr Gln Lys Gly Asn Thr Gly
1               5                   10                  15

Trp Asp Ile Gly Asn Ile Ser Thr Pro Leu Lys Glu Tyr Ile Asp His
            20                  25                  30

Leu His Lys Lys Glu Leu Lys Ile Leu Ile Pro Gly Ala Gly Asn Ser
        35                  40                  45

```
Tyr Glu Ala Glu Tyr Leu Phe Glu Lys Gly Phe Lys Asn Ile Trp Ile
             50                  55                  60

Cys Asp Ile Ala Lys Glu Pro Ile Glu Asn Phe Lys Lys Arg Leu Pro
 65                  70                  75                  80

Glu Phe Pro Glu Ser Gln Ile Leu Asn Arg Asp Phe Glu Leu Lys
                 85                  90                  95

Asp Gln Phe Asp Leu Ile Leu Glu Gln Thr Phe Phe Cys Ala Leu Pro
                100                 105                 110

Val Asn Phe Arg Glu Asn Tyr Ala Lys Lys Val Phe Glu Leu Leu Lys
            115                 120                 125

Val Asn Gly Lys Ile Ser Gly Val Leu Phe Asp Phe Pro Leu Thr Pro
130                 135                 140

Asp Gly Pro Pro Phe Gly Gly Ser Lys Glu Glu Tyr Leu Ala Tyr Phe
145                 150                 155                 160

Ser Pro Tyr Phe Lys Ile Asn Thr Phe Glu Arg Cys Tyr Asn Ser Ile
                165                 170                 175

Asn Pro Arg Gln Gly Lys Glu Leu Phe Phe Asn Phe Ser Lys Lys
                180                 185                 190

<210> SEQ ID NO 67
<211> LENGTH: 198
<212> TYPE: PRT
<213> ORGANISM: Anaeromyxobacter dehalogenans

<400> SEQUENCE: 67

Met Gly Thr Ser Tyr Arg Leu Ala Tyr Leu Ile Gly Phe Thr Pro Trp
 1               5                  10                  15

Glu Asp Gln Pro Leu Pro Pro Glu Leu Ser Ala Leu Val Glu Gly Leu
             20                  25                  30

Arg Ala Arg Pro Pro Gly Arg Ala Leu Asp Leu Gly Cys Gly Arg Gly
         35                  40                  45

Ala His Ala Val Tyr Leu Ala Ser His Gly Trp Lys Val Thr Gly Val
     50                  55                  60

Asp Leu Val Pro Ala Ala Leu Ala Lys Ala Arg Gln Arg Ala Thr Asp
 65                  70                  75                  80

Ala Gly Val Asp Val Gln Phe Leu Asp Gly Asp Val Thr Arg Leu Asp
                 85                  90                  95

Thr Leu Gly Leu Ser Pro Gly Tyr Asp Leu Leu Leu Ala Gly Cys
                100                 105                 110

Phe His Gly Leu Ser Asp Pro Glu Arg Ala Ala Tyr Ala Arg Gly Val
            115                 120                 125

Thr Ala Leu Arg Ala Pro Arg Ala Ala Met Leu Leu Phe Ala Phe Lys
130                 135                 140

Pro Gly Trp Arg Gly Pro Ala Pro Arg Gly Ala Ser Ala Glu Asp Leu
145                 150                 155                 160

Thr Ser Ala Phe Gly Pro Ser Trp Arg Leu Val Arg Ser Glu Arg Ala
                165                 170                 175

Arg Glu Ser Arg Leu Pro Leu Pro Leu Arg Asn Ala Asp Pro Arg Trp
                180                 185                 190

His Leu Leu Glu Ala Ala
            195

<210> SEQ ID NO 68
<211> LENGTH: 211
<212> TYPE: PRT
<213> ORGANISM: Mycobacterium smegmatis
```

<400> SEQUENCE: 68

Met Asp Thr Thr Pro Thr Arg Glu Leu Phe Asp Glu Ala Tyr Glu Ser
1               5                   10                  15

Arg Thr Ala Pro Trp Val Ile Gly Glu Pro Gln Pro Ala Val Val Glu
            20                  25                  30

Leu Glu Arg Ala Gly Leu Ile Arg Ser Arg Val Leu Asp Val Gly Cys
        35                  40                  45

Gly Ala Gly Glu His Thr Ile Leu Leu Thr Arg Leu Gly Tyr Asp Val
    50                  55                  60

Leu Gly Ile Asp Phe Ser Pro Gln Ala Ile Glu Met Ala Arg Glu Asn
65                  70                  75                  80

Ala Arg Gly Arg Gly Val Asp Ala Arg Phe Ala Val Gly Asp Ala Met
                85                  90                  95

Ala Leu Gly Asp Leu Gly Asp Gly Ala Tyr Asp Thr Ile Leu Asp Ser
            100                 105                 110

Ala Leu Phe His Ile Phe Asp Asp Ala Asp Arg Gln Thr Tyr Val Ala
        115                 120                 125

Ser Leu His Ala Gly Cys Arg Pro Gly Gly Thr Val His Ile Leu Ala
    130                 135                 140

Leu Ser Asp Ala Gly Arg Gly Phe Gly Pro Glu Val Ser Glu Glu Gln
145                 150                 155                 160

Ile Arg Lys Ala Phe Gly Asp Gly Trp Asp Leu Glu Ala Leu Glu Thr
                165                 170                 175

Thr Thr Tyr Arg Gly Val Val Gly Pro Val His Ala Glu Ala Ile Gly
            180                 185                 190

Leu Pro Val Gly Thr Gln Val Asp Glu Pro Ala Trp Leu Ala Arg Ala
        195                 200                 205

Arg Arg Leu
    210

<210> SEQ ID NO 69
<211> LENGTH: 201
<212> TYPE: PRT
<213> ORGANISM: Unknown
<220> FEATURE:
<223> OTHER INFORMATION: Marine gamma proteobacterium HTCC2080,
      synthetic polypeptide of thiopurine S-methyltransferase thereof

<400> SEQUENCE: 69

Met Glu Lys Phe Gly Ala Ser Ala Met Glu Pro Val Leu Asp Trp Glu
1               5                   10                  15

Ala Arg Tyr Gln Glu Ser Ser Val Pro Trp Glu Arg Thr Gly Leu Asn
            20                  25                  30

Pro Ala Phe Val Ala Trp Gln Ser Trp Leu Arg Asp His Gln Gly Gly
        35                  40                  45

Thr Val Val Val Pro Gly Cys Gly Arg Ser Pro Glu Leu Gln Ala Phe
    50                  55                  60

Ala Asp Met Gly Phe Asn Val Ile Gly Val Asp Leu Ser Pro Ser Ala
65                  70                  75                  80

Ala Gln Phe Gln Glu Thr Val Leu Ala Ala Lys Gly Leu Asp Gly Lys
                85                  90                  95

Leu Val Val Ser Asn Leu Phe Asp Trp Ser Pro Asp Thr Pro Val Asp
            100                 105                 110

Phe Val Tyr Glu Gln Thr Cys Leu Cys Ala Leu Lys Pro Asp His Trp
        115                 120                 125

```
Arg Ala Tyr Glu Asn Leu Leu Thr Arg Trp Leu Arg Pro Gly Gly Thr
            130                 135                 140

Leu Leu Ala Leu Phe Met Gln Thr Gly Glu Ser Gly Gly Pro Pro Phe
145                 150                 155                 160

His Cys Gly Lys Ala Ala Met Glu Gln Leu Phe Ser Glu Gln Arg Trp
                165                 170                 175

Ile Trp Asp Glu Thr Ser Val Arg Ser Glu His Pro Leu Gly Val His
                180                 185                 190

Glu Leu Gly Phe Arg Leu Thr Leu Arg
            195                 200

<210> SEQ ID NO 70
<211> LENGTH: 199
<212> TYPE: PRT
<213> ORGANISM: Artificial Sequence
<220> FEATURE:
<223> OTHER INFORMATION: Synthetic polypeptide of hypothetical protein
      KAOT1_18457 from Kordia algicida

<400> SEQUENCE: 70

Met Asn Ser Asp Ala Thr Lys Glu Tyr Trp Ser Gln Arg Tyr Lys Asp
1               5                   10                  15

Asn Ser Thr Gly Trp Asp Ile Gly Ser Pro Ser Thr Pro Leu Lys Thr
            20                  25                  30

Tyr Ile Asp Gln Leu Lys Asp Arg Asn Leu Lys Ile Leu Ile Pro Gly
        35                  40                  45

Ala Gly Asn Ala Tyr Glu Ala Glu Tyr Leu Leu Gln Gln Gly Phe Thr
50                  55                  60

Asn Ile Tyr Ile Leu Asp Ile Ser Glu Ile Pro Leu Gln Glu Phe Lys
65                  70                  75                  80

Gln Arg Asn Pro Glu Phe Pro Ser Asp Arg Leu Leu Cys Asp Asp Phe
                85                  90                  95

Phe Thr His Lys Asn Thr Tyr Asp Leu Ile Ile Glu Gln Thr Phe Phe
            100                 105                 110

Cys Ser Phe Pro Pro Leu Pro Glu Thr Arg Ala Gln Tyr Ala Lys His
        115                 120                 125

Met Ala Asp Leu Leu Asn Pro Asn Gly Lys Leu Val Gly Leu Trp Phe
130                 135                 140

Asp Phe Pro Leu Thr Asp Asp Leu Glu Lys Arg Pro Phe Gly Gly Ser
145                 150                 155                 160

Lys Glu Glu Tyr Leu Glu Tyr Phe Lys Pro Tyr Phe Asp Val Lys Thr
                165                 170                 175

Phe Glu Lys Ala Tyr Asn Ser Ile Ala Pro Arg Ala Gly Asn Glu Leu
            180                 185                 190

Phe Gly Ile Phe Ile Lys Ser
        195

<210> SEQ ID NO 71
<211> LENGTH: 239
<212> TYPE: PRT
<213> ORGANISM: Alkaliphilus metalliredigens

<400> SEQUENCE: 71

Met Asn Asp Lys Leu Asp Gln Glu Val Ile Leu Asn Gln Glu Asp Leu
1               5                   10                  15

Leu Asn Met Leu Asp Ser Leu Leu Glu Lys Trp Asp Glu Glu Trp Trp
            20                  25                  30
```

```
Asn Glu Phe Tyr Ser Asp Lys Gly Lys Pro Ile Pro Phe Val Asn
            35                  40                  45

Ala Pro Asp Glu Asn Leu Val Thr Tyr Phe Asp Lys Tyr Phe Asp Asp
 50                  55                  60

Ile Gly Arg Ala Leu Asp Val Gly Cys Gly Asn Gly Arg Asn Ser Arg
 65                  70                  75                  80

Phe Ile Ala Ser Arg Gly Tyr Asp Val Glu Gly Leu Asp Phe Ser Lys
                 85                  90                  95

Lys Ser Ile Glu Trp Ala Lys Glu Glu Ser Lys Lys Thr Gly Asp Ile
            100                 105                 110

Ala Leu Tyr Val Asn Asp Ser Phe Phe Asn Ile Asn Arg Glu Leu Ser
            115                 120                 125

Ser Tyr Asp Leu Ile Tyr Asp Ser Gly Cys Leu His His Ile Lys Pro
130                 135                 140

His Arg Arg Ser Gln Tyr Leu Glu Lys Val His Arg Leu Leu Lys Pro
145                 150                 155                 160

Gly Gly Tyr Phe Gly Leu Val Cys Phe Asn Leu Lys Gly Gly Ala Asn
                165                 170                 175

Leu Ser Asp His Asp Val Tyr Lys Lys Ser Ser Met Ala Gly Gly Leu
            180                 185                 190

Gly Tyr Ser Asp Ile Lys Leu Lys Lys Ile Leu Gly Thr Tyr Phe Glu
            195                 200                 205

Ile Val Glu Phe Arg Glu Met Arg Glu Cys Ala Asp Asn Ala Leu Tyr
            210                 215                 220

Gly Lys Asp Ile Cys Trp Ser Ile Leu Met Arg Arg Leu Ala Lys
225                 230                 235

<210> SEQ ID NO 72
<211> LENGTH: 195
<212> TYPE: PRT
<213> ORGANISM: Artificial Sequence
<220> FEATURE:
<223> OTHER INFORMATION: Synthetic polypeptide of hypothetical protein
      MA2137 from Methanosarcina acetivorans

<400> SEQUENCE: 72

Met Phe Trp Asp Glu Val Tyr Lys Gly Thr Pro Pro Trp Asp Ile Asp
 1               5                  10                  15

His Pro Gln Pro Ala Phe Gln Ala Leu Ile Glu Ser Gly Glu Ile Arg
            20                  25                  30

Pro Gly Arg Ala Leu Asp Ile Gly Cys Gly Arg Gly Glu Asn Ala Ile
            35                  40                  45

Met Leu Ala Lys Asn Gly Cys Asp Val Thr Gly Ile Asp Leu Ala Lys
 50                  55                  60

Asp Ala Ile Ser Asp Ala Lys Ala Lys Ala Ile Glu Arg His Val Lys
 65                  70                  75                  80

Val Asn Phe Ile Val Gly Asn Val Leu Glu Met Asp Gln Leu Phe Thr
                 85                  90                  95

Glu Asp Glu Phe Asp Ile Val Ile Asp Ser Gly Leu Phe His Val Ile
            100                 105                 110

Thr Asp Glu Glu Arg Leu Leu Phe Thr Arg His Val His Lys Val Leu
            115                 120                 125

Lys Glu Gly Gly Lys Tyr Phe Met Leu Cys Phe Ser Asp Lys Glu Pro
            130                 135                 140

Gly Glu Tyr Glu Leu Pro Arg Arg Ala Ser Lys Ala Glu Ile Glu Ser
```

```
145                 150                 155                 160
Thr Phe Ser Pro Leu Phe Asn Ile Ile Tyr Ile Lys Asp Val Ile Phe
                165                 170                 175

Asp Ser Leu Leu Asn Pro Gly Arg Arg Gln Ala Tyr Leu Leu Ser Ala
            180                 185                 190

Thr Lys Ser
        195

<210> SEQ ID NO 73
<211> LENGTH: 221
<212> TYPE: PRT
<213> ORGANISM: Legionella pneumophila

<400> SEQUENCE: 73

Met Asn Lys Gly Gln Tyr Phe Trp Asn Glu Leu Trp Cys Gly Arg
1               5                   10                  15

Ile Ser Phe His Lys Lys Glu Val Asn Pro Asp Leu Ile Ala Tyr Val
                20                  25                  30

Ser Ser Leu Asn Ile Pro Ala Lys Gly Arg Val Leu Val Pro Leu Cys
            35                  40                  45

Gly Lys Ser Val Asp Met Leu Trp Leu Val Arg Gln Gly Tyr His Val
50                  55                  60

Val Gly Ile Glu Leu Val Glu Lys Ala Ile Leu Gln Phe Val Gln Glu
65                  70                  75                  80

His Gln Ile Thr Val Arg Glu Asn Thr Ile Gly Gln Ala Lys Gln Tyr
                85                  90                  95

Phe Thr Asp Asn Leu Asn Leu Trp Val Thr Asp Ile Phe Ala Leu Asn
            100                 105                 110

Ser Ala Leu Ile Glu Pro Val Asp Ala Ile Tyr Asp Arg Ala Ala Leu
        115                 120                 125

Val Ala Leu Pro Lys Lys Leu Arg Pro Ala Tyr Val Asp Ile Cys Leu
130                 135                 140

Lys Trp Leu Lys Pro Gly Gly Ser Ile Leu Leu Lys Thr Leu Gln Tyr
145                 150                 155                 160

Asn Gln Glu Lys Val Gln Gly Pro Pro Tyr Ser Val Ser Pro Glu Glu
                165                 170                 175

Ile Ala Leu Ser Tyr Gln Gln Cys Ala Lys Ile Lys Leu Leu Lys Ser
            180                 185                 190

Gln Lys Arg Ile Gln Glu Pro Asn Asp His Leu Phe Asn Phe Gly Ile
        195                 200                 205

Ser Glu Val Asn Asp Ser Val Trp Cys Ile Arg Lys Gly
210                 215                 220

<210> SEQ ID NO 74
<211> LENGTH: 201
<212> TYPE: PRT
<213> ORGANISM: Unknown
<220> FEATURE:
<223> OTHER INFORMATION: Vibrio species, synthetic polypeptide of
      hypothetical protein VEx2w_02000031 thereof

<400> SEQUENCE: 74

Met Lys Gln Ala Pro Thr Ile Asn Gln Gln Phe Trp Asp Asn Leu Phe
1               5                   10                  15

Thr Gln Gly Thr Met Pro Trp Asp Ala Lys Thr Thr Pro Gln Glu Leu
                20                  25                  30

Lys Ala Tyr Leu Glu Asn Ala Leu His Ser Gly Gln Ser Val Phe Ile
```

```
                      35                  40                  45
Pro Gly Cys Gly Ala Ala Tyr Glu Leu Ser Ser Phe Ile Gln Tyr Gly
             50                  55                  60

His Asp Val Ile Ala Met Asp Tyr Ser Glu Gln Ala Val Lys Met Ala
 65                  70                  75                  80

Gln Ser Thr Leu Gly Lys His Lys Asp Lys Val Val Leu Gly Asp Val
                 85                  90                  95

Phe Asn Ala Asp Ser Thr His Ser Phe Asp Val Ile Tyr Glu Arg Ala
            100                 105                 110

Phe Leu Ala Ala Leu Pro Arg Asp Gln Trp Pro Glu Tyr Phe Ala Met
        115                 120                 125

Val Asp Lys Leu Leu Pro Arg Gly Gly Leu Leu Ile Gly Tyr Phe Val
    130                 135                 140

Ile Asp Asp Asp Tyr His Ser Arg Phe Pro Pro Phe Cys Leu Arg Ser
145                 150                 155                 160

Gly Glu Leu Glu Gly Tyr Leu Glu Pro Val Phe Lys Leu Val Glu Ser
                165                 170                 175

Ser Val Val Ala Asn Ser Val Glu Val Phe Lys Gly Arg Glu Arg Trp
            180                 185                 190

Met Val Trp Gln Lys Ser Cys Arg Ile
        195                 200

<210> SEQ ID NO 75
<211> LENGTH: 209
<212> TYPE: PRT
<213> ORGANISM: Mycobacterium vanbaalenii

<400> SEQUENCE: 75

Met Asp Leu Thr Pro Arg Leu Ser Arg Phe Asp Glu Phe Tyr Lys Asn
  1               5                  10                  15

Gln Thr Pro Pro Trp Val Ile Gly Glu Pro Gln Gln Ala Ile Val Glu
                 20                  25                  30

Leu Glu Gln Ala Gly Leu Ile Gly Gly Arg Val Leu Asp Val Gly Cys
             35                  40                  45

Gly Thr Gly Glu His Thr Ile Leu Leu Ala Arg Ala Gly Tyr Asp Val
         50                  55                  60

Leu Gly Ile Asp Gly Ala Pro Thr Ala Val Glu Gln Ala Arg Arg Asn
 65                  70                  75                  80

Ala Glu Ala Gln Gly Val Asp Ala Arg Phe Glu Leu Ala Asp Ala Leu
                 85                  90                  95

His Leu Gly Pro Asp Pro Thr Tyr Asp Thr Ile Val Asp Ser Ala Leu
            100                 105                 110

Phe His Ile Phe Asp Asp Ala Asp Arg Ala Thr Tyr Val Arg Ser Leu
        115                 120                 125

His Ala Ala Thr Arg Pro Gly Ser Val Val His Leu Leu Ala Leu Ser
    130                 135                 140

Asp Ser Gly Arg Gly Phe Gly Pro Glu Val Ser Glu His Thr Ile Arg
145                 150                 155                 160

Ala Ala Phe Gly Ala Gly Trp Glu Val Glu Ala Leu Thr Glu Thr Thr
                165                 170                 175

Tyr Arg Gly Val Val Ile Asp Ala His Thr Glu Ala Leu Asn Leu Pro
            180                 185                 190

Ala Gly Thr Val Val Asp Glu Pro Ala Trp Ser Ala Arg Ile Arg Arg
        195                 200                 205
```

-continued

Leu

<210> SEQ ID NO 76
<211> LENGTH: 218
<212> TYPE: PRT
<213> ORGANISM: Saccharopolyspora erythraea

<400> SEQUENCE: 76

```
Met Asp Asp Glu Leu Ala Glu Ser Gln Arg Ala His Trp Gln Asp Thr
1 5 10 15

Tyr Ser Ala His Pro Gly Met Tyr Gly Glu Glu Pro Ser Ala Pro Ala
20 25 30

Val His Ala Ala Gly Val Phe Arg Ala Ala Gly Ala Arg Asp Val Leu
35 40 45

Glu Leu Gly Ala Gly His Gly Arg Asp Ala Leu His Phe Ala Arg Glu
50 55 60

Gly Phe Thr Val Gln Ala Leu Asp Phe Ser Ser Ser Gly Leu Gln Gln
65 70 75 80

Leu Arg Asp Ala Ala Arg Ala Gln Gln Val Glu Gln Arg Val Thr Thr
85 90 95

Ala Val His Asp Val Arg His Pro Leu Pro Ser Ala Asp Ala Ser Val
100 105 110

Asp Ala Val Phe Ala His Met Leu Leu Cys Met Ala Leu Ser Thr Glu
115 120 125

Glu Ile His Ala Leu Val Gly Glu Ile His Arg Val Leu Arg Pro Gly
130 135 140

Gly Val Leu Val Tyr Thr Val Arg His Thr Gly Asp Ala His His Gly
145 150 155 160

Thr Gly Val Ala His Gly Asp Asp Ile Phe Glu His Asp Gly Phe Ala
165 170 175

Val His Phe Phe Pro Arg Gly Leu Val Asp Ser Leu Ala Asp Gly Trp
180 185 190

Thr Leu Asp Glu Val His Ala Phe Glu Glu Gly Asp Leu Pro Arg Arg
195 200 205

Leu Trp Arg Val Thr Gln Thr Leu Pro Arg
210 215
```

<210> SEQ ID NO 77
<211> LENGTH: 207
<212> TYPE: PRT
<213> ORGANISM: Artificial Sequence
<220> FEATURE:
<223> OTHER INFORMATION: Synthetic polypeptide of hypothetical protein Bxe_A4046 from Burkholderia xenovorans

<400> SEQUENCE: 77

```
Met Ser Asp Pro Thr Gln Pro Ala Val Pro Asp Phe Glu Thr Arg Asp
1 5 10 15

Pro Asn Ser Pro Ala Phe Trp Asp Glu Arg Phe Glu Arg Arg Phe Thr
20 25 30

Pro Trp Asp Gln Ala Gly Val Pro Ala Ala Phe Gln Ser Phe Ala Ala
35 40 45

Arg His Ser Gly Ala Ala Val Leu Ile Pro Gly Cys Gly Ser Ala Tyr
50 55 60

Glu Ala Val Trp Leu Ala Gly Gln Gly Asn Pro Val Arg Ala Ile Asp
65 70 75 80

Phe Ser Pro Ala Ala Val Ala Ala Ala His Glu Gln Leu Gly Ala Gln

```
                      85                  90                  95

His Ala Gln Leu Val Glu Gln Ala Asp Phe Phe Thr Tyr Glu Pro Pro
                100                 105                 110

Phe Thr Pro Ala Trp Ile Tyr Glu Arg Ala Phe Leu Cys Ala Leu Pro
            115                 120                 125

Leu Ala Arg Arg Ala Asp Tyr Ala His Arg Met Ala Asp Leu Leu Pro
        130                 135                 140

Gly Gly Ala Leu Leu Ala Gly Phe Phe Leu Gly Ala Thr Pro Lys
145                 150                 155                 160

Gly Pro Pro Phe Gly Ile Glu Arg Ala Glu Leu Asp Ala Leu Leu Thr
                165                 170                 175

Pro Tyr Phe Asp Leu Ile Glu Asp Glu Ala Val His Asp Ser Ile Ala
            180                 185                 190

Val Phe Ala Gly Arg Glu Arg Trp Leu Thr Trp Arg Arg Arg Ala
        195                 200                 205

<210> SEQ ID NO 78
<211> LENGTH: 207
<212> TYPE: PRT
<213> ORGANISM: Burkholderia phytofirmans

<400> SEQUENCE: 78

Met Ser Asp Pro Thr Gln Pro Ser Ala Pro Glu Phe Glu Ser Arg Asp
1               5                   10                  15

Pro Asn Ser Pro Glu Phe Trp Asp Glu Arg Phe Glu Arg Gly Phe Met
            20                  25                  30

Pro Trp Asp Gln Ala Gly Val Pro Ser Ala Phe Glu Ser Phe Ala Ala
        35                  40                  45

Arg His Ala Gly Ala Ala Val Leu Ile Pro Gly Cys Gly Ser Ala Tyr
    50                  55                  60

Glu Ala Val Trp Leu Ala Gly His Gly Tyr Pro Val Arg Ala Ile Asp
65                  70                  75                  80

Phe Ser Pro Ala Ala Val Ala Ala His Glu Gln Leu Gly Ala Gln
                85                  90                  95

His Ala Asp Leu Val Glu Gln Ala Asp Phe Phe Thr Tyr Glu Leu Pro
                100                 105                 110

Phe Thr Pro Ala Trp Ile Tyr Glu Arg Ala Phe Leu Cys Ala Leu Pro
            115                 120                 125

Leu Ala Arg Arg Ala Asp Tyr Ala Arg Arg Met Ala Asp Leu Leu Pro
        130                 135                 140

Gly Gly Ala Leu Leu Ala Gly Phe Phe Ile Gly Ala Thr Pro Lys
145                 150                 155                 160

Gly Pro Pro Phe Gly Ile Glu Arg Ala Glu Leu Asp Gly Leu Leu Lys
                165                 170                 175

Pro Tyr Phe Glu Leu Ile Glu Asp Glu Pro Val His Asp Ser Ile Ala
            180                 185                 190

Val Phe Ala Gly Arg Glu Arg Trp Leu Thr Trp Arg Arg Arg Val
        195                 200                 205

<210> SEQ ID NO 79
<211> LENGTH: 245
<212> TYPE: PRT
<213> ORGANISM: Burkholderia thailandensis

<400> SEQUENCE: 79

Met Thr Ser Glu Ala Asn Lys Gly Asp Ala Ala Val Gln Ala Ala Gly
```

```
1               5                   10                  15
Asp Ala Gln Pro Ala Ser Pro Ala Ser Pro Ser Ala Asp Val Gln
                20                  25                  30
Pro Ala Arg Ala Ala Leu Ala Pro Ser Ser Val Pro Pro Ala Pro Ser
            35                  40                  45
Ala Ala Asn Phe Ala Ser Arg Asp Pro Gly Asp Ala Ser Phe Trp Asp
        50                  55                  60
Glu Arg Phe Glu Arg Gly Val Thr Pro Trp Asp Ser Ala Arg Val Pro
65                  70                  75                  80
Asp Ala Phe Ala Ala Phe Ala Ala Arg His Pro Arg Cys Pro Val Leu
                85                  90                  95
Ile Pro Gly Cys Gly Ser Ala Tyr Glu Ala Arg Trp Leu Ala Arg Ala
                100                 105                 110
Gly Trp Pro Val Arg Ala Ile Asp Phe Ser Ala Gln Ala Val Ala Ala
            115                 120                 125
Ala Arg Arg Glu Ser Gly Ala Asp Ala Ala Leu Val Glu Gln Ala Asp
        130                 135                 140
Phe Phe Ala Tyr Val Pro Pro Phe Val Pro Gln Trp Ile Tyr Glu Arg
145                 150                 155                 160
Ala Phe Leu Cys Ala Ile Pro Thr Ser Arg Arg Ala Asp Tyr Ala Arg
                165                 170                 175
Arg Val Ala Glu Leu Leu Pro Ala Gly Gly Phe Leu Ala Gly Phe Phe
                180                 185                 190
Phe Ile Gly Ala Thr Pro Lys Gly Pro Pro Phe Gly Ile Glu Arg Ala
            195                 200                 205
Glu Leu Asp Ala Leu Leu Ser Pro Asn Phe Glu Leu Val Glu Asp Glu
        210                 215                 220
Pro Val Ala Asp Ser Leu Pro Val Phe Ala Gly Arg Glu Arg Trp Leu
225                 230                 235                 240
Ala Trp Arg Arg Ser
                245

<210> SEQ ID NO 80
<211> LENGTH: 208
<212> TYPE: PRT
<213> ORGANISM: Burkholderia vietnamiensis

<400> SEQUENCE: 80

Met Ser Asn Pro Thr Gln Pro Pro Pro Ser Ala Ala Asp Phe Ala
1               5                   10                  15
Thr Arg Asp Pro Ala Asn Ala Ser Phe Trp Asp Glu Arg Phe Ala Arg
                20                  25                  30
Gly Val Thr Pro Trp Glu Phe Gly Gly Val Pro Asp Gly Phe Arg Ala
            35                  40                  45
Phe Ala Gln Arg Arg Ala Pro Cys Thr Val Leu Ile Pro Gly Cys Gly
        50                  55                  60
Ser Ala Gln Glu Ala Gly Trp Leu Ala Gln Ala Gly Trp Pro Val Arg
65                  70                  75                  80
Ala Ile Asp Phe Ala Glu Gln Ala Val Val Ala Ala Lys Ala Thr Leu
                85                  90                  95
Gly Ala His Ala Asp Val Val Glu Gln Ala Asp Phe Phe Ala Tyr Gln
                100                 105                 110
Pro Pro Phe Val Val Gln Trp Val Tyr Glu Arg Ala Phe Leu Cys Ala
            115                 120                 125
```

```
Leu Pro Pro Ser Leu Arg Ala Gly Tyr Ala Ala Arg Met Ala Glu Leu
        130                 135                 140

Leu Pro Ala Gly Gly Leu Leu Ala Gly Tyr Phe Phe Val Met Lys Lys
145                 150                 155                 160

Pro Lys Gly Pro Pro Phe Gly Ile Glu Arg Ala Glu Leu Asp Ala Leu
                165                 170                 175

Leu Ala Pro Ser Phe Glu Leu Ile Glu Asp Leu Pro Val Thr Asp Ser
                180                 185                 190

Leu Ala Val Phe Asp Gly His Glu Arg Trp Leu Thr Trp Arg Arg Arg
        195                 200                 205

<210> SEQ ID NO 81
<211> LENGTH: 208
<212> TYPE: PRT
<213> ORGANISM: Burkholderia cenocepacia

<400> SEQUENCE: 81

Met Ser Asp Pro Lys Gln Pro Ala Ala Pro Ser Ala Ala Glu Phe Ala
1               5                   10                  15

Thr Arg Asp Pro Gly Ser Ala Ser Phe Trp Asp Glu Arg Phe Ala Arg
                20                  25                  30

Gly Val Thr Pro Trp Glu Phe Gly Gly Val Pro Asp Gly Phe Arg Ala
            35                  40                  45

Phe Ala Gln Arg His Glu Pro Cys Ala Val Leu Ile Pro Gly Cys Gly
    50                  55                  60

Ser Ala Gln Glu Ala Gly Trp Leu Ala Gln Ala Gly Trp Pro Val Arg
65                  70                  75                  80

Ala Ile Asp Phe Ala Ala Gln Ala Val Ala Ala Lys Val Gln Leu
                85                  90                  95

Gly Ala His Ala Asp Val Val Glu Gln Ala Asp Phe Phe Gln Tyr Arg
            100                 105                 110

Pro Pro Phe Asp Val Gln Trp Val Tyr Glu Arg Ala Phe Leu Cys Ala
        115                 120                 125

Leu Pro Pro Ser Leu Arg Ala Asp Tyr Ala Ala Arg Met Ala Glu Leu
        130                 135                 140

Leu Pro Thr Gly Gly Leu Leu Ala Gly Tyr Phe Phe Val Val Ala Lys
145                 150                 155                 160

Pro Lys Gly Pro Pro Phe Gly Ile Glu Arg Ala Glu Leu Asp Ala Leu
                165                 170                 175

Leu Ala Pro His Phe Glu Leu Leu Glu Asp Leu Pro Val Thr Asp Ser
                180                 185                 190

Leu Ala Val Phe Asp Gly His Glu Arg Trp Leu Thr Trp Arg Arg Arg
        195                 200                 205

<210> SEQ ID NO 82
<211> LENGTH: 261
<212> TYPE: PRT
<213> ORGANISM: Burkholderia mallei

<400> SEQUENCE: 82

Met Lys Asp Arg Leu Met Ser Gln Gly Asp Gly Val Thr Asn Glu Ala
1               5                   10                  15

Asn Gln Pro Glu Ala Ala Gly Gln Ala Ala Gly Asp Ala Gln Pro Ala
                20                  25                  30

Ser Pro Ala Gly Pro Ala His Ile Ala Asn Pro Ala Asn Pro Ala Asn
            35                  40                  45
```

```
Pro Pro Ala Leu Pro Ser Phe Ser Pro Pro Ala Ala Ala Ser Ser Ser
    50                  55                  60

Ala Ser Ser Ala Ala Pro Phe Ser Arg Asp Pro Gly Asp Ala Ser
65                  70                  75                  80

Phe Trp Asp Glu Arg Phe Glu Gln Gly Val Thr Pro Trp Asp Ser Ala
                85                  90                  95

Arg Val Pro Asp Ala Phe Ala Ala Arg His Ala Arg Val Pro Val Leu
            100                 105                 110

Ile Pro Gly Cys Gly Ser Ala Tyr Glu Ala Arg Trp Leu Ala Arg Ala
            115                 120                 125

Gly Trp Pro Val Arg Ala Ile Asp Phe Ser Ala Gln Ala Val Ala Ala
130                 135                 140

Ala Arg Arg Glu Leu Gly Glu Asp Ala Gly Leu Val Glu Gln Ala Asp
145                 150                 155                 160

Phe Phe Thr Tyr Ala Pro Pro Phe Val Pro Gln Trp Ile Tyr Glu Arg
                165                 170                 175

Ala Phe Leu Cys Ala Ile Pro Arg Ser Arg Ala Asp Tyr Ala Arg
            180                 185                 190

Arg Met Ala Glu Leu Leu Pro Pro Gly Gly Phe Leu Ala Gly Phe Phe
            195                 200                 205

Phe Ile Gly Ala Thr Pro Lys Gly Pro Pro Phe Gly Ile Glu Arg Ala
    210                 215                 220

Glu Leu Asp Ala Leu Leu Cys Pro His Phe Ala Leu Val Glu Asp Glu
225                 230                 235                 240

Pro Val Ala Asp Ser Leu Pro Val Phe Ala Gly Arg Glu Arg Trp Leu
                245                 250                 255

Ala Trp Arg Arg Ser
            260

<210> SEQ ID NO 83
<211> LENGTH: 267
<212> TYPE: PRT
<213> ORGANISM: Burkholderia pseudomallei

<400> SEQUENCE: 83

Met Lys Asp Arg Leu Met Ser Gln Gly Asp Gly Val Thr Asn Glu Ala
1               5                   10                  15

Asn Gln Pro Glu Ala Ala Gly Gln Ala Thr Gly Asp Ala Gln Pro Ala
            20                  25                  30

Ser Pro Ala Gly Pro Ala His Ile Ala Asn Pro Ala Asn Pro Ala Asn
        35                  40                  45

Pro Ala Asn Pro Pro Ala Leu Pro Ser Leu Ser Pro Ala Ala Ala
    50                  55                  60

Pro Ser Ser Ala Ser Ala Ala His Phe Ser Arg Asp Pro Gly
65                  70                  75                  80

Asp Ala Ser Phe Trp Asp Glu Arg Phe Glu Gln Gly Val Thr Pro Trp
                85                  90                  95

Asp Ser Ala Arg Val Pro Asp Ala Phe Ala Ala Phe Ala Ala Arg His
            100                 105                 110

Ala Arg Val Pro Val Leu Ile Pro Gly Cys Gly Ser Ala Tyr Glu Ala
            115                 120                 125

Arg Trp Leu Ala Arg Ala Gly Trp Pro Val Arg Ala Ile Asp Phe Ser
        130                 135                 140

Ala Gln Ala Val Ala Ala Ala Arg Arg Glu Leu Gly Glu Asp Ala Gly
145                 150                 155                 160
```

Leu Val Glu Gln Ala Asp Phe Phe Thr Tyr Ala Pro Pro Phe Val Pro
            165                 170                 175

Gln Trp Ile Tyr Glu Arg Ala Phe Leu Cys Ala Ile Pro Arg Ser Arg
        180                 185                 190

Arg Ala Asp Tyr Ala Arg Arg Met Ala Glu Leu Leu Pro Pro Gly Gly
            195                 200                 205

Phe Leu Ala Gly Phe Phe Ile Gly Ala Thr Pro Lys Gly Pro Pro
210                 215                 220

Phe Gly Ile Glu Arg Ala Glu Leu Asp Ala Leu Leu Cys Pro His Phe
225                 230                 235                 240

Ala Leu Val Glu Asp Glu Pro Val Ala Asp Ser Leu Pro Val Phe Ala
            245                 250                 255

Gly Arg Glu Arg Trp Leu Ala Trp Arg Arg Ser
            260                 265

<210> SEQ ID NO 84
<211> LENGTH: 208
<212> TYPE: PRT
<213> ORGANISM: Burkholderia cenocepacia

<400> SEQUENCE: 84

Met Ser Asp Pro Lys Gln Pro Ala Ala Pro Ser Ala Ala Asp Phe Ala
1               5                   10                  15

Thr Arg Asp Pro Gly Ser Ala Ser Phe Trp Asp Glu Arg Phe Ala Arg
            20                  25                  30

Gly Val Thr Pro Trp Glu Phe Gly Gly Val Pro Asp Gly Phe Arg Val
        35                  40                  45

Phe Ala Gln Arg Arg Glu Pro Cys Ala Val Leu Ile Pro Gly Cys Gly
    50                  55                  60

Ser Ala Gln Glu Ala Gly Trp Leu Ala Gln Ala Gly Trp Pro Val Arg
65                  70                  75                  80

Ala Ile Asp Phe Ala Ala Gln Ala Val Ala Ala Lys Ala Gln Leu
                85                  90                  95

Gly Ala His Ala Asp Val Val Glu Gln Ala Asp Phe Phe Gln Tyr Arg
            100                 105                 110

Pro Pro Phe Asp Val Gln Trp Val Tyr Glu Arg Ala Phe Leu Cys Ala
        115                 120                 125

Leu Pro Pro Gly Leu Arg Ala Gly Tyr Ala Ala Arg Met Ala Glu Leu
    130                 135                 140

Leu Pro Thr Gly Gly Leu Leu Ala Gly Tyr Phe Phe Val Val Ala Lys
145                 150                 155                 160

Pro Lys Gly Pro Pro Phe Gly Ile Glu Arg Ala Glu Leu Asp Ala Leu
                165                 170                 175

Leu Ala Pro His Phe Glu Leu Leu Glu Asp Leu Pro Val Thr Asp Ser
            180                 185                 190

Leu Ala Val Phe Asp Gly His Glu Arg Trp Leu Thr Trp Arg Arg Arg
        195                 200                 205

<210> SEQ ID NO 85
<211> LENGTH: 215
<212> TYPE: PRT
<213> ORGANISM: Burkholderia dolosa

<400> SEQUENCE: 85

Met Thr Gly Arg Ser Phe Ala Met Ser Asp Pro Lys Gln Pro Gly Thr
1               5                   10                  15

```
Pro Thr Ala Ala Asp Phe Ala Thr Arg Asp Pro Gly Asp Ala Ser Phe
            20                  25                  30

Trp Asp Glu Arg Phe Ala Arg Gly Val Thr Pro Trp Glu Phe Gly Gly
        35                  40                  45

Val Pro Asp Gly Phe Arg Ala Phe Ala Gln Arg Leu Glu Arg Cys Ala
    50                  55                  60

Val Leu Ile Pro Gly Cys Gly Ser Ala Gln Glu Ala Gly Trp Leu Ala
65                  70                  75                  80

Asp Ala Gly Trp Pro Val Arg Ala Ile Asp Phe Ala Ala Gln Ala Val
                85                  90                  95

Ala Thr Ala Lys Ala Gln Leu Gly Ala His Ala Asp Val Val Glu Leu
            100                 105                 110

Ala Asp Phe Phe Thr Tyr Arg Pro Pro Phe Asp Val Arg Trp Ile Tyr
        115                 120                 125

Glu Arg Ala Phe Leu Cys Ala Leu Pro Pro Ala Arg Arg Ala Asp Tyr
    130                 135                 140

Ala Ala Gln Met Ala Ala Leu Leu Pro Ala Gly Gly Leu Leu Ala Gly
145                 150                 155                 160

Tyr Phe Phe Val Thr Ala Lys Pro Lys Gly Pro Pro Phe Gly Ile Glu
                165                 170                 175

Arg Ala Glu Leu Asp Ala Leu Leu Ala Pro Gln Phe Asp Leu Ile Asp
            180                 185                 190

Asp Trp Pro Val Thr Asp Ser Leu Pro Val Phe Glu Gly His Glu Arg
        195                 200                 205

Trp Leu Thr Trp Arg Arg Arg
    210                 215

<210> SEQ ID NO 86
<211> LENGTH: 208
<212> TYPE: PRT
<213> ORGANISM: Burkholderia ambifaria

<400> SEQUENCE: 86

Met Ser Glu Pro Lys Gln Pro Ser Thr Pro Gly Ala Ala Asp Phe Ala
1               5                   10                  15

Thr Arg Asp Pro Gly Asp Ala Ser Phe Trp Asp Glu Arg Phe Ala Arg
            20                  25                  30

Gly Val Thr Pro Trp Glu Phe Gly Gly Val Pro Glu Gly Phe Arg Ala
        35                  40                  45

Phe Ala Gln Arg Leu Gly Pro Cys Ala Val Leu Ile Pro Gly Cys Gly
    50                  55                  60

Ser Ala Gln Glu Ala Gly Trp Leu Ala Gln Ala Gly Trp Pro Val Arg
65                  70                  75                  80

Ala Ile Asp Phe Ala Ala Gln Ala Val Ala Ala Lys Ala Gln Leu
                85                  90                  95

Gly Ala His Ala Asp Val Val Glu Gln Ala Asp Phe Phe Met Tyr Arg
            100                 105                 110

Pro Pro Phe Asp Val Gln Trp Val Tyr Glu Arg Ala Phe Leu Cys Ala
        115                 120                 125

Leu Pro Pro Ser Leu Arg Ala Gly Tyr Ala Ala Arg Met Ala Glu Leu
    130                 135                 140

Leu Pro Ala Gly Ala Leu Leu Ala Gly Tyr Phe Phe Val Thr Lys Lys
145                 150                 155                 160

Pro Lys Gly Pro Pro Phe Gly Ile Glu Arg Ala Glu Leu Asp Ala Leu
```

```
                165                 170                 175
Leu Ala Pro His Phe Glu Leu Ile Asp Asp Leu Pro Val Thr Asp Ser
        180                 185                 190

Leu Ala Val Phe Glu Gly His Glu Arg Trp Leu Thr Trp Arg Arg Arg
        195                 200                 205

<210> SEQ ID NO 87
<211> LENGTH: 210
<212> TYPE: PRT
<213> ORGANISM: Unknown
<220> FEATURE:
<223> OTHER INFORMATION: Burkholderia species, synthetic polypeptide
      of thiopurine S-methyltransferase thereof

<400> SEQUENCE: 87

Met Ser Asp Pro Lys Gln Pro Lys Pro Asn Ala Pro Ala Ala Ala Asp
1               5                   10                  15

Phe Thr Thr Arg Asp Pro Gly Asn Ala Ser Phe Trp Asn Glu Arg Phe
            20                  25                  30

Glu Arg Gly Val Thr Pro Trp Glu Phe Gly Val Pro Glu Gly Phe
        35                  40                  45

Ser Val Phe Ala His Arg Leu Glu Leu Cys Ala Val Leu Ile Pro Gly
    50                  55                  60

Cys Gly Ser Ala Gln Glu Ala Gly Trp Leu Ala Glu Ala Gly Trp Pro
65                  70                  75                  80

Val Arg Ala Ile Asp Phe Ala Ala Gln Ala Val Ala Ala Lys Ala
                85                  90                  95

Gln Leu Gly Ala His Ala Gly Val Val Glu Gln Ala Asp Phe Ala
            100                 105                 110

Tyr Arg Pro Pro Phe Asp Val Gln Trp Val Tyr Glu Arg Ala Phe Leu
            115                 120                 125

Cys Ala Leu Pro Pro Ala Met Arg Ala Asp Tyr Ala Ala Arg Met Ala
    130                 135                 140

Glu Leu Leu Pro Ala Asp Gly Leu Leu Ala Gly Tyr Phe Phe Leu Met
145                 150                 155                 160

Ala Lys Pro Lys Gly Pro Pro Phe Gly Ile Glu Arg Ala Glu Leu Asp
                165                 170                 175

Ala Leu Leu Thr Pro His Phe Glu Leu Ile Glu Asp Leu Pro Val Thr
            180                 185                 190

Asp Ser Leu Ala Val Phe Glu Gly His Glu Arg Trp Leu Thr Trp Arg
        195                 200                 205

Arg Arg
    210

<210> SEQ ID NO 88
<211> LENGTH: 208
<212> TYPE: PRT
<213> ORGANISM: Burkholderia multivorans

<400> SEQUENCE: 88

Met Ser Asp Pro Lys His Ala Ala Ala Pro Ala Ala Ala Ser Phe Glu
1               5                   10                  15

Thr Arg Asp Pro Gly Asp Ala Ser Phe Trp Asp Glu Arg Phe Ala Arg
            20                  25                  30

Gly Met Thr Pro Trp Glu Phe Gly Val Pro Ala Gly Phe Arg Ala
        35                  40                  45

Phe Ala Ser Ala Arg Pro Pro Cys Ala Val Leu Ile Pro Gly Cys Gly
```

```
Ser Ala Arg Glu Ala Gly Trp Leu Ala Gln Ala Gly Trp Pro Val Arg
 65                  70                  75                  80

Ala Ile Asp Phe Ser Ala Gln Ala Val Ala Ala Lys Ala Gln Leu
                 85                  90                  95

Gly Ala His Ala Asp Val Val Glu Gln Ala Asp Phe Phe Ala Tyr Arg
            100                 105                 110

Pro Pro Phe Asp Val Gln Trp Ile Tyr Glu Arg Ala Phe Leu Cys Ala
        115                 120                 125

Leu Pro Pro Ala Arg Arg Ala Asp Tyr Ala Ala Thr Met Ala Ala Leu
    130                 135                 140

Leu Pro Ala Gln Gly Leu Leu Ala Gly Tyr Phe Val Ala Asp Lys
145                 150                 155                 160

Gln Lys Gly Pro Pro Phe Gly Ile Thr Arg Gly Glu Leu Asp Ala Leu
                165                 170                 175

Leu Gly Ala His Phe Glu Leu Ile Asp Asp Ala Pro Val Ser Asp Ser
            180                 185                 190

Leu Pro Val Phe Glu Gly His Glu Arg Trp Leu Ala Trp Arg Arg Arg
        195                 200                 205

<210> SEQ ID NO 89
<211> LENGTH: 151
<212> TYPE: PRT
<213> ORGANISM: Burkholderia cenocepacia

<400> SEQUENCE: 89

Met Leu Ile Pro Gly Cys Gly Ser Ala Gln Glu Ala Gly Trp Leu Ala
  1               5                  10                  15

Gln Ala Gly Trp Pro Val Arg Ala Ile Asp Phe Ala Ala Gln Ala Val
                 20                  25                  30

Ala Ala Ala Lys Ala Gln Leu Gly Ala His Ala Asp Val Val Glu Gln
             35                  40                  45

Ala Asp Phe Phe Ala Tyr Arg Pro Pro Phe Asp Val Gln Trp Val Tyr
 50                  55                  60

Glu Arg Ala Phe Leu Cys Ala Leu Pro Pro Ser Leu Arg Ala Gly Tyr
 65                  70                  75                  80

Ala Ala Arg Met Ala Glu Leu Leu Pro Thr Gly Gly Leu Leu Ala Gly
                 85                  90                  95

Tyr Phe Val Val Ala Lys Pro Lys Gly Pro Pro Phe Gly Ile Glu
            100                 105                 110

Pro Ala Glu Leu Asp Ala Leu Leu Ala Pro His Phe Ala Leu Leu Glu
        115                 120                 125

Asp Leu Pro Val Thr Asp Ser Leu Ala Val Phe Asp Gly His Glu Arg
    130                 135                 140

Trp Leu Thr Trp Arg Arg Arg
145                 150

<210> SEQ ID NO 90
<211> LENGTH: 200
<212> TYPE: PRT
<213> ORGANISM: Artificial Sequence
<220> FEATURE:
<223> OTHER INFORMATION: Synthetic polypeptide of hypothetical protein
      VPA1146 from Vibrio parahaemolyticus

<400> SEQUENCE: 90

Met Lys Ser Lys Asp Ser Pro Ile Ile Asn Glu Gln Phe Trp Asp Ala
```

```
1               5                   10                  15
Leu Phe Phe Asn Gly Thr Met Pro Trp Asp Arg Ser Gln Thr Pro Asn
                20                  25                  30

Glu Leu Lys His Tyr Leu Lys Arg Ile Ala Asp Lys Thr His Ser Val
            35                  40                  45

Phe Ile Pro Gly Cys Gly Ala Ala Tyr Glu Val Ser His Phe Val Asp
        50                  55                  60

Cys Gly His Asp Val Ile Ala Met Asp Tyr Ser Ala Glu Ala Val Asn
65                  70                  75                  80

Leu Ala Lys Ser Gln Leu Gly Gln His Gln Asp Lys Val Met Leu Gly
                85                  90                  95

Asp Val Phe Asn Ala Asp Phe Ser Arg Glu Phe Asp Val Ile Tyr Glu
            100                 105                 110

Arg Ala Phe Leu Ala Ala Leu Pro Arg Glu Ile Trp Gly Asp Tyr Phe
        115                 120                 125

Ala Met Ile Glu Arg Leu Leu Pro Ser Asn Gly Leu Leu Val Gly Tyr
    130                 135                 140

Phe Val Ile Ser Asp Asp Tyr Arg Ser Arg Phe Pro Pro Phe Cys Leu
145                 150                 155                 160

Arg Ser Gly Glu Ile Glu Gln Lys Leu Glu Ala Asn Phe His Leu Ile
                165                 170                 175

Glu Ser Thr Pro Val Thr Asp Ser Val Asp Val Phe Lys Gly Lys Glu
            180                 185                 190

Gln Trp Met Val Trp Gln Lys Lys
        195                 200

<210> SEQ ID NO 91
<211> LENGTH: 198
<212> TYPE: PRT
<213> ORGANISM: Artificial Sequence
<220> FEATURE:
<223> OTHER INFORMATION: Synthetic polypeptide of hypothetical protein
      V12G01_01280 from Vibrio alginolyticus

<400> SEQUENCE: 91

Met Lys Gln Ala Pro Met Ile Asn Thr Gln Phe Trp Asp Asp Leu Phe
1               5                   10                  15

Ile Arg Gly Thr Met Pro Trp Asp Ala Gln Ser Thr Pro Gln Glu Leu
                20                  25                  30

Lys Asp Tyr Leu Asp Asn Ser Leu His Val Gly Gln Ser Val Phe Ile
            35                  40                  45

Pro Gly Cys Gly Ala Ala Tyr Glu Leu Ser Thr Phe Ile Gln Tyr Gly
        50                  55                  60

His Asp Val Ile Ala Met Asp Tyr Ser Gln Glu Ala Val Lys Met Ala
65                  70                  75                  80

Gln Ser Ala Leu Gly Asn Tyr Lys Asp Lys Val Val Leu Gly Asp Val
                85                  90                  95

Phe Asn Ala Asp Phe Ser His Ser Phe Asp Val Ile Tyr Glu Arg Ala
            100                 105                 110

Phe Leu Ala Ala Leu Pro Arg Asp Met Trp Ser Glu Tyr Phe Ser Thr
        115                 120                 125

Val Asp Lys Leu Leu Pro Ser Gly Gly Phe Leu Ile Gly Phe Phe Val
    130                 135                 140

Ile Asp Asp Asp Tyr Cys Ser Arg Phe Pro Pro Phe Cys Leu Arg Ser
145                 150                 155                 160
```

Gly Glu Leu Ala Ser Phe Leu Glu Pro Thr Phe Glu Leu Val Lys Ser
                165                 170                 175

Ser Val Val Ala Asn Ser Val Glu Val Phe Lys Gly Arg Glu Gln Trp
            180                 185                 190

Met Val Trp Gln Lys Arg
        195

<210> SEQ ID NO 92
<211> LENGTH: 210
<212> TYPE: PRT
<213> ORGANISM: Unknown
<220> FEATURE:
<223> OTHER INFORMATION: Synechococcus species, synthetic polypeptide
      of thiopurine S-methyltransferase thereof

<400> SEQUENCE: 92

Met Thr Asn Val His Leu Pro Gln Ala Trp Asp Ala Arg Tyr Gln His
1               5                   10                  15

Gly Thr Asp Gly Trp Glu Leu Gly Lys Ala Ala Pro Leu Gln Ala
            20                  25                  30

Phe Leu Glu His His Pro Arg Ala Pro Gln Pro Glu Gly Thr Val Leu
        35                  40                  45

Val Pro Gly Cys Gly Arg Gly His Glu Ala Ala Leu Leu Ala Arg Leu
    50                  55                  60

Gly Phe Glu Val Ile Gly Leu Asp Phe Ser Ser Glu Ala Ile Arg Glu
65                  70                  75                  80

Ala Arg Arg Leu His Gly Glu His Pro Arg Leu Arg Trp Leu Gln Ala
                85                  90                  95

Asp Leu Phe Asp Ala Asp Ala Leu Ser Gly Ala Gly Leu Ala Ser Gly
            100                 105                 110

Ser Leu Ser Gly Val Leu Glu His Thr Cys Phe Cys Ala Ile Asp Pro
        115                 120                 125

Ser Gln Arg Ala His Tyr Arg Ser Thr Val Asp Arg Leu Leu Arg Ala
    130                 135                 140

Glu Gly Trp Leu Leu Gly Leu Phe Phe Cys His Pro Arg Pro Gly Gly
145                 150                 155                 160

Pro Pro Phe Gly Ser Asp Pro Glu Gln Leu Ala Ala Ser Trp Ala Gln
                165                 170                 175

Ile Gly Phe Tyr Pro Leu Ile Trp Glu Pro Ala Arg Gly Ser Val Ala
            180                 185                 190

Gly Arg Ser Glu Glu Trp Leu Gly Phe Trp Arg Lys Pro Gln Arg
        195                 200                 205

Ser Ala
    210

<210> SEQ ID NO 93
<211> LENGTH: 225
<212> TYPE: PRT
<213> ORGANISM: Unknown
<220> FEATURE:
<223> OTHER INFORMATION: Synechococcus species, synthetic
      polypeptide of thiol methyltransferase 1-like protein thereof

<400> SEQUENCE: 93

Met Gln Leu Asp Gly Ala Ser Ser Ala Pro Thr Leu Thr Ala Arg Asp
1               5                   10                  15

Trp Asp Ala Arg Tyr Arg Gln Gly Thr Asp Arg Trp Leu Gly Met
            20                  25                  30

```
Ala Ala Pro Pro Leu Gln Ala Phe Leu Glu Gln His Pro Leu Ala Pro
            35                  40                  45

Lys Pro Thr Gly Thr Val Leu Val Pro Gly Cys Gly Arg Gly His Glu
 50                      55                  60

Ala Ala Leu Leu Ala Arg Leu Gly Phe Asp Val Val Gly Leu Asp Phe
 65                  70                  75                  80

Ser Val Glu Ala Ile Arg Glu Ala Arg Arg Leu Gln Gly Glu His Glu
                85                  90                  95

Asn Leu Arg Trp Leu Gln Ala Asp Leu Phe Asn Gly Ala Ala Leu Asp
            100                 105                 110

Arg Ala Gly Leu Gly Ala His Ser Leu Ser Gly Val Val Glu His Thr
            115                 120                 125

Cys Phe Cys Ala Ile Asp Pro Ser Gln Arg Asp His Tyr Arg Ser Thr
130                 135                 140

Val Asp Arg Leu Leu Glu Pro Gly Gly Trp Leu Leu Gly Val Phe Phe
145                 150                 155                 160

Cys His Asp Arg Pro Gly Gly Pro Pro Tyr Gly Ser Asp Ala Glu Gln
                165                 170                 175

Leu Ala Ala Ser Trp Ser Gln Ile Gly Phe Thr Gly Val Ile Trp Glu
            180                 185                 190

Pro Ala Gln Gly Ser Val Ala Gln Arg Ser Asp Glu Trp Leu Gly Leu
            195                 200                 205

Trp Arg Lys Pro Ser Gln Ala Asp Asn Glu Ala Ile Pro Ala Gly Ser
210                 215                 220

Arg
225

<210> SEQ ID NO 94
<211> LENGTH: 219
<212> TYPE: PRT
<213> ORGANISM: Unknown
<220> FEATURE:
<223> OTHER INFORMATION: Rhodococcus species, synthetic polypeptide of
      3-demethylubiquinone-9 3-methyltransferase thereof

<400> SEQUENCE: 94

Met Val Asp Ala Pro Arg Phe Pro Tyr Pro Gly Ser Pro Pro Val His
 1               5                  10                  15

Gly Pro Asp Asp Leu Tyr Val Thr Pro Pro Trp Ile Gly Arg
            20                  25                  30

Ala Gln Pro Val Phe Val Ala Leu Ala Glu Gly Gly Ala Ile Arg Gly
            35                  40                  45

Arg Val Leu Asp Cys Gly Cys Gly Thr Gly Glu His Val Leu Leu Ala
 50                  55                  60

Ala Gly Leu Gly Leu Asp Ala Thr Gly Val Asp Leu Ala Ala Thr Ala
 65                  70                  75                  80

Leu Arg Ile Ala Glu Gln Lys Ala Arg Asp Arg Gly Leu Thr Ala Arg
                85                  90                  95

Phe Leu His His Asp Ala Arg Arg Leu Ala Glu Leu Gly Glu Arg Phe
            100                 105                 110

Asp Thr Val Leu Asp Cys Gly Leu Phe His Ile Phe Asp Pro Asp Asp
            115                 120                 125

Arg Ala Ala Tyr Val Asp Ser Leu Arg Asp Val Leu Val Pro Gly Gly
130                 135                 140

Arg Tyr Leu Met Leu Gly Phe Ser Asp Gln Gln Pro Gly Asp Trp Gly
145                 150                 155                 160
```

```
Pro His Arg Leu Thr Arg Asp Glu Ile Thr Thr Ala Phe Asp Asp Gly
            165                 170                 175

Trp Thr Ile Asp Ser Leu Glu Ser Ala Thr Leu Glu Val Thr Leu Asp
            180                 185                 190

Pro Ala Gly Met Arg Ala Trp Gln Leu Ala Ala Thr Arg Thr Trp Pro
            195                 200                 205

His Pro Ile Glu Arg Glu Cys Ser Ala Pro Cys
            210                 215
```

<210> SEQ ID NO 95
<211> LENGTH: 256
<212> TYPE: PRT
<213> ORGANISM: Burkholderia mallei

<400> SEQUENCE: 95

```
Met Ser Gln Gly Asp Gly Val Thr Asn Glu Ala Asn Gln Pro Glu Ala
1               5                   10                  15

Ala Gly Gln Ala Ala Gly Asp Ala Gln Pro Ala Ser Pro Ala Gly Pro
            20                  25                  30

Ala His Ile Ala Asn Pro Ala Asn Pro Ala Asn Pro Pro Ala Leu Pro
            35                  40                  45

Ser Phe Ser Pro Pro Ala Ala Ala Ser Ser Ala Ser Ser Ala Ala
 50                 55                  60

Pro Phe Ser Ser Arg Asp Pro Gly Asp Ala Ser Phe Trp Asp Glu Arg
65                  70                  75                  80

Phe Glu Gln Gly Val Thr Pro Trp Asp Ser Ala Arg Val Pro Asp Ala
            85                  90                  95

Phe Ala Ala Arg His Ala Arg Val Pro Val Leu Ile Pro Gly Cys Gly
            100                 105                 110

Ser Ala Tyr Glu Ala Arg Trp Leu Ala Arg Ala Gly Trp Pro Val Arg
            115                 120                 125

Ala Ile Asp Phe Ser Ala Gln Ala Val Ala Ala Arg Arg Glu Leu
            130                 135                 140

Gly Glu Asp Ala Gly Leu Val Glu Gln Ala Asp Phe Phe Thr Tyr Ala
145                 150                 155                 160

Pro Pro Phe Val Pro Gln Trp Ile Tyr Glu Arg Ala Phe Leu Cys Ala
            165                 170                 175

Ile Pro Arg Ser Arg Arg Ala Asp Tyr Ala Arg Arg Met Ala Glu Leu
            180                 185                 190

Leu Pro Pro Gly Gly Phe Leu Ala Gly Phe Phe Ile Gly Ala Thr
            195                 200                 205

Pro Lys Gly Pro Pro Phe Gly Ile Glu Arg Ala Glu Leu Asp Ala Leu
            210                 215                 220

Leu Cys Pro His Phe Ala Leu Val Glu Asp Glu Pro Val Ala Asp Ser
225                 230                 235                 240

Leu Pro Val Phe Ala Gly Arg Glu Arg Trp Leu Ala Trp Arg Arg Ser
            245                 250                 255
```

<210> SEQ ID NO 96
<211> LENGTH: 250
<212> TYPE: PRT
<213> ORGANISM: Burkholderia mallei

<400> SEQUENCE: 96

```
Met Thr Asn Glu Ala Asn Gln Pro Glu Ala Ala Gly Gln Ala Ala Gly
1               5                   10                  15
```

-continued

Asp Ala Gln Pro Ala Ser Pro Ala Gly Pro Ala His Ile Ala Asn Pro
            20                  25                  30

Ala Asn Pro Ala Asn Pro Pro Ala Leu Pro Ser Phe Ser Pro Pro Ala
        35                  40                  45

Ala Ala Ser Ser Ser Ala Ser Ser Ala Ala Pro Phe Ser Ser Arg Asp
50                  55                  60

Pro Gly Asp Ala Ser Phe Trp Asp Glu Arg Phe Glu Gln Gly Val Thr
65                  70                  75                  80

Pro Trp Asp Ser Ala Arg Val Pro Asp Ala Phe Ala Ala Arg His Ala
                85                  90                  95

Arg Val Pro Val Leu Ile Pro Gly Cys Gly Ser Ala Tyr Glu Ala Arg
            100                 105                 110

Trp Leu Ala Arg Ala Gly Trp Pro Val Arg Ala Ile Asp Phe Ser Ala
        115                 120                 125

Gln Ala Val Ala Ala Arg Arg Glu Leu Gly Glu Asp Ala Gly Leu
    130                 135                 140

Val Glu Gln Ala Asp Phe Phe Thr Tyr Ala Pro Pro Phe Val Pro Gln
145                 150                 155                 160

Trp Ile Tyr Glu Arg Ala Phe Leu Cys Ala Ile Pro Arg Ser Arg Arg
                165                 170                 175

Ala Asp Tyr Ala Arg Arg Met Ala Glu Leu Leu Pro Pro Gly Gly Phe
            180                 185                 190

Leu Ala Gly Phe Phe Phe Ile Gly Ala Thr Pro Lys Gly Pro Pro Phe
        195                 200                 205

Gly Ile Glu Arg Ala Glu Leu Asp Ala Leu Leu Cys Pro His Phe Ala
    210                 215                 220

Leu Val Glu Asp Glu Pro Val Ala Asp Ser Leu Pro Val Phe Ala Gly
225                 230                 235                 240

Arg Glu Arg Trp Leu Ala Trp Arg Arg Ser
                245                 250

<210> SEQ ID NO 97
<211> LENGTH: 267
<212> TYPE: PRT
<213> ORGANISM: Burkholderia pseudomallei

<400> SEQUENCE: 97

Met Lys Asp Arg Leu Met Ser Gln Gly Asp Gly Val Thr Asn Glu Ala
1               5                   10                  15

Asn Gln Pro Glu Ala Ala Gly Gln Ala Ala Gly Asp Ala Gln Pro Ala
            20                  25                  30

Ser Pro Ala Gly Pro Ala His Ile Ala Asn Pro Ala Asn Pro Ala Asn
        35                  40                  45

Pro Ala Asn Pro Pro Ala Leu Pro Ser Leu Ser Pro Pro Ala Ala Ala
50                  55                  60

Pro Ser Ser Ala Ser Ser Ala Ala His Phe Ser Arg Asp Pro Gly
65                  70                  75                  80

Asp Ala Ser Phe Trp Asp Glu Arg Phe Glu Gln Gly Val Thr Pro Trp
                85                  90                  95

Asp Ser Ala Arg Val Pro Asp Ala Phe Ala Ala Phe Ala Ala Arg His
            100                 105                 110

Ala Arg Val Pro Val Leu Ile Pro Gly Cys Gly Ser Ala Tyr Glu Ala
        115                 120                 125

Arg Trp Leu Ala Arg Ala Gly Trp Leu Val Arg Ala Ile Asp Phe Ser

```
                        130                 135                 140
Ala Gln Ala Val Ala Ala Arg Arg Glu Leu Gly Glu Asp Ala Arg
145                 150                 155                 160

Leu Val Glu Gln Ala Asp Phe Phe Thr Tyr Ala Pro Pro Phe Val Pro
                    165                 170                 175

Gln Trp Ile Tyr Glu Arg Ala Phe Leu Cys Ala Ile Pro Arg Ser Arg
                180                 185                 190

Arg Ala Asp Tyr Ala Arg Arg Met Ala Glu Leu Leu Pro Pro Gly Gly
            195                 200                 205

Phe Leu Ala Gly Phe Phe Ile Gly Ala Thr Pro Lys Gly Pro Pro
210                 215                 220

Phe Gly Ile Glu Arg Ala Glu Leu Asp Ala Leu Leu Cys Pro Arg Phe
225                 230                 235                 240

Ala Leu Val Glu Asp Glu Pro Val Ala Asp Ser Leu Pro Val Phe Ala
                245                 250                 255

Gly Arg Glu Arg Trp Leu Ala Trp Arg Arg Ser
                260                 265
```

<210> SEQ ID NO 98
<211> LENGTH: 213
<212> TYPE: PRT
<213> ORGANISM: Artificial Sequence
<220> FEATURE:
<223> OTHER INFORMATION: Synthetic polypeptide of conserved hypothetical
      protein of Chromobacterium violaceum

<400> SEQUENCE: 98

```
Met Ala Asp Ser Ser Arg Ala Asp Phe Trp Glu Gln Arg Tyr Arg Glu
1               5                   10                  15

Gly Val Thr Pro Trp Glu Gly Gly Gln Leu Pro Pro Arg Ala Arg Ala
                20                  25                  30

Phe Phe Ala Ala Gln Arg Pro Leu Arg Val Leu Met Pro Gly Cys Gly
            35                  40                  45

Ser Ala Ala Asp Leu Pro Pro Leu Leu Ala Met Gly His Asp Val Leu
50                  55                  60

Ala Val Asp Phe Ser Glu Ala Ala Ile Glu Leu Ala Ala Arg Gln Trp
65                  70                  75                  80

Pro Glu Ala Ala Gly Arg Leu Leu Leu Ala Asp Phe Phe Gln Leu Gln
                85                  90                  95

Met Pro Ala Phe Asp Cys Leu Phe Glu Arg Ala Phe Leu Cys Ala Leu
            100                 105                 110

Pro Val Gly Met Arg Ser Gln Tyr Ala Glu Arg Val Ala Ala Leu Ile
        115                 120                 125

Ala Pro Gly Gly Ala Leu Ala Gly Val Phe Val Ala Asp Thr Glu
130                 135                 140

Arg Gly Pro Pro Phe Gly Met Gln Ala Glu Ala Leu Arg Glu Leu Leu
145                 150                 155                 160

Ser Pro Trp Phe Glu Leu Glu Asp Leu Ala Leu Asp Glu Ser Val
                165                 170                 175

Ala Val Phe Arg Asn Arg Glu Arg Trp Met Val Trp Arg Arg Arg Gly
            180                 185                 190

Phe Asp Leu Gly Gln Val Ser Glu His Glu Ser Thr Gly Asn Cys Gly
        195                 200                 205

Ala His Arg Lys Glu
    210
```

<210> SEQ ID NO 99
<211> LENGTH: 413
<212> TYPE: PRT
<213> ORGANISM: Artificial Sequence
<220> FEATURE:
<223> OTHER INFORMATION: Synthetic polypeptide of hypothetical protein
      CHGG_03529 from Chaetomium globosum

<400> SEQUENCE: 99

```
Met Ala His Pro Lys Ser Asp Pro Gly Arg Leu Ile Thr His Phe
1               5                   10                  15

Ala Asn Arg Asp Arg Gln Ser Gln Lys Ala Gly Trp Ser Glu Leu Trp
            20                  25                  30

Asp Ser Asp Gln Thr Asp Leu Trp Asp Arg Gly Met Pro Ser Pro Ala
        35                  40                  45

Leu Ile Asp Phe Ile Thr Thr Arg Arg Asp Ile Ile Gly Arg Leu Gly
    50                  55                  60

Gly Gly Arg Arg Pro Arg Ala Leu Val Pro Gly Cys Gly Arg Gly
65                  70                  75                  80

Tyr Asp Val Val Met Leu Ala Phe His Gly Phe Asp Ala Ile Gly Leu
                85                  90                  95

Glu Val Ser Gln Thr Ala Val Asn Ser Ala Arg Ala Tyr Ala Glu Val
            100                 105                 110

Glu Leu Ser Asp Pro Ser Ala Tyr Asn Phe Ala Thr Glu Asp Asp Glu
        115                 120                 125

Lys Arg Arg Ala Thr Cys Gln Pro Gly Thr Val Ser Phe Val Cys Gly
    130                 135                 140

Asp Phe Phe Gln Arg Glu Trp Glu Thr Ser Cys Phe Ala Pro Gly Asp
145                 150                 155                 160

Asp Gly Gly Phe Asp Leu Ile Tyr Asp Tyr Thr Phe Leu Cys Ala Leu
                165                 170                 175

Leu Pro Glu Met Arg Lys Asp Trp Ala Gln Gln Met Arg Glu Leu Ile
            180                 185                 190

Arg Pro Thr Gly Val Leu Val Cys Leu Glu Phe Pro Leu Tyr Lys Asp
        195                 200                 205

Val Thr Ala Asp Gly Pro Pro Trp Gly Leu Gln Gly Ile Tyr Trp Asn
    210                 215                 220

Leu Leu Ala Glu Gly Gly Asn Gly Arg Met Asp Gly Pro Ala Ala Thr
225                 230                 235                 240

Asp Gly Gly Arg Gly Pro Phe Ser Arg Val Ala Tyr Ile Lys Pro Ser
                245                 250                 255

Arg Ser Tyr Glu Met Gly Arg Gly Thr Asp Met Leu Ser Val Trp Ala
            260                 265                 270

Pro Gln Glu Pro Ser Gly Asp Arg Lys Arg Pro Ala Thr Ala Ala Thr
        275                 280                 285

Pro Ile Pro Trp Cys Ala His Tyr Leu Leu Asn Asp Thr Pro Ala Pro
    290                 295                 300

Phe Pro Leu Ala Tyr Thr Thr Ser Ile Val Val Asn Arg Val Cys Val
305                 310                 315                 320

Arg Pro Ser Ser Gln Lys Gln Leu Ala Glu Ala Arg Val Ala Val Pro
                325                 330                 335

Val Ala Gly Ala Arg Ser Tyr Met Lys Gly Arg Leu Ala Arg Val Val
            340                 345                 350

Arg Leu Pro Ala Arg Arg Ser His Phe Gln Lys Gly Leu Gly Gly Trp
        355                 360                 365
```

```
Val Lys Leu Glu Leu Tyr Cys Ala Leu Glu Ile Arg Pro Gly Cys Val
    370                 375                 380
Ala Gly Leu His Leu Ser Tyr Arg Ala Pro Leu Asp Met Arg Cys Ala
385                 390                 395                 400
Arg Asn Leu Glu Pro Ala Ala Ser Pro Ser Glu Leu Asp
            405                 410

<210> SEQ ID NO 100
<211> LENGTH: 273
<212> TYPE: PRT
<213> ORGANISM: Magnaporthe grisea

<400> SEQUENCE: 100

Met Gly Thr Pro Glu Gln Thr Asn Lys Leu Ser Asn Leu Phe Leu Asp
1               5                   10                  15
Gln Pro Leu Ser Glu His Gly Lys Arg Trp Asp Gly Leu Trp Lys Glu
            20                  25                  30
Asp Tyr Thr Pro Trp Asp Arg Ala Gly Pro Ser Met Ala Leu Tyr Asp
        35                  40                  45
Val Leu Thr Gly Arg Pro Asp Leu Val Pro Pro Thr Gly Gly Gln
50                  55                  60
Lys Lys Arg Ala Leu Val Pro Gly Cys Gly Arg Gly Tyr Asp Val Leu
65                  70                  75                  80
Leu Leu Ser Arg Leu Gly Tyr Asp Val Trp Gly Leu Asp Tyr Ser Glu
                85                  90                  95
Glu Ala Thr Lys Gln Ser Ile Ile Tyr Glu Lys Lys Val Glu Gln Gly
            100                 105                 110
Asp Asp Gly Thr Tyr Ala Glu Leu Glu Arg Glu Gly Val Lys Lys Gly
        115                 120                 125
Lys Val Thr Trp Leu Thr Gly Asp Phe Phe Ser Asp Glu Trp Val Asn
130                 135                 140
Lys Ala Gly Val Gln Gln Phe Asp Leu Thr Tyr Asp Tyr Thr Phe Leu
145                 150                 155                 160
Cys Ala Leu Pro Ile Ser Ala Arg Pro Ala Trp Ala Arg Arg Met Ala
                165                 170                 175
Asp Leu Leu Ala His Glu Gly Arg Leu Val Cys Leu Gln Trp Pro Thr
            180                 185                 190
Ala Lys Pro Trp Ser Gly Gly Pro Pro Trp Gly Val Leu Pro Glu
        195                 200                 205
His Tyr Ile Ala Gln Leu Ala Arg Pro Gly Lys Val Glu Tyr Glu
    210                 215                 220
Ser Asp Gly Lys Ile Pro Ala Gln Ala Met Pro Lys Val Val Glu Gln
225                 230                 235                 240
Gly Gly Leu Arg Arg Leu Glu Leu Val Val Pro Ser Arg Thr His Asn
                245                 250                 255
Ser Gly Ile Ala Asp Gly Val Leu His Asp Arg Ile Ala Val Phe Ala
            260                 265                 270
His

<210> SEQ ID NO 101
<211> LENGTH: 381
<212> TYPE: PRT
<213> ORGANISM: Bacillus methanolicus

<400> SEQUENCE: 101
```

```
Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
            85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Thr Ala Gly Thr Gly Ser Glu Thr
        130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Ala Lys Gly Ala Thr Pro
        195                 200                 205

Val Thr Asp Ala Phe Ala Ile Gln Ala Met Lys Leu Ile Asn Glu Tyr
210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly
                245                 250                 255

Leu Gly Leu Val His Ser Ile Ser His Gln Val Gly Gly Val Tyr Lys
            260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
290                 295                 300

Leu Gly Glu Asn Val Ser Gly Leu Ser Thr Ala Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Glu Asp Ile Glu Leu Leu Ala
            340                 345                 350

Lys Asn Ala Phe Glu Asp Val Cys Thr Gln Ser Asn Pro Arg Val Ala
        355                 360                 365

Thr Val Gln Asp Ile Ala Gln Ile Ile Lys Asn Ala Leu
370                 375                 380

<210> SEQ ID NO 102
<211> LENGTH: 465
<212> TYPE: PRT
<213> ORGANISM: Saccharomyces cerevisiae

<400> SEQUENCE: 102
```

```
Met Leu Gly Ile Thr Tyr Ala Val Asn Ser Thr Lys Gln Leu Ile Phe
1               5                   10                  15
Cys Cys Leu Lys Tyr Leu Thr Leu Leu Gly Tyr Ile Leu Leu Ser Asn
                20                  25                  30
Arg Lys Lys Gly Gln Arg Thr Asn Met Tyr Lys Arg Val Ile Ser Ile
            35                  40                  45
Ser Gly Leu Leu Lys Thr Gly Val Lys Arg Phe Ser Ser Val Tyr Cys
    50                  55                  60
Lys Thr Thr Ile Asn Asn Lys Phe Thr Phe Ala Thr Thr Asn Ser Gln
65                  70                  75                  80
Ile Arg Lys Met Ser Ser Val Thr Gly Phe Tyr Ile Pro Pro Ile Ser
                85                  90                  95
Phe Phe Gly Glu Gly Ala Leu Glu Thr Ala Asp Tyr Ile Lys Asn
            100                 105                 110
Lys Asp Tyr Lys Lys Ala Leu Ile Val Thr Asp Pro Gly Ile Ala Ala
            115                 120                 125
Ile Gly Leu Ser Gly Arg Val Gln Lys Met Leu Glu Glu Arg Asp Leu
    130                 135                 140
Asn Val Ala Ile Tyr Asp Lys Thr Gln Pro Asn Pro Asn Ile Ala Asn
145                 150                 155                 160
Val Thr Ala Gly Leu Lys Val Leu Lys Glu Gln Asn Ser Glu Ile Val
                165                 170                 175
Val Ser Ile Gly Gly Gly Ser Ala His Asp Asn Ala Lys Ala Ile Ala
            180                 185                 190
Leu Leu Ala Thr Asn Gly Gly Glu Ile Gly Asp Tyr Glu Gly Val Asn
        195                 200                 205
Gln Ser Lys Lys Ala Ala Leu Pro Leu Phe Ala Ile Asn Thr Thr Ala
210                 215                 220
Gly Thr Ala Ser Glu Met Thr Arg Phe Thr Ile Ile Ser Asn Glu Glu
225                 230                 235                 240
Lys Lys Ile Lys Met Ala Ile Ile Asp Asn Asn Val Thr Pro Ala Val
                245                 250                 255
Ala Val Asn Asp Pro Ser Thr Met Phe Gly Leu Pro Pro Ala Leu Thr
            260                 265                 270
Ala Ala Thr Gly Leu Asp Ala Leu Thr His Cys Ile Glu Ala Tyr Val
    275                 280                 285
Ser Thr Ala Ser Asn Pro Ile Thr Asp Ala Cys Ala Leu Lys Gly Ile
    290                 295                 300
Asp Leu Ile Asn Glu Ser Leu Val Ala Ala Tyr Lys Asp Gly Lys Asp
305                 310                 315                 320
Lys Lys Ala Arg Thr Asp Met Cys Tyr Ala Glu Tyr Leu Ala Gly Met
                325                 330                 335
Ala Phe Asn Asn Ala Ser Leu Gly Tyr Val His Ala Leu Ala His Gln
            340                 345                 350
Leu Gly Gly Phe Tyr His Leu Pro His Gly Val Cys Asn Ala Val Leu
    355                 360                 365
Leu Pro His Val Gln Glu Ala Asn Met Gln Cys Pro Lys Ala Lys Lys
    370                 375                 380
Arg Leu Gly Glu Ile Ala Leu His Phe Gly Ala Ser Gln Glu Asp Pro
385                 390                 395                 400
Glu Glu Thr Ile Lys Ala Leu His Val Leu Asn Arg Thr Met Asn Ile
                405                 410                 415
```

Pro Arg Asn Leu Lys Glu Leu Gly Val Lys Thr Glu Asp Phe Glu Ile
            420                 425                 430

Leu Ala Glu His Ala Met His Asp Ala Cys His Leu Thr Asn Pro Val
        435                 440                 445

Gln Phe Thr Lys Glu Gln Val Val Ala Ile Ile Lys Lys Ala Tyr Glu
    450                 455                 460

Tyr
465

<210> SEQ ID NO 103
<211> LENGTH: 350
<212> TYPE: PRT
<213> ORGANISM: Pichia pastoria

<400> SEQUENCE: 103

Met Ser Pro Thr Ile Pro Thr Thr Gln Lys Ala Val Ile Phe Glu Thr
1               5                   10                  15

Asn Gly Gly Pro Leu Glu Tyr Lys Asp Ile Pro Val Pro Lys Pro Lys
            20                  25                  30

Ser Asn Glu Leu Leu Ile Asn Val Lys Tyr Ser Gly Val Cys His Thr
        35                  40                  45

Asp Leu His Ala Trp Lys Gly Asp Trp Pro Leu Asp Asn Lys Leu Pro
    50                  55                  60

Leu Val Gly Gly His Glu Gly Ala Gly Val Val Ala Tyr Gly Glu
65                  70                  75                  80

Asn Val Thr Gly Trp Glu Ile Gly Asp Tyr Ala Gly Ile Lys Trp Leu
                85                  90                  95

Asn Gly Ser Cys Leu Asn Cys Glu Tyr Cys Ile Gln Gly Ala Glu Ser
            100                 105                 110

Ser Cys Ala Lys Ala Asp Leu Ser Gly Phe Thr His Asp Gly Ser Phe
        115                 120                 125

Gln Gln Tyr Ala Thr Ala Asp Ala Thr Gln Ala Ala Arg Ile Pro Lys
    130                 135                 140

Glu Ala Asp Leu Ala Glu Val Ala Pro Ile Leu Cys Ala Gly Ile Thr
145                 150                 155                 160

Val Tyr Lys Ala Leu Lys Thr Ala Asp Leu Arg Ile Gly Gln Trp Val
                165                 170                 175

Ala Ile Ser Gly Ala Gly Gly Leu Gly Ser Leu Ala Val Gln Tyr
            180                 185                 190

Ala Lys Ala Leu Gly Leu Arg Val Leu Gly Ile Asp Gly Gly Ala Asp
        195                 200                 205

Lys Gly Glu Phe Val Lys Ser Leu Gly Ala Glu Val Phe Val Asp Phe
    210                 215                 220

Thr Lys Thr Lys Asp Val Val Ala Glu Val Gln Lys Leu Thr Asn Gly
225                 230                 235                 240

Gly Pro His Gly Val Ile Asn Val Ser Val Ser Pro His Ala Ile Asn
                245                 250                 255

Gln Ser Val Gln Tyr Val Arg Thr Leu Gly Lys Val Val Leu Val Gly
            260                 265                 270

Leu Pro Ser Gly Ala Val Val Asn Ser Asp Val Phe Trp His Val Leu
        275                 280                 285

Lys Ser Ile Glu Ile Lys Gly Ser Tyr Val Gly Asn Arg Glu Asp Ser
    290                 295                 300

Ala Glu Ala Ile Asp Leu Phe Thr Arg Gly Leu Val Lys Ala Pro Ile
305                 310                 315                 320

```
Lys Ile Ile Gly Leu Ser Glu Leu Ala Lys Val Tyr Glu Gln Met Glu
                325                 330                 335

Ala Gly Ala Ile Ile Gly Arg Tyr Val Val Asp Thr Ser Lys
            340                 345                 350

<210> SEQ ID NO 104
<211> LENGTH: 296
<212> TYPE: PRT
<213> ORGANISM: Sphingobium paucimobilis

<400> SEQUENCE: 104

Met Ser Leu Gly Ala Lys Pro Phe Gly Glu Lys Lys Phe Ile Glu Ile
1               5                   10                  15

Lys Gly Arg Arg Met Ala Tyr Ile Asp Glu Gly Thr Gly Asp Pro Ile
            20                  25                  30

Leu Phe Gln His Gly Asn Pro Thr Ser Ser Tyr Leu Trp Arg Asn Ile
        35                  40                  45

Met Pro His Cys Ala Gly Leu Gly Arg Leu Ile Ala Cys Asp Leu Ile
    50                  55                  60

Gly Met Gly Asp Ser Asp Lys Leu Asp Pro Ser Gly Pro Glu Arg Tyr
65                  70                  75                  80

Thr Tyr Ala Glu His Arg Asp Tyr Leu Asp Ala Leu Trp Glu Ala Leu
                85                  90                  95

Asp Leu Gly Asp Arg Val Val Leu Val Val His Asp Trp Gly Ser Val
            100                 105                 110

Leu Gly Phe Asp Trp Ala Arg Arg His Arg Glu Arg Val Gln Gly Ile
        115                 120                 125

Ala Tyr Met Glu Ala Val Thr Met Pro Leu Glu Trp Ala Asp Phe Pro
    130                 135                 140

Glu Gln Asp Arg Asp Leu Phe Gln Ala Phe Arg Ser Gln Ala Gly Glu
145                 150                 155                 160

Glu Leu Val Leu Gln Asp Asn Val Phe Val Glu Gln Val Leu Pro Gly
                165                 170                 175

Leu Ile Leu Arg Pro Leu Ser Glu Ala Glu Met Ala Ala Tyr Arg Glu
            180                 185                 190

Pro Phe Leu Ala Ala Gly Glu Ala Arg Arg Pro Thr Leu Ser Trp Pro
        195                 200                 205

Arg Gln Ile Pro Ile Ala Gly Thr Pro Ala Asp Val Val Ala Ile Ala
    210                 215                 220

Arg Asp Tyr Ala Gly Trp Leu Ser Glu Ser Pro Ile Pro Lys Leu Phe
225                 230                 235                 240

Ile Asn Ala Glu Pro Gly His Leu Thr Thr Gly Arg Ile Arg Asp Phe
                245                 250                 255

Cys Arg Thr Trp Pro Asn Gln Thr Glu Ile Thr Val Ala Gly Ala His
            260                 265                 270

Phe Ile Gln Glu Asp Ser Pro Asp Glu Ile Gly Ala Ala Ile Ala Ala
        275                 280                 285

Phe Val Arg Arg Leu Arg Pro Ala
    290                 295
```